US012624333B2

(12) United States Patent
Kellar et al.

(10) Patent No.: US 12,624,333 B2
(45) Date of Patent: May 12, 2026

(54) STABLE INOCULANT COMPOSITIONS AND METHODS FOR PRODUCING SAME

(71) Applicant: NOVOZYMES BIOAG A/S, Bagsvaerd (DK)

(72) Inventors: Kenneth Edmund Kellar, Fuquay-Varina, NC (US); Megan Fruchte, Durham, NC (US); Mike Jerry Schweiner, Durham, NC (US); Jarrod Leland, Blacksburg, VA (US); Anna Wysinski, Roanoke, VA (US); Emily Looze, Bedford, VA (US); Kimberley Clarke, Durham, NC (US); William Pasutti, Durham, NC (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 1002 days.

(21) Appl. No.: 16/471,644

(22) PCT Filed: Dec. 18, 2017

(86) PCT No.: PCT/US2017/066929

§ 371 (c)(1),
(2) Date: Jun. 20, 2019

(87) PCT Pub. No.: WO2018/118740

PCT Pub. Date: Jun. 28, 2018

(65) Prior Publication Data

US 2020/0085065 A1 Mar. 19, 2020

Related U.S. Application Data

(60) Provisional application No. 62/436,562, filed on Dec. 20, 2016, provisional application No. 62/436,529, filed on Dec. 20, 2016, provisional application No. 62/436,517, filed on Dec. 20, 2016.

(51) Int. Cl.
*C12N 1/04* (2006.01)
*A01N 43/80* (2006.01)
*A01N 63/20* (2020.01)

(52) U.S. Cl.
CPC ............... *C12N 1/04* (2013.01); *A01N 43/80* (2013.01); *A01N 63/20* (2020.01)

(58) Field of Classification Search
CPC ........... A01N 63/20; A01N 43/80; C12N 1/04
See application file for complete search history.

(56) References Cited

U.S. PATENT DOCUMENTS

| | | | | |
|---|---|---|---|---|
| 5,014,437 | A | 5/1991 | Sun | |
| 5,104,437 | A | 4/1992 | Hadwiger | |
| 5,358,863 | A | 10/1994 | Quimby, Jr. | |
| 5,484,464 | A | 1/1996 | Gleddie | |
| 5,527,760 | A | 6/1996 | Rensing et al. | |
| 5,586,411 | A | 12/1996 | Gleddie | |
| 5,695,541 | A | 12/1997 | Kosanke | |
| 5,780,023 | A | 7/1998 | McLaughlin et al. | |
| 5,804,208 | A | 9/1998 | Andersch | |
| 5,916,029 | A | 6/1999 | Smith | |
| 5,928,469 | A | 7/1999 | Franks | |
| 6,426,210 | B1 | 7/2002 | Franks | |
| 6,569,425 | B2 | 5/2003 | Drahos | |
| 6,808,917 | B1 | 10/2004 | Johnson | |
| 6,824,772 | B2 | 11/2004 | Drahos | |
| 7,037,708 | B1 | 5/2006 | Runge | |
| 7,037,709 | B2 | 5/2006 | Blumenfeld | |
| 7,429,477 | B2 | 9/2008 | Johnson | |
| 8,011,132 | B2 | 9/2011 | Pearce | |
| 8,148,138 | B2 | 4/2012 | Johnson | |
| 8,278,247 | B2 | 10/2012 | Hnatowich | |
| 8,445,256 | B2 | 5/2013 | Woods | |
| 8,883,679 | B2 | 11/2014 | Woods | |
| 8,921,089 | B2 | 12/2014 | Kang | |
| 8,940,510 | B2 | 1/2015 | Subramanian | |
| 8,999,698 | B2 | 4/2015 | Kang | |
| 9,017,442 | B2 | 4/2015 | Johnson | |
| 9,055,746 | B2 * | 6/2015 | Smith | C05F 11/00 |
| 9,090,884 | B2 | 7/2015 | Harman | |

(Continued)

FOREIGN PATENT DOCUMENTS

| | | | |
|---|---|---|---|
| CA | 2254431 | A1 | 11/1998 |
| CN | 86102971 | A | 12/1986 |

(Continued)

OTHER PUBLICATIONS

Agnes Sri Harti, Dwi Susi Haryati, Sunarto, Wiwik Setyaningsih and Sri Yatmihatun, "The Potential Chito-Oligosaccharide (COS) as Natural Prebiotic and Preservatives on Synbiotic Tofu in Indonesia" International Journal of Pharma Medicine and Biological Sciences, vol. 4, No. 3, pp. 204-208, Jul. 2015 (Year: 2015).*

Hofman DL, van Buul VJ, Brouns FJ. Nutrition, Health, and Regulatory Aspects of Digestible Maltodextrins. Crit Rev Food Sci Nutr. 2016;56(12):2091-2100 doi:10.1080/10408398.2014.940415 (Year: 2016).*

Marguerite Rinaudo, Chitin and chitosan: Properties and applications, Progress in Polymer Science, vol. 31, Issue 7, 2006, pp. 603-632, ISSN 0079-6700 (Year: 2006).*

DB Haytowitz, S Bhagwat, J Harnly, JM Holden, SE Gebhardt Sources of flavonoids in the US diet using USDA's updated database on the flavonoid content of selected foods J Nutr, 137 (2007), pp. 280S-281S. (Year: 2007).*

(Continued)

*Primary Examiner* — Robert J Yamasaki
*Assistant Examiner* — Trevor Kane
(74) *Attorney, Agent, or Firm* — Adam Rucker

(57) ABSTRACT

The present disclosure provides stable inoculant compositions and methods for enhancing the survival and/or stability of microorganisms in an inoculant composition. In some embodiments, the microorganisms in an inoculant compositions are stabilized by the presence of one or more sugar alcohols, humic acids and/or fulvic acids and one or more maltodextrins, monosaccharides, disaccharides, oxidation control components and/or UV protectants.

22 Claims, 23 Drawing Sheets

(56) References Cited

U.S. PATENT DOCUMENTS

| | | | |
|---|---|---|---|
| 9,101,088 B2 | 8/2015 | Hnatowich | |
| 9,102,893 B2 | 8/2015 | Custis | |
| 9,234,251 B2 | 1/2016 | Snyder | |
| 9,340,464 B2 | 5/2016 | Hnatowich | |
| 10,820,594 B2 | 11/2020 | Kellar | |
| 10,856,552 B2 | 12/2020 | Greenshields et al. | |
| 11,076,603 B2 | 8/2021 | Greenshields et al. | |
| 2002/0015988 A1 | 2/2002 | Enzmann | |
| 2003/0012819 A1 | 1/2003 | Ko | |
| 2003/0060371 A1 | 3/2003 | Asrar et al. | |
| 2003/0138936 A1 | 7/2003 | Mizuguchi | |
| 2004/0022860 A1 | 2/2004 | Johson | |
| 2004/0038825 A1* | 2/2004 | Leland | A01N 63/30 504/117 |
| 2004/0077498 A1 | 4/2004 | Lynch | |
| 2006/0150488 A1 | 7/2006 | Pearce et al. | |
| 2006/0229203 A1 | 10/2006 | Peltanen | |
| 2007/0254353 A1 | 11/2007 | Stavnsbjerg | |
| 2008/0013411 A1 | 1/2008 | Thorp et al. | |
| 2008/0107689 A1 | 5/2008 | Seiskari | |
| 2009/0093365 A1 | 4/2009 | Walsh | |
| 2009/0142303 A1 | 6/2009 | Edwards | |
| 2010/0144534 A1 | 6/2010 | Pullen | |
| 2010/0160160 A1 | 6/2010 | Hewlett | |
| 2012/0015806 A1 | 1/2012 | Paikray et al. | |
| 2012/0039956 A1 | 2/2012 | Harel | |
| 2012/0135017 A1 | 5/2012 | Harel | |
| 2012/0283094 A1 | 11/2012 | Meng | |
| 2013/0061645 A1 | 3/2013 | Smith | |
| 2013/0096002 A1 | 4/2013 | Smith et al. | |
| 2013/0323362 A1 | 12/2013 | Penhasi | |
| 2014/0112899 A1 | 4/2014 | Jeschke et al. | |
| 2014/0143909 A1 | 5/2014 | Greenshields | |
| 2014/0308249 A1 | 10/2014 | Tyler et al. | |
| 2014/0342905 A1 | 11/2014 | Bullis et al. | |
| 2015/0230478 A1* | 8/2015 | Vujanovic | A01N 63/28 504/100 |
| 2015/0307409 A1 | 10/2015 | Hnatowich et al. | |
| 2016/0298201 A1* | 10/2016 | Siepe | C12P 7/42 |
| 2019/0014787 A1 | 1/2019 | Greenshields et al. | |
| 2019/0029262 A1 | 1/2019 | Kellar | |
| 2020/0315183 A1 | 10/2020 | Clary et al. | |
| 2021/0219554 A1 | 7/2021 | Greenshields et al. | |

FOREIGN PATENT DOCUMENTS

| | | | | |
|---|---|---|---|---|
| CN | 1489476 A | 4/2004 | | |
| CN | 1922305 A | 2/2007 | | |
| CN | 101106900 A | 1/2008 | | |
| CN | 101341818 A | 1/2009 | | |
| CN | 101709277 A | 5/2010 | | |
| CN | 102070368 A | 5/2011 | | |
| CN | 102246750 A | 11/2011 | | |
| CN | 102433287 A | 2/2012 | | |
| CN | 102459568 A | 5/2012 | | |
| CN | 102987055 A | 3/2013 | | |
| CN | 103039439 A | 4/2013 | | |
| CN | 103421693 A | 4/2013 | | |
| CN | 103140145 A | 6/2013 | | |
| CN | 103283948 A | 9/2013 | | |
| CN | 103347395 A | 10/2013 | | |
| CN | 103404703 A | 11/2013 | | |
| CN | 103444786 A | 12/2013 | | |
| CN | 103766407 A | 5/2014 | | |
| CN | 103787758 A | 5/2014 | | |
| CN | 103911314 A | 9/2014 | | |
| CN | 104080337 A | 10/2014 | | |
| CN | 104255809 A | 1/2015 | | |
| CN | 104628485 A | 5/2015 | | |
| CN | 104797701 A | 7/2015 | | |
| CN | 105101776 A | 11/2015 | | |
| CN | 106190929 A * | 12/2016 | | |
| EP | 0203708 A1 | 3/1986 | | |
| EP | 0906951 A2 | 4/1999 | | |
| JP | 45021632 B | 7/1970 | | |
| JP | 2002176969 A | 6/2002 | | |
| JP | 2004231626 A | 8/2004 | | |
| JP | 2006124337 A | 5/2006 | | |
| JP | 2008525022 A | 7/2008 | | |
| JP | 2009540825 A | 11/2009 | | |
| JP | 2013516193 A | 5/2013 | | |
| JP | 2014501500 A | 1/2014 | | |
| JP | 2015519051 A | 7/2015 | | |
| JP | 2019503714 A | 2/2019 | | |
| JP | 2022010176 A | 1/2022 | | |
| RU | 2345975 C2 | 2/2009 | | |
| RU | 2428467 C2 | 9/2011 | | |
| SU | 922104 T | 4/1982 | | |
| UA | 40992078 A | 7/1992 | | |
| WO | 9957959 A1 | 11/1999 | | |
| WO | 2005095580 A1 | 10/2005 | | |
| WO | 2006071369 A2 | 7/2006 | | |
| WO | 2008002371 A1 | 1/2008 | | |
| WO | 2009/010561 A1 | 1/2009 | | |
| WO | 2009/049747 A2 | 4/2009 | | |
| WO | 2010/037228 A1 | 4/2010 | | |
| WO | 2011085221 A2 | 7/2011 | | |
| WO | 2012058730 A1 | 5/2012 | | |
| WO | 2013/044208 A2 | 3/2013 | | |
| WO | 2013/044214 A1 | 3/2013 | | |
| WO | 2013/096883 A2 | 6/2013 | | |
| WO | 2013090628 A1 | 6/2013 | | |
| WO | 2013169923 A2 | 11/2013 | | |
| WO | WO-2014138490 A1 * | 9/2014 | A01N 43/16 | |
| WO | 2014160827 A1 | 10/2014 | | |
| WO | WO-2015003908 A1 * | 1/2015 | A01N 63/22 | |
| WO | 2015/063090 A2 | 5/2015 | | |
| WO | 2015069708 A1 | 5/2015 | | |
| WO | 2015100432 A2 | 7/2015 | | |
| WO | 2015130911 A1 | 9/2015 | | |
| WO | 2017/044473 A1 | 3/2017 | | |
| WO | 2017044545 A1 | 3/2017 | | |
| WO | 2017/116837 A1 | 7/2017 | | |
| WO | 2017/116846 A1 | 7/2017 | | |
| WO | 2017131971 A1 | 8/2017 | | |

OTHER PUBLICATIONS

Cruz, Renato Souza, Geany Peruch Camilloto, and Ana Clarissa dos Santos Pires. "Oxygen scavengers: an approach on food preservation." in: Structure and function of food engineering 2 (IntechOpen) pp. 21-42 (2012). (Year: 2012).*

Sara Gaucher., 5 benefits of Lactobacillus bacteria, Mar. 2020, [serialonline], [retrieved Nov. 9, 2021] retrieved from the internet <URL: https://symsoil.com/benefits-of-lactobacillus-bacteria/> (Year: 2020).*

Scarmeas, Nikolaos, Costas A. Anastasiou, and Mary Yannakoulia. "Nutrition and prevention of cognitive impairment." The Lancet Neurology 17.11 (2018): 1006-1015 (Year: 2018).*

Chi, Feng, et al. "Ascending migration of endophytic rhizobia, from roots to leaves, inside rice plants and assessment of benefits to rice growth physiology." Applied and environmental microbiology 71.11 (2005): 7271-7278. (Year: 2005).*

Harti, A. S., Haryati, D. S., Setyaningsih, W., & Yatmihatun, S. (2015). The potential chito-oligosaccharide (COS) as natural prebiotic and preservatives on synbiotic tofu in Indonesia. International Journal of Pharma Medicine and Biological Sciences, 4(3), 204. (Year: 2015).*

Rong, Y., Sillick, M., & Gregson, C. M. (2009). Determination of dextrose equivalent value and number average molecular weight of maltodextrin by osmometry. Journal of Food Science, 74(1), C33-C40 (Year: 2009).*

CN-106190929-A, Dec. 2016, Liu Peng Machine translation. (Year: 2016).*

Diange, E. A., & Lee, S. S. (2013). *Rhizobium halotolerans* sp. nov., isolated from chloroethylenes contaminated soil. Current microbiology, 66(6), 599-605 (Year: 2013).*

Storz, Elizabeth, and Klaus-Jürgen Steffens. "Feasibility study for determination of the dextrose equivalent (DE) of starch hydrolysis

(56) References Cited

OTHER PUBLICATIONS products with near-infrared spectroscopy (NIRS)." Starch-Stärke 56.2 (2004): 58-62. (Year: 2004).*
Behboudi-Jobbehdar et al, 2013, Drying Technology 31(11), 1274-1283.
Anonymous, 2013, Jumpstart LCO Extended Label, Internet website.
Colaco et al, 1992, Biotechnology 10(9), 1007-1011.
Oldenhof et al, 2005, Biotechnol Progr 21(3), 885-892.
Friesen et al, 2005, Appl Microbiol Biotechnol 68(3), 397-404.
Shahidi et al, 1993, Crit Rev Food Sci Nutri 33(6), 501-547.
Fu et al, 2011, Food Res Int 44(5), 1127-1149.
Campos et al, 2014, World J Microbiol Biotechnol 30(9), 2371-2378.
Hewitt et al, 2013, Food and bioproducts processing 91, 362-369.
Mary et al, 1994, Soil Biol Biochem 26(9), 1125-1132.
Schoebitz et al, 2013, Agronomy for Sustainable Development 33(4), 751-765.
Streeter, 2003, J Appl Microbiol 95(3), 484-491.
Boos et al, 1998, Microbiol Mol Biol Revs, vol. 62, No. 1, pp. 204-229.
Fu et al, 2008, China traditional Chinese Medicine Press, pp. 109-112.
Batsam et al, 2012, African journal of food, vol. 12, No. 3, pp. 1-10.
Kawai et al, 2005, Pharmaceutical research, vol. 22, No. 3, pp. 490-495.
Pispan et al, 2013, Food and bioproducts processing, vol. 91, No. 4, pp. 362-369.
Semyonov et al, 2011, LWT-Food science and technology, vol. 44, No. 9, pp. 1844-1852.
Yao et al, 2007, China traditional Chinese Medicine Press, pp. 232-234.
Zhang(Ed) et al, 2009, China Light Industry Press, p. 291.
Zhao(Ed) et al, 1988, Beijing Agricultural University Press, p. 228.
Zhao(Ed), 1986, Agricultural Press, pp. 497-499.
Lai et al., Vaccine, 2013, 4759-4764, 31.
Bashan et al., 2014, Plant and Soil, 378(1), 1-33.
Chi et al., 2005, Applied and Environmental Microbiology, 71(11), 7271-7278.
Cunningham et al., 1990, Can. J. Bot., 68(10), 2270-2274.
Gaucher, 2020, 5 Benefits of Lactobacillus bacteria, 1-7.
Guangzhou Glam Biotechnology Co Ltd., 2013, abstract of CN103283948A.
Guangzhou Glam Biotechnology Co. Ltd., 2013, abstract of CN103404703A.
Harbin Inst of Technology, 2010, abstract of CN101709277A.
Idemitsu Kosan Co et al., 2005, Abstract of WO2005095580A1.
Inst of Microbiology Heilongjiang Acedemy of Sciences et al., abstract of CN103421693.
Kleespies et al., Biocontrol Science and Technology, 4, 309-319, 1994.
Leading Green Biolog Zhenjiang Co. Ltd. et al., abstract of CN103911314.
Li Xueping, 2013, abstract of CN102987055A.
Mariupol I Metallurgical Works et al., abstract of UA26928U.
Meng Honglin, 2015, abstract of CN104628485A.
Monsanto Company, 2015, Safety Data Sheet, Commercial Product.
Oregel-Zamudio et al., 2017, Scientia Horticulturae, 214, 273-279.
Patil et al., 2012, International journal of environmental sciences, 3(3), 1116-1129.
Takahashi, 1967, The Japanese Journal of Tuberculosis, 14(3-4), 67-95.
Tianjin Univ of Science and Technology et al., abstract of CN102433287.
Torres et al., 2003, Journal of Applied Microbiology, 94, 330-339.
Universitet China Agricultural, 2011, Abstract of CN102070368.
Vnii Sel'Skokhozyaystvennoy Mikrobiologii Inst. et al. 1982, abstract of SU922104A1.
Zongyang County Baiyun Ecological Garden Co. Ltd., 2014, abstract of CN103787758A.

* cited by examiner

STABLE INOCULANT COMPOSITIONS AND METHODS FOR PRODUCING SAME

CROSS-REFERENCE TO RELATED APPLICATIONS

This application is a 35 U.S.C. 371 national application of international application no. PCT/US2017/066929 filed Dec. 18, 2017, which claims priority or the benefit under 35 U.S.C. 119 of U.S. application nos. 62/436,517, 62/436,529 and 62/436,562 each of which were filed Dec. 20, 2016, the contents of which are fully incorporated herein by reference.

NAMES OF PARTIES TO A JOINT RESEARCH AGREEMENT

The inventive concepts described herein were developed as pan of a joint research agreement between Monsanto Company and Novozymes BioAg A/S. The activities giving rise to the claimed invention were undertaken within the scope of the joint research agreement, said agreement having been in effect on or before the date the claimed invention was made.

FIELD OF THE INVENTION

The present disclosure relates to compositions and methods for enhancing the stability and survival of microorganisms in inoculant compositions.

BACKGROUND OF THE INVENTION

Inoculant compositions comprising agriculturally beneficial microorganisms are well known in the an. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Because the effectiveness of such inoculant compositions generally depends on the ability of the microorganisms therein to survive and propagate following application, much effort has been made to increase the stability of agriculturally beneficial microorganisms in inoculant compositions. See, e.g., U.S. Pat. No. 8,011,132 (describing a method of adding trehalose, sucrose or glycerol to the substantially stationary phase of fermentation) and U.S. Pat. No. 9,090,884 (describing the microencapsulation of microorganisms in a water-soluble encapsulating material).

Nevertheless, there remains a need for improved compositions and methods for enhancing the stability and survival of microorganisms in inoculant compositions.

SUMMARY OF THE CLAIMED SUBJECT MATTER

The present disclosure provides compositions and methods for enhancing the survival and/or stability of microorganisms in inoculant compositions.

A first aspect of the present disclosure is an inoculant composition comprising one or more maltodextrins, one or more sugar alcohols and one or more microorganisms. In some embodiments, the inoculant composition further comprises one or more humic acids, one or more fulvic acids, one or more monosaccharides, one or more disaccharides, one or more oligosaccharides, one or more pest attractants, one or more pesticides, one or more lipo-chitooligosaccharides, one or more chitooligosaccharides, one or more chitinous compounds, one or more flavonoids, one or more oxidation control components, and/or one or more drying agents.

A second aspect of the present disclosure is a method that comprises applying an inoculant composition of the present disclosure to a plant propagation material.

A third aspect of the present disclosure is a method that comprises applying an inoculant composition of the present disclosure to a plant.

A fourth aspect of the present disclosure is a coated plant propagation material comprising a plant propagation material and a coating that covers at least a portion of an outer surface of the plant propagation material, said coating comprising an inoculant composition of the present disclosure.

A fifth aspect of the present disclosure is a kit comprising an inoculant composition of the present disclosure and a container housing the inoculant composition.

A sixth aspect of the present disclosure is a kit comprising a coated plant propagation material of the present disclosure and a container housing the coated plant propagation material.

A seventh aspect of the present disclosure is a method that comprises planting a coated plant propagation material of the present disclosure.

DETAILED DESCRIPTION

Figure 1:
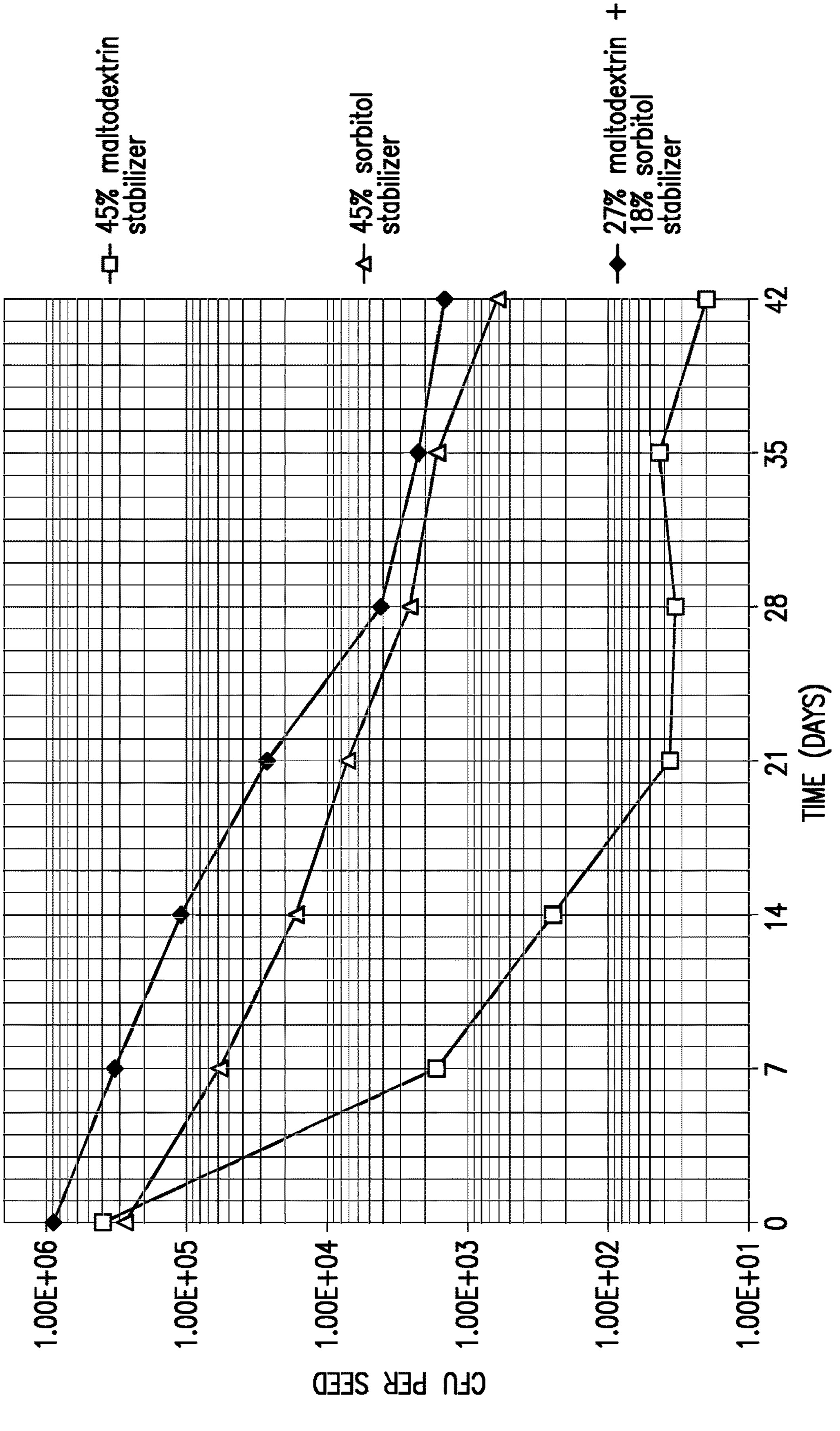
FIGS. 1-5 are graphs showing the survivability of desiccated *Yersinia entomaphaga* O82KB8 on soybean seeds stored at room temperature and 54% relative humidity.

The present disclosure is explained in greater detail below. This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure Hence, the following specification is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms “a,” “an,” and “the” are intended to include the plural forms as well, unless the context clearly indicates otherwise Thus, unless the context clearly indicates otherwise, “a maltodextrin” is to be interpreted as “one or more maltodextrins,” “a microorganism” is to be interpreted as “one or more microorganisms,” “a lipo-chitooligosaccharide” is to be interpreted as “one or more lipo-chitooligosaccharides.” etc.

As used herein, the term “about.” when used in reference to a measurable value such as an amount of mass, dose, time, temperature and the like, is meant to encompass variations of 0.1%, 0.25%, 0.5%, 0.75%, 1%, 2%, 3%, 4%, 5%, 6%, 7% 8%, 9%, 10%, 11%, 12%, 13%, 14%, 15%, 16%, 17%, 18%, 19% or 20% of the specified amount Unless otherwise indicated, all numerical values in the specification are to be understood as being modified by the term “about.”

As used herein, the term “agriculturally beneficial agent” refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., acaricides, fungicides, herbicides, insecticides, and nematicides) and plant signal molecules.

As used herein, the term “agriculturally beneficial microorganism” refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term “agriculturally acceptable carrier” refers to a material that can be used to deliver an agriculturally beneficial agent to a plant, plant part or plant growth medium (e.g., soil). As used herein, the term “soil-compatible carrier” refers to a material that can be added to a soil without causing/having an unduly adverse effect on plant growth, soil structure, soil drainage, or the like. As used herein, the term “seed-compatible carrier” refers to a material that can be added to a seed without causing/having an unduly adverse effect on the seed, the plant that grows from the seed, seed germination, or the like. As used herein, the term “foliar-compatible carrier” refers to a material that can be added to a plant or plant part without causing/having an unduly adverse effect on the plant, plant part, plant growth, plant health, or the like.

As used herein, the term “and/or” is intended to include any and all combinations of one or more of the associated listed items, as well as the lack of combinations when interpreted in the alternative (“or”).

As used herein, the term “aqueous” refers to a composition that contains more than a trace amount of water (i.e., more than 0.5% water by weight, based upon the total weight of the composition).

As used herein, the term “biostimulant” refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term “BRADY” is to be interpreted as a shorthand substitute for the phrase “*Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129 and/or *Bradyrhizobium japonicum* USDA 532C.”

As used herein, the term “colony forming unit” refers to a microbial cell/spore capable of propagating on or in a substrate (e.g., a soil) when conditions (e.g., temperature, moisture, nutrient availability, pH, etc.) are favorable for microbial growth.

As used herein, the terms “comprise,” “comprises,” “comprising,” “include,” “includes” and “including” specify the presence of stated features, steps, operations, elements and/or components, but do not preclude the presence or addition of one or more other features, steps, operations, elements, components and/or groups thereof.

As used herein, the term “consists essentially of” (and grammatical variants thereof), as applied to the compositions and methods of the present disclosure, means that the compositions/methods may contain additional components so long as the additional components do not materially alter the composition method. The term “materially alter.” as applied to a composition/method, refers to an increase or decrease in the effectiveness of the composition/method of at least about 20% or more. For example, a component added to an inoculant composition of the present disclosure "materially alters" the composition if it increases or decreases the composition's ability to enhance microbial survival by at least about 50%.

As used herein, the terms "effective amount." "effective concentration," and "effective dosage" (and grammatical variants thereof) refer to an amount, concentration or dosage that is sufficient to cause a desired effect (e.g., enhanced microbial survival). The absolute value of the amount/concentration/dosage that is sufficient to cause the desired effect may be affected by factors such as the type and magnitude of effect desired, the type, size and volume of seeds to which the inoculant composition will be applied, the type(s) of microorganisms in the composition, the number of microorganisms in the composition, the stability of the microorganisms in the inoculant composition and the storage conditions (e.g., temperature, relative humidity, duration) Those skilled in the art will understand how to select an effective amount/concentration/dosage using routine dose-response experiments.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced growth" and "enhanced plant growth" refer to an improvement in one or more characteristics of plant growth and/or development as compared to one or more control plants (e.g., a plant germinated from an untreated seed or an treated plant). Exemplary plant growth/development characteristics include, but are not limited to, biomass, carbohydrate biosynthesis, chlorophyll content, cold tolerance, drought tolerance, height, leaf length, leaf mass, leaf number, leaf surface area, leaf volume, nutrient uptake (e.g., calcium, magnesium, nitrogen, phosphorous and/or potassium uptake), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stomatal conductance and survival rate. Unless otherwise indicated, references to enhanced plant growth are to be interpreted as meaning that compositions and methods of the present disclosure may be capable of enhancing plant growth by enhancing nutrient availability, improving soil characteristics, etc. and are not to be interpreted as suggesting that compositions and methods of the present disclosure act as plant growth regulators.

As used herein, the term "enhanced stability" refers to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to germinate and/or propagate after being coated on a seed and/or stored for a defined period of time and the ability to cause a desired effect (e.g., enhanced plant yield and/or increased pesticidal activity) after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the term "enhanced survival" refers to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a "stable inoculant composition."

As used herein, the terms "enhanced yield" and "enhanced plan yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content, percentage of plants in a given area (e.g., plot) that fail to produce grain, yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that compositions and methods of the present disclosure may be capable of enhancing plant yield by enhancing nutrient availability, improving soil characteristics, etc. and are not to be interpreted as suggesting that compositions and methods of the present disclosure act as plant growth regulators. As used herein, the term "foliage" refers to those portions of a plant that normally grow above the ground, including, but not limited to, leaves, stalks, stems, flowers, limiting bodies and fruits.

As used herein, the terms "foliar application," "foliarly applied" and grammatical variations thereof, refer to the application of one or more active ingredients to the foliage of a plant (e.g., to the leaves of the plant) Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the term "fulvic acid" encompasses pure fulvic acids and fulvic acid salts (fulvates). Non-limiting examples of fulvic acids include ammonium fulvate, boron fulvate, potassium fulvate, sodium fulvate, etc. In some embodiments, the fulvic acid comprises, consists essentially of or consists of MDL Number MFCD09838488 (CAS Number 479-66-3).

As used herein, the term "humic acid" encompasses pure humic acids and humic acid salts (humates). Non-limiting examples of humic acids include ammonium humate, boron humate, potassium humate, sodium humate, etc. In some embodiments, the humic acid comprises, consists essentially of or consists of one or more of MDL Number MFCD00147177 (CAS Number 1415-93-6). MDL Number MFCD00135560 (CAS Number 68131-04-4), MDL Number MFCS22495372 (CAS Number 68514-28-3), CAS Number 93924-35-7 and CAS Number 30806745-0.

As used herein, the terms "inoculant composition" and "inoculum" refer to compositions comprising microbial cells and/or spores, said cells/spores being capable of propagating/germinating on or in a substrate (e.g., a soil) when conditions (e.g., temperature, moisture, nutrient availability, pH, etc.) are favorable for microbial growth.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer, where embodiments disclose a (L)-enantiomer, that embodiment also includes the (D)-enantiomer. Where embodiments disclose a (+)-enantiomer, that embodiment also includes the (−)-enantiomer, where embodiments disclose a (−)-enantiomer, that embodiment also includes the (+)-enantiomer. Where embodiments disclose a (S)-enantiomer, that embodiment also includes the (R)-enantiomer, where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with am different microbial strain; and any combination of the foregoing. The term modified microbial strains includes a strain with (a) one of more heterologous nucleotide sequences. (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4$+), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "PENI" is to be interpreted as a shorthand substitute for the phrase "*Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Pecullium bilaiae* RS7B-SD1, *Penicillium brevicompactum* AgRF18, *Penicillium canesens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490."

As used herein, the term "*Penicillium bilaiae*" is intended to include all iterations of the species name, such as "*Penicillium bilaji*" and "*Penicillium bilaii.*"

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., caterpillars, thrips, weevils, white flies, etc.), nematodes (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, bactericides, fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated Examples of plant propagation materials include, but are not limited to, cuttings (e.g., leaves, stems), rhizomes, seeds, tubers and cells/tissues that can be cultured into a whole plant.

As used herein, the term "stabilizer" refers to an agent or combination of agents the application of which enhances the survival and/or stability of a microorganism in an inoculant composition.

As used herein, the terms "spore" and "microbial spore" refer to a microorganism in its dormant, protected state. As used herein with respect to inoculant compositions, the term "stable" refers to an inoculant composition in which one or more microorganisms exhibit enhanced stability and/or survival. In general, an inoculant composition may be labeled "stable" if it improves the survival rate and/or at least one microbial stability characteristic of at least one microorganism contained therein.

As used herein with respect to microbial spores, the term "survival rate" refers to the percentage of microbial spores that are viable (i.e., capable of propagating on or in a substrate (e.g., on a seed and/or in a soil) when conditions (e.g., temperature, moisture, nutrient availability. pH, etc.) are favorable for microbial growth) at a given period of time.

As used herein, the term "UV protectant" refers to an agent or combination of agents the application of which reduces one or more of the detrimental effects experienced by microorganisms upon being exposed to ultraviolet radiation. In some embodiments, the UV protectant acts by filtering and/or absorbing a portion of the ultraviolet radiation, thereby reducing a microorganism's exposure thereto.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides stable inoculant compositions and methods for enhancing the stability and/or survival of microorganisms.

Inoculant compositions of the present disclosure comprise, consist essentially of, or consist of one or more microorganisms in a stabilizing medium that comprises, consists essentially of or consists of one or more sugar alcohols (e.g., arabitol, mannitol, sorbitol and/or xylitol), one or more humic acids (e.g., ammonium humate, boron humate, potassium humate and/or sodium humate), and/or one or more fulvic acids (e.g., ammonium fulvate, boron fulvate, potassium fulvate and/or sodium fulvate).

Sugar alcohols, humic acids and fulvic acids may be used to stabilize myriad microorganisms, including, but not limited to, agriculturally beneficial microorganisms such as diazotrophs, phosphate-solubilizing microorganisms and biopesticides. Selection of additional microbes (if any) will depend on the intended application(s).

In some embodiments, inoculant compositions of the present disclosure comprise one or more bacteria (e.g., one or more Gram-negative bacteria and/or one or more Gram-positive bacteria). Non-limiting examples of bacteria that may be useful in inoculant compositions of the present disclosure include *Azospirillum brasilense* INTA Az-39, *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA4658) and *Bacillus amyloliquefaciens* BS18 (deposited as NRRL B-50633), *Bacillus cereus* I-1562, *Bacillus firmus* 1-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus*

*subtilis* 3BP5 (deposited as NRRL B-50510), *Bacillus thuringiensis* ATC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, *Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129, *Bradyrhizobium japonicum* USDA 532C, *Pseudomonas jessenii* PSO6, *Rhizobium leguminosarum* SO12A-2 (IDAC 080305-01). *Sinorhizobium fredii* CCBAU114, *Sinorhizobium fredii* USDA 205, *Yersinia entomophaga* O82KB8 and combinations thereof, as well as microorganisms having at least at least 75%, 80%, 85%, 90%, 95%, 96%, 97%, 98%, 99% or more identical to any of the aforementioned strains on the basis of 16S rDNA sequence identity.

In some embodiments, inoculant compositions of the present disclosure comprise one or more fungi. Non-limiting examples of fungi that may be useful in inoculant compositions of the present disclosure include *Gliocladium virens* ATCC 52045, *Gliocladium virens* GL-21, *Glomus intraradices* RTI-801, *Metarhizium anisopliae* F52, *Penicillium bilaiae* (formerty known as *P. bilaiae* and *P. bilaji*) ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777. *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SDI, *Penicillium breviocompactum* AgRF18. *Penicillium canescens* ATCC 10419, *Penicillium expansum* ATCC 24692, *Penicillium expansum* YT02, *Peculium fellatanum* ATCC 48694, *Penicillium gaestrivorus* NRRL 50170, *Penicillium glabrum* DAOM 239074, *Penicillium glabrum* CBS 229.28, *Penicillium janthinellium* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium raistrickii* ATCC 10490, *Trichoderma asperellum* SKT-1, *Trichoderma asperellum* ICC 012, *Trichoderma atroviride* LC52, *Trichoderma atroviride* CNCM 1-1237*Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* GL-3, *Trichoderma virens* GL-21, *Trichoderma virens* G-41. *Trichoderma viridae* ATCC 52440, *Trichoderma viridae* ICC080, *Trichoderma viridae* TV1 and combinations thereof, as well as microorganisms having at least at least 75%, 80%, 85%, 90%, 95%, 96%, 97%, 98%, 99% or more identical to any of the aforementioned strains on the basis of internal transcribed spacer (ITS) and/or cytochrome c oxidase (COI) sequence identity.

In some embodiments, inoculant compositions of the present disclosure comprise one or more mycorrhizal fungi (e.g., one or more endomycorrhizal fungi, one or more ectomycorrhizal fungi and/or one or more ericoid mycorrhizal fungi). Non-limiting examples of myconthizal strains that may be useful in inoculant compositions of the present disclosure include mycorrhizal strains such as *Gigaspora margarita, Glomus aggregatum, Glomus brasilianum, Glomus clarum, Glomus deserticola, Glomus etunicatum, Glomus intraradices, Glomus monosporum, Glomus mosseae, Laccaria bicolor, Laccaria laccata, Paraglomus brazilianum, Pisolithus tinctorius, Rhizopogon amylopogon, Rhizopogon fulvigleba, Rhizopogon luteolus, Rhizopogon villosuh, Scleroderma cepa* and *Scleroderma citrinum* and combinations thereof.

In some embodiments, inoculant compositions of the present disclosure comprise one or more biopesticides (e.g., one or more biofungicides, bioherbicides, bioinsectides and/or bionematicades). See generally Burges, Formulation of Microbial Biopesticides: Beneficial Microorganisms, Nematodes and Seed Treartments (Springer Science & Business Media) (2012); Hall & Menn, Biopestictde Use and Delivery (Humana Press) (1998); McCoy, et al., *Entomogenous fungi*, in CRC Handbook of Natural Pesticides. Microbial Pesticides, Part A. Entomogenous Protozoa and Fungi (C. M. Inoffo, ed), Vol. 5:151-236 (1988); Samson, et al., Atlas of Entomopathogenic Fungi (Springer-Verlag, Berlin) (1988); deFaria and Wraight, *Mycoinsecticides and Mycoacaricides: A comprehensive list with worldwide coverage and international classification of formulation types*, Biol. Control (2007), doi: 10 1016/j.biocontrol.2007.08 001; and WO 2016/096821. Non-limiting examples of biopesticidal strains that may be useful in compositions of the present disclosure include *Ampelomyces quisqualis* AQ 10® (Intrachem Bio GmbH & Co. KG, Germany), *Aspergillus flavus* AFLA-GUARD® (Syngenta Crop Protection, Inc. CH). *Aureobasidium pullulans* BOTECTOR® (bio-ferm GmbH, Germany), *Bacillus* AQ175 (ATCC 55608), *Bacillus* AQ177 (ATCC 55609), *Bacillus amyloliquefaciens* FZB24, *Bacillus*

*amyloliquefaciens* FZB42, *Bacillus amyloliquefaciens* NRRL B-50349, *Bacillus amyloliquefaciens* TJJ1000 (also known as iBE, isolate ATCC BAA-390), *Bacillus firmus* 1-1582, *Bacillus mycoides* AQ726 (NRRL B-21664); *Bacillus pumilus* AQ717 (NRRL B-21662), *Bacillus pumilus* NRRL B-30087, *Bacillus subtilis* AQ713 (NRRL B-21661), *Bacillus subtilis* AQ743 (NRRL B-21665), *Bacillus subtilis* ATCC 55078, *Bacillus subtilis* ATCC 55079, *Bacillus thuringiensis* AQ52 (NRRL B-21619), *Beauveria bassiana* ATCC-74040, *Beauveria bassiana* ATCC-74250, *Burkholderia* sp. A3% sp, nov. rinojensis, NRRL B-50319, *Candida oleophila* 1-182 (e.g., ASPIRE®, Ecogen Inc., USA), *Candida saitoana, Chromobacterium subtsugae* NRRL B-30655, *Chromobacterium vaccinii* NRRL B-50880, *Clonostachys rosea* f, *catenulata* (also referred to as *Ghocladium catenulatum*) J1446 (PRESTOP®, Verdera, Finland), *Coniothyrium munitans* CONTANS® (Prophyta, Germany), *Cryphonectria parasitica* (CNICM, France), *Cryptococcus albidus* YIELD PLUS® (Anchor Bio-Technologies. South Africa), *Flavobacterium* H492, NRRL B-50584, *Fusarium oxysporum* BIOFOXA (from S.I.A.P.A., Italy) and FUSACLEAN® (Natural Plant Protection, France), *Gliocladium virens* GL-21 (SOILGARD®, Certis LLC, USA), *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD 170 and ARSEF 7711), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Paeclomyces fumosoroseus* FE991, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVER SUM®, Remeslo SSRO, Biopreparaty, Czech Rep.), *Reynoutria sachlinensis* (e.g., REGALIA®, Marrone BioInnovations, USA), *Streptomyces* NRRL B-30145, *Streptomyces* MI064, *Streptomyces galbus* NRRL 30232, *Streptomyces lydicus* WYEC 108 (ATCC 55445), *Streptomyces violaceusniger* YCED 9 (ATCC 55660), *Streptomyces* WYE 53 (ATCC 55750), *Talaromyces flavus* VI 17b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELDI®, BioWorks Inc, USA), *Trichoderma harzianum* TH-35 (ROOT PRO®, Mycontrol Ltd., Israel), *Trichoderma harzianum* T-39 (TRICHODEX®, Mycontrol Ltd., Israel, *TRICHODERMA* 2000®, Makhteshim Ltd., Israel), *Trichoderma harzianum* ICC012 and *Trichoderma viride* TRICHOPEL (Agrimm Technologies Ltd. NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E P.L.A.C., Brazil), *Trichoderma virens* GL-3 (ATCC 58678), *Trichoderma viride* TRIECO® (Ecosense Labs. (India) PNt. Ltd., India, BIO-CURE® F, T. Stanes & Co. Ltd., Indica, *Trichoderma viride* TV1 (Agribiotec srl, Italy), *Trichoderma viride* ICC080, *Ulocladium oudemansii* HRU3 (BOTRY-ZEN®, Botry-Zen Ltd, NZ) and combinations thereof.

In some embodiments, inoculant compositions of the present disclosure comprise one or more modified microbial strains.

Additional examples of microorganisms that may be useful in compositions of the present disclosure are set forth in Appendix A.

Microorganisms may be incorporated into inoculant compositions of the present disclosure in any suitable amount(s)/concentration(s).

In some embodiments, the microorganism(s) comprise about 0.1 to about 95% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% or more (by weight) of one or more agriculturally beneficial microorganisms (e.g., BRADY and/or PENI) In some embodiments, the microorganism(s) amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, the microorganism(s) is/are present in an amount/concentration ranging from about $1\times10^{1}$ to about $1\times10^{12}$ colony-forming units (cfu) per gran and/or milliliter of inoculant composition. For example, inoculant compositions of the present disclosure may comprise about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$ or more cfu of one or more agriculturally beneficial microorganisms per gram and/or milliliter of inoculant composition (e.g., about $1\times10^{2}$ to about $1\times10^{2}$ cfu of BRADY and/or PENI per gram and/or milliliter of inoculant composition).

In some embodiments, the microorganism(s) is/are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is introduced into a plant growth medium (e.g., a soil).

In some embodiments, the microorganism(s) is/are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is applied to a plant or plant part.

It is to be understood that sugar alcohols, humic acids and fulvic acids may be used to stabilize microbes in vegetative form, spore form and combinations thereof. In some embodiments, inoculant compositions of the present disclosure comprise are devoid of spores. In some embodiments, inoculant compositions of the present disclosure comprise are devoid of vegetative cells.

In some embodiments, microbial spores comprise about 0.1 to about 95% (by weight) of the inoculant composition. For example, inoculant compositions of the present disclosure may comprise about 0.1, 0.2, 0.3, 0.4, 0.5, 0.6.0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95% or more (by weight) of one or more microbial spores. In some embodiments, the microbial spore amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, microbial spores are present in an amount/concentration ranging from about $1\times10^{1}$ to about $1\times10^{12}$ colony-forming units (cfu) per gram and/or milliliter of inoculant composition. For example, inoculant compositions of the present disclosure may comprise about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$ or more microbial spores per gram and/or milliliter of inoculant composition (e.g., about $1\times10^{4}$ to about $1\times10^{9}$ *Bacillus amyloliquefaciens* TJJ000 (also known as 1BE, isolate ATCC BAA-390), *Metarhisium anisopliae* F52, *Penicillium bilaiae* ATCC 20851, *Penicillium bilaiae* RS7B-SD1 and/or *Trichoderma virens* GL-3 spores per gram/milliliter).

In some embodiments, microbial spores are present in an amount/concentration effective for mixing atmospheric nitrogen, solubilizing phosphate, controlling one or more phytopathogenic pests, enhancing plant growth, enhancing plant stress tolerance and/or enhancing plant yield when the inoculant composition is introduced into a plant growth medium (e.g., a soil).

In some embodiments, microbial spores are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is applied to a plant or plant part.

Microorganisms included in inoculant compositions of the present disclosure may be produced using any suitable method(s), including, but not limited to, liquid state fermentation and solid state fermentation. See, generally, Cunningham et al., Can. J. Bot. 68:2270 (1990); Friesen et al., Appl. Microbiol. Boitech. 68:397 (2005).

Microorganisms included in inoculant compositions of the present disclosure may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

Microorganisms may be harvested and incorporated into inoculant compositions of the present disclosure during any suitable growth phase. In general, microorganisms are allowed to reach the stationary growth phase before they are harvested and incorporated into inoculant compositions of the present disclosure.

The stabilizing medium may comprise any suitable sugar alcohol(s), including, but not limited to, arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and xylitol. In some embodiments, one or more of arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and xylitol is/are excluded from inoculant compositions of the present disclosure.

The stabilizing medium may comprise any suitable humic acid(s), including, but not limited to, leonardite humic acids, lignite humic acids, peat humic acids and water-extracted humic acids. In some embodiments, the stabilizing medium comprises ammonium humate, boron humate, potassium humate and/or sodium humate. In some embodiments, one or more of ammonium humate, boron humate, potassium humate and sodium humate is/are excluded from inoculant compositions of the present disclosure Nonlimiting examples of humic acids that may be useful in embodiments of the present disclosure include MDL Number MFCD00147177 (CAS Number 1415-93-6), MDL Number MFCD00135560 (CAS Number 68131-04-4). MDL Number MFCS22495372 (CAS Number 68514-28-3), CAS Number 93924-35-7 and CAS Number 308067-45-0.

The stabilizing medium may comprise any suitable fulvic acid(s), including, but not limited to, leonardite fulvic acids, lignite fulvic acids, peat fulvic acids and water-extracted fulvic acids. In some embodiments, the stabilizing medium comprises ammonium fulvate, boron fulvate, potassium fulvate and/or sodium fulvate. In some embodiments, one or more of ammonium fulvate, boron fulvate, potassium fulvate and sodium fulvate is/are excluded from inoculant compositions of the present disclosure. Nonlimiting examples of fulvic acids that may be useful in embodiments of the present disclosure include MDL Number MFCD09838488 (CAS Number 479-66-3).

Sugar alcohols, humic acids, and fulvic acids may be incorporated into inoculant compositions of the present disclosure in any suitable form(s), including, but not limited to, powders, flakes, crystals and suspensions. In some embodiments, the sugar alcohol(s), humic acid(s) and/or fulvic acid(s) included in inoculant compositions of the present disclosure is/are at least 70, 75, 80, 85, 90, 91, 92, 93, 94, 95, 96, 97, 98, 99, 99.5% or more pure when incorporated into the inoculant composition. In some embodiments, the sugar alcohol(s), humic acid(s) and/or fulvic acid(s) is/are incorporated into the inoculant composition as part of a mixture containing one or more additional substances. Non-limiting examples of such mixtures include CAS Number 68514-28-3.

Sugar alcohols, humic acids and fulvic acids may be incorporated into inoculant compositions of the present disclosure in any suitable amount(s)/concentration(s). The absolute value of the amount(s)/concentration (s) that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration) Those skilled in the art will understand how to select an effective amount/concentration/dosage using routine dose-response experiments.

In some embodiments, sugar alcohol(s) comprise(s) about 0.001 to about 95% or more (by weight) of the inoculant composition. In some embodiments, sugar alcohol(s) (e.g., arabitol, mannitol, sorbitol and/or xylitol) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more sugar alcohols (e.g., arabitol, mannitol, sorbitol and/or xylitol).

In some embodiments, humic acid(s) comprise(s) about 0.001 to about 95% or more (by weight) of the inoculant composition. In some embodiments, humic acid(s) (e.g., ammonium humate, boron humate, potassium humate and/or sodium humate) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85.190, 95% or more (by weight) of one or more humic acid (e.g., ammonium humate, boron humate, potassium humate and/or sodium humate).

In some embodiments, humic acid(s) is/are present in a concentration ranging from about $1\times10^{-20}$ M to about $1\times10^{-1}$ M. For example one or more humic acids may be included at a concentration of $1\times10^{-26}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$M, $1\times10^{-10}$M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more.

In some embodiments, fulvic acid(s) comprise(s) about 0.001 to about 95% or more (by weight) of the inoculant composition. In some embodiments, fuhic acid(s) (e.g., ammonium fulvate, boron fulvate, potassium fulvate and/or sodium fulvate) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more fulvic acid (e.g., ammonium humate, boron humate, potassium humate and/or sodium humate).

In some embodiments, fulvic acid(s) is/are present in a concentration ranging from about $1\times10^{-20}$ M to about $1\times10^{-1}$ M. For example one or more fulvic acids may be included at a concentration of $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$, $1\times10^{-9}$ M, $1\times10^{-8}$ M, $1\times10^{-7}$ M, $1\times10^{-6}$M, $1\times10^{-5}$ M, $1\times10^{-4}$M, $1\times10^{-3}$ M, $1\times10^{-2}$ M, $1\times10^{-1}$ M or more.

In some embodiments, the stabilizing medium comprises one or more sugar alcohols, one or more humic acids and/or one or more fulvic acids in an amount/concentration sufficient to ensure microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed), application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the stabilizing medium comprises one or more sugar alcohols, one or more humic acids and/or one or more fulvic acids in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 61, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed), application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the stabilizing medium comprises one or more sugar alcohols, one or more humic acids and/or one or more fulvic acids in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units per gram and/or milliliter of inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at of below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more, application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more sugar alcohols, one or more humic acids and/or one or more fulvic acids in an amount/concentration sufficient to ensure the deliquescence relative humidity (DRH) of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C.).

In some embodiments, inoculant compositions of the present disclosure comprise two or more sugar alcohols, humic acids and/or fulvic acids that synergistically enhance the stability and/or survival of one or more microorganisms in the inoculant composition.

In the interest of maximizing the teaching of the present application and without intending to be limited by any particular theory, applicants submit that sugar alcohols may enhance the stability and survival of microorganisms in an inoculant composition by passing through, intercalating into and/or binding to the cell membranes of the microorganisms and causing/allowing the cell membranes of the microorganisms to remain in a fluid state. The stabilizing effects of sugar alcohols may be particularity beneficial in those instances in which the inoculant composition is desiccated (e.g., when an inoculant composition is coated on a seed/leaf and then dried).

In the interest of maximizing the teaching of the present application and without intending to be limited by any particular theory, applicants submit that humic acids and fulvics may enhance the stability and survival of microorganisms in an inoculant composition by optimizing the DRH of the inoculant composition. The stabilizing effects of humic acids and fluvic acids may be particularly beneficial in those instances in which the inoculant composition is desiccated (e.g., when an inoculant composition is coated on a seed/leaf and then dried).

The stabilizine medium may comprise additional stabilizer(s), including, but not limited to, maltodextrins, monosaccharides, disaccharides, oligosaccharides, malt extracts, peat extracts, betaines, prolines, sarcosines, peptones, skim milks, oxidation control components, hygroscopic polymers, and/or UV protectants.

The stabilizine medium may comprise any suitable maltodextrin(s), including, but not Hinted to, maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25, In some embodiments, the stabilizine medium comprises one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 of 20, or about 15 to about 16, 17, 18, 19 or 20, In some embodiments, the stabilizine medium comprises a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. Non-limiting examples of maltodextrins that may be useful in compositions of the present disclosure include MALTRIN® M040 (DEV=5; molecular weight=3600; Grain Processing Corporation, Muscatine, IA), MALTRIN® M100 (DEV=10; molecular weight=1800; Grain Processing Corporation, Muscatine, IA), MALTRIN® M150 (DEV=15, molecular weight=12W, Grain Processing Corporation, Muscatine, IA), MALTRIN® M180 (DEV=18; molecular weight=1050; Grain Processing Corporation. Muscatine, IA), MALTRIN® M200 (DEV=20; molecularweight=900; Grain Processing Corporation, Muscatine, IA), MALTRIN® M250 (DEV=25; molecular weight=720; Grain Processing Corporation, Muscatine, IA); MALTRIN QD® M580 (DEV=16.5-19.9, Grain Processing Corporation, Muscatine, IA); MALTRIN QD® M585 (DEV=150-19.9; Grain Processing Corporation. Muscatine, IA); MALTRIN QD® M600 (DEV=20.0-23.0; Grain Processing Corporation, Muscatine. IA); GLOBE® Plus 15 DE (Ingredion Inc., Westchester, IL); and combinations thereof.

The stabilizine medium may comprise any suitable monosaccharide(s), including, but not limited to, allose, altrose, arabinose, fructose, galactose, glucose, gulose, iodose, lyxose, mannose, ribose, talose, threose and/or xylose. In some embodiments, one or more of allose, altrose, arabinose, fructose, galactose, glucose, gulose, iodose, lyxose, mannose, ribose, talose, threose and xylose is/ae excluded from inoculant compositions of the present disclosure.

The stabilizine medium may comprise any suitable disaccharide(s), including, but not limited to, cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, meibiulose, nigerose, palatinose, mtinose, rutinulose, sophorose, sucrose, trehalose (e.g., trehalose dihydrate, anhydrous trehalosc), turanose and/or xylobiose. In some embodiments, one or more of cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, utinulose, sophorose, sucrose, trehalose (e.g., trehalose dihydrate, anhydrous trehalose), turanose and xylobiose is/ar excluded from inoculant compositions of the present disclosure.

The stabilizine medium may comprise any suitable oligosacchandets), including, but not limited to, fructo-oligosaccharides, galacto-oligosaccharides, mannon-oligosaccharides and/or raffinose.

The stabilizine medium may comprise any suitable betaine(s), including, but not limited to, trimethylglycine.

The stabilizine medium may comprise any suitable peptone(s), including, but not limited to, bacterial peptones, meat peptones, milk peptones, vegetable peptones and yeast peptones.

The stabilizine medium may comprise any suitable oxidation control component(s), including, but not limited to, antioxidants and/or oxygen scavengers. In some embodiments, the oxidation control component is/comprises ascorbic acid and/or glutathione.

In some embodiments, the stabilizine medium comprises one or more antioxidants. For example, in some embodiments, the stabilizine medium comprises ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid. Non-limiting examples of antioxidants that may be useful in compositions of the present disclosure include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition.

In some embodiments, the stabilizine medium comprises one or more oxygen scavengers. For example, in some embodiments, the stabilizine medium comprises ascorbic acid, ascorbate salts, catechol and/or sodium hydrogen carbonate.

The stabilizine medium may comprise any suitable hygroscopic polymer(s), including, but not limited to, hygroscopic agars, albumins, alginates, carrageenans, celluloses, gums e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylemines (PEI), polylactides, polymethylacrylates (PMA), polyurethanes, polyvinyl alcohols (PVA), polyvinylpyrrolidones (PVP), propylene glycols, sodium carboxymethyl celluloses and/or starches. Non-limiting examples of polymers that may be useful in compositions of the present disclosure include AGRIMER™ polymers (e.g., 30, AL-10 LC, AL-22, AT/ATF, VA 3E, VA 3I, VA 5E, VA 5I, VA 6, VA 6E, VA 7E, VA 7I, VEMA AN-216, VEMA AN-990, VEMA AN-1200, VEMA AN-1980, VEMA H-815MS; Ashland Specialty Ingredients, Wilmington, DE), EASYSPERSE™ polymers (Ashland Specialty Ingredients, Wilmington, DE), DISCO™ AG polymers (e.g., L-250, L-280, L-285, L-286, L-320, L-323, L-517, L-519. L-520, L800; incotec Inc., Salinas. CA), KELZAN® polymers (Bri-Chem Supply Ltd., Calgary, Alberta, CA), SEEDWORX™ polymers (e.g., Bio 200; Aginnovation, LLC, Walnut Groove, CA), TICAXAN® xanthan powders, such as PRE-HYDRATED, TICAXAN® Rapid-3 Powder (TIC Gums, White Marsh, MD) and combinations thereof. Additional examples of polymers that may be included in inoculant compositions of the present disclosure may be found in Pouci, et al Am. J. Agric. Biol. Sci. 3(1):299 (2008).

The stabilizine medium may comprise any suitable UV protectant(s), including, but not limited to, and/or aromatic amino acids (e.g., tryptophan, tyrosine), carotenoids, cinnamates, lignosulfonates (e.g., calcium lignostlfonate, sodium lignosulfonate), melanins, mycosporines, polyphenols and/or salicylates Non-limiting examples of UV protectants that may be useful in compositions of the present disclosure include Borregaard LIGNOTECH™ lignosulfonates (e.g., BORRESPERSE® 3A, BORRESPERSE® CA, BORRESPERSE® NA, MARASPERSE® AG, NORLIG® A, NORLIG® 11D, UFOXANE® 3A, ULTRAZINE® NA, VANISPERSE® CB; Borregaard LIGNOTECH™, Sarpsborg, Norway) and combinations thereof. Additional examples of UV protectants that may be included in inoculanc compositions of the present disclosure may be found in Burges, Formulation of Microbial Biopesticides: Beneficial Microorganisms, Nematodes and Seed Treatments (Springer Science & Business Media) (2012).

In some embodiments, the stabilizine medium comprises one or more additional stabilizers having a deliquescence relative humidity (DRH) at 0, 5, 10, 15, 20, 25 and/or 30° C. less than 5, 10, 15, 20, 25, 30, 35, 40, 45, 50, 55, 60, 65, 70, 75, 80, 85 or 90. In some embodiments, the DRH of the additional stabilizer(s) at the temperature(s) at which the inoculant composition will be stored is less than 5, 10, 15, 20, 25, 30, 35, 40, 45, 50, 55, 60, 65, 70, 75, 80, 85 or 90.

In some embodiments, the stabilizine medium comprises one or more additional stabilizers that reduce the DRH of the inoculant composition at 0, 5, 10, 15, 20, 25 and/or 30° C. until it is less than 5, 10, 15, 20, 25, 30, 35, 40, 45, 50, 55, 60, 65, 70, 75, 80, 85 or 90. In some embodiments, the additional stabilizer(s) reduce(s) the DRH of the inoculant composition at the temperature(s) at which the inoculant composition will be stored is less than 5, 10, 15, 20, 25, 30, 35, 40, 45, 50, 55, 60, 65, 70, 75, 80, 85 or 90.

In some embodiments, the stabilizine medium comprises one or more additional stabilizers that reduce the DRH of the inoculant composition at the temperature at which the inoculant composition is to be stored until it is less than 5, 10, 15, 20, 25, 30, 35, 40, 45, 50, 55, 60, 65, 70, 75, 80, 85 or 90

In some embodiments, the additional stabilizer(s) reduce(s) the DRH of the inoculant composition at the temperature at which the inoculant composition is to be stored until it less than 5, 10, 15, 20, 25, 30, 35, 40, 45, 50, 55, 60, 65, 70, 75, 80, 85 or 90.

Additional stabilizers may be incorporated into inoculant compositions of the present disclosure in any suitable form. In some embodiments, the additional stabilizer(s) included in inoculant compositions of the present disclosure is/are at least 70, 75, 80, 85, 90, 91, 92, 93, 94, 95, 96, 97, 98, 99, 99.5% or more pure.

Additional stabilizers may be incorporated into inoculant compositions of the present disclosure in any suitable amount(s)/concentration(s). The absolute value of the amount(s/concentration(s) that is/are sufficient to cause the desired effect(s) may be affected by factors such as the type, size and volume of material to which the composition will be applied, the type(s) of microorganisms in the composition, the number of microorganisms in the composition, the stability of the microorganism(s) in the composition and storage conditions (e.g., temperature, relative humidity, duration). Those skilled in the art will understand how to select effective amounts/concentrations using routine dose-response experiments Guidance for the selection of appropriate amounts/concentrations can be found, for example, in International Patent Publication Nos. WO2017/044473, WO2017/044545, WO2017/116837, WO2017/116846, WO2017/210163 and WO2017/210166, and in U.S. Provisional Patent Application Nos. 62/511,408; 62/511,420 and 62/511,434.

In some embodiments, inoculant compositions of the present disclosure comprise one or more additional stabilizers in an amount/concentration of about 0.0001 to about 95% or more (by weight, based upon the total of the inoculant composition). For example, inoculant compositions of the present disclosure may comprise about 0.0001 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95%, of one or more maltodextrins, monosaccharides, disaccharides, betaines, prolines, sarcosines, peptones, oxidation control components, hygroscopic polymers and/or UV protectants.

In some embodiments, inoculant compositions of the present disclosure comprise one or more additional stabilizers at a concentration of about $1\times10^{-20}$ M to about $1\times10^{-1}$ M. For example, inoculant compositions of the present disclosure may comprise about $1\times10^{-15}$ M to about $1\times10^{10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M, optionally about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more, of one or more maltodextrins, monosaccharides, disaccharides, betaines, prolines, sarcosines, peptones, oxidation control components, hygroscopic polymers and/or UV protectants.

In some embodiments, inoculant compositions of the present disclosure comprise one or more maltodextrins in an amount/concentration of about 0.001 to about 95% or more (by weight) of the inoculant composition. In some embodiments, the maltodextrin(s) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 0.05, 0.06, 0.07, 0.08, 0.09, 0.1.0.2, 0.3, 0.4, 0.5, 1, 1.5.2, 2.5, 3, 3.5, 4, 4.5, 5, 5.5, 6.6.5, 7, 7.5.8, 8.5, 9, 9.5, 10, 15, 20, 25, 30, 35, 40, 45, 50, 55, 60, 65, 70, 75, 80, 85, 90, 95% or more (by weight) of one or more maltodextrins (e.g., one or more maltodextrins (each and/or collectively) having a DEV value of about 15 to about 20).

In some embodiments, inoculant compositions of the present disclosure comprise one or more monosaccharides in an amount/concentration of about 0.001 to about 95% of more (by weight) of the inoculant composition. In some embodiments, the monosaccharide(s) (e.g., arabinose, fructose and/or glucose) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more monosaccharides (e.g., arabinose, fructose and/or glucose).

In some embodiments, inoculant compositions of the present disclosure comprise one or more disaccharides in an amount/concentration of about 0.001 to about 95% or more (by weight) of the inoculant composition. In some embodiments, the disaccharide(s) (e.g., maltose, sucrose and/or trehalose) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more disaccharides (e.g., maltose, sucrose and/or trehalose).

In some embodiments, inoculant compositions of the present disclosure comprise one or more oxidation control components in an amount/concentration of about 0.0001 to about 95% or more (by weight) of the inoculant composition. In some embodiments, the oxidation control component(s) (e.g., ascorbic acid and/or glutathione) comprise(s) about 0.0001 to about 0.001, about 0.001 to about 1%, about 0.25 to about 5%, (by weight) of the inoculant composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more (by weight) of one or more oxidation control components (e.g., ascorbic acid and/or glutathione).

In some embodiments, inoculant compositions of the present disclosure comprise one or more UV protectants in an amount/concentration of about 0.0001 to about 5% of more (by weight) of the inoculant composition. In some embodiments, the UV protectant(s) (e.g., calcium lignosulfate and/or sodium lignosulfate) comprise(s) about 0.0001 to about 0.001, about 0.001 to about 1%, about 0.25 to about 5%, (by weight) of the inoculant composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4.4, 5.5% or more (by weight) of one or more UV protectants (e.g., calcium lignosulfate and/or sodium lignosulfate).

In some embodiments, inoculant compositions of the present disclosure comprise two or more stabilizers that synergistically enhance the stability and/or survival of one or more microorganisms in the inoculant composition.

Stabilizers may be incorporated into inoculant compositions of the present disclosure in any suitable ratio(s). In some embodiments, inoculant compositions of the present disclosure comprise a (sugar alcohol(s), humic acid(s) and/or fulvic acid(s)):(maltodextrin(s), monosaccharide(s), disaccharide(s), oxidation control component(s) and/or UV protectant(s)) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 45:55, 50:50, 55:45, 60:40, 65:35, 70:30, 75:25, 80:20, 85:15, 90:10, 95:5 or more. For example, inoculant compositions of the present disclosure may comprise one or more sugar alcohols (e.g., arabitol, mannotiol, sorbitol and/or xylitol), one or more humic acids (e.g., ammonium humate, boron humate, potassium humate and/or sodium humate), and/or one or more fulvic acids (e.g., ammonium fulvate, boron fulvate, potassium fulvate and/or sodium fulvate), with one or more maltodextrins (e.g., one or more maltodextrins (each and/or collectively) having a DEV of about 15 to about 20) and/or one or more disaccharides (e.g., maltose) in a (sugar alcohol/humic acid/fulvic acid):(maltodextrin/disaccharide) ratio of about 5:95, about 15:85, about 25:75 or about 50:50.

In some embodiments, the inoculant composition comprises one or more sugar alcohols, humic acids and/or fulvic acids and one or more additional stabilizers in amounts/concentrations sufficient to ensure microorganisms remain viable in inoculant compositions of the present disclosure following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more, desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation maternal (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application, foliar application and desiccation by about 5, 10, 15, 20, 25, 30, 35, 40, 45, 50, 55, 60, 65, 70, 75, 80, 85, 90, 95% or more, and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the inoculant composition comprises one or more sugar alcohols, humic acids and/or fulvic acids and one or more additional stabilizers in amounts/concentrations sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C., and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C., and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C., for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more, and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C., and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 day s or more.

In some embodiments, the inoculant composition comprises one or more sugar alcohols, humic acids and/or fulvic acids and one or more additional stabilizers in amounts/concentrations sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units per gram and/or milliliter of inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storge at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the inoculant composition comprises one or more sugar alcohols, humic acids and/or fulvic acids and one or more additional stabilizers in amounts/concentrations sufficient to ensure the DRH of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40C).

In some embodiments, inoculant compositions of the present disclosure comprise one or more sugar alcohols, humic acids and/or fluvic acids and one or more additional stabilizers that synergistically enhance the stability and/or survival of one or more microorganisms in the inoculant composition.

In some embodiments, the stabilizing medium acts as a carrier for the microorganism(s).

In some embodiments, the microorganism(s) and the stabilizing medium are incorporated into one or more agriculturally acceptable carriers.

Inoculant compositions of the present disclosure may comprise any suitable agriculturally acceptable carrier(s), including, but not limited to, seed-compatible carriers, foliar-compatible carriers and soil-compatible carriers.

In some embodiments, inoculant compositions of the present disclosure comprise one or more liquid and/or gel carriers. For example, in some embodiments, inoculant compositions of the present disclosure comprise an aqueous solvent and/or a nonaqueous solvent. In some embodiments, inoculant compositions of the present disclosure comprise one or more inorganic solvents, such as decane, dodecane, hexylether and nonane; one or more organic solvents, such as acetone, dichloromethane, ethanol, hexane, methanol, propan-2-01 and trichloroethlene; and/or water. Non-limiting examples of liquid/gel carriers that may be useful in compositions of the present disclosure include oils (e.g., mineral oil, olive oil, peanut oil, soybean oil, sunflower oil), polyethylene glycols (e.g., PEG 200, PEG 300, PEG 400, etc.), propylene glycols (e.g., PPG-9, PPG-10, PPG-17, PPG-20. PPG-26, etc.), ethoxylated alcohols (e.g., TOMADOL® (Air Products and Chemicals, Inc, Allentown, PA), TERGITOL™ 15-S surfactants such as TERGITOL™ 15-S-9 (The Dow Chemical Company, Midland. MI), etc), polysorbates (e.g. polysorbate 20, polysorbate 40, polysorbate 60, polysorbate 80, etc.), silicones (siloxanes, trisiloxanes, etc.) and combinations thereof. Additional examples of solvents that may be included in inoculant compositions of the present disclosure may be found in Burges, Formulation of Microbial Biopesticides: Beneficial Microorganisms, Nematodes and Seed Treatments (Springer Science & Business Media) (2012); Inoue & Horikoshi, J. Fermentation Bioeng. 71(3):194 (1991).

In some embodiments, inoculant compositions of the present disclosure comprise one or more solid carriers. For example, in some embodiments, inoculant compositions of the present disclosure comprise one or more powders (e.g., wettable powders) and/or granules. Non-limiting examples of solid carriers that may be useful in compositions of the present disclosure include clays (e.g., attapulgite clays, montmorillonite clay, etc.), peat-based powders and granules, freeze-dried powders, spray-dried powders, spray-freeze-dried powders and combinations thereof. Additional examples of solid carriers that may be included in inoculant compositions of the present disclosure may be found in Burges, Formulation of Microbial Biopesticides: Beneficial Microorganisms, Nematodes and Seed Treatments (Springer Science & Business Media) (2012).

Carriers incorporated into inoculant compositons of the present disclosure may comprise a growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Selection of appropriate carrier materials will depend on the intended application(s) and the microorganism(s) present in the inoculant composition. In some embodiments, the carrier material(s) will be selected to provide an inoculant composition in the form of a liquid, gel, slurry, or solid.

As noted above, inoculant compositions of the present disclosure may comprise agriculturally beneficial microorganisms, such as diazotrophs, phosphate-solubilizing microorganisms and biopesticides. It is to be understood that other agriculturally beneficial constituents, such as biostimulants, microbial extracts, nutrients, pesticides and plant signal molecules, may also be included in inoculant compostions of the present disclosure.

Inoculant compositions of the present disclosure may comprise any suitable biostimulant(s), including, but not limited to, seaweed extracts (e.g., *Ascophyllum nodosum* extracts, such as alginate, *Ecklonia maxima* extracts, etc.), myo-inositol, glycine and combinations thereof.

Inoculant compositions of the present disclosure may comprise any suitable microbial extract(s), including, but not limited to, bacterial extracts, fungal extracts and combinations thereof. In some embodiments, inoculant compositions of the present disclosure comprise one or more extracts of media comprising one or more diazotrophs, phosphate-solubilizing microorganisms and/or biopesticides. In some embodiments, inoculant compositions of the present disclosure comprise one or more *Azospirillum* extracts (e.g., an extract of media comprising *A. brasilense* INTA Az-39), one or more *Bradyrhizobium* extracts (e.g., an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C), one or more *Rhizobium* extracts (e.g., an extract of media comprising *R. leguminosarum* SO12A-2), one or more *Sinorhizobium* extracts (e.g., an extract of media comprising *S. fredii* CCBAU114 and/or *S. fredii* USDA 205), one or more *Penicillium* extracts (e.g., an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490), one or more *Pseudomonas* extracts (e.g., an extract of media comprising *P. jensenii* PS06), one or more acaridical, insecticidal and/or nematicidal extracts (e.g., an extract of media comprising *Bacillus firmus* I-1582, *Bacillus mycoides* AQ726, NRRL B-21664; *Beauveria bassiana* ATCC-74040, *Beauveria bassiana* ATCC-74250, *Burkholderia* sp. A396 sp, nov. rinojensis, NRRL B-50319, *Chromobacterium subtsugae* NRRL B-30655, *Chromobacterium vaccinii*, NRRL B-50880, *Flavobacterium* H492, NRRL B-50584, *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD 170 and AR SEF 7711) and/or *Paecilomyces fumosoroseus* FE991), and/or one or more fungicidal extracts (e.g., an extract of media comprising *Ampelomyces quisqualis* AQ 10® (Intrachem Bio GmbH & Co. KG, Germamy), *Aspergillus flavus* AFLA-GUARD® (Syngenta Crop Protection, Inc., CH), *Aureobasidium pullulans* BOTECTOR® (bio-ferm GmbH. Germany), *Bacillus pumilus* AQ717 (NRRL B-21662), *Bacillus pumilus* NRRL B-30087, *Bacillus* AQI75 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* NRRL B-50349, *Bacillus amyloliquefaciens* TJ1000 (also known as IBE, isolate ATCC BAA-390), *Bacillus thuringiensis* AQ52 (NRRL B-21619), *Candida oleophila* I-82 (e.g., ASPIRE®, Ecogen Inc., USA), *Candida saitoana* BIO-CURE® (in mixture with lysozyme; BASF, USA) and BIOCOAT® (ArystaLife Science, Ltd., Cary, NC), *Clonostachys rosea* f, *catenulata* (also referred to as *Gliocladium catenulatum*) J1446 (PRESTOP®, Verdera, Finland), *Coniothyrium munitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Gliocladium virens* GL-21 (SOILGARD®, Certis LLC, USA), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® D (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachalinensis* (e.g., REGALIA®, Marrone BioInnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660), *Streptomyces* WYE 53 (ATCC 55750), *Talaromyces flavus* V117b (PROTUS®, Prophyta, Germany), *Trichoderma asperellum* SKT-1 (ECO-HOPE®, Kuniai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, BioWorks Inc., USA), *Trichoderma harzianum* TH-35 (ROOT PRO®, Mycontrol Ltd., Israel). *Trichoderma harzianum* T-39 (TRICHODEX®, Mycontrol Ltd., Israel; *TRICHODERMA* 2000®, Makhteshim Ltd, Israel), *Trichoderma harzianum* ICC012 and *Trichoderma viride* TRICHOPEL (Agrimm Technologies Ltd, NZ), *Trichoderma harzianum* ICC012 and *Trichoderma viride* ICCO80 (REMEDIER® WP, Isagro Ricerca, Italy), *Trichoderma polysporum* and *Trichoderma harzianum* (BINAB®, BINAB Bro-Innovation AB, Sweden), *Trichoderma stromaticum* TRICOVAB® (C.E-.P.L.A.C., Brazil), *Trichoderma virens* GL-3, ATCC 58678, *Trichoderma viride* TRIECO® (Ecosense Labs. (India) Pvt. Ltd., India, BIO-CURE®, F, T. Stanes & Co. Ltd., India), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ)).

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins. (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutern, lycopene, zeaxanthin, etc.) and combinations thereof. In some embodiments, noculant compositions of the present disclosure comprise phosphorous, boron, chlorine, copper, iron, manganese, molybdenum and/or zinc.

Inoculant compositions of the present disclosure may comprise any suitable pest attractant(s) and/or feeding stimulant(s), including, but not limited to, brevicomin, ceralure, codlelure, cue-hure, disparlure, dominicalure, eugenol, frontalin, gossyplure, grandlure, hexalure, ipsdienol, ipsenol, japonilure, latitlure, lineatin, litlure, looplure, medium, megatomic acid, methyl eugenol, moguchun, α-multistriatin, muscalure, orfalure, oryctalure, ostramone, rescalure, siglure, sulcatol, tnmedlure and/or trunc-call.

Inoculant compositions of the present disclosure may comprise any suitable pesticide(s), including, but not limited to, acaricides, fungicides, herbicides, insecticides and nematicides.

Fungicides may be selected to provide effective control against a broad spectrum of phytopathogenic fungi (and fungus-like organisms), including, but not limited to, soil-borne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes According to some embodiments, the inoculant composition comprises a fungicide (or combination of fungicides) that is toxic to one or more strains of *Albugo* (e.g., *A. candida*), *Alternaria* (e.g., *A. alternata*), *Aspergillus* (e.g., *A. candidus, A. clavatus, A. flavus, A. fumigatus, A. parasiticus, A. restrictus, A. sojae, A. solanii*), *Blumeria* (e.g., *B. graminis*), *Botrytis* (e.g., *B. cinerea*), *Cladosporum* (e.g., *C. cladosporioides*), *Colletotrichum* (e.g., *C. acutatum, C boninense, C. capsici, C. caudatum, C. coccodes, C. crassipes, C. dematium, C. destructivum, C. fragariae, C. gloeosporioides, C. graminicola, C. kehawee, C. lindemuthianum, C. musae. C, orbiculare, C. spinaceae, C. sublineolum, C. trifolii, C. truncatum*), *Fusarium* (e.g., *F. graminearum, F. moniliforme, F. oxysporum, F. roseum, F. tricinctum*), *Helminthosporium, Magnaporthe* (e.g., *M. grisea, M. oryzae*), *Melamspora* (e.g., *M. lini*), *Mycosphaerella* (e.g., *M. graminicola*), *Nematospora, Penicillium* (e.g., *P. rugulosum, P. verrucosum*), *Phakopsora* (e.g., *P. pachyrhizi*), *Phomopsis, Phytiphtoria* (e.g., *P. infestans*), *Puccinia* (e.g., *P. graminis, P. striiformis, P. tritici, P. triticina*), *Pucivinia* (e.g., *P. graministice*), *Pythium, Phytophthora, Rhizoctomia* (e.g., *R. solanii*), *Scopulariopsis, Selerotinia, Thielaviopsis* and/or *Ustilago* (e.g., *U. maydis*). Additional examples of fungi may be found in Bradley. *Managing Diseases*, in Illinois Agronomy Handbook (2008).

Herbicides may be selected to provide effective control against a broad spectrum of plants, including, but not limited to, plants from the families Asteraceae. Caryophyllaceae. Poaceae and Polygonaceae According to some embodiments, the inoculant composition comprises an herbicide (or combination of herbicides) that is toxic to one or more strains of *Echinochloa* (e.g., *E. brevipedicellata, E. callopus, E. chacoensis, E. colona, E. crus-galh, E. crus-pavonis, E. elliptica, E. esculenta, E. frumentacea, E, glabrescens, E. haploclada, E. helodes, E. holciformis, E. inundata, E. jaliscana, E. jubata, E. kimberleyensis, E. lacunaria, E. macrandra, E. muricata, E. obtusifora, E. oplismenoides, E. orzyoides, E. paludigena, E. picta, E. pithopus, E. polystachya, E. praestans, E. pyramidalis, E. rotundiflora, E. stagnina, E. telmatophila, E. turneriana, E. ugandensis, E. walteri*), *Fallopia* (e.g., *F. baldschuanica, F. japonica, F. sachalinensis*), *Stellaria* (e.g., *S. media*) and/or *Taraxacum* (e.g., *T. albidum, T. aphrogenes, T. brevicorniculatum, T. californicum, T. centrasiatum, T. ceratophorum, T. erythrospermum, T. farinosum, T. holmboei, T. japonicum, T. kok-saghyz, T. laevigatum, T. officinale, T. platycarpum*). Additional species of plants that may be targeted by inoculant compositions of the present disclosure may be found in Hager, *Weed Management*, in *ILLINOIS AGRONOMY HANDBOOK* (2008) and Loux et al, Weed Control Guide for Ohio, Indiana and Illinois (2015).

Insecticides may be selected to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae. Bruchidae, Cecidomyiidae, Cerambycidae. Cercopidae, Chrysomelidae, Cicadellidae, Coccinellidae. Cryllotalpidae, Cucujidae, Curculionidae, Dennestidae, Elateridae. Gelechiidae, Lygaeidae, Meloidae, Membracidae. Miridae, Noctuidae, Pentatomidae, Pyralidae, Scarabaeidae, Silvanidae, Spingidae, Tenebrionidae and/or Thripidae. According to some embodiments, the inoculant composition comprises an insecticide (or combination of insecticides) that is toxic to one or more species of *Acalymma, Acanthoscelides* (e.g., *A. obtectus*), *Anasa* (e.g., *A. tritis*), *Anastrepha* (e.g., *A. ludens*), *Anoplophora* (e.g., *A. glabripennis*), *Anthonomus* (e.g., *A. eugenii*), *Acyrthosiphon* (e.g., *A. pisum*), *Bactrocera* (e.g., *B. dosalis*), *Bemisia* (e.g., *B. argentifolii, B. tabaci*), *Brevicoryne* (e.g., *B. brassicae*), *Bruchidius* (e.g., *B. atrolineatus*), *Bruchus* (e.g., *B. atomarius, B. dentipes, B. lentis, B. pisorum* and/or *B. rufipes*), *Callosobruces* (e.g., *C. chinensis, C. maculatus, C. rhodesianus, C. subinnotalus, C. theobromae*), *Caryedon* (e.g., *C. serratus*), *Cassadinae, Ceratitis* (e.g., *C. capitata*), *Chrysomeliae, Circulifer* (e.g., *C. tenellus*), *Criocerinae, Cryptocephalinae, Cryptolestes* (e.g., *C. ferrugineus, C. pusillis, C. pussilloides*), *Cylas* (e.g., *C. formicarius*), *Delia* (e.g., *D. antiqua*), *Diabrotica, Diaphania* (e.g., *D. nitidalis*), *Diaphorina* (e.g., *D. citri*), *Donaciinae, Ephestia* (e.g. *E. cautella, E. elutella, E. keuhniuella*), *Epilachna* (e.g., *E. varivestis*),

*Epiphyas* (e.g., *E. postvittana*), *Eumolpinae, Galerucinae, Helicoverpa* (e.g., *H. zea*), *Heteroligus* (e.g., *H. meles*), *Iobesia* (e.g., *I. botrana*), *Lamprosomatinae, Lasioderma* (e.g., *L. serricorne*), *Leptinotarsa* (e.g., *L. decemlineata*), *Leptoglossus, Liriomyza* (e.g., *L. trifolii*), *Manducca, Melittia* (e.g., *M. cucurbitae*), *Myzus* (e.g., *M. persicae*), *Nezara* (e.g., *N. viridula*), *Orzaephilus* (e.g., *O. merator, O. surinamensis*), *Ostrinia* (e.g., *O. nubilalis*), *Phthorimaea* (e.g., *P. operculella*), *Pieris* (e.g., *P. rapae*), *Plodia* (e.g., *P. interpunctella*), *Plutella* (e.g., *P. xylostella*), *Popillia* (e.g., *P. japonica*), *Prostephanus* (e.g., *P. truncates*), *Psila, Rhizopertha* (e.g., *R. dominica*), *Rhopalosiphum* (e.g., *R. maidis*), *Sagrinae, Solenopsis* (e.g., *S. Invicta*), *Spilopyrinae, Sitophilus* (e.g., *S. granaries, S. oryzae* and/or *S. zeamais*), *Sitotroga* (e.g., *S. cerealella*), *Spodoptera* (e.g., *S. frugiperda*), *Stegobium* (e.g., *S. paniceum*), *Synetinae, Tenebrio* (e.g., *T. malens* and/or *T. molitor*), *Thrips* (e.g., *T. tabaci*), *Trialeurodes* (e.g., *T. vaporariorum*), *Tribolium* (e.g., *T. castaneum* and/or *T. confusum*), *Trichoplusia* (e.g. *T. ni*), *Trogoderma* (e.g., *T. granarium*) and *Trogossitidae* (e.g., *T. mauritanicus*). Additional species of insects that may be targeted by inoculant compositions of the present disclosure may be found in Capinera, Handbook of Vegetable Pests (2001) and Steffey and Gray, *Managing Insect Pests*, in Illinois Agronomy Handbook (2008).

Nematicides may be selected to provide effective control against a broad spectrum of nematodes, including, but not limited to, phytoprasitic nematodes from the classes Chromadorea and Enoplea According to some embodiments, the inoculant composition comprises a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/or *Xiphinema*. Additional species that may be targeted by inoculant compositions of the present disclosure may be found in Capinera, Handbook of Vegetable Pests (2001) and Niblack, *Nematodes*, in Illinois Agronomy Handbook (2008).

In some embodiments, inoculant compositions of the present disclosure comprise one or more chemical fungicides.

Non-limiting examples of chemical fungicides include strobiluuins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl)-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilide (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, fenehexamid, mandiproamid, oxytetracyclin, silthiofam, spiroxamine, and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles e.g., cyazofamid, imazalil, pefurazoate, prochloraz, triflumizol); heterocyclic compounds, such as pyridines (e.g., fluazinam, pyrifenox (cf.D1b), 3-{5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin), dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-44-methylpiperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A); nitrophenyl derivates (e.g., binapacryl, dicloran, dinobuton, dinocap, nitrothal-isopropyl, tecnazene); organometal compounds (e.g., fentin salts, such as fentin-acetate, fentin chloride, fentin hydroxide); sulfur-containing heterocyclyl compounds (e.g., dithianon, isoprothiolane); organophosphorus compounds (e.g., edifenphos, fosetyl, fosetyl-aluminum, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorophenol and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-AI, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, miraculan compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram. In some embodiments, inoculant compositions of the present disclosure comprise one or more aromatic hydrocarbons, benzimidazoles, benzothiadiazole, carboxamides, carboxylic acid amides, morpholines, phenylamides, phosphonates, quinone outside inhibitors (e.g. strobilurins), thiazolidines, thiophanates, thiophene carboxamides and/or triazoles.

In some embodiments, inoculant compositions of the present disclosure comprise one or more chemical herbicides. Non-limiting examples of chemical herbicides include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluron, clethodim, clodinafop, clomazone, cyanazine, cycloxydim, cyhalofop, desmedipham, desmetryn, dicamba, diclofop, diflufenican, dimefuron, diuron, dithiopyr, ethofumesate, fenoxaprop, fluazifop, fluazifop-P, flufenacet, fluometuron, flufenpyr-ethyl, flumiclorac-pentyl, flumioxazin, fluoroglycofen, fluthiacet-methyl, fomesafen, fomesafen, foramsulfuron, glyphosate, glufosinate, haloxyfop, hexazinone, imazamox, imazaquin, imazethapyr, indaziflam, iodosulfuron, ioxynil, isoproturon, isoxaflutole, lactofen, linuron, mecoprop, mecoprop-P, mesosulfuron, mesotrione, metamitron, metazochlor, methibenzuron, metolachlor (and S-metolachlor), metoxuron, metribuzin, monolinuron, oxadiargyl, oxadiazon, oxaziclomefone, oxyfluorfen, phenmedipham, pretilachlor, profoxydim, prometon, prometry, propachlor, propanil, propaquizafop, propisochlor, propoxycarbazone, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, thiencarbazone-methyl, tralkoxydim, triclopyr, trietazine, topramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/or ethyl 2-((3-(2-chloro-4-fluoro-5-(3-methy-2,6-dioxo-4-(trifluoromethyl)-2,3-dihydropyrimidin-(6H)-yl)phenoxy)pyridin-2-yl)oxy)acetate. In some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof.

In some embodiments, inoculant compositions of the present disclosure comprise one or more chemical insecticides and/or nematicides. Non-limiting examples of chemical insecticides and nematicides include abamectin, acrinathrin, aldicarb, aldoxycarb, alpha-cypermethrin, betacyfluthrin, bifenthrin, cyhalothrin, cypermethrin, deltamethrin, esfenvalerate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thramethoxam, nitenpyram, thiacloprid, dinotefuran, clothianidin, chlorfluazuron, diflubenzuron, lufenuron, teflubenzuron, triflumuon, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole, cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacatb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino)furan-2(5H)-one, 3,5-disubstituted-1,2,4-oxadiazole compounds, 3-phenyl-5-(thien-2-yl)-1,2,4-oxadiazole, cadusaphos, carbaryl, carbofuran, ethoprophos, thiodicarb, aldicarb, aldoxycarb, methamidophos, methiocarb, sulfoxaflor, methamidophos, cyantraniliprole and tioxazafen and combinations thereof. In some embodiments, inoculant compositions of the present disclosure comprise abamectin, aldicarb, aldoxycarb, bifenthrin, carbofuran, chlorantraniliprole, clothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-chalothane, milbemectin, nitenpyram, oxamyl, permethrin, spinetoram, spinosad, spirodiclofen, spirotetramat, tefluthrin, thiacloprid, thioredoxin, tioxazafen and/or thiodicarb. In some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

In some embodiments, inoculant compositions of the present disclosure comprise one or more biopesticides (e.g., one or more biofungicides, bioinsecticides and/or bionematicides). Examples of microbial strains that exhibit biopesticidal activity are included in Appendix A, along with strains that exhibit nitrogen-fixing activity, phosphate-solubilizing activity, etc. Additional examples of pesticides may be found in Bradley, *Managing Diseases*, in Illinois Agronomy Handbook (2008); Hager, *Weed Management*, M Illinois Agronomy Handbook (2008); Loux et al., Weed Control Guide for Ohio, Indiana and Illinois (2015); Niblack, *Nematodes*, in Illinois Agronomy Handbook (2008), and Steffey and Gray, *Managing Insect Pests*, in Illinois Agronomy Handbook (2008).

Inoculant compositions of the present disclosure may comprise any suitable plant signal molecule(s), including, but not limited to, lipo-chitooligosaccharides (LCOs), chitin oligomers, chitosan oligomers, chitinous compounds, flavonods, non-flavonoid node-gene inducers, jasmonic acid or derivatives thereof, linoleic acid or derivatives thereof, linolenic acid or derivatives thereof and karrikins.

Inoculant compositions of the present disclosure may comprise any suitable LCOs. LCOs, sometimes referred to as symbiotic nodulation (Nod) signals or Nod factors, consist of an oligosaccharide backbone of β-1,4-linked N-acetyl-D-glucosamine ("GlcNAc") residues with an N-linked fatty acyl chain condensed at the non-reducing end. LCOs differ in the number of GlcNAc residues in the backbone, in the length and degree of saturation of the fatty acyl chain and in the substitutions of reducing and non-reducing sugar residues. See, e.g., Denarie, et al., Ann Rev. Biochem. 65:503 (1996; Hamel, et al., Planta 232:787 (2010); Prome, et al. Pure & Appl. Chem. 70(1):55 (1998).

In some embodiments, inoculant compositions of the present disclosure comprise one or more LCOs represented by formula I:

(I)

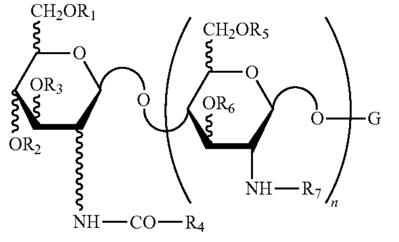

in which G is a hexosamine which can be substituted, for example, by an acetyl group on the nitrogen, a sulfate group, an acetyl group and/or an ether group on an oxygen; $R_1$, $R_2$, $R_3$, $R_5$, $R_6$ and $R_7$, which may be identical or different, represent H, $CH_3CO$—. $C_xH_y$ CO— where is an integer between 0 and 17 and y is an integer between 1 and 35, or any other acyl group such as, for example, a carbamoyl; $R_4$ represents a saturated or mono-, di- or tri-unsaturated aliphatic chain containing at least 12 carbon atoms; and n is an integer between 1 and 4.

In some embodiments, inoculant compositions of the present disclosure comprise one or more LCOs represented by formula II:

(II)

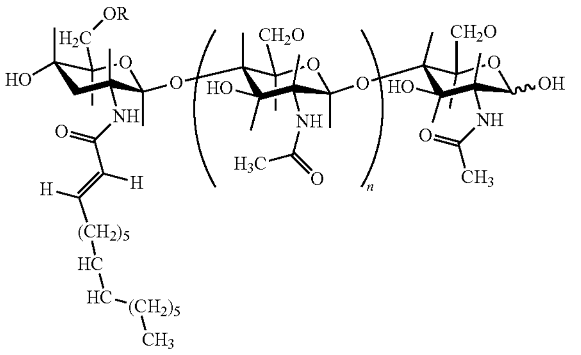

in which R represents H or $CH_3CO$— and n is equal to 2 or 3. See, e.g., U.S. Pat. No. 5,549,718. A number of *Bradyrhizobium japonicum*-derived LCOs have also been described, including BjNod-V ($C_{18:1}$), BjNod-V (Ac, $C_{18:1}$), BjNod-V ($C_{16:1}$) and BjNod-V (Ac, $C_{16:1}$) (with "V" indicating the presence of five N-acetylglucosamines, "Ac" an acetylation, the number following the "C" indicating the number of carbons in the fatty acid side chain and the number following the ";" indicating the number of double bonds). See, e.g., U.S. Pat. Nos. 5,175,149 and 5,321,011. Additional LCOs obtained from bacterial strains include NodRM, NodRM-1, NodRM-3. When acetylated (the R=$CH_3CO$—), they become AcNodRM-1 and AcNodRM-3, respectively (U.S. Pat. No. 5,545,718).

In some embodiments, inoculant compositions of the present disclosure comprise one or more LCOs represented by formula III:

(III)

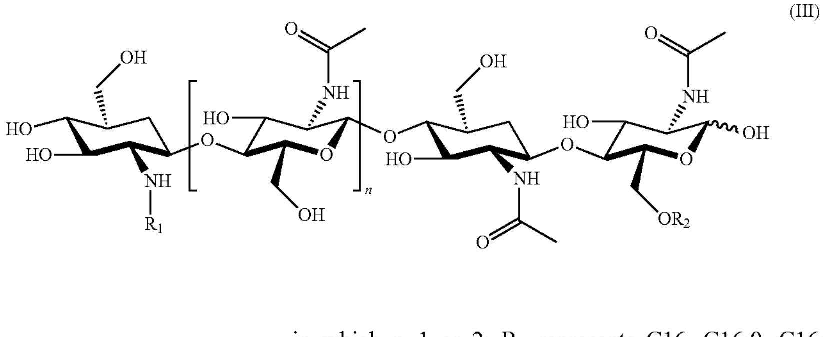

in which n=1 or 2; $R_1$ represents C16, C16:0, C16:1, C16:2, C18:0, C18:1Δ9Z or C18:1Δ11Z; and $R_2$ represents hydrogen or $SO_3H$.

In some embodiments, inoculant compositions of the present disclosure comprise one or more LCOs represented by formula IV:

(IV)

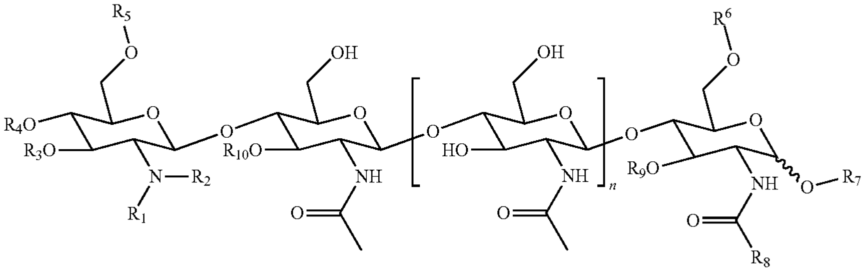

in which $R_1$ represents C14:0, 3OH—C14:0, iso-C15:0, C16:0, 3-OH-C16:0, iso-C15:0, C16:1, C16:2, C16:3, iso-C17:0, iso-C17:1, C18:0, 3OH—C18:0, C18:0/3-OH, C18:1, OH—C18:1, C18:2, C18:3, C18:4, C19:1 carbamoyl, C20:0, C20:1, 3-OH-C20:1, C20:1/3-OH, C20:2, C20:3, C22:1 and C18-26(ω-1)-OH (which according to D'Haeze, et al., Glycobiology 12:79R-105R (2002), includes C18, C20, C22, C24 and C26 hydroxylated species and C16:1Δ9, C16:2 (Δ2,9) and C16:3 (Δ2,4,9)); $R_2$ represents hydrogen or methyl; $R_3$ represents hydrogen, acetyl or caibamoyl, $R_4$ represents hydrogen, acetyl orcarbamoyl; $R_5$ represents hydrogen, acetyl or carbamoyl; $R_6$ represents hydrogen, arabinosyl, fucosyl, acetyl, $SO_3H$, sulfate ester, 3-0-S-2-0-MeFuc, 2-0-MeFuc and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. Naturally occurring LCOs embraced by this structure are described in D'Haeze, et al., supra.

Further examples of LCOs (and derivatives thereof) that may be useful in compositions and methods of the present disclosure are provided below as structures V-XXXIII:

(V)

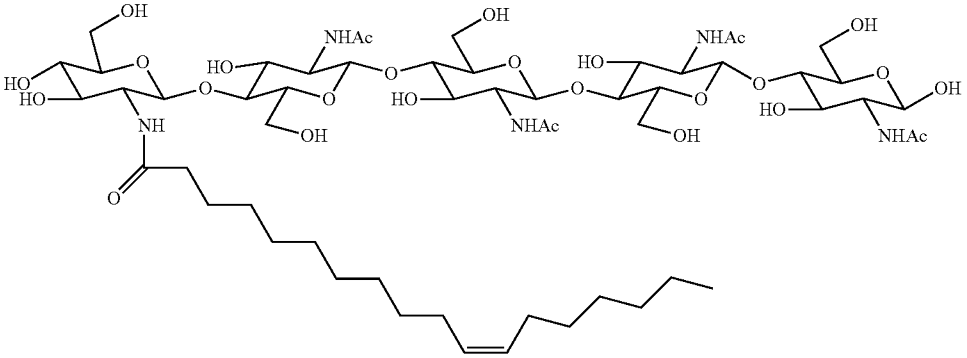

-continued
(VI)
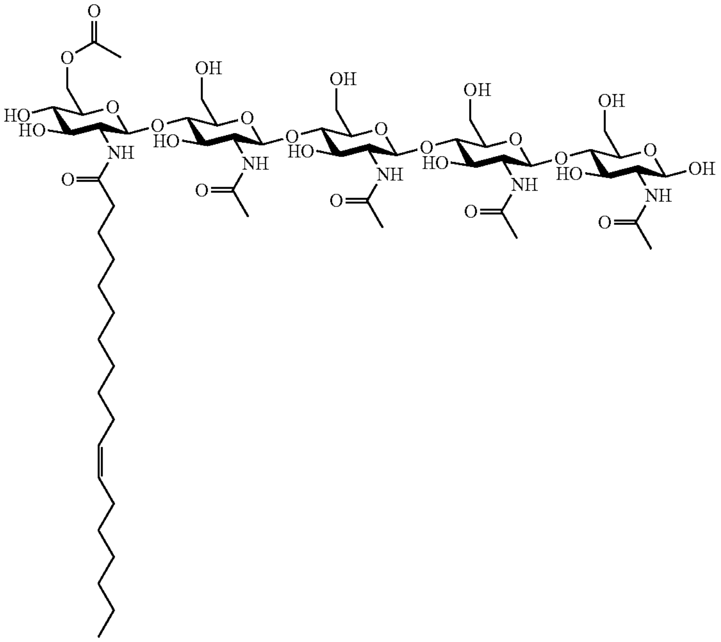
(VII)
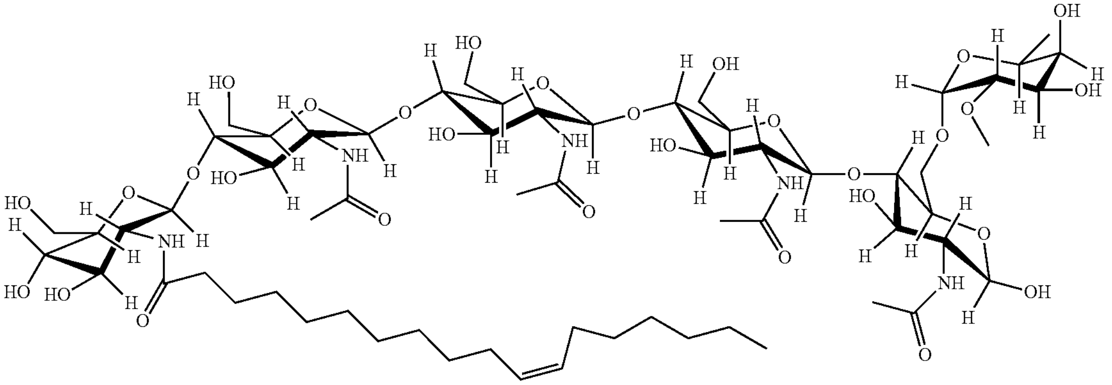

-continued
(VIII))
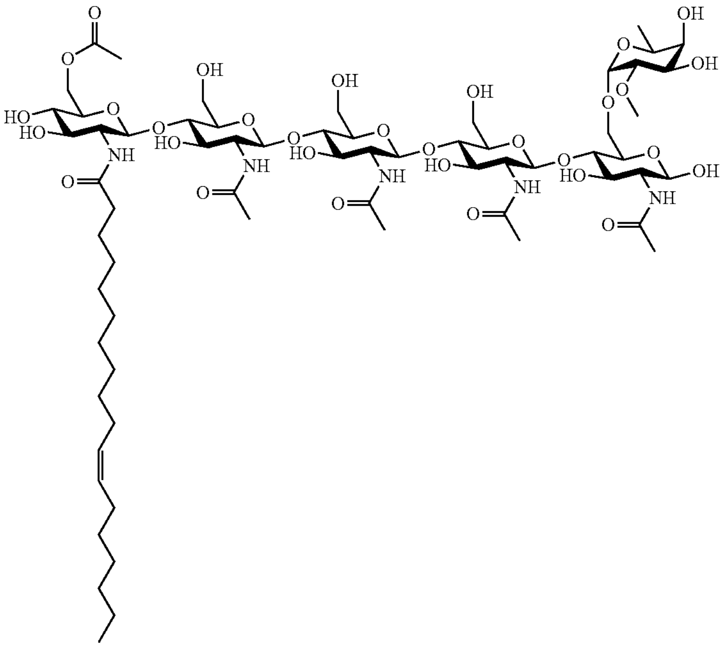
(IX)
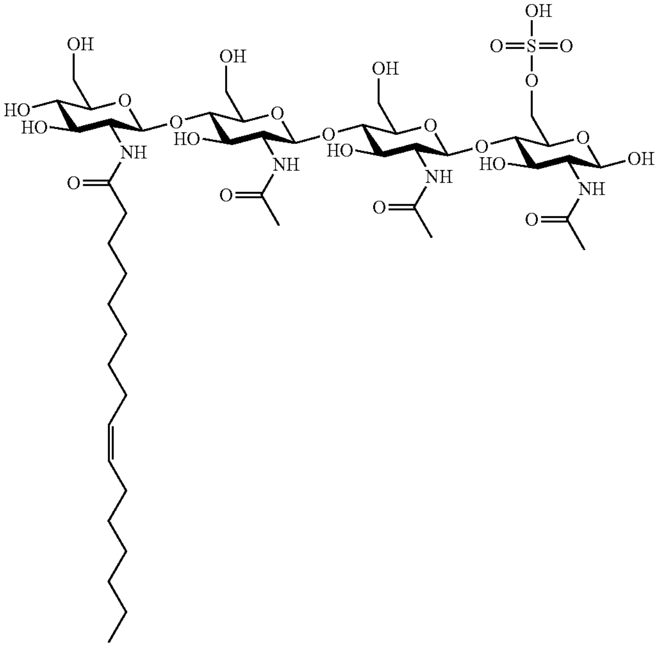

-continued
(X)
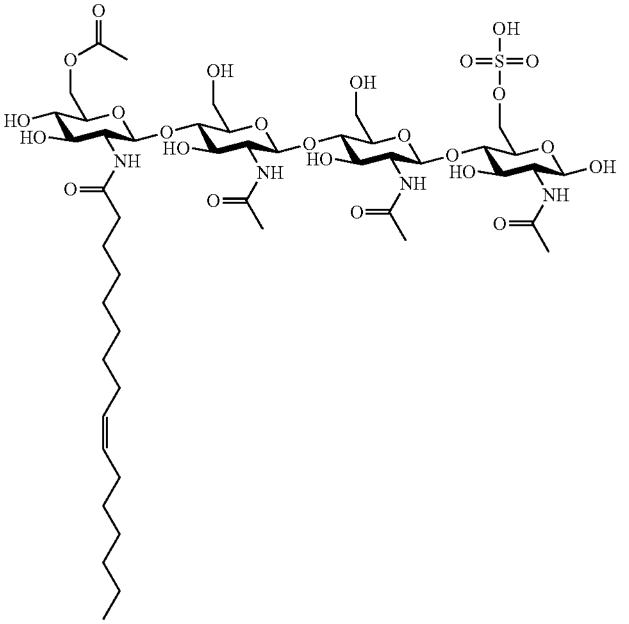
(XI)
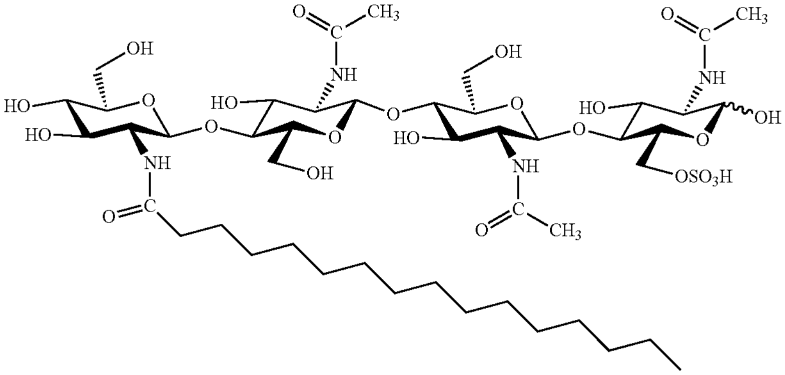
(XII)
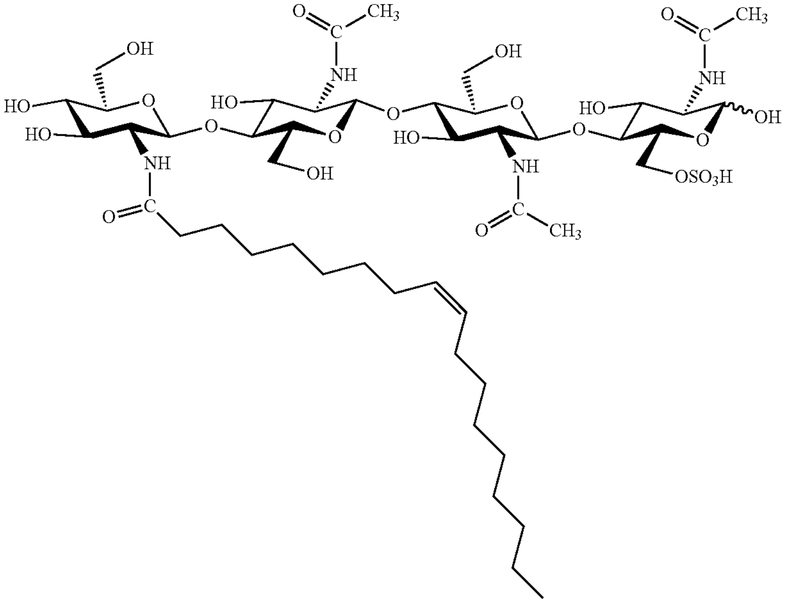

-continued
(XIII)
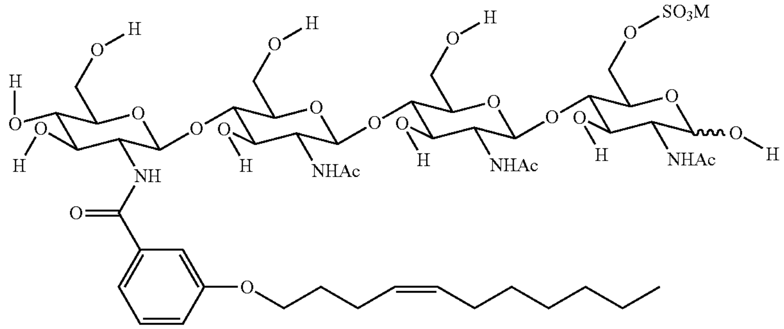
(XIV)
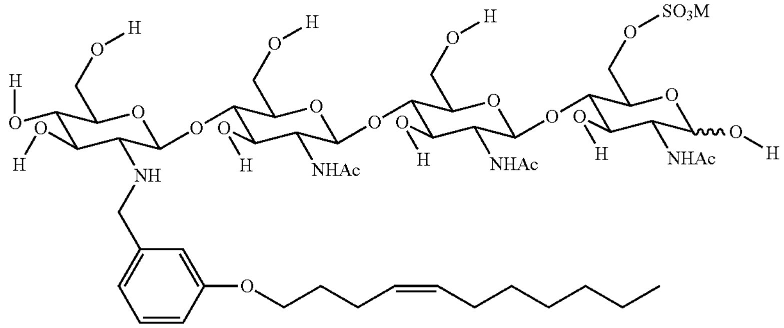
(XV)
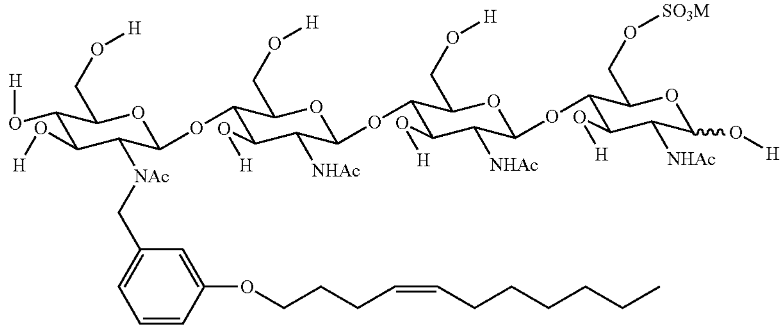
(XVI)
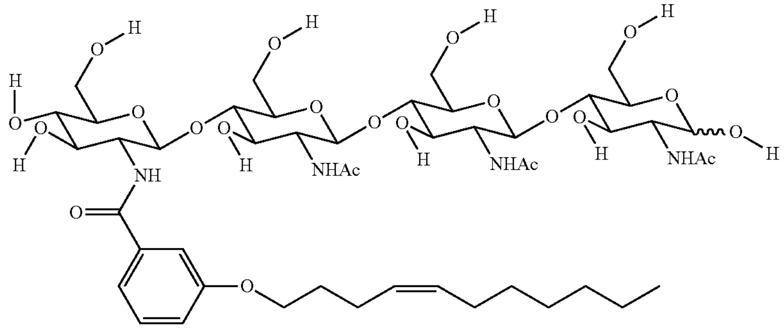

-continued
(XVII)
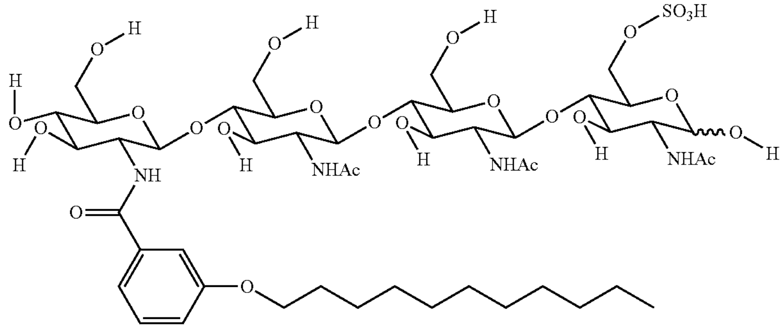
(XVIII)
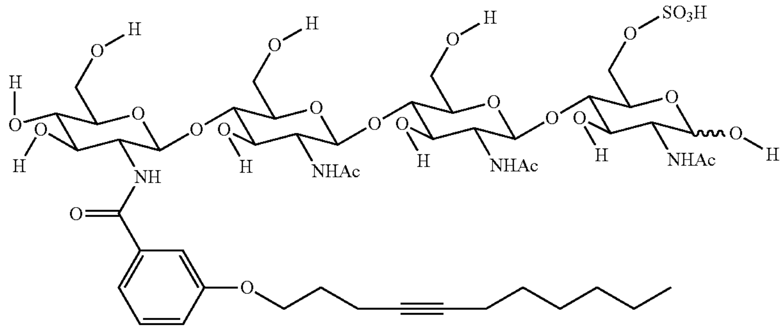
(XIX)
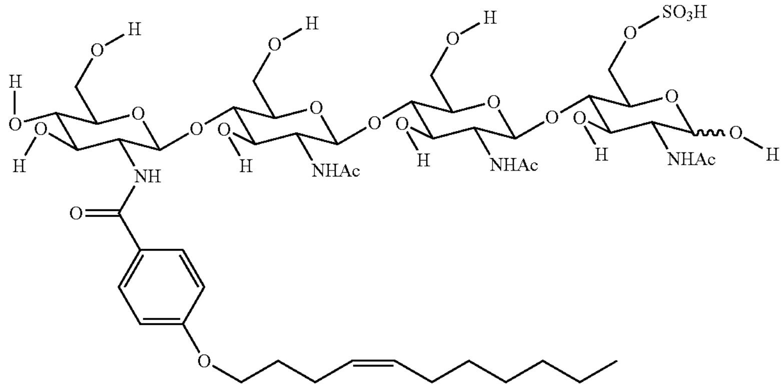
(XX)
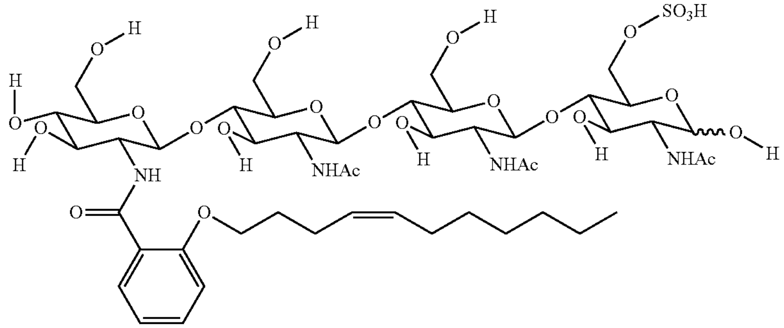

-continued
(XXI)
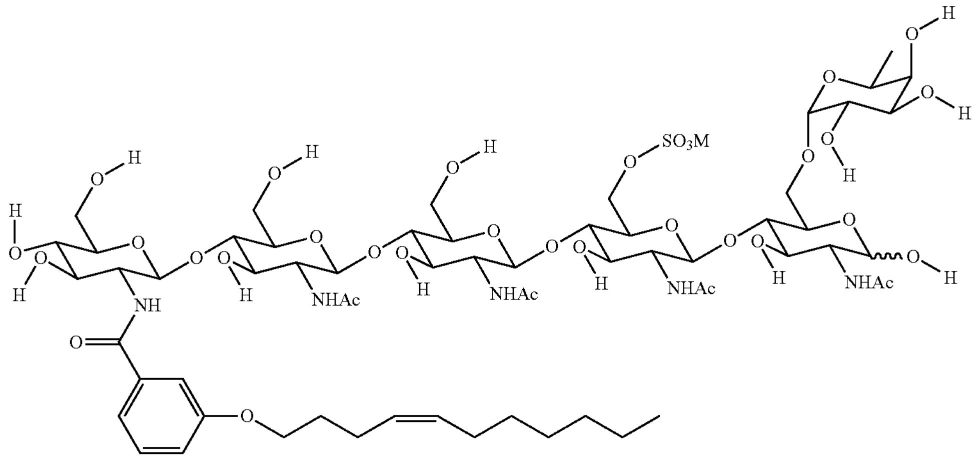
(XXII)
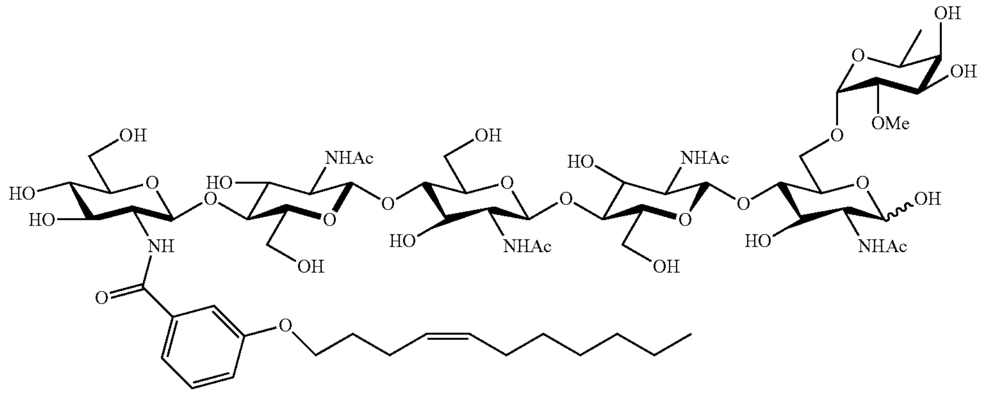
(XXIII)
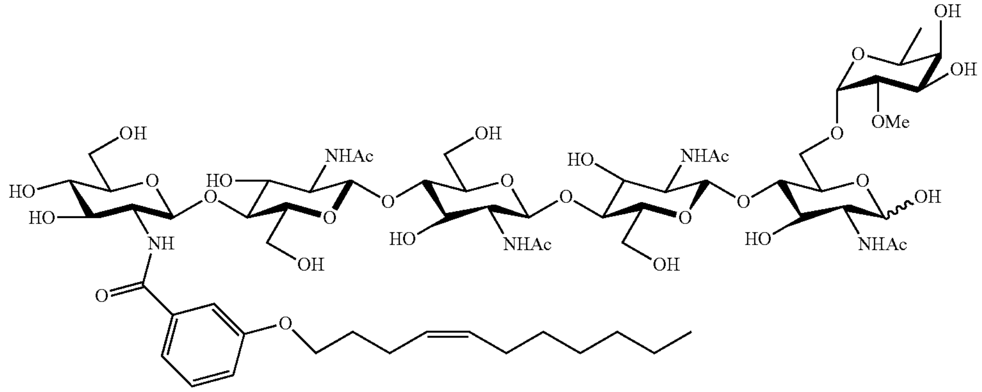
(XXIV)
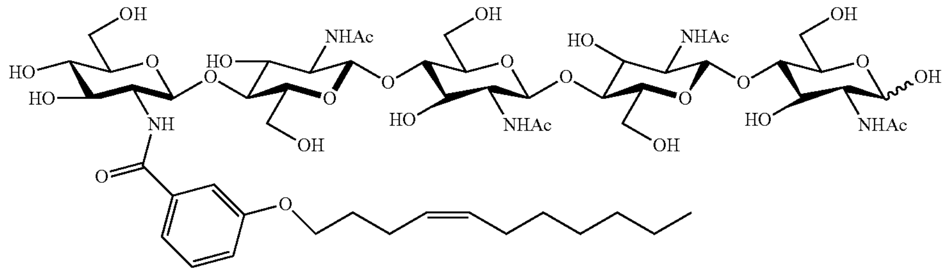

-continued
(XXV)
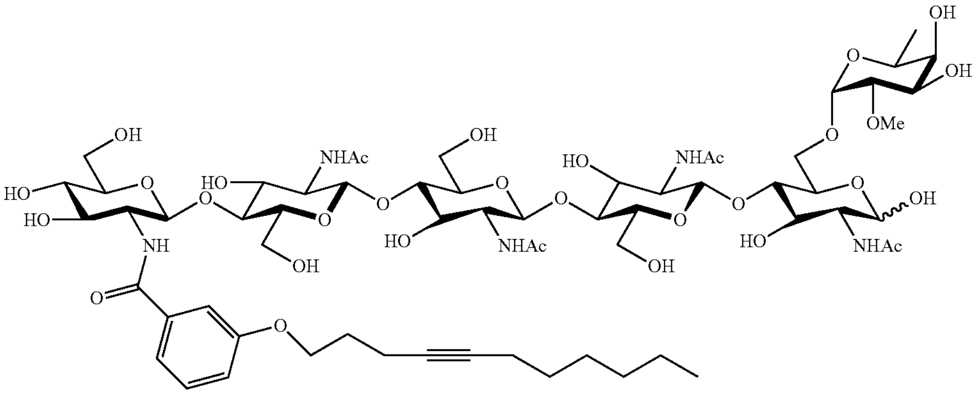
(XXVI)
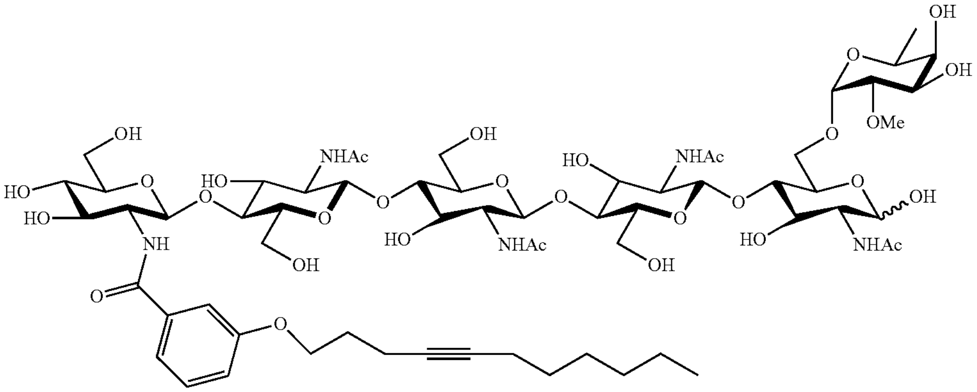
(XXVII)
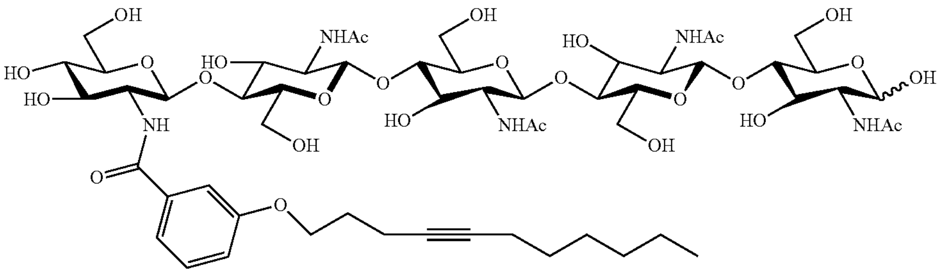
(XXVIII)
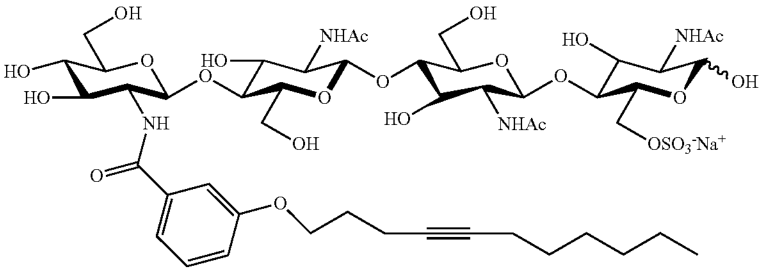

-continued
(XXIX)
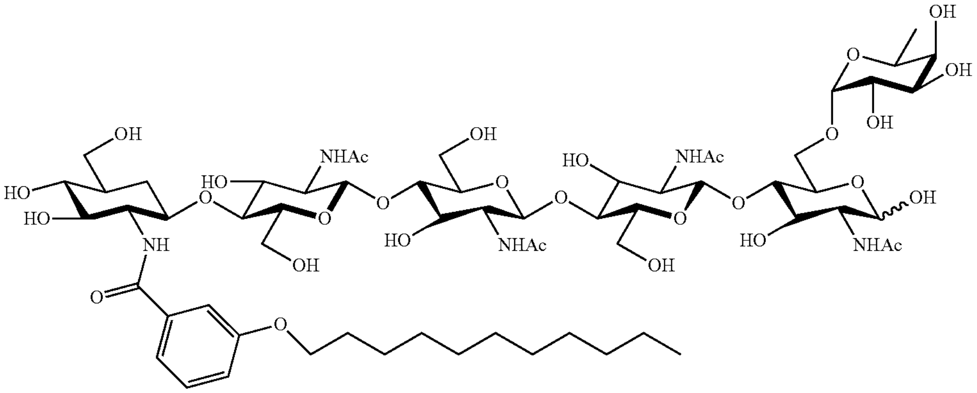
(XXX)
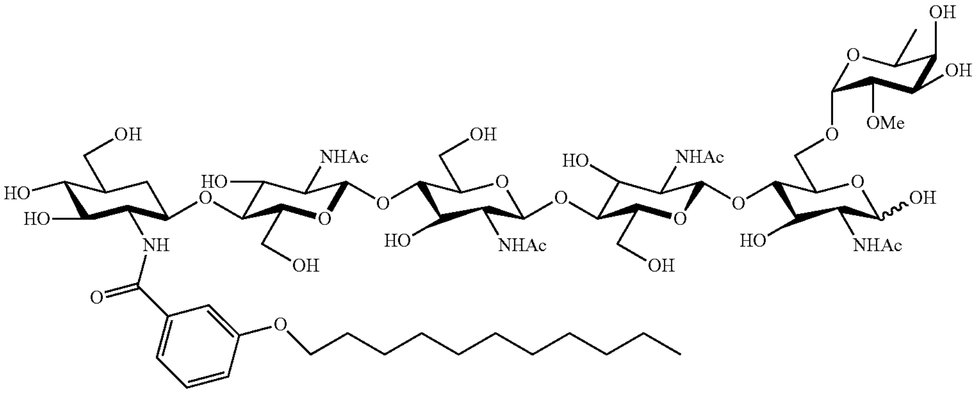
(XXXI)
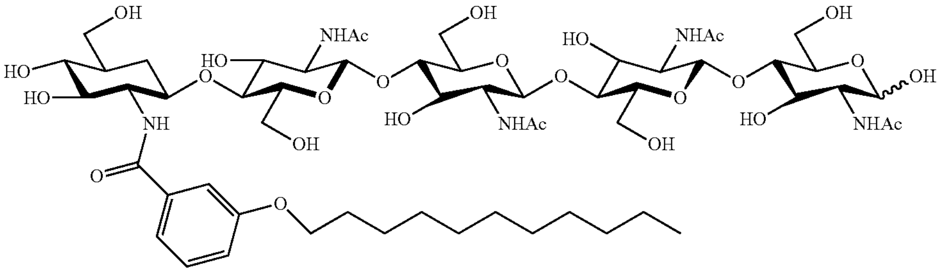
(XXXII)
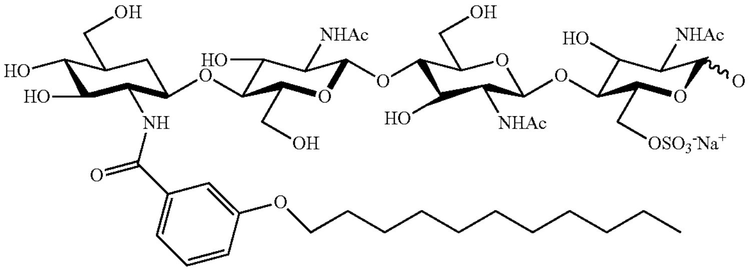
(XXXIII)
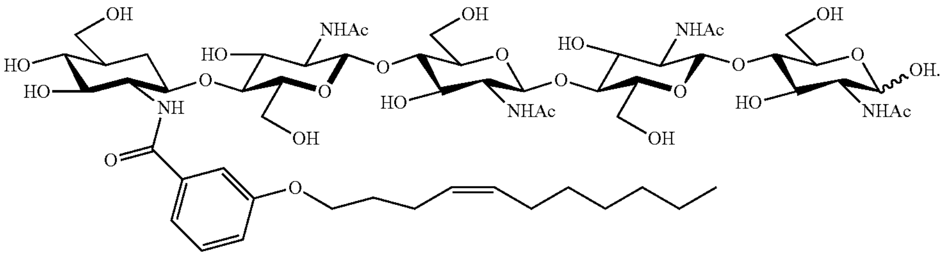

LCOs may be obtained from any suitable source. In some embodiments, the LCO is obtained (i.e., isolated and/or purified) from a bacterial strain. For example, in some embodiments, inoculant compositions of the present disclosure comprise one or more LCOs obtained from a of *Azorhizobium, Bradyrhizobium* (e.g., *B. japonicum*), *Mesorhizobium, Rhizobium* (e.g., *R. leguminosarum*), or *Sinorhizobium* (e.g., *S. meliloti*). In some embodiments, the LCO is obtained (i.e., isolated and/or purified) from a mycorrhizal fungus. For example, in some embodiments, inoculant compositions of the present disclosure comprise one or more LCOs obtained from a strain of Glomeromycota (e.g., *Glomus intraradicus*). See, e.g., WO 2010/049751 (in which the LCOs are referred to as "Myc factors") In some embodiments, the LCO is synthetic. For example, in some embodiments, inoculant compositions of the present disclosure comprise one or more of the synthetic LCOs described in WO 2005/063784, WO 2007/117500 and/or WO 2008/071674. In some embodiments, the synthetic LCO contains one or more modifications or substitutions, such as those described in Spaink. Cit. Rev. Plant Sci. 54:257 (2000) and D1-laeze, supra. LCOs and precursors for the construction of LCOs (e.g., chitin oligomers, which are themselves useful as plant signal molecules) may be synthesized by genetically engineered organisms. See, e.g., Samain et al., Carbohydrate Res. 302:35 (1997); Cottaz, et al. Meth. Eng. 7(4):311 (2005); and Samain, et al., J. Biotechnol. 72:33 (1999).

It is to be understood that compositions and methods of the present disclosure may comprise analogues, derivatives, hydrates, isomers, salts and/or solvates of LCOs Thus, in some embodiments, inoculant compositions of the present disclosure comprise one, two, three, four, five, six, seven, eight, nine, ten, or more LCOs represented by one or more of formulas I-IV and/or structures V-XXXIII and/or one, two, three, four, five, six, seven, eight, nine, ten, or more analogues, derivatives, hydrates, isomers, salts and/or solvates of LCOs represented by one or more of formulas I-IV and/or structures V-XXXIII.

LCOs (and derivatives thereof) may be utilized in various forms of purity and may be used alone or in the form of a culture of LCO-producing bacteria or fungi. In some embodiments, the LCO(s) included in inoculant compositions of the present disclosure is/are at least 50%, 55%, 60%, 65%, 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitin oligomer(s) and/or chitosan oligomer(s). Se, e.g., D'Haeze et al., Glycobiol. 12(6):79R (2002); Demont-Caulet et al., Plant Physiol. 120(1):83 (1999); Hanel et al, Planta 232:787 12010); Muller et al., Plant Physiol. 124:733 (2000); Robina et al., Tetrahedron 58:521-530 (2002); Rouge et al., *Docking of Chitn Oligomers and Nod Factors on Lectin Domains of the LysM-RLK Receptors an the Medicago-Rhizobium Symbiosis*, in The Molecular Immunology of Complex Carbohydrates-3 (Springer Science. 2011); Van der Holst et al., Curr. Opin. Struc. Biol. 11:608 (2001); Wan et al., Plant Cell 21:1053 (2009); and PCT/F100/00803 (2000).

In some embodiments, inoculant compositions of the present disclosure comprise one or more chitin oligosaccharides represented by formula XXXIV:

(XXXIV)

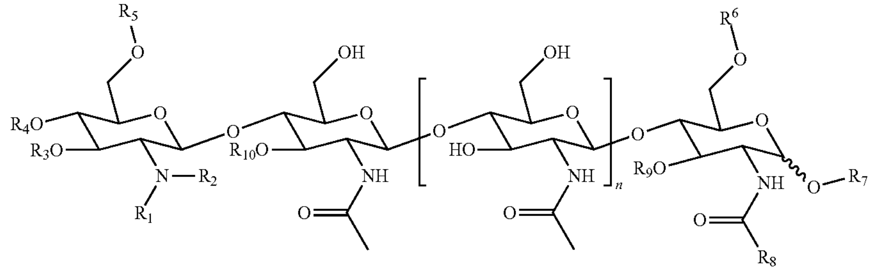

in which $R_1$ represents hydrogen or methyl; $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3.

In some embodiments, inoculant compositions of the present disclosure comprise one or more chitin oligosaccharides represented by formula XXXV:

(XXXV)

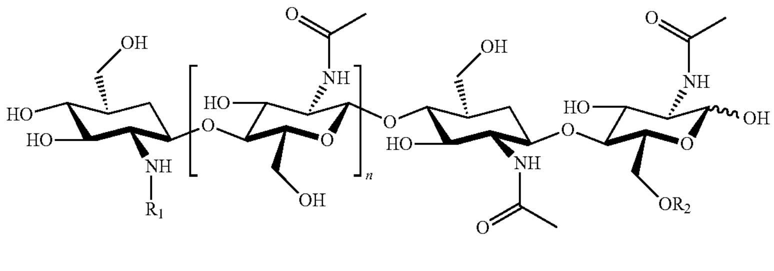

in which n=1 or 2; $R_1$ represents hydrogen or methyl; and $R_2$ represents hydrogen or $SO_3H$.
Further examples of oligosaccharides (and derivatives thereof) that may be useful in compositions and methods of the present disclosure are provided below as structures XXXVI-LXXXIII:
(XXXVI)
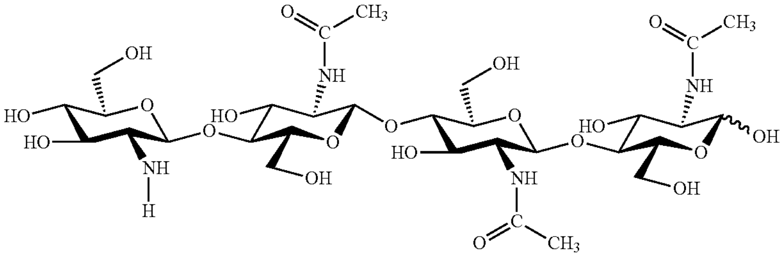
(XXXVII)
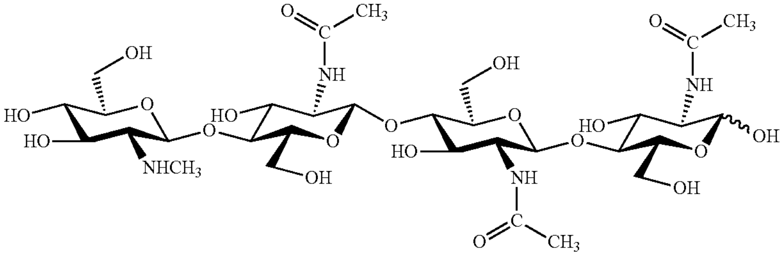
(XXXVIII)
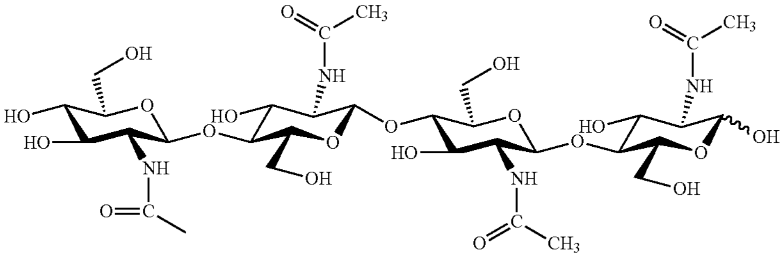
(XXXIX)
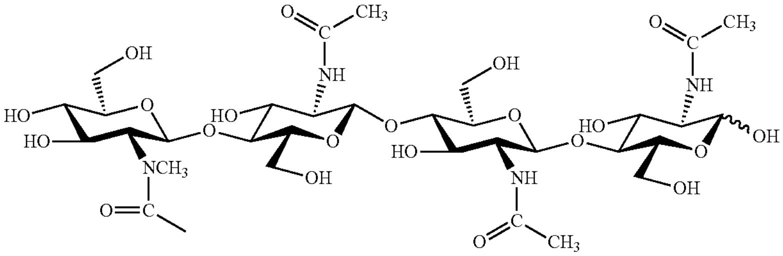
(XXXX)
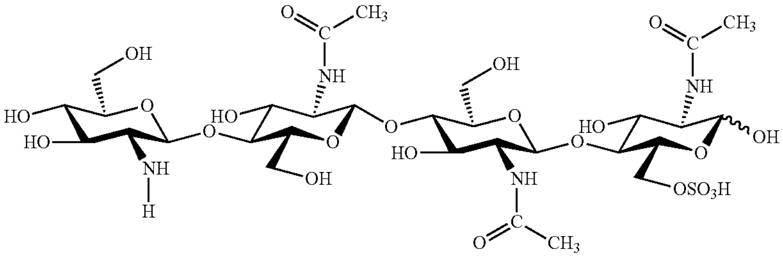

-continued
(XXXXI)
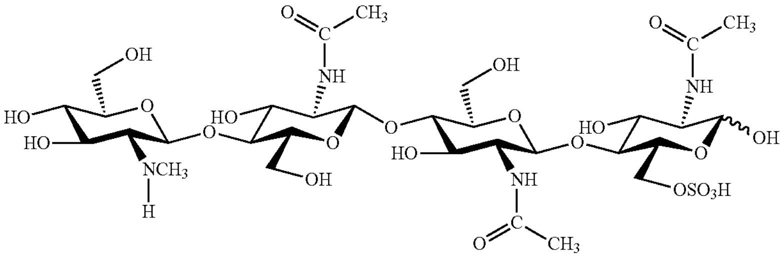
(XXXXII)
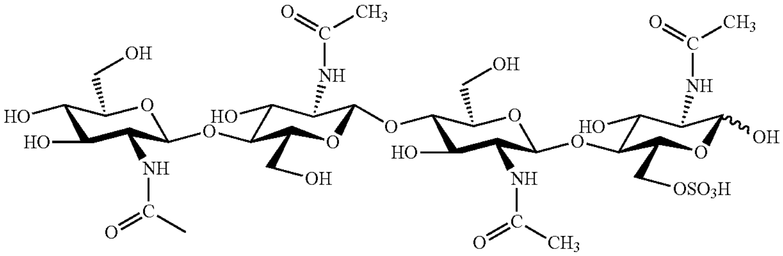
(XXXXIII)
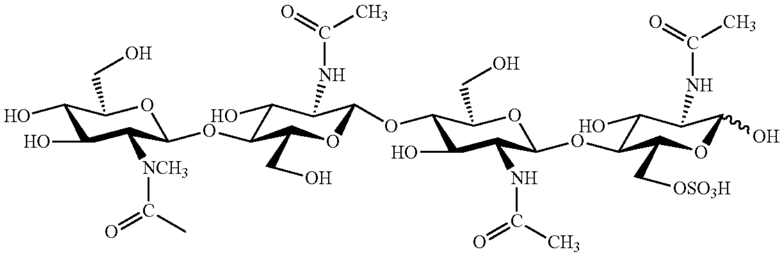
(XXXXIV)
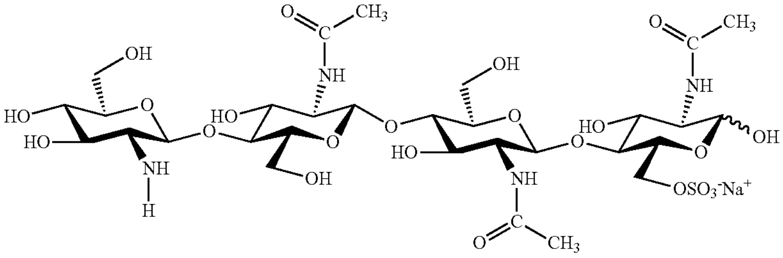
(XXXXV)
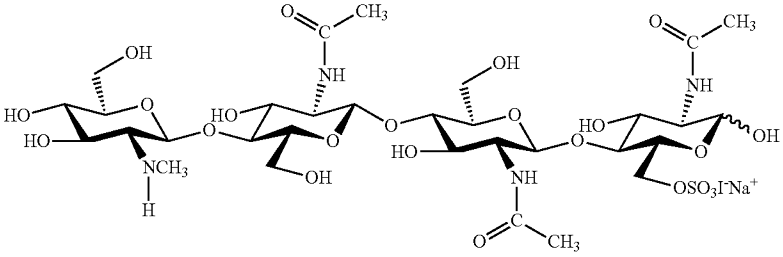
(XXXXVI)
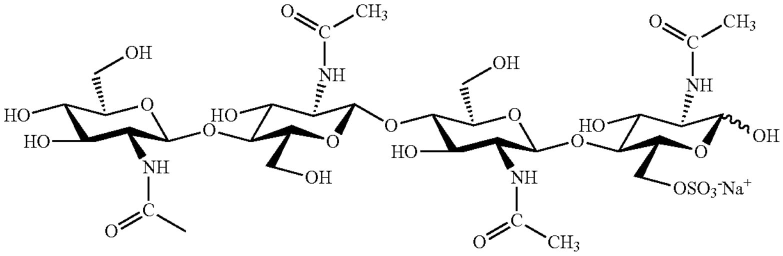

-continued
(XXXXVII)
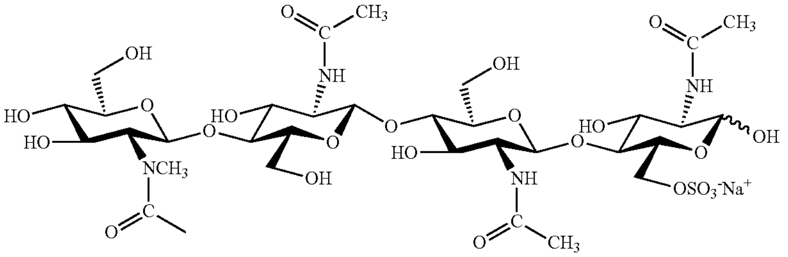
(XXXXVIII)
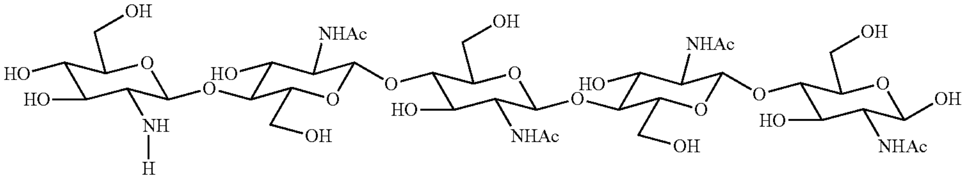
(XXXXIX)
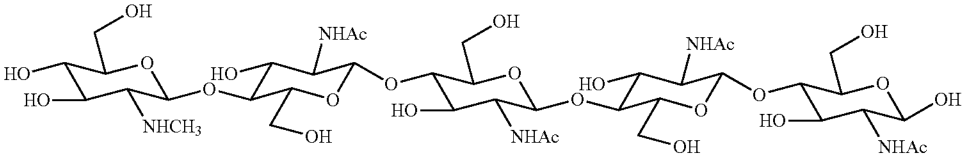
(L)
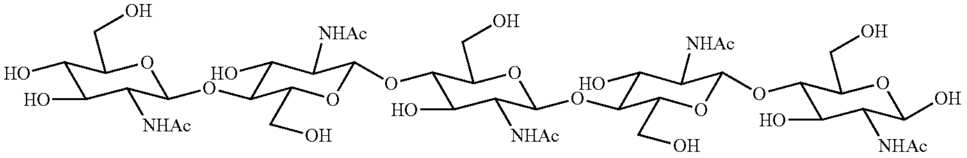
(LI)
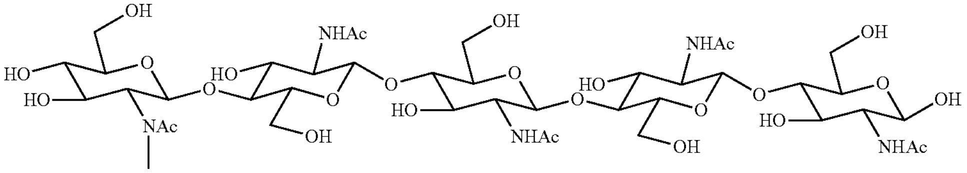
(LII)
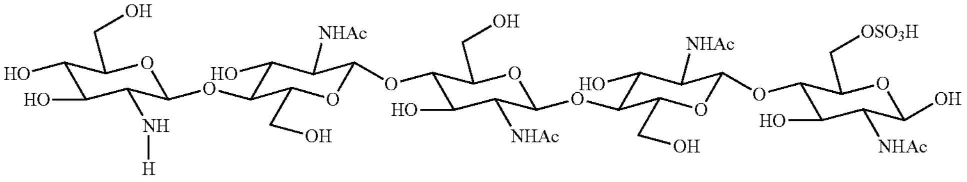
(LIII)
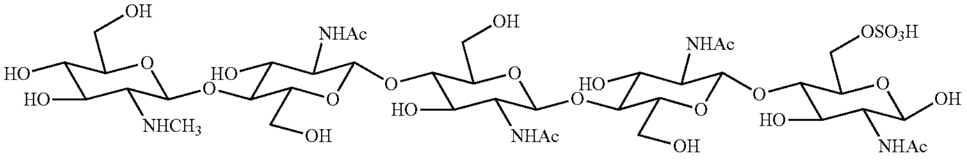
(LIV)
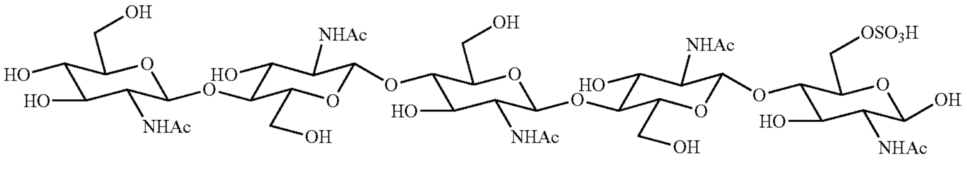

-continued
(LV)
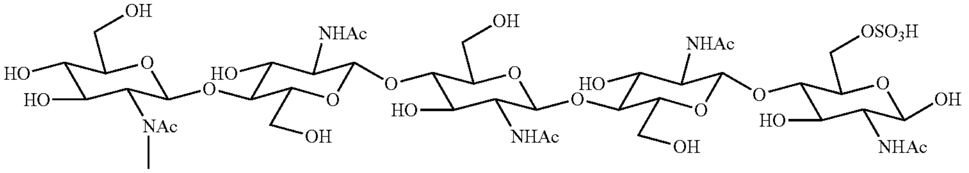
(LVI)
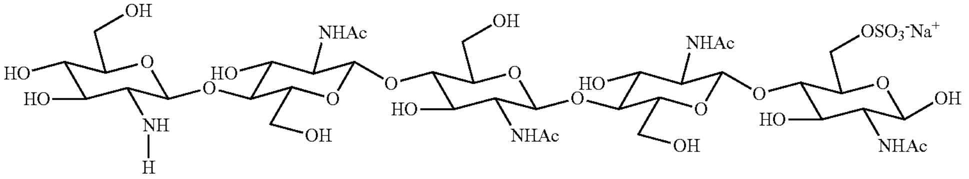
(LVII)
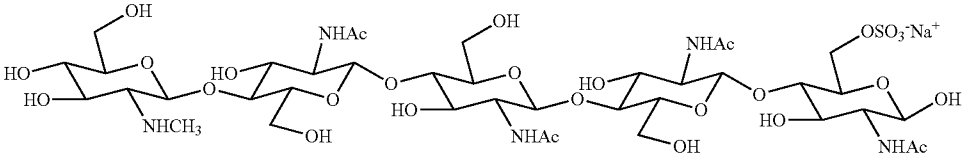
(LVIII)
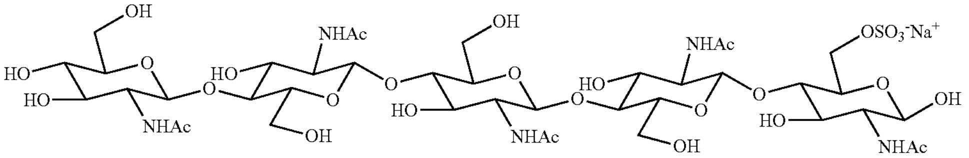
(LIX)
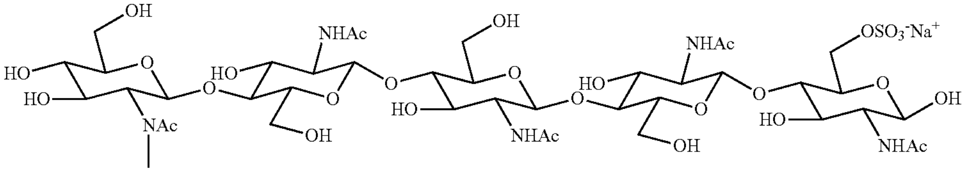
(LX)
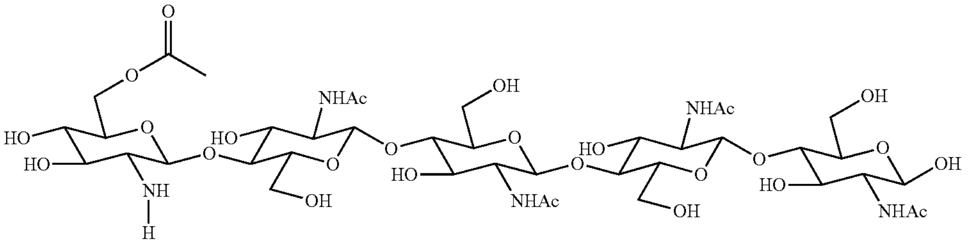
(LXI)
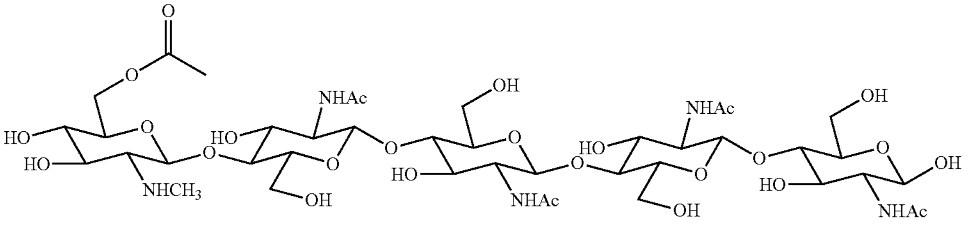
(LXII)
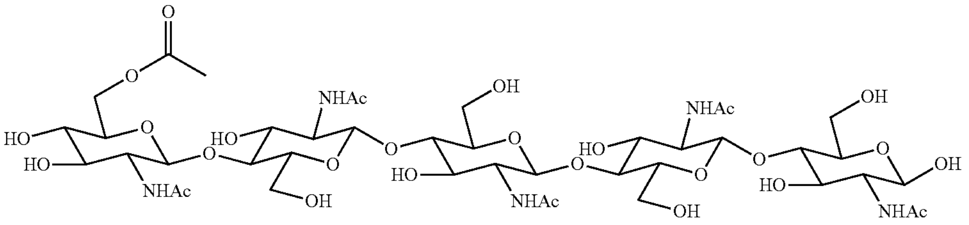

-continued
(LXIII)
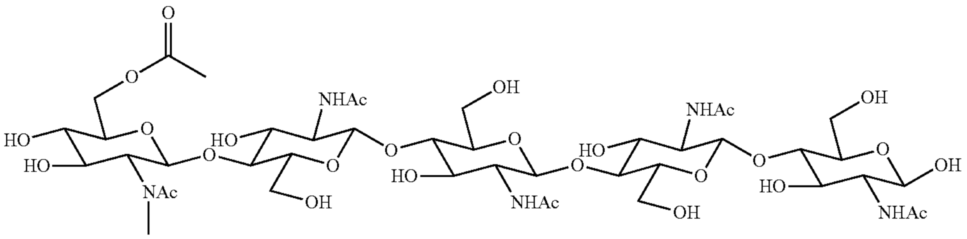
(LXIV)
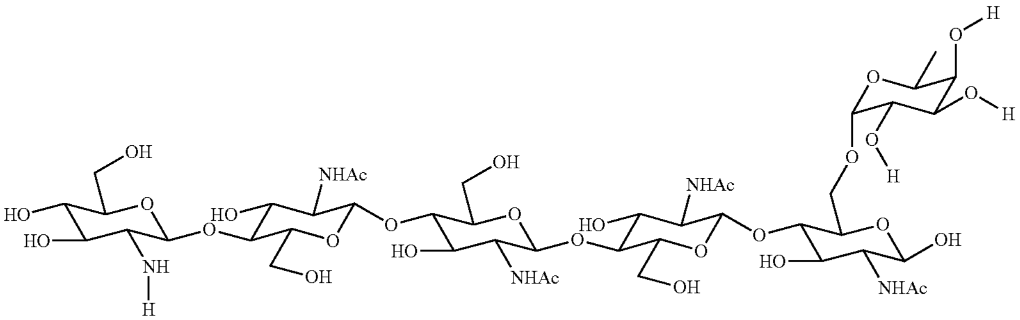
(LXV)
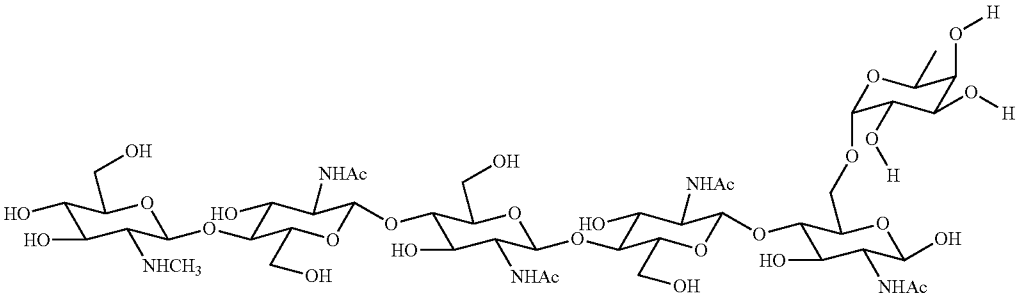
(LXVI)
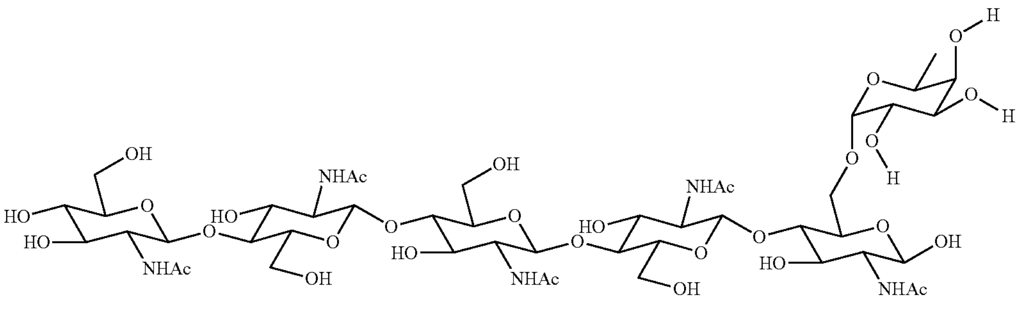
(LXVII)
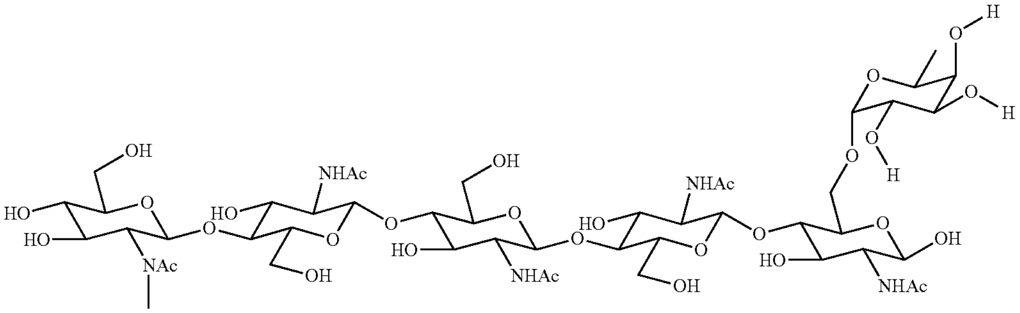

-continued
(LXVIII)
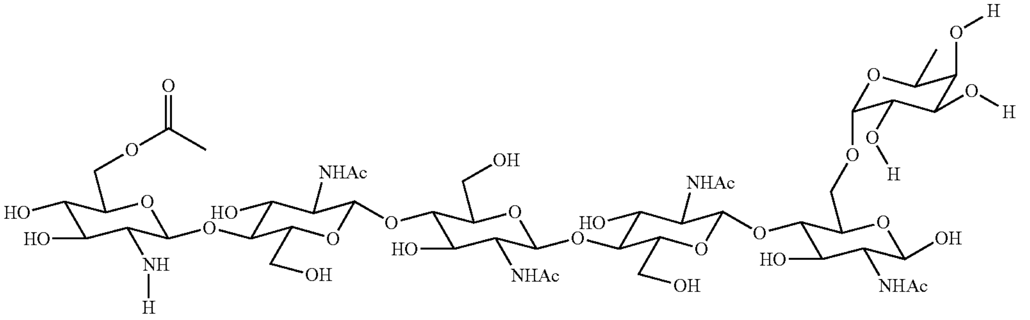
(LXIX)
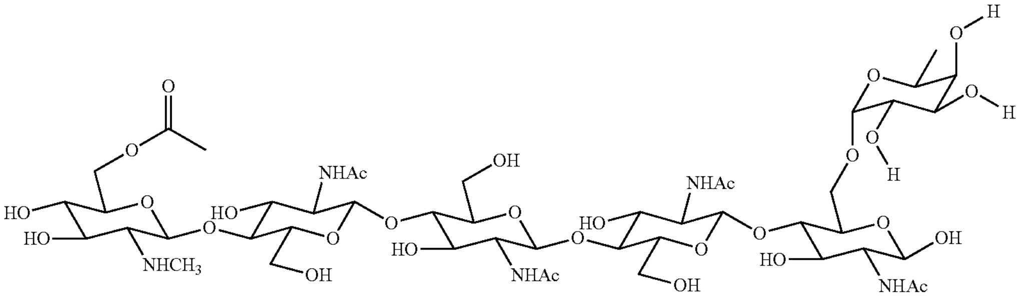
(LXX)
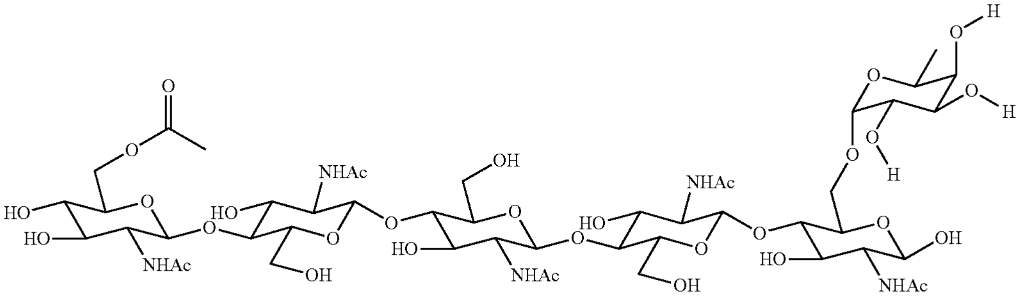
(LXXI)
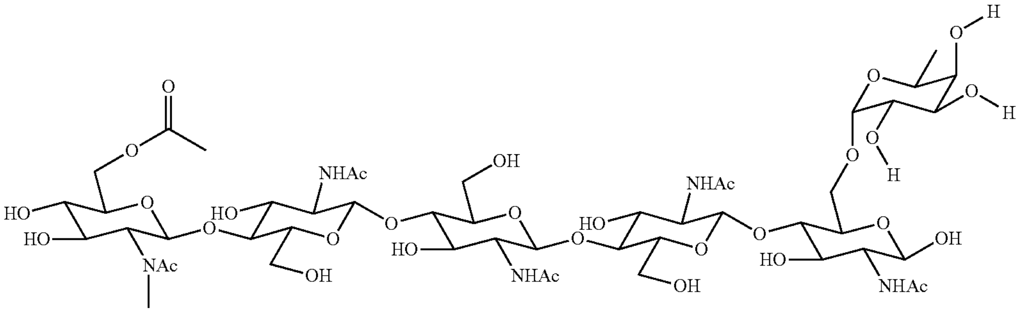
(LXXII)
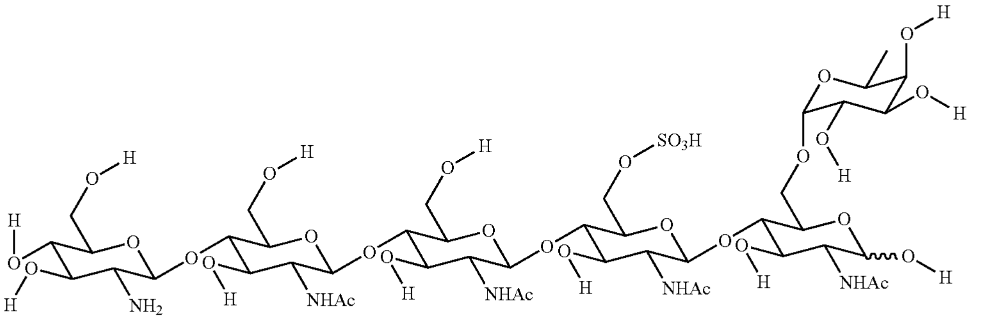

-continued
(LXXIII)
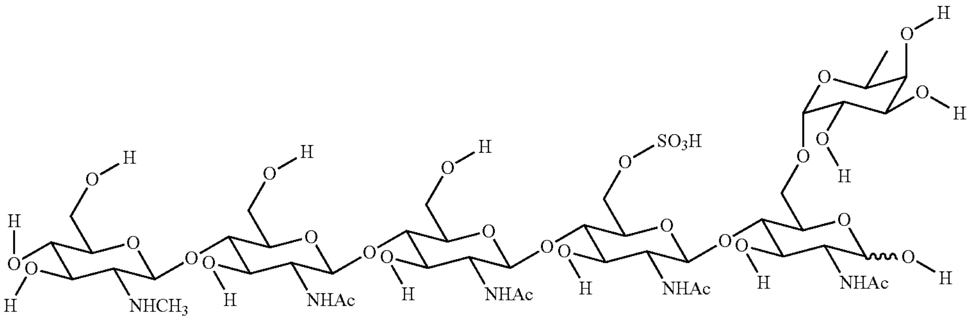
(LXXIV)
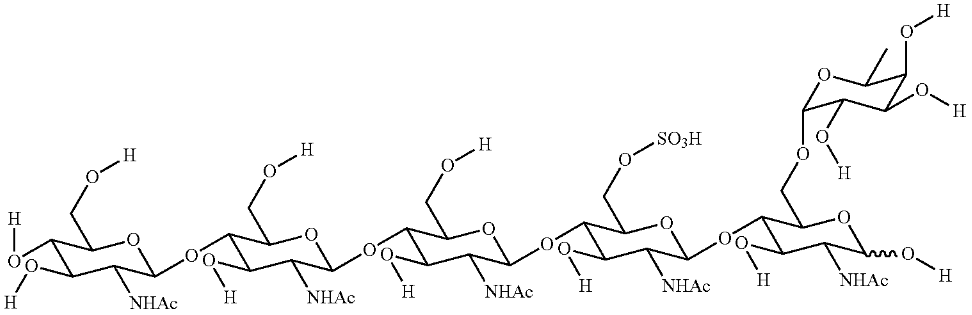
(LXXV)
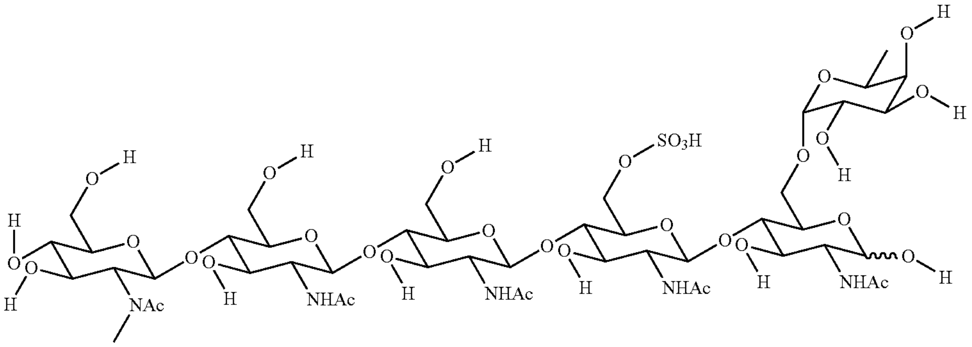
(LXXVI)
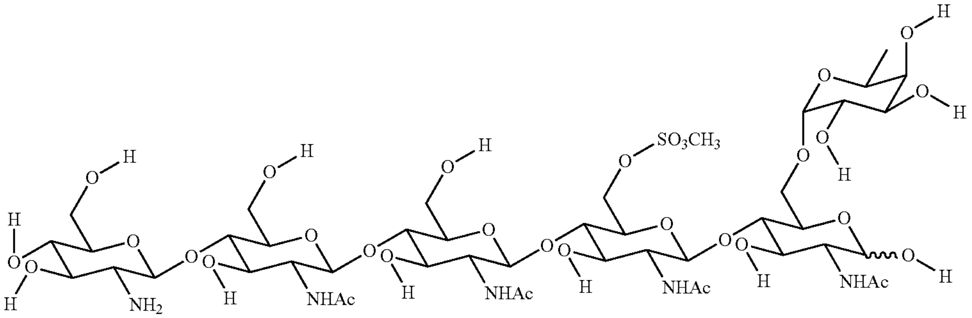
(LXXVII)
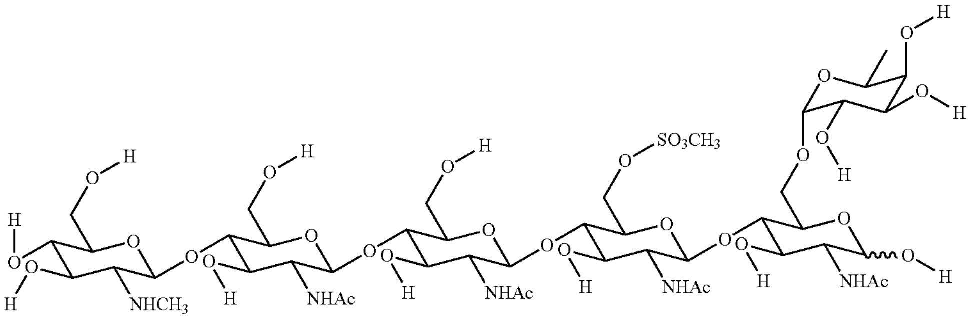

-continued
(LXXVIII)
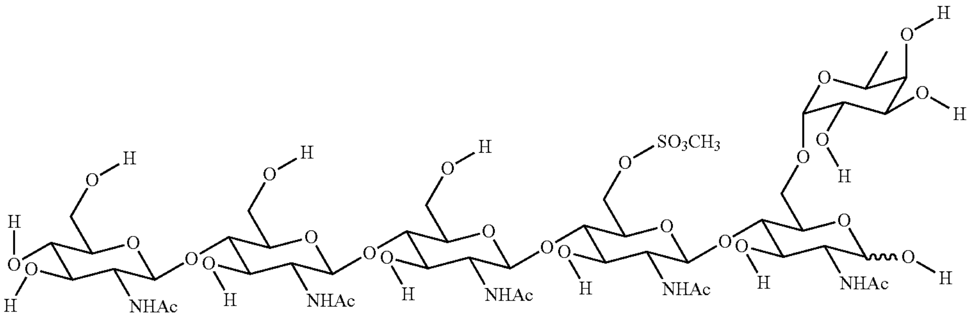
(LXXIX)
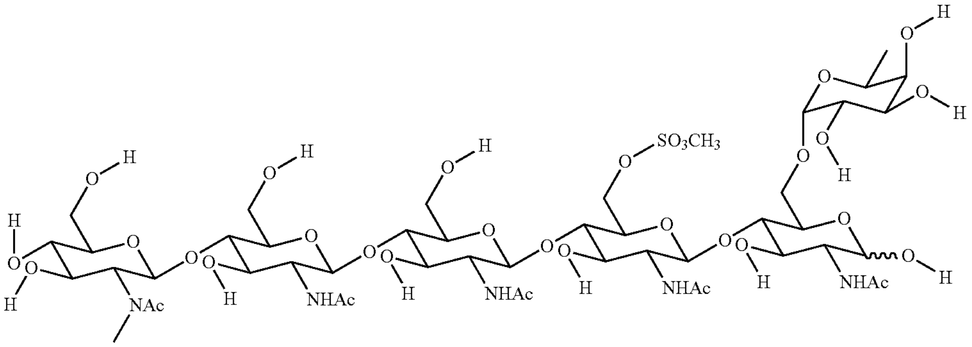
(LXXX)
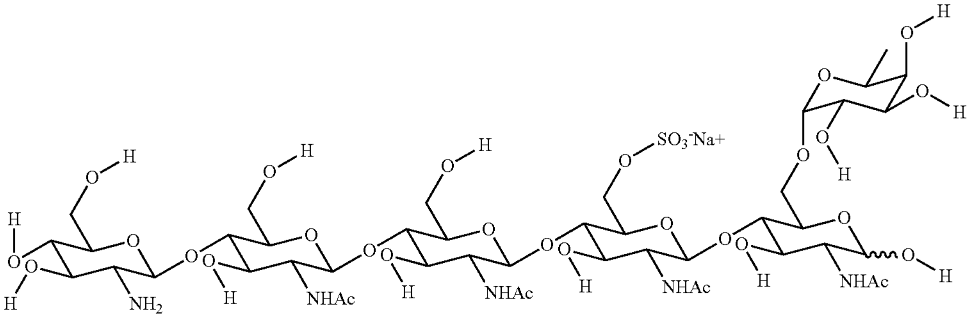
(LXXXI)
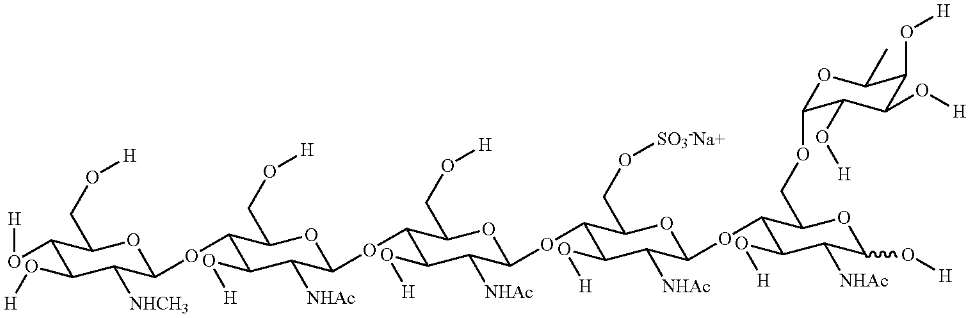
(LXXXII)
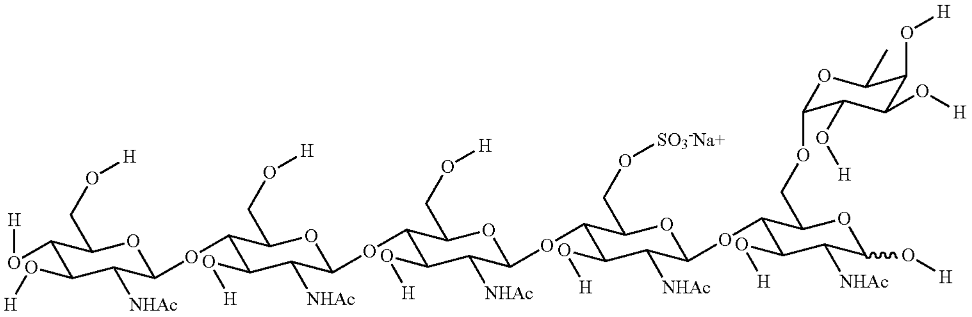

-continued (LXXXIII)

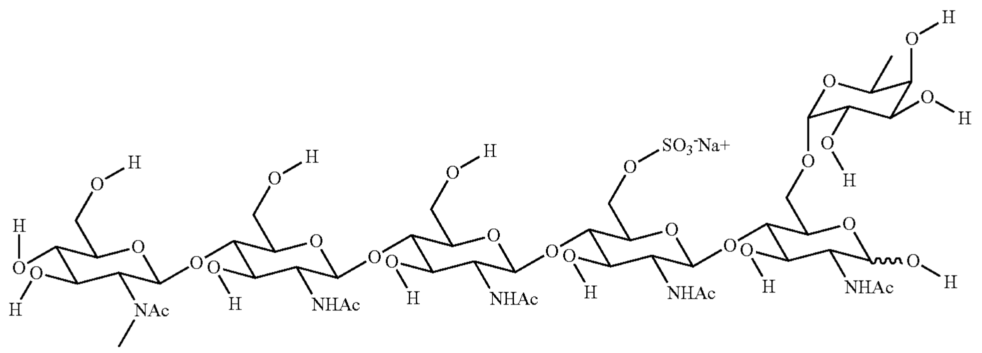

In some embodiments, inoculant compositions of the present disclosure comprise one or more of the oligosaccharides set forth above as structures XXXVI-LXXXIII in a deacetylated form (e.g., an oligosaccharide corresponding to structure XXXVI above except that one or more of the acetyl groups has been removed, optionally replaced by a hydrogen or methyl group).

Chitin oligosaccharides and chitosan oligosaccharides may be obtained from any suitable source. Chitin oligosaccharides and chitosan oligosaccharides may be harvested from chitin/chitosan (see, e.g., Aam et al., Mar. Drugs 8:1482 (2010); D'Haeze et al., Glycobiol. 12(6):79R (2002); Demont-Caulet et al., Plant Physiol. 120(1):83 (1999), Hanel et al., Planta 232:787 (2010). Limpanavech et al., Scientia Horticulture 116:65 (2008); Lodhi et al., Biomed Res. Intl. Vol. 2014 Art. 654913 (March 2014); Mourya et al., Polymer Sci. 53(7):583 (2011); Muller et al., Plant Physiol. 124:733 (2000); Robina et al., Tetrahedron 58:521 (2002); Rouge et al., *The Molecular Immunology of Complex Carbohydrates*, in Advances In Experimental Medicine and Biology (Springer Science, 2011); Van der Hoist et al, Curr. Opin. Struc. Biol. 11:608 (2001); Wan et al, Plant Cell 21:1053 (2009); Xia et al., Food Hydrocolloids 25:170 (2011); PCT/F100/00803 (2000)) They may also be synthetically generated (see, e.g., Cottaz et al., Meth. Eng. 7(4):311 (2005); Samain et al., Carbohydrate Res. 302:35 (1997); Samain et al., J. Biotechnol. 72:33 (1999)). In some embodiments, they are derived from a naturally occurring LCO. For example, in some embodiments, inoculant compositions of the present disclosure comprise one or mom chitin/chitosan oligosaccharides derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, inoculant compositions of the present disclosure comprise one or more chitin oligosaccharides and/or chitosan oligosaccharides derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, the chitin oligosaccharide(s) and/or chitosan oligosaccharide(s) is/are derived from an LCO represented by one or more of formulas I-IV and/or structures V-XXXIII. Thus, in some embodiments, inoculant compositions of the present disclosure may comprise one or more chitin oligosaccharides represented by one or more of formulas I-IV and/or structures V-XXXIII except that the pendant fatty acid is replaced with a hydrogen or methyl group.

It is to be understood that compositions of the present disclosure may comprise analogues, derivatives, hydrates, isomers, salts and/or solvates of chitin oligosaccharides and/or chitosan oligosaccharides. Thus, in some embodiments, inoculant compositions of the present disclosure comprise one, two, three, four, five, six, seven, eight, nine, ten, or more chitin oligosaccharides represented by one or more of formulas XXXIV-XXXV and/or structures XXXVI-LXXXIII and/or one, two, three, four, five, six, seven, eight, nine, ten, or more analogues, derivatives, hydrates, isomers, salts and/or solvates of chitin oligosaccharides represented by one or more of formulas XXXIV-XXXV and/or structures XXXVI-LXXXIII.

Chitin oligosaccharides and chitosan oligosaccharides (and analogues, derivatives, hydrates, isomers, salts and/or solvates thereof) may be utilized in various forms of purity and may be used alone or in the form of a culture of CO-producing bacteria or fungi. In some embodiments, the chitin oligosaccharides and/or chitosan oligosaccharides included in inoculant compositions of the present disclosure is/are at least 50%, 55%, 60%, 65%, 70%, 75%, 80%, 85%, 90%, 91%, 92%, 93%, 94%, 95%, 96% 97%, 98%, 99%, 99.5% or more pure.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2 yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan(IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2(hydroxymethyl)oxane-3,4-diol) and isomers, salts and solvates thereof.

Chitins and chitosans, which are major components of the cell walls of fungi and the exoskeletons of insects and crustaceans, are composed of GlcNAc residues.

Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and U.S. Pat. No. 5,965,545 (preparation from crab shells and hydrolysis of commercial chitosan); Pochanavanich, et al., Lett. Appl. Microbiol. 35:17 (2002) (preparation from fungal cell walls).

Deacetylated chitins and chitosans may be obtained that range from less than 35% to greater than 90% deacetylation and cover a broad spectrum of molecular weights. e.g., low molecular weight chitosan oligomers of less than 15 kD and chitin oligomers of 0.5 to 2 kD, "practical grade" chitosan with a molecular weight of about 15 kD, and high molecular weight chitosan of up to 70 kD. Chitin and chitosan compositions formulated for seed treatment are commercially available. Commercial products include, for example. ELEXA® (Plant Defense Boosters, Inc.) and BEYOND™ (Agrihouse, Inc.).

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof.

Flavonoids are phenolic compounds having the general structure of two aromatic rings connected by a three-carbon bridge. Classes of flavonoids include are known in the art. See, e.g., Jain et al., J. Plant Biochem. & Biotechnol. 11:1 (2002), Shaw et al, Environ. Microbiol. 11:1867 (2006). Flavonoid compounds are commercially available, e.g., from Novozymes BioAg, Saskatoon, Canada; Natland International Corp., Research Triangle Park, NC; MP Biomedicals, Irvine, CA; LC Laboratories, Wobum MA. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston et al., Plant Physiol. 137:1375 (2005).

In some embodiments, inoculant compositions of the present disclosure comprise one or more anthocyanidins. According to some embodiments, the inoculant composition comprises cyanidin, delphinidin, malvidin, pelargonidin, peonidin and/or petunidin.

In some embodiments, inoculant compositions of the present disclosure comprise one or more anthoxanthins. According to some embodiments, the inoculant composition comprises one or more flavones (e.g., apigenin, baicalein, chrysin. 7,8-dihydroxyflavone, diosmin, flavoxate, 6 hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, prenylflavonols quercetin, quercetin, rhamnazin, rhamnetin, robinin, rutin, spiraeoside, troxerutin and/or zanthortamnin).

In some embodiments, inoculant compositions of the present disclosure comprise one or more flavanones. According to some embodiments, the inoculant composition comprises butin, eriodictyol, hesperetin, hesperidin, homoeriodictyol, isosakuranetin, naringenin, naringin, pinocembrin, poncirin, sakuranetin, sakuranin and/or sterubin.

In some embodiments, inoculant compositions of the present disclosure comprise one or more flavanonols. According to some embodiments, the inoculant composition comprises dihydrokaempferol and/or taxifolin.

In some embodiments, inoculant compositions of the present disclosure comprise one or more flavans. According to some embodiments, the inoculant composition comprises one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. According to some embodiments, the inoculant composition comprises one or more isoflavones (e.g. biochanin A, daidzein, formononetin, genistein and/or glycitein), isoflavones (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids.

Inoculant compositions of the present disclosure may comprise any suitable flavonoid derivative, including, but not limited to, neoflavonoids (e.g., calophyllolide, coutarmagenin, dalbergichromene, dalbergin, nivetin) and pterocarpans (e.g., bitucarpin A, bitucarpin B, erybraedin A, erbraedin B, erythrabyssin II, erthyrabissin-I, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compositions of the present disclosure in any suitable form, including, but not limited to, polymorphic and crystalline forms.

Inoculant compositions of the present disclosure may comprise any suitable non-flavonoid nod-gene inducer(s), including, but not limited to, jasmonic acid ([1R-[1α,2β (Z)]]-3-oxo-2-(pentenyl)cyclopentaneacetic acid; JA), linoleic acid ((Z,Z)-9,12-Octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae, Gibbrella fujikuroi*), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. Plant Physiol Biochem. 44(11):759 (2006). Mabood et al., Agr J. 98(2):289 (2006); Mabood, et al., Field Crops Res. 95(2-3):412 (2006); Mabood & Smith, *Linoleic and linolenic acid induce the expression of nod genes in Bradyrhizobium japonicum USDA* 3, Plant Biol. (2001) Non-limiting examples of derivatives of jasmonic acid, linoleic acid, linolenic acid include esters, amides, glycosides and salts. Representative esters are compounds in which the carboxyl group of linoleic acid, linolenic acid, or jasmonic acid has been replaced with a —COR group, where R is an —$OR^1$ group, in which $R^1$ is; an alkyl group, such as a $C_1$-$C_8$ unbranched or branched alkyl group. e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an $NR^2R^3$ group, in which $R^2$ and $R^3$ are independently; hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salts may be precipitated from solution and be collected by filtration or may be recovered by other means such as by evaporation of the solvent.

Inoculant compositions of the present disclosure may comprise any suitable karrakin(s), including, but not limited to, 2H-furo[2,3-c]pyran-2-ones, as well as analogues, derivatives, hydrates, isomers, polymers, salts and solvates thereof.

In some embodiments, the inoculant composition comprises one or more karrakins represented by formula LXXXIV:

(LXXXIV)

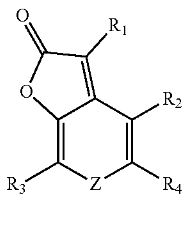

in which Z is O, S or $NR_5$; $R_1$, $R_2$, $R_3$ and $R_4$ are each independently H, alkyl, alkenyl, alkynyl, phenyl, benzyl, hydroxy, hydroxy alkyl, alkoxy, phenyloxy, benzyloxy, CN, $COR_6$, COOR=, halogen, $NR_6R_7$, or $NO_2$; and $R_5$, $R_6$ and $R_7$ are each independently H, alkyl or alkenyl, or a biologically acceptable salt thereof.

Examples of biologically acceptable salts of karrakins include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where $R_1$—$CH_3$, $R_2$, $R_3$, $R_4$═H), 2H-furo[2,3-c]pyran-2-one (where $R_1$, $R_2$, $R_3$, $R_4$=H), 7-methyl-2H-furo[2,3-c]pyran-2-one (where $R_1$, $R_2$, $R_4$=H, $R_3$=$CH_3$), 5-methyl-2H-furo[2,3-c]pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trimethyl-2H-furo[2,3-c]pyran-2-one (where $R_1$, $R_3$, $R_4$=$CH_3$, $R_2$=H), 5-methoxymethyl-3-methyl-2H-furo[2,3-c]pyran-2-one (where $R_1$=$CH_3$, $R_2$, $R_3$=H, $R_4$—$CH_2OCH$), 4-bromo-3,7-dimethyl-2H-furo[2,3-c]pyran-2-one (where $R_1$, $R_3$=$CH_3$, $R_2$=Br, $R_4$=H), 3-methylfuro[2,3-c]pyridin-2(3H)-one (where Z=NH, $R_1$=$CH_3$, $R_2$, $R_3$, $R_4$=H) and 3,6-dimethylfuro[2,3-c]pyridin-2(6H)-one (where Z=N—$CH_3$, $R_1$=$CH_3$, $R_2$, $R_3$, $R_4$=H). See, e.g., U.S. Pat. No. 7,576,213; Halford, *Smoke Signals*, in CHEM. ENG. NEWS (Apr. 12, 2010) (reporting that karrikins or butenolides contained in smoke act as growth stimulants and spur seed germination after a forest fire and can invigorate seeds such as corn, tomatoes, lettuce and onions that had been stored).

Inoculant compositions of the present disclosure may comprise gluconolactone and/or one or more analogues, derivatives, hydrates, isomers, polymers, salts and/or solvates thereof.

Inoculant compositions of the present disclosure may comprise any suitable excipient(s), including, but not limited to, dispersants, drying agents, anti-freezing agents, seed flowability agents, safeners, anti-settling agents, pH buffers, adhesives and effect pigments.

Inoculant compositions of the present disclosure may comprise any suitable agriculturally acceptable dispersant(s), including, but not limited to, surfactants and wetting agents Selection of appropriate dispersants will depend on the intended application(s) and the microorganism(s) present in the inoculant composition. In general, the dispersant(s) will have low toxicity for the microorganism(s) in the inoculant composition and for the plant part(s) to which the inoculant composition is to be applied. In some embodiments, the dispersant(s) will be selected to wet and/or emulsify one or more soils. Non-limiting examples of dispersants include Atlox™ (e.g., 4916, 4991; Croda Intemational PLC. Edison, NJ). Atlox METASPERSE™ (Croda International PLC, Edison, NJ), BIO-SOFT® (e.g., N series, such as N1-3, N1-7, N1-5, N1-9, N23-3, N2.3-6.5, N25-3, N25-7, N25-9, N91-2.5, N91-6, N91-8, Stepan Company, Northfield, IL), MAKON® nonionic surfactants (e.g., DA-4, DA-6 and DA-9; Stepan Company, Northfield, IL), MORWET® powders (Akzo Nobel Surface Chemistry LLC, Chicago, IL). MULTIWET™ surfactants (e.g., MO-85P-PW-(AP); Croda International PLC, Edison. NJ), SILWET®, L-77 (Helena Chemical Company. Collierville, TN), SPAN™ surfactants (e.g., 20, 40, 60, 65, 80 and 85; Croda Inc, Edison NJ), TAMOL™ dispersants (The Dow Chemical Company, Midland, MI), TERGITOL™ surfactants (e.g., TMN-6 and TMN-100X; The Dow Chemical Company, Midland, MI), TERSPERSE surfactants (e.g., 2001, 2020, 2100, 2105, 2158, 2700, 4894 and 4896, Hunstman Corp., The Woodlands, TX), TRITON™ surfactants (e.g., X-100; The Dow Chemical Company, Midland, MI), TWEEN®; surfactants (e.g., TWEEN® 20, 21, 22, 23, 28, 40, 60, 61, 65, 80, 81 and 85; Croda International PLC, Edison, NJ) and combinations thereof. Additional examples of dispersants may be found in BAIRD & ZUBLENA 1993. SOIL FACTS: USING WETTING AGENTS (NONIONIC SURFACTANTS) ON SOIL (North Carolina Cooperative Extension Service Publication AG-439-25) (1993): BURGES, FORMULATION OF MICRObial Biopesticides: Beneficial Microorganisms, Nematodes and Seed Treatments (Springer Science & Business Media) (2012). McCarty, Wettings Agents (Clemson University Cooperative Extension Service Publication) (2001).

In some embodiments, inoculant compositions of the present disclosure comprise one or more anionic surfactants According to some embodiments, the inoculant composition comprises one or more water-soluble anionic surfactants and/or one or more water-insoluble anionic surfactants, optionally one of more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarcosinates, acyl isethionates. N-acyl taurates, N-acyl-N-alkyltaurines, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. According to some embodiments, the inoculant composition comprises one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride. 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. According to some embodiments, the inoculant composition comprises one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™ 15-S-9 (The Dow Chemical Company, Midland, MI)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinolate, polysorbate, polyoxyethylenated fatty acids, polyoxyethylenated mercaptans, polyoxyethylenated polyoxypropylene glycols, polyoxyethylene glycol sorbitan alkyl esters, polyethylene glycol-polypropylene glycol copolymers, polyoxyethylene glycol octylphenol ethers, polyvinyl pyrolidone, sugar-based alkyl polyglycosides, sulfonylamide, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonmonic surfactant. According to some embodiments, the inoculant composition comprises at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants According to some embodiments, the inoculant composition comprises one or more betaines and/or one or mote sultaines, optionally one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. According to some embodiments, the inoculant composition comprises one or more alkali metal salts of fatty acids.

In some embodiments, inoculant compositions of the present disclosure comprise one or more wetting agents. According to some embodiments, the inoculant composition comprises one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Inoculant compositions of the present disclosure may comprise any suitable drying agent(s), including, but not limited to, drying powders. Non-limiting examples of drying agents include AEROSIL® hydrophobic fumed silica powders (Evonik Corporation, Parsippany, NJ), BENTOLITE® powders (BYK-Chemie GmbH, Wesel, German). INCOTEC® powders (INCOTEC Inc., Salinas. CA), SIPERNAT® silica powders (Evonik Corporation, Parsippany, NJ) and combinations thereof. Additional examples of drying agents may be found in Burges, Formulation of Microbial Biopesticides: Beneficial Microorganisms, Nematodes and Seed Treatments (Springer Science & Business Media) (2012). In some embodiments, moculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Inoculant compositions of the present disclosure may comprise any suitable anti-freezing agent(s), including, but not limited to, ethylene glycol, glycerin, propylene glycol and urea.

Inoculant compositions of the present disclosure may comprise am seed flowability agent to improve the lubricity of the treated seeds. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material. Non-limiting examples of wax materials that can be incorporated into the liquid seed treatment composition include plant and animal-derived waxes such as carnauba wax, candelilla wax, ouricury wax, beeswax, spermaceti, and petroleum derived waxes, such as paraffin wax. For example, in some instances, the flowability agent comprises caranuba wax. In some instances, the flowability agent comprises an oil. For example, the flowability agent may comprise soybean oil. Non-limiting examples of commercially available wax materials suitable for use as flowability agents include AQUAKLEAN 418 supplied by Micro Powders, Inc tan anionic aqueous emulsion comprising extra light carnauba wax at 35% solids content).

Inoculant compositions of the present disclosure may comprise any suitable safener(s), including, but not limited to, naphthalic anhydride.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof.

Inoculant compositions of the present disclosure may comprise any suitable pH buffer(s), including, but not limited to, potassium phosphate monobasic and potassium phosphate dibasic. In some embodiments, the inoculant composition comprises one or more pH buffers selected to provide a composition having a pH of less than 10, typically from about 4.5 to about 9.5, from about 6 to about 8, or about 7.

Inoculant compositions of the present disclosure may comprise any suitable adhesive(s), including, but not limited to, adhesive compositions comprising, consisting essentially of or consisting of one or more disaccharides (e g, maltose), gums (e.g., cellulose gum, guar gum, gum arabic, gum combretum, xantham gum), maltodextrins (e.g., one or more maltodextrins (each and/or collectively) having a DEV of about 10 to about 20), monosaccharides, oils (e.g., mineral oil, olive oil, peanut oil, soybean oil and/or sunflower oil) and/or oligosaccharides.

Inoculant compositions of the present disclosure may comprise any suitable effect pigment(s) Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate Non-limiting examples of particulate silicates that can be incorporated into the dry powder coating include mica coated with titanium dioxide (e.g., SUNMICA FINE WHITE 2800102, which is commercially available from Sun Chemical Corp.) Other non-limiting examples of commercially available effect pigments that can be incorporated into the dry powder include MAGNA PEARL, LUMINA and MEARLIN pigments from BASF Corporation: PHIBRO PEARL from PhibroChem; and IRIDESIUM 120 from Aakash Chemicals. In some instances, the dry powder has a mean particle size of from about 1 to about 25 microns.

Inoculant compositions of the present disclosure may comprise any suitable growth medium suitable for culturing one or mom of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Carriers, biostimulants, microbial extracts, nutrients, pest attractants and/or feeding stimulants, pesticides, plant signal molecules, dispersants, drying agents, anti-freezing agents, seed flowability agents, safeners, anti-settling agents, pH buffers, adhesives and effect pigments may be incorporated into inoculant compositions of the present disclosure in any suitable amount(s)/concentration(s). The absolute value of the amount(s)/concentration(s) that is/arc sufficient to cause the desired effect(s) may be affected by factors such as the type, size and volume of material to which the composition will be applied, the types) of microorganisms in the composition, the number of microorganisms in the composition, the stability of the microorganism(s) in the composition and storage conditions (e.g., temperature, relative humidity, duration) Those skilled in the art will understand how to select effective amounts/concentrations using routine dose-response experiments. Guidance for the selection of appropriate amounts/concentrations can be found, for example, in International Patent Publication Nos. WO2017/044473, WO2017/044545, WO2017/116837, WO2017/116846, WO2017/210163 and WO2017/210166, and in U.S. Provisional Patent Application Nos. 62/511,408; 62/511,420 and 62/511,434.

In some embodiments, one or more biostimulants, microbial extracts, nutrients, pest attractants and/or feeding stimulants comprise about/at least 0.0001 to about/less than 5% (by weight) of the inoculant composition. In some embodiments, the biostimulant(s) (e.g., glycine and/or seaweed extract), microbial extract(s), nutrient(s) (e.g., phosphorous, boron, chlorine, copper, iron, manganese, molybdenum and/or zinc), pest attractant(s) and/or feeding stimulant(s) comprise(s) about about 0.0001, 0.0002, 00003, 0.0004, 0.0005, 00006, 0.0007, 0.0008, 00009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more biostimulants (e.g., glycine and/or seaweed extract), microbial extracts, nutrients (e.g., phosphorous, boron, chlorine, copper, iron, manganese, molybdenum and/or zinc), pest attractants and/or feeding stimulants.

In some embodiments, inoculant compositions of the present disclosure comprise one or more LCOs at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M For example, inoculant compositions of the present disclosure may comprise about $1\times10^{-20}$ M, $1\times10^{-19}$ M, $1\times10^{-18}$ M, $1\times10^{-17}$, $1\times10^{-16}$, $1\times10^{-15}$ M, $1\times10^{-14}$ M, $1\times10^{-13}$, $1\times10^{-12}$, $1\times10^{-11}$ M, $1\times10^{-10}$ M, $1\times10^{-9}$ $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more LCOs (e.g., one, two, three, four or more of the LCOs set forth as structures V-XXXIII above).

In some embodiments, inoculant compositions of the present disclosure comprise one or more chitin oligomers at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitin oligomers e.g., one, two, three, four or more of the chitin oligomers set forth as structures XXXVI-LXXXIII above).

In some embodiments, inoculant compositions of the present disclosure comprise one or more chitosan oligomers at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-6}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$M, $1\times10^{-16}$ M, $1\times10^{-15}$ M, $1\times10^{-14}$ M, $1\times10^{-13}$ M, $1\times10^{-12}$ M, $1\times10^{-11}$, $1\times10^{-10}$ M, $1\times10^{-9}$ M, $1\times10^{-8}$ M, $1\times10^{-7}$ M, $1\times10^{-6}$ M, $1\times10^{-5}$M, $1\times10^{-4}$ M, $1\times10^{-3}$ M, $1\times10^{-2}$ M, $1\times10^{-1}$ M or more of one or more chitosan oligomers (e.g., one, two, three, four or more of the oligosaccharides set forth as structures XXXVI-LXXXIII above in a deacetylated form).

In some embodiments, inoculant compositions of the present disclosure comprise one or more chitins at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-8}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-11}$, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitins.

In some embodiments, inoculant compositions of the present disclosure comprise one or more chitosans at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitosans.

In some embodiments, inoculant compositions of the present disclosure comprise one or more dispersants in an amount/concentration of about 0.001 to about 25% or more (by weight) of the inoculant composition. In some embodiments, the dispersant(s) comprise(s) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20% or more (by weight) of one or more dispersants (e.g., one or more surfactants and/or wetting agents).

In some embodiments, inoculant compositions of the present disclosure comprise one or more drying agents in an amount/concentration of about 0.001 to about 95% or more (by weight) of the inoculant composition. In some embodiments, the drying agent(s) comprise(s) about) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more drying agents (e.g., lecithin and/or talc).

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

In some embodiments, inoculant compositions of the present disclosure comprise one or more pH buffers in an amount/concentration of about 0.0001 to about 5% or more (by weight) of the inoculant composition. In some embodiments, the pH buffer(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more pH buffers (e.g., potassium phosphate monobasic and/or potassium phosphate dibasic).

In some embodiments, inoculant compositions of the present disclosure comprise one or more commercial biostimulants, microbial extracts, nutrients, pest attractants and/or feeding stimulants, pesticides, plant signal molecules, dispersants, drying agents, anti-freezing agents, seed flowability agents, safeners, anti-setting agents, pH buffers, adhesives and/or effect pigments used in accordance with the manufacturer's recommended amounts/concentrations.

Inoculant compositions of the present disclosure may be formulated into any suitable type of composition, including, but not limited to, seed coatings, soil inoculants and foliar inoculants.

In some embodiments, inoculant compostions of the present disclosure are formulated as pesticidal baits.

In some embodiments, inoculant compositions of the present disclosure are formulated as amorphous solids.

In some embodiments, inoculant compositions of the present disclosure are formulated as amorphous liquids.

In some embodiments, inoculant compositions of the present disclosure are formulated as wettable powders.

In some embodiments, inoculant compositions of the present disclosure are formulated as liquid compositions that are subsequently dried to produce a powder or granules. For example, in some embodiments, liquid inoculant compositions of the present disclosure are drum dried, evaporation dried, fluidized bed dried, freeze dried, spray dried, spray-freeze dried, tray dried and/or vacuum dried to produce powders/granules Such powders/granules may be further processed using any suitable methods), including, but not limited to, flocculation, granulation and milling, to achieve a desired particle size or physical format. The precise method(s) and parameters of processing dried powders/granules that are appropriate in a given situation may be affected by factors such as the desired particle size(s), the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

In some embodiments, inoculant compositions of the present disclosure are frozen for cryopreservation. For example, in some embodiments, liquid inoculant compositions of the present disclosure are flash-frozen and stored in a cryopreservation storage unit/facility. The precise method(s) and parameters of freezing and preserving inoculant compositions of the present disclosure that are appropriate in a given situation may be affected by factors such as the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

Inoculant compositions of the present disclosure may be formulated as aqueous or non-aqueous compositions. In some embodiments, inoculant compositions of the present disclosure comprise no water. In some embodiments, inoculant compositions of the present disclosure comprise a trace amount of water. In some embodiments, inoculant compositions of the present disclosure comprise less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5% water by weight, based upon the total weight of the composition.

In some embodiments, inoculant compositions of the present disclosure are formulated to have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

Inoculant compositions of the present disclosure may be formulated for the treatment of any suitable plant type, including, but not limited to, row crops and vegetables. In some embodiments, strains of the present disclosure and inoculant compositions of the present disclosure are formulated for the treatment of one or more plants selected from the families Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch). Malvaceae (e.g., cacao, cotton, durian, hibiscus, kenaf, kola, okra), Poaceae (e.g., bamboo, barley, corn, fonio, lawn grass (e.g., Bahia grass. Bermudagrass, bluegrass, Buffalograss. Centipede grass, Fescue, or *Zoysia*), millet, oats, ornamental grasses, rice, rye, sorghum, sugar cane, triticale, wheat and other cereal crops, Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). In some embodiments, strains of the present disclosure and inoculant compositions of the present disclosure are formulated for the treatment of one or more plants with which the strain(s) is/are not naturally associated (e.g., one or more plants that does not naturally exist in the geographical location(s) from which the strain(s) was/were isolated). In some embodiments, strains of the present disclosure and inoculant compositions of the present disclosure are formulated for the treatment of one or more acaricide-, fungicide-, gastropodicide-, herbicide-, insecticide-, nematicide-, rodenticide- and/or virucide-resistant plants (e.g., one or more plants resistant to acetolactate synthase inhibitors (e.g., imidazolinone, pryimidinyoxy(thio)benzoates, sulfonylaminocarbonyltriazolinone, sulfonylurea, triazolopyrimidines), bialaphos, glufosinate, glyphosate, hydroxyphenylpyruvatedioxygenase inhibitors and/or phosphinothricin). Non-limiting examples of plants that may be treated with inoculant compositions of the present disclosure include plants sold by Monsanto Company (St. Louis, MO) under the BOLLGARD 18®, DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

Inoculant compositions of the present disclosure may be designed and formulated to improve not only the stability and survival of microorganisms therein, but also the dispersion of those microorganisms within the composition.

In some embodiments, inoculant compositions of the present disclosure improve one or more microbial stability characteristics of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the ability of one or more of the microorganisms contained therein to germinate/propagate and/or to enhance plant yield by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the sugar alcohols, humic acids or fulvic acids found in the inoculant composition and/or comprises a reduced amount of one or more of the sugar alcohols, humic acids or fulvic acids found in the inoculant composition.

In some embodiments, inoculant compositions of the present disclosure improve the survival rate of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the survival rate of one or more of the microorganisms contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the sugar alcohols, humic acids or fulvic acids found in the inoculant composition and/or comprises a reduced amount of one or more of the sugar alcohols, humic acids or fulvic acids found in the inoculant composition.

In some embodiments, inoculant compositions of the present disclosure improve both the survival rate and one, two, three, four, five, six, seven, eight, nine, ten or more microbial stability characteristics of the microorganism(s) contained therein.

In some embodiments, inoculant compositions of the present disclosure improve the dispersion of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the dispersion of one or more of the microorganisms contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the stabilizers/dispersants found in the inoculant composition and/of comprises a reduced amount/concentration of one or more of the stabilizers/dispersants found in the inoculant composition.

In some embodiments, inoculant compositions of the present disclosure improve the dispersion of one or more of the microorganisms contained therein to the extent that at least about 50, 55, 60, 65, 70, 75, 80, 85, 90, 95% or more of the microorganisms are present as single cells/spores (rather than as members of a clump comprising two or more cells/spores).

In some embodiments, inoculant compositions of the present disclosure exhibit enhanced flowability as compared to a control composition (e.g., a control composition that is identical to the inoculant composition of the present disclosure except that it lacks one or more of the components found in the inoculant composition and/or contains one or more components not found in the inoculant composition of the present disclosure). For example, the flowability of inoculant compositions of the present disclosure may be improved by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the stabilizers/dispersants found in the inoculant composition and/or comprises a reduced amount/concentration of one or more of the stabilizers/dispersants found in the inoculant composition.

The present disclosure extends to methods and uses for stable inoculant compositions.

In some embodiments, the present disclosure provides kits comprising, consisting essentially of, or consisting of an inoculant composition of the present disclosure and a container housing the inoculant composition. According to some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The containers may comprise any suitable material(s), including, but not limited to, materials that reduce the amount of light, moisture and/or oxygen that contact the coated plant propagation material when the container is sealed. In some embodiments, the containers comprise, consist essentially of, or consist of a material having light permeability of less than about 1, 2, 3, 4, 5, 6, 7, 8, 9, 10, 15, 20, 25, 30, 35, 40, 45, 50, 55, 60, 65, 70 or 75% In some embodiments, the containers comprise, consist essentially of, or consist of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2$ day (as measured in accordance with ASTM D3985).

In some embodiments, the containers reduce the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the containers reduce the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the containers reduce the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

In some embodiments, oxygen is actively removed from the container. Amy suitable method(s) may be used to remove oxygen from the container, including, but not limited to, vacuum sealing and gas flushing methods. See generally WO2016/096821. In some embodiments, ambient air is evacuated from the container under vacuum and replaced with one or more inert gases (e.g., hydrogen, nitrogen, helium, neon, argon, krypton, xenon, radon, carbon dioxide, nitrous oxide, hydrogen sulfide, lower alkane and/or halo alkane).

In some embodiments, kits of the present disclosure comprise 1, 2, 3, 4, 5 or more additional containers. The additional containers may comprise any suitable component(s) or composition(s), including, but not limited to, biostimulants, microbial extracts, nutrients, pest attractants and/or feeding stimulants, pesticides, plant signal molecules, dispersants, drying agents, anti-freezing agents, seed flowability agents, safeners, anti-settling agents, pH buffers, adhesives and effect pigments. Examples of biostimulants, microbial extracts, nutrients, pest attractants, pesticides, plant signal molecules, dispersants, drying agents, anti-freezing agents, seed flowability agents, safeners, anti-settling agents, pH buffers, adhesives and effect pigments that may be included in the additional containers are described above.

In some embodiments, the microorganism(s) and the stabilizing medium are housed in separate containers for long-term storage and then mixed together for application to plants or plant propagation materials. Optional constituents may be included in the microorganism container, the stabilizing medium container and/or one or more separate containers during the long-term storage period.

In some embodiments, the present disclosure provides plant propagation materials treated with an inoculant composition of the present disclosure (e.g., seeds coated with an inoculant composition of the present disclosure), plants grown from plant propagation materials treated with an inoculant composition of the present disclosure, plants treated with an inoculant composition of the present disclosure, plant parts harvested from plants grown from plant propagation materials treated with an inoculant composition of the present disclosure, plant parts harvested from plants treated with an inoculant composition of the present disclosure, processed products derived from plants grown from plant propagation materials treated with an inoculant composition of the present disclosure, processed products derived from plants treated with an inoculant composition of the present disclosure, crops comprising a plurality of plants grown from plant propagation materials treated with an inoculant composition of the present disclosure and crops comprising a plurality of plants treated with an inoculant composition of the present disclosure. Examples of methods that may be used to treat plants and plant parts with inoculant compositions of the present disclosure are discussed in further detail below.

In some embodiments, treated plant propagation materials comprise, consist essentially of or consist of a plant propagation material and a coating that covers at least a portion of the outer surface of the plant propagation material, said coating comprising, consisting essentially of, or consisting of an inoculant composition of the present disclosure.

The coating may cover any suitable portion of the plant propagation material. In some embodiments, the coating covers at least 20, 25, 30, 35, 40, 45, 50, 55, 60, 65, 70, 75, 80, 85, 90, 95% or more of the outer surface of the plant propagation material. In some embodiments, the coating completely covers the outer surface of the plant propagation material.

The coating may comprise one, two, three, four, five or more layers. In some embodiments, the coating comprises at least one layer that is free or substantially free of microorganisms. For example, in some embodiments, the coating comprises an inner layer that contains one or more microorganisms and one or more outer layers free or substantially free of microorganisms. In some embodiments, the coating comprises at least one layer that is free or substantially free of stabilizing compounds. For example, in some embodiments, the coating comprising an inner layer that contains one or more microorganisms but is free or substantially free of sugar alcohols, humic acids and/or fulvic acids and and an outer layer that is equivalent to an inoculant composition of the present disclosure except insofar as it lacks one or more microorganisms.

In some embodiments, coatings of the present disclosure comprise, consist essentially of or consist of an the inner layer that comprises, consists essentially of or consists of an inoculant composition of the present disclosure and an outer layer that is equivalent to an inoculant composition of the present disclosure except insofar as it lacks one or more microorganisms. For example, coated plant propagation materials of the present disclosure may comprise a seed that is coated with an inner layer comprising one or more maltodextrins (e.g., one or more maltodextrins having a DEV of about 15 to about 20), one or more sugar alcohols (e.g., arabitol, mannitol, sorbitol and/or xylitol) and one or more microorganisms (e.g., one or more strains of *Bradyrhizobium*, such as BRADY; and/or one or more strains of *Penicillium*, such as PENI) and an outer layer that comprises one or more maltodextrins (e.g., one or more maltodextrins having a DEV of about 15 to about 20) and one or more sugar alcohols (e.g., arabitol, mannitol, sorbitol and/or xylitol) but is free of microorganisms.

In some embodiments, coatings of the present disclosure comprise, consist essentially of or consist of an inoculant composition of the present disclosure and a drying powder. For example, coated plant propagation materials of the present disclosure may comprise a seed that is coated with an inoculant composition comprising one or more maltodextrins (e.g., one or more maltodextrins having a DEV of about 15 to about 20)), one or more sugar alcohols (e.g., arabitol, mannitol, sorbitol and/or xylitol) and one or more microorganisms (e.g., one or more strains of *Bradyrhizobium*, such as BRADY; and/or one or more strains of *Penicillium*, such as PENI) and then covered with a drying powder (e.g., a drying power that comprises calcium stearate, one or more clays, graphite, magnesium stearate, magnesium sulfate, powdered milk, silica, soy lecithin and/or talc).

The coating may have any suitable thickness. The absolute value of the thickness that is sufficient to cause the desired effect may be affected by factors such as the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select an effective amount/concentration/dosage using routine dose-response experiments. In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 μm or more. In some embodiments, the average thickness of the coating is about 1.5 to about 3.0 μm.

Plant propagation materials treated with inoculant compositions of the present disclosure may exhibit a high degree of flowability. In some embodiments, inoculant compositions of the present disclosure enhance the flowability of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiments, seeds coated with inoculant compositions of the present disclosure may exhibit a basic flowability energy of less than 5, 6, 7, 8, 9, 10, 20, 30, 40, 50, 60, 70, 80, 90, 100, 125, 150, 175, 200, 225, 2500, 275, 300, 325, 350, 375, 400, 425, 450, 475, 500, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000 mJ or less when measured at an airflow rate of 200, 300, 400, 500, 600, 700, 800, 900 and/or 1000 ml per minute using an FT4 Powder Rheometer® (Freeman Technology, Tewkesbury, UK).

Plant propagation materials treated with inoculant compositions of the present disclosure may exhibit a high degree of plantability. In some embodiments, inoculant compositions of the present disclosure enhance the plantability of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiments, seeds coated with inoculant compositions of the present disclosure may exhibit a plantability of at least 70, 75, 80, 85, 90, 91, 92, 93, 94, 95, 95.5, 96, 96.5, 97, 97.5, 98, 98.5, 99, 99.5% or more when measured using a brush-type seed meter, a vacuum seed meter and/or a finger pickup seed meter.

Plant propagation materials treated with inoculant compositions of the present disclosure may exhibit a low degree of dust-off. In some embodiments, inoculant compositions of the present disclosure enhance the dust-off of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiments, seeds coated with inoculant compositions of the present disclosure exhibit a dust-off value of less than 0.01, 0.02, 0.03, 0.04, 0.05, 0.06, 0.07, 0.07, 0.08, 0.09, 0.1, 0.2, 0.3, 0.4, 0.5, 0.6, 0.7, 0.8, 0.9, 1 gram per 100 kilograms of seed when tested at room temperature (20-25° C.) and 30-50% relative humidity using a Type I HEUBACH DUSTMETER® (Heubach GmbH, Langelsheim, Germany) set to 30 rotations per minute, an air throughput of 20 liters per minute and total rotation time of 120 seconds. In some embodiments, seeds coated with inoculant compositions of the present disclosure may exhibit a Heubach dust value of less than about 0.01, 0.02, 0.03, 0.04, 0.05, 0.06, 0.07, 0.07, 0.08, 0.09, 0.1, 0.2, 0.3, 0.4, 0.5, 0.6, 0.7, 0.8, 0.9, 1 gram per 100 kilogram of treated seed when tested in accordance with the European Seed Association's Heubach Test ("Assessment of free floating dust and abrasion particles of treated seeds as a parameter of the quality of treated seeds" version 1.0).

Inoculant compositions of the present disclosure may be used to coat any suitable plant propagation materials, including, but not limited to, cuttings (e.g., leaves, stems), rhizomes, seeds and tubers. In some embodiments, the plant propagation material is a seed.

Inoculant compositions of the present disclosure may be used to coat plant propagation materials of any suitable plant type, including, but not limited to, row crops and vegetables. In some embodiments, inoculant compositions of the present disclosure are coated on propagation material derived from one or more plants selected from the families listed in Appendix B.

Non-limiting examples of plant propagation materials that may be coated with inoculant compositions of the present disclosure include seeds sold by Monsanto Company (St. Louis, MO) under the BOLLGARD II®, DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

In some embodiments, the present disclosure provides kits comprising, consisting essentially of, or consisting of a coated plant propagation material of the present disclosure and a container housing the coated plant propagation material. According to some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is scaled.

In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

In some embodiments, the container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches said plant propagation material by about 5, 10, 15, 20, 25, 30, 35, 40, 45, 50, 55, 60, 65, 70, 75, 80, 85, 90, 95 of 100% when sealed.

In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 5(0 $cm^3$/$m^2$·day (as measured in accordance with ASTM D3985).

In some embodiments, the container reduces the amount of ambient oxygen that reaches said plant propagation material by about 5, 10, 15, 20, 25, 30, 35, 40, 45, 50, 55, 60, 65, 70, 75, 80, 85, 90, 95 or 100/when sealed.

In some embodiments, oxygen is actively removed from the container Any suitable method(s) may be used to remove oxygen from the container, including, but not limited to, vacuum sealing and gas flushing methods. See generally WO2016/096821. In some embodiments, ambient air is evacuated from the container under vacuum and replaced with one or more inert gases (e.g., hydrogen, nitrogen, helium, neon, argon, krypton, xenon, radon, carbon dioxide, nitrous oxide, hydrogen sulfide, lower alkane and/or halo alkane).

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, microbial extracts, nutrients, pest attractants, pesticides, plant signal molecules, dispersants and drying agents. Examples of agriculturally beneficial microorganisms, biostimulants, microbial extracts, nutrients, pest attractants, pesticides, plant signal molecules, dispersants and drying agents that may be included in the additional containers are described above.

In some embodiments, the present disclosure provides methods of treating plants and plant parts with inoculant compositions of the present disclosure.

In some embodiments, the present disclosure provides uses for inoculant compositions of the present disclosure. According to some embodiments, inoculant compositions of the present disclosure are used for fixing atmospheric nitrogen, solubilizing phosphate, controlling one or more phytopathogenic pests, enhancing plant growth, enhancing plant stress tolerance and/or enhancing plant yield.

In some embodiments, methods and uses of the present disclosure comprise, consist essentially of, of consist of applying an inoculant composition of the present disclosure to a plant or plant part.

Inoculant compositions of the present disclosure may be applied to plants and plant pails at any suitable time(s), including, but not limited to, prior to planting, at the time of planting and/or after planting. In some embodiments, a plant propagation material is treated at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks prior to planting the plant propagation material in a growth medium. In some embodiments, a plant propagation material is treated less than 1, 2, 3, or 4 weeks prior to planting the plant propagation material in a growth medium. In some embodiments, a plant propagation material is treated at the time of planting the plant propagation material in a growth medium. In some embodiments, plants are treated after germination (e.g., by soil amendment and/or foliar application).

Inoculant compositions of the present disclosure may be applied to plants and plant parts using any suitable method(s), including, but not limited to, on-seed application, in-furrow application, soil application and foliar application. The appropriate application method may be affected by factors such as the type, size and volume of material to which the inoculant composition will be applied, the timing of application, the type(s) of microorganisms in the composition, the number of microorganisms in the composition, the stability of the microorganisms in the inoculant composition and the storage conditions (e.g., temperature, relative humidity, duration). Those skilled in the art will understand how to select an effective method using routine dose-response experiments.

In some embodiments, inoculant compositions of the present disclosure are applied using a batch system in which predetermined batch sizes of plant material and inoculant composition are combined (e.g., by delivering both the plant material and inoculation composition into a mixer).

In some embodiments, inoculant compositions of the present disclosure are applied using a continuous treatment system calibrated to apply inoculant composition at a predefined rate in proportion to a continuous flow of plant material.

In some embodiments, plant propagation materials are soaked in a liquid inoculant composition of the present disclosure for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours or more.

In some embodiments, plant propagation materials are coated in an inoculant composition of the present disclosure. For example, in some embodiments, a liquid inoculant composition of the present disclosure is applied to the inside wall of a round container, seeds are added to the container, then the container is rotated such that the seeds come into contact with the composition, a process known in the art as "container coating."

In some embodiments, liquid inoculant compositions of the present disclosure are applied directly to plant materials. For example, in some embodiments, liquid inoculant compositions of the present disclosure are mixed with another liquid composition (e.g., a composition comprising one or more pesticides) to form a treatment composition, which is applied to plants or plant propagation materials.

In some embodiments, liquid inoculant compositions of the present disclosure are dried prior to application. For example, in some embodiments, liquid inoculant compositions of the present disclosure are dried to produce a powder or granule, which is applied to plants or plant propagation materials.

Inoculant compositions of the present disclosure may be applied to plants and plant parts in any suitable amount(s)/concentration(s). The absolute value of the amount/concentration/dosage of inoculant composition that is sufficient to cause the desired effect may be affected by factors such as the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select an effective amount/concentration/dosage using routine dose-response experiments.

In some embodiments, the inoculant composition is applied in an amount/concentration ranging from about 0.01 to about 10 milliliters of inoculant composition per kilogram of treated plant material. For example, in some embodiments, about/at least/less than 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, or 10 milliliters of inoculant composition is applied per kilogram of seed.

In some embodiments, the inoculant composition is applied in an amount/concentration ranging from about 0.01 to about 10 milligrams of inoculant composition per kilogram of treated plant material. For example, in some embodiments, about/at least/less than 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, or 10 milligrams of inoculant composition is applied per kilogram of seed.

In some embodiments, the inoculant composition is applied in an amount/concentration sufficient to ensure the treated plant material is coated with at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, $1\times10^{20}$ or more cfu of the microorganism(s) in the inoculant composition. For example, in some embodiments, the inoculant composition is applied in an amount/concentration sufficient to ensure the treated plant material is coated with at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of the microorganism(s) (e.g., one or more strains of *Bradyrhizobium*, such as BRADY; and/or one or more strains of *Penicillium*, such as PENI) per kilogram of plant propagation material.

In some embodiments, methods and uses of the present disclosure further comprise applying one or more drying powders to the plant or plant part.

Drying powders may be applied in an suitable amount(s)/concentration(s). The absolute value of the amount/concentration/dosage of drying powder(s) that is sufficient to cause the desired effect may be affected by factors such as the type, size and volume of material to which the composition will be applied, the stability of the microorganisms in the composition and the storage conditions (e.g., temperature, relative humidity, duration) Those skilled in the art will understand how to select an effective amount/concentration/dosage using routine dose-response experiments.

In some embodiments, the drying powder is applied in an amount/concentration ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, soy lecithin and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition comprising one or more maltodextrins (e.g., one or more maltodextrins having a DEV of about 15 to about 20) and one or more microorganisms (e.g., one or more strains of *Bradyrhizobium*, such as BRADY; and/or one or more strains of *Penicillium*, such as PENI) at a rate of about 1, 1.25, 1.5, 1.75, 2, 2.25, 2.5, 2.75, or 3 grams per kilogram of seed.

In some embodiments, methods of the present disclosure further comprise applying one or more additional agriculturally beneficial components (e.g., one or more biostimulants, microbial extracts, nutrients, pesticides and/or plant signal molecules) to the plant or plant part. For example, in some embodiments, an inoculant composition of the present disclosure is applied to a seed and a second composition comprising one or more pesticides is applied to the seed and/or to the plant that grows from the seed.

Additional agriculturally beneficial components may be applied in any suitable amount(s)/concentration(s). The absolute value of the amount/concentration/dosage of drying powder(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the an will understand how to select an effective amount/concentration/dosage using routine dose-response experiments.

In some embodiments, the present disclosure provides methods comprising, consisting essentially of, or consisting of growing a plant from a plant propagation material that has been treated with a composition of the present disclosure.

As noted above, inoculant compositions of the present disclosure may comprise myriad agriculturally beneficial constituents in addition to any agriculturally beneficial microorganisms contained therein, including, but not limited to, biostimulants, microbial extracts, nutrients, pest attractants, pesticides and plant signal molecules. It is to be understood that such agriculturally beneficial constituents may also be used in conjunction with inoculant compositions of the present disclosure (rather than incorporated into inoculant compositions of the present disclosure). Thus, the present disclosure extends to systems and methods of using inoculant compositions of the present disclosure in conjunction with additional compositions comprising one or more agriculturally beneficial constituents. The additional composition(s) may comprise any suitable agriculturally beneficial constituent(s), including, but not limited to, the agriculturally beneficial constituents described above.

In some embodiments, inoculant compositions of the present disclosure are used in conjunction with one or more on-seed compositions, one or more in-furrow compositions, one or more soil-applied compositions and/or one or more foliar-applied compositions.

In some embodiments, inoculant compositions of the present disclosure are used as part of an integrated disease and/or pest management system.

The present disclosure extends to animal feed compositions comprising, consisting essentially of, or consisting of a food component and a microbial component, said microbial component comprising, consisting essentially of, or consisting of an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

In some embodiments, the present disclosure provides methods of enhancing the survival and/or stability of microorganisms in a composition, said methods comprising, consisting essentially of, or consisting of adding an effective amount/concentration of one or more sugar alcohols, one or more humic acids and/or one or more fulvic acids to said composition.

Any suitable sugar alcohol(s) may be added to the composition, including, but not limited to, arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and xylitol.

Any suitable humic acid(s) may be added to the composition, including, but not limited to leonardite humic acids, lignite humic acids, peat humic acids and water-extracted humic acids. In some embodiments, potassium humate and/or sodium humate is/are added to the composition.

Any suitable fulvic acid(s) may be added to the composition, including, but not limited to, leonardite fulvic acids, lignite fulvic acids, peat fulvic acids and water-extracted fulvic acids. In some embodiments, potassium fulvate and/or sodium fulvate is/are added to the composition.

Sugar alcohols, humic acids and fulvic acids may be added to the composition in any suitable form(s), including, but not limited to, powders, flakes, crystals and suspensions. In some embodiments, the sugar alcohol(s), humic acid(s) and/or fulvic acid(s) is/arc included in inoculant compositions of the present disclosure is/are at least 70, 75, 80, 85, 90, 91, 92, 93, 94, 95, 96, 97, 98, 99, 99.5% or more pure.

Sugar alcohols, humic acids and fulvic acids may be added to the composition in any suitable amount(s)/concentration(s). The absolute value of the amount(s)/concentration(s) of sugar alcohol(s), humic acid(s) and/or fulvic acid(s) that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration/dosage using routine dose-response experiments.

In some embodiments, the sugar alcohol(s), humic acid(s) and fulvic acid(s) is/are added to the composition until it/they are present in the amount(s)/concentration(s) described above with respect to inoculant compositions of the present disclosure. For example, in some embodiments, the sugar alcohol(s) (e.g., arabitol, mannitol, sorbitol and/or xylitol), humic acid(s) (e.g., ammonium humate, boron humate, potassium humate and/or sodium humate), and/or fulvic acid(s) (e.g., ammonium fulvate, boron fulvate, potassium fulvate and/or sodium fulvate) is/are added to the composition until it/they comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. In some embodiments, the sugar alcohol(s), humic acid(s) and/or fulvic acid(s) is/are added to the composition in an amount/concentration sufficient to ensure microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more, application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the sugar alcohol(s), humic acid(s) and/or fulvic acid(s) is/are added to the composition in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application, foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the sugar alcohol(s), humic acid(s) and/or fulvic acid(s) is/are added to the composition in an amount/concentration sufficient to ensure at least $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$ or more colony-forming units per gram and/or milliliter of inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40.44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% of more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application, foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, two or more sugar alcohol(s) (e.g., arabitol, mannitol, sorbitol and/or xylitol), humic acid(s) (e.g., ammonium humate, boron humate, potassium humate and/or sodium humate), and/or fulvic acid(s) (e.g., ammonium fulvate, boron fulvate, potassium fulvate and/or sodium fulvate), are added to composition in amounts/concentrations that synergistically enhance the stability and/or survival of one or more microorganisms in the inoculant composition. In some embodiments, one or more additional stabilizers is/are added to the composition.

Any suitable additional stabilizer(s), may be added to the composition, including, but not limited to, maltodextrins, monosaccharides, disaccharides, oligosaccharides, malt extracts, peat extracts, betaines, prolines, sarcosines, peptones, skim milks, oxidation control components, hygroscopic polymers, and/or UV protectants.

Any suitable maltodextrin(s) may be added to the composition, including, but not limited to, maltodextrins having a DEV of about 3, 4, 5, 6, 7, 8, 9, 10, 11, 12, 13, 14, 15, 16, 17, 18, 19, 20, 21, 22, 23, 24, or 25. In some embodiments, one or more maltodextrins having a DEV of about 10 to about 20 (e.g., one or more maltodextrins having a DEV of about 15 to about 20) is added to the composition. In some embodiments, a combination of maltodextrins having a DEV of about 10 to about 20 (e.g., a combination of maltodextrins having a DEV of about 15 to about 20) is added to the composition. Non-limiting examples of maltodextrins that may be useful in methods of the present disclosure include MALTRIN® M040 (DEV=5; molecular weight=3600; Grain Processing Corporation, Muscatine, IA), MALTRIN® M100 (DEV=10; molecular weight=1800; Grain Processing Corporation. Muscatine, IA), MALTRIN® M150 (DEV=15; molecular weight=1200; Grain Processing Corporation, Muscatine, IA), MALTRIN® M200 (DEV=20; molecular weight=900; Grain Processing Corporation, Muscatine, IA), MALTRIN® M250 (DEV=25; molecular weight=720; Grain Processing Corporation, Muscatine, IA); GLOBE® Plus 15 DE (Ingredion Inc., Westchester, IL); and combinations thereof.

Any suitable monosaccharide(s) may be added to the composition, including, but not limited to, allose, altrose, arabinose, fructose, galactose, glucose, gulose, iodose, lyxose, mannose, ribose, talose, threose and/or xylose. In some embodiments, glucose is added to the composition. In some embodiments, a monosaccharide other than glucose is added to the composition.

Any suitable disaccharide(s) may be added to the composition, including, but not limited to, cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose. In some embodiments, maltose is added to the composition. In some embodiments, a disaccharide other than maltose is added to the composition. In some embodiments, trehalose is added to the composition. In some embodiments, a disaccharide other than trehalose is added to the composition.

Any suitable oligosaccharide(s) may be added to the composition, including, but not limited to, fructo-oligosaccharides, galacto-oligosaccharides, mannon-oligosaccharides and/or raffinose.

Any suitable betaine(s) may be added to the composition, including, but not limited to, trimethylglycine.

Any suitable peptone(s) may be added to the composition, including, but not limited to, bacterial peptones, meat peptones, milk peptones, vegetable peptones and yeast peptones.

Any suitable oxidation control component(s) may be added to the composition, including, but not limited to, antioxidants and/or oxygen scavengers. In some embodiments, one or more antioxidants is added to the composition. For example, in some embodiments, ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid is/are added to the composition. Non-limiting examples of antioxidants that may be added to the composition include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition. In some embodiments, one or more oxygen scavengers is added to the composition. For example, in some embodiments, ascorbic acid, ascorbate salts, catechol and/or sodium hydrogen carbonate is/are added to the composition.

Any suitable hygroscopic polymer may be added to the composition, including, but not limited to, hygroscopic agars, albumins, alginates, carrageenans, celluloses, gums (e.g., cellulose gun, guar gum, gun arabic, gum combretum, xantham gum), methyl celluloses, nylons, pectins, polyacrylic acids, polycaprolactones, polycarbonates, polyethylene glycols (PEG), polyethylenimines (PET), polylactides, polymethylacrylates (PMA), polyurethanes, polyvinyl alcohols (PVA), polyvinvlpyrrolidones (PVP), propylene glycols, sodium carboxymethyl celluloses and/or starches. Non-linuting examples of polymers that may be added to the composition include AGRIMER™ polymers (e.g., 30, AL-10 LC, AL-22, AT/ATF, VA 3E, VA 3I, VA 5E, VA 5I, VA 6, VA 6E, VA 7E, VA 7I, VEMA AN-216, VEMA AN-990, VEMA AN-1200, VEMA AN-1980, VEMA H-815MS; Ashland Specialty Ingredients, Wilmington, DE), EASYSPERSE™ polymers (Ashland Specialty Ingredients, Wilmington, DE); DISCO™ AG polymers (e.g., L-250, L-280, L-285, L-286, L-320, L-323, L-517, L-519, L-520, L800; Incotec Inc., Salinas, CA), KELZAN® polymers (Bri-Chem Supply Ltd., Calgary. Alberta, CA), SEEDWORX™ polymers (e.g., Bio 200; Aginnovation, LLC, Walnut Groove, CA), TICAXAN® xanthan powders, such as PRE-HYDRATED® TICAXAN® Rapid-3 Powder (TIC Gums, White Marsh, MD) and combinations thereof. Additional examples of polymers that may be added to the composition may be found in Pouci, et al AM. J. AGRIC. BIOL. SCI. 3(1):299 (2008).

Any suitable UV protectant(s) may be added to the composition, including, but not limited to, and/or aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates. Non-limiting examples of UV protectants that may be added to the composition include Borregaard LIGNOTECH™ lignosulfonates (e.g., BORRESPERSE® 3A, BORRESPERSE® CA, BORRESPERSE® NA, MARASPERSE® AG, NORLIG® A, NORLIG® 11D, UFOXANE® 3A, ULTRAZINE® NA, VANISPERSE® CB; Borregaard LIGNOTECH™, Sarpsborg, Norway) and combinations thereof. Additional examples of UV protectants that may be included in inoculant compositions of the present disclosure may be found in BURGES, FORMULATION OF MICROBIAL BIOPESTICIDE BENEFICIAL MICROORGANISMS, NEMATODES AND SEED TREATMENTS (Springer Science & Business Media) (2012).

Additional stabilizers may be added to the composition in any suitable form. In some embodiments, the additional stabilizer(s) added to the composition is/are at least 70, 75, 80, 85, 90, 91, 92, 93, 94, 95, 96, 97, 98, 99, 99.5% or more pure.

Additional stabilizers may be added to the composition in any suitable amount(s)/concentration(s). The absolute value of the amount/concentration that is/are sufficient to cause the desired effect(s) may be affected by factors such as the type, size and volume of material to which the composition will be applied, the type(s) of microorganisms in the composition, the number of microorganisms in the composition, the stability of the microorganism(s) in the composition and storage conditions (e.g., temperature, relative humidity, duration). Those skilled in the art will understand how to select effective amounts/concentrations using routine dose-response experiments. Guidance for the selection of appropriate amounts/concentrations can be found, for example, in International Patent Publication Nos. WO2017/044473, WO2017/044545, WO2017/116837, WO2017/116846, WO2017/210163 and WO2017/210166, and in U.S. Provisional Patent Application Nos. 62/296,798; 62/271,857; 62/347,773; 62/343,217; 62/296,784; 62/271,873; 62/347,785; 62/347,794; and 62/347,805.

In some embodiments, one or more additional stabilizers is/are added to the composition until it/they are present in the amount/concentration/dosage described above with respect to inoculant compositions of the present disclosure.

In some embodiments, one or more additional stabilizers is/are added to the composition in an amount/concentration of about 0.0001 to about 95% or more (by weight, based upon the total of the inoculant composition) For example, inoculant compositions of the present disclosure may comprise about 0.0001 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95%, of one or more maltodextrins, monosaccharides, disaccharides, betaines, prolines, sarcosines, peptones, oxidation control components, hygroscopic polymers and/or UV protectants.

In some embodiments, one or more additional stabilizers is/are added to the composition at a concentration of about $1\times10^{-20}$ M to about $1\times10^{-1}$ M. For example, inoculant compositions of the present disclosure may comprise about $1\times10^{-15}$ M to about $1\times10^{-10}$ M, about $1\times10^{-14}$ to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M, optionally about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more, of one or more maltodextrins, monosaccharides, disaccharides, betaines, prolines, sarcosines, peptones, oxidation control components, hygroscopic polymers and/or UV protectants.

In some embodiments, two or more additional stabilizers are added to the composition in amounts/concentrations that synergistically enhance the stability and/or survival of one or more microorganisms in the inoculant composition.

Stabilizers may be added to the composition in any suitable ratio(s). In some embodiments, one or more sugar alcohols, humic acids and/or fulvic acids and one or more additional stabilizing compounds are added to the composition at a (sugar alcohol(s), humic acid(s) and/or fulvic acid(s)), additional stabilizing compound ratio of about 1:99 to about 99:1 (by weight, based upon the respective weight percentages of the sugar alcohol(s)/humic acid(s)/fulvic acid(s) and the additional stabilizer(s) in the inoculant composition). For example, in some embodiments, one or more sugar alcohols, humic acids and/or fulvic acids and one or more additional stabilizing compounds are added to the composition at a (sugar alcohol/humic acid/fulvic acid): additional stabilizing compound ratio of about 5:95, 10:90, 15:85, 20:80, 25:75, 30:70, 35:65, 40:60, 45:55, 50:50, 55:45, 60:40, 65:35, 70:30, 75:25, 80.20, 85:15, 90:10, 95:5 or more, preferably about 45:55, 50.50, 55:45, 60:40, 65.35, 70.30, 75:25, 80:20, 85:15, 90:10, 95:5 or more. In some embodiments, one or more sugar alcohols, humic acids and/or fulvic acids and one or more additional stabilizing compounds are added to the composition at a (sugar alcohol/humic acid/fulvic acid):additional stabilizing compound ratio of about 5:95 to about 95:5, optionally about 50:50 to about 85:15, optionally about 75:25. In some embodiments, one or more maltodextrins (e.g., one or more maltodextrins (each and/or collectively) having a DEV of about 15 to about 20) and one or more sugar alcohols (e.g., sorbitol and/or xylitol)/humic acids (e.g., ammonium humate, boron humate, potassium humate and/or sodium humate)/fulvic acids (e.g., ammonium fulvate, boron fulvate, potassium fulvate and/or sodium fulvate) are added to the composition at a maltodextrin:(sugar alcohol/humic acid/fulvic acid) ratio of about 5:95, about 15:85, about 25:75 or about 50:50.

In some embodiments, the amount(s)/concentration(s) of the stabilizer(s) added to the inoculant composition is/are selected to ensure microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more, desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the amount(s)/concentration(s) of the stabilizer(s) added to the inoculant composition is/are selected to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more desiccation by about 5, 10, 15, 20, 25, 30, 35, 40, 45, 50, 55, 60, 65, 70, 75, 80, 85, 90, 95% or more, desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; ctyopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40C and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 das or more.

In some embodiments, the amount(s)/concentration(s) of the stabilizer(s) added to the inoculant composition is/are selected to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colon-forming units per gram and/or milliliter of inoculant composition remain viable following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 6, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 10, 104 weeks or more; cryopreservation at or below 40° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 1K), 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more, application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more, and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the amount(s)/concentration(s) of the stabilizer(s) added to the inoculant composition is/are selected to ensure the deliquescence relative humidity (DRH) of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C.).

As indicated above, sugar alcohols, humic acids and fulvic acids may be used in conjunction with additional stabilizers to enhance the stability and/or survival of microorganisms in an inoculant composition Indeed, sugar alcohols, humic acids and fulvic acids may be used to further enhance the stability and/or survival of microorganisms in inoculant compositions comprising other stabilizers (e.g., inoculant compositions comprising one or more maltodextrins, humic acids, monosaccharides, disaccharides, oxidation control components, hygroscopic polymers, and/or UV protectants). Thus, in some embodiments of the present disclosure, one or more sugar alcohols, humic acids and/or fulvic acids is/are added to an inoculant composition as described in one or more of International Patent Publication Nos. WO2017/044473, WO2017/044545, WO2017/116837, WO2017/11646, WO2017/210163 and WO2017/210166, and in U.S. Provisional Patent Application Nos. 62/511,408; 62/511,420 and 62/511,434.

Particular embodiments of the present disclosure are described in the following numbered paragraphs:

1. An inoculant composition, comprising, consisting essentially of, or consisting of one or more sugar alcohols, humic acids and/or fulvic acids; one or more maltodextrins, one or more monosaccharides, one or more disaccharides, one or more oxidation control components and/or one or more UV protectants; and one or more microorganisms.
2. The inoculant composition of paragraph 1, wherein said one more sugar alcohols, humic acids and/or fulvic acids comprises, consists essentially of or consists of one or more sugar alcohols, optionally sorbitol and/or xylitol.
3. The inoculant composition of paragraph 1, wherein said one more sugar alcohols, humic acids and/or fulvic acids comprises, consists essentially of or consists of one or more humic acids, optionally potassium humate and/or sodium humate.
4. The inoculant composition of paragraph 1, wherein said one more sugar alcohols, humic acids and/or fulvic acids comprises, consists essentially of or consists of one or more fulvic acids, optionally potassium fulvate and/or sodium fulvate.
5. The inoculant composition of any one of the preceding paragraphs, wherein said one or more sugar alcohols, humic acids and/or fulvic acids comprise(s) 0.001 to about 1%, about 0.25 to about 5%, about 1 to about 10%, about 5 to about 25%, about 10% to about 30%, about 20% to about 40%, about 25% to about 50% (by weight), of said inoculant composition.

6. The inoculant composition of any one of the preceding paragraphs, wherein said one or more sugar alcohols, humic acids and/or fulvic acids comprise(s) about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of said inoculant composition.
7. The inoculant composition of any one of the preceding paragraphs, wherein said one or more sugar alcohols, humic acids and/or fulvic acids is/are present in an amount/concentration sufficient to ensure microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application, foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.
8. The inoculant composition of any one of the preceding paragraphs, wherein said one or more sugar alcohols, humic acids and/or fulvic acids is/are present in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −8° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed), application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.
9. The inoculant composition of any one of the preceding paragraphs, wherein said one or more sugar alcohols, humic acids and/or fulvic acids is/are present in an amount/concentration sufficient to ensure at least $1\times10^1$, $1\times10^2$, $1\times10^3$, $1\times10^4$, $1\times10^5$, $1\times10^6$, $1\times10^7$, $1\times10_8$, $1\times10^9$, $1\times10^{10}$ or more colony-forming units per gram and/or milliliter of inoculanm composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 6, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed), application to plait propagation material and desiccation by about 5, 10, 15, 20, 25, 30, 35, 40, 45, 50, 55, 60, 65, 70, 75, 80, 85, 90, 95% or more; application to a plant propagation material and storage at 0, 1.2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

10. The inoculant composition of any one of the preceding paragraphs, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 10, 11, 12, 13, 14, 15, 16, 17, 18, 19, 20, 21, 22, 23, 24 or 25.

11. The inoculant composition of any one of the preceding paragraphs, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 15 to about 20.

12. The inoculant composition of any one of the preceding paragraphs, wherein said one or more maltodextrins, one or more monosaccharides, one or more disaccharides, one or more oxidation control components and/or one or more UV protectants comprises, consists essentially of, or consists of one or more monosaccharides, optionally arabinose, fructose and/or glucose.

13. The inoculant composition of any one of the preceding paragraphs, wherein said one or more maltodextrins, one or more monosaccharides, one or more disaccharides, one or more oxidation control components and/or one or more UV protectants comprises, consists essentially of, or consists of one or more disaccharides, optionally maltose, sucrose and/or trehalose.

14. The inoculant composition of any one of paragraphs 1-9, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 10, 11, 12, 13, 14, 15, 16, 17, 18, 19, 20, 21, 22, 23, 24 or 25, and one or more monosaccharides, optionally arabinose, fructose and/or glucose.

15. The inoculant composition of any one of paragraphs 1-9, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 10, 11, 12, 13, 14, 15, 16, 17, 18, 19, 20, 21, 22, 23, 24 or 25, and one or more disaccharides, optionally maltose, sucrose and/or trehalose.

16. The inoculant composition of any one of paragraphs 1-9, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 15 to about 20, and one or more monosaccharides, optionally arabinose, fructose and/or glucose.

17. The inoculant composition of any one of paragraphs 1-9, wherein said one or more maltodextrins, one or more monosaccharides, one or more disaccharides, one or more oxidation control components and/or one or more UV protectants comprises, consists essentially of, or consists of one or more maltodextrins, optionally one or more maltodextrins having a dextrose equivalent value of about 15 to about 20, and one or more disaccharides, optionally maltose, sucrose and/or trehalose.

18. The inoculant composition of any one of the preceding paragraphs, wherein said one or more maltodextrins, one or more monosaccharides, one or more disaccharides, one or more oxidation control components and/or one or more UV protectants comprise(s) about 0.001 to about 95% (by weight), optionally about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight), of said inoculant composition.

19. The inoculant composition of any one of the preceding paragraphs, wherein said one or more maltodextrins, one or more monosaccharides, one or more disaccharides, one or more oxidation control components and/or one or more UV protectants comprise(s) about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of said inoculant composition.

20. The inoculant composition of any one of the preceding paragraphs, wherein said one or more sugar alcohols, humic acids and/or fulvic acids and said one or more maltodextrins, one or more monosaccharides, one or more disaccharides, one or more oxidation control components and/or one or more UV protectants are present in a (sugar alcohol/humic acid/fulvic acid): (maltodextrin/monosaccharide/disaccharide/oxidation control component/UV protectant) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, optionally about 45:55, 50:50, 55:45, 60:40, 65:35, 70:30, 75:25, 80:20, 85:15, 90:10, 95:5 or more 21. The inoculant composition of any one of the preceding paragraphs, wherein said one or more microorganisms comprises, consists essentially of, or consists of one or more microorganisms that improve the availability of a soil nutrient.

22. The inoculant composition of any one of the preceding paragraphs, wherein said one or more microorganisms comprises, consists essentially of, or consists of one or more diazotrophs.

23. The inoculant composition of any one of the preceding paragraphs, wherein said one or more microorganisms comprises, consists essentially of, or consists of one or more rhizobacteria.

24. The inoculant composition of any one of the preceding paragraphs, wherein said one or more microorganisms comprises, consists essentially of, or consists of one or more strains of *Bradyrhizobium*, optionally one or more strains of *Bradyrhizobium japonicum.*

25. The inoculant composition of any one of the preceding paragraphs, wherein said one or more microorganisms comprises, consists essentially of, or consists of one or more strains of *Rhizobium*, optionally one or more strains of *Rhizobium leguminosarum.*

26. The composition of any one of the preceding paragraphs, wherein said one or more microorganisms comprises, consists essentially of, or consists of one or more strains of *Sinorhizobium*, optionally one or more strains of *Sinorhizobium meliloti.*

27. The composition of any one of the preceding paragraphs, wherein said one or more microorganisms comprises, consists essentially of, or consists of one or more strains of *Mesorhizobium.*

28. The inoculant composition of any one of the preceding paragraphs, wherein said one or more microorganisms comprises, consists essentially of, or consists of one or more strains of *Azorhizobium.*

29. The inoculant composition of any one of the preceding paragraphs, wherein said one or more microorganisms comprises, consists essentially of, or consists of *Azospirillum brasilense* INTA Az-39, *Bradyrhizobium elkanii* SEMIA 501. *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571, *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129, *Bradyrhizobium japonicum* USDA 532C, *Rhizobium leguminosarum* SO12A-2 (IDAC 080305-01), *Sinorhizobium fredii* CCBAU114, *Sinorhizobium fredii* USDA 205 and/or *Yersinia entomophaga* O82KB8.

30. The inoculant composition of any one of the preceding paragraphs, wherein said one or more microorganisms comprises, consists essentially of, or consists of one or more strains having a genomic sequence that is at least 75, 80, 85, 90, 95, 96, 97, 98, 99% or more identical to any of the strains recited in the preceding paragraph on the basis of 16S rDNA sequence identity.

31. The inoculant composition of any one of the preceding paragraphs, wherein said one or more microorganisms comprises, consists essentially of, or consists of one or more phosphate-solubilizing microorganisms.

32. The inoculant composition of any one of the preceding paragraphs, wherein said one or more microorganisms comprises, consists essentially of, or consists of one or more strains of *Penicillium*, optionally one or more strains of *P. bilaiae* and/or one or more strains of *P. gaestrivorus.*

33. The inoculant composition of any one of the preceding paragraphs, wherein said one or more microorganisms comprises, consists essentially of, or consists of *Penicillium bilaiae* (formerly known as *P. bilaii* and *P. bilaii* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SDI, *Penicillium brevicompactum* AgRF18, *Penicillium canescens* ATCC 10419, *Penicillium expansum* ATCC 24692, *Penicillium expansum* YT02, *Penicillium fellatanum* ATCC 48694*Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium rastrickii* ATCC 10490 and/or *Pseudomonas jessenii* PS06.

34. The inoculant composition of any one of the preceding paragraphs, wherein said one or more microorganisms comprises, consists essentially of, or consists of one or more strains having a genomic sequence that is at least 75, 80, 85, 90, 95, 96, 97, 98, 99% or more identical to any of the strains recited in the preceding paragraph on the basis of 165 rDNA sequence identity.
35. The inoculant composition of any one of the preceding paragraphs, wherein said one or more microorganisms comprises, consists essentially of, or consists of one or more myconthizal fungi.
36. The inoculant composition of any one of the preceding paragraphs, wherein said one or more microorganisms comprises, consists essentially of, or consists of one or more biopesticides, optionally one or more acaricides, one or more biofungicides, one or more bioinsecticides and/or one or more bionematicides.
37. The inoculant composition of any one of the preceding paragraphs, wherein said one or more microorganisms is present in said inoculant composition in a concentration ranging from about $1\times10^{1}$ to about $1\times10^{12}$ colony-forming units of said one or more microorganisms per gram and/or milliliter of said inoculant composition, optionally $1\times10^{4}$, $1\times10^{5}$, $1\times10^{6}$, $1\times10^{7}$, $1\times10^{8}$, $1\times10^{9}$, $1\times10^{10}$ or more colony-forming units per gram and/or milliliter of said inoculant composition
38. The inoculant composition of any one of the preceding paragraphs, wherein said inoculant composition comprises one or more biostimulants, optionally one or more seaweed extracts, myo-inositol and/or glycine.
39. The inoculant composition of any one of the preceding paragraphs, wherein said inoculant composition comprises one or more nutrients, optionally one or more vitamins e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine).
40. The inoculant composition of any one of the preceding paragraphs, wherein said inoculant composition comprises one or more pest attractants, optionally brevicomin, ceralure, codlelue, cue-lure, dispardure, dominicalum, eugenol, frontalin, gossyplure, grandlure, hexalure, ipsdienol, ipsenol, japonilure, latitlure. Ineatin, litlure, looplure, medlure, megatomic acid, methyl eugenol, moguchun, α-muitistriatin, muscalure, orfalure, oryctalure, ostramone, rescalure, siglure, sulcatol, trimedlure and/or trunc-call.
41. The inoculant composition of any one of the preceding paragraphs, wherein said inoculant composition comprises one or more pesticides, optionally.

one or more fungicides, optionally one or more of the fungicides expressly disclosed above;

one or more herbicides, optionally one or more of the herbicides expressly disclosed above;

one or more insecticides, optionally one or more of the insecticides expressly disclosed above; and/or one or more nematicides, optionally one or more of the nematicides expressly disclosed on above.

42. The inoculant composition of an one of the preceding paragraphs, wherein said inoculant composition comprises one or more plant signal molecules.
43. The inoculant composition of any one of the preceding paragraphs, wherein said inoculant composition comprises one or more lipo-chitooligosaccharides, optionally one or more of the lipo-chitooligosaccharides represented by formulas I-IV
44. The inoculant composition of any one of the preceding paragraphs, wherein said inoculant composition comprises one or more of the lipo-chitooligosaccharides represented by structures V-XXXIII.
45. The inoculant composition of any one of the preceding paragraphs, wherein said inoculant composition comprises one or more chitooligosaccharides, optionally one or more of the chitooligosaccharides represented by formulas XXXIV-XXXV.
46. The inoculant composition of any one of the preceding paragraphs, wherein said inoculant composition comprises one or more of the chitooligosaccharides represented by structures XXXVI-XXXIX.
47. The inoculant composition of any one of the preceding paragraphs, wherein said inoculant composition comprises one or more chitinous compounds, optionally one or more chitins and/or one or more chitosans.
48. The inoculant composition of any one of the preceding paragraphs, wherein said inoculant composition comprises one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallocatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g. biochanin A, daidzein, formononetin, genistein and/or glycitein), isoflavones (e.g., equol, ionchocarpane and/or laxifloranone), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one or more analogues, derivatives, hydrates, isomers, polymers, salts and solvates thereof, such as neoflavonoids (e.g., calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-I, erycristagallin, glycinol, glyceollidins, glyceollins, glycyrrhizol, maackiain, medicarpin, morisianine, orientanol, phaseolin, pisatin, striatine and/or trifolirhizin).

49. The inoculant composition of any one of the preceding paragraphs, wherein said inoculant composition comprises jasmonic acid and/or one or more derivatives thereof.

50. The inoculant composition of any one of the preceding paragraphs, wherein said inoculant composition comprises linoleic acid and/or one or more derivatives thereof.

51. The inoculant composition of any one of the preceding paragraphs, wherein said inoculant composition comprises linolenic acid and/or one or more derivatives thereof.

52. The inoculant composition of any one of the preceding paragraphs, wherein said inoculant composition comprises one or more karrakins, optionally one or more karrakins represented by formula XXXX.

53. The inoculant composition of any one of the preceding paragraphs, wherein said inoculant composition comprises gluconolactone 54. The inoculant composition of an one of the preceding paragraphs, wherein said inoculant composition comprises one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

55. The inoculant composition of any one of the preceding paragraphs, wherein said inoculant composition comprises one or more agriculturally acceptable carriers, optionally one or more soil-compatible carriers, seed-compatible carriers and/or foliar-compatible carriers.

56. The inoculant composition of any one of the preceding paragraphs, wherein said inoculant composition comprises one or more non-aqueous solvents.

57. The inoculant composition of any one of the preceding paragraphs, wherein said inoculant composition comprises one or more inorganic solvents, optionally decane, dodecane, hexylether and/or nonane.

58. The inoculant composition of any one of the preceding paragraphs, wherein said inoculant composition comprises one or more organic solvents.

59. The inoculant composition of any one of the preceding paragraphs, wherein said inoculant composition comprises water.

60. The inoculant composition of any one of the preceding paragraphs, wherein said inoculant composition is non-aqueous 61. The inoculant composition of any one of the preceding paragraphs, wherein said inoculant composition comprises one or more growth media, optionally YEM media mannitol yeast extract, glycerol yeast extract. Czapek-Dox media and/or potato dextrose broth.

62. The inoculant composition of any one of the preceding paragraphs, wherein said inoculant composition comprises one or more agriculturally acceptable polymers, optionally agar, alginate, carrageenan, cellulose, guar gum, locust bean gum, methylcellulose, pectin, polycaprolactone, polylactide, polyvinyl alcohol, polyvinyl pyrrolidone, sodium carboxymethyl cellulose, starch and/or xanthan gum.

63. The inoculant composition of any one of the preceding paragraphs, wherein said inoculant composition comprises one or more agriculturally acceptable wetting agents, optionally one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

64. The inoculant composition of any one of the preceding paragraphs, wherein said inoculant composition comprises one or more agriculturally acceptable drying agents, optionally calcium stearate, attapulgite clay, montmorillonite clay, graphite, magnesium stearate, silica (e.g., fumed silica, hydrophobically-coated silica and/or precipitated silica) and/or talc.

65. The inoculant composition of any one of the preceding paragraphs, wherein said inoculant composition comprises one or more agriculturally acceptable surfactants, optionally one or more anionic surfactants (e.g., one or more anionic surfactants selected from the group consisting of alkyl carboxylates (e.g., sodium steatite), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarcosinates, acyl isethionates, N-acyl taurates, N-acyl-N-alkyltaurines, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates), cationic surfactants (e.g., one or more cationic surfactants selected from the group consisting of alkyltrimethylammonium salts (e.g., cetyl trimethylammonium-bromide, cetyl trimethylammonium chloride), cetylpyridinium chloride, benzalkonium chloride, benzethonium chloride. 5-Bromo-5-nitro-1,3-dioxane, dimethyldioctadecylammonium chloride, cetrimonium bromide, dioctadecyldimethylammonium bromide and octenidine dihydrochloride), ionic surfactants (e.g., one or more ionic surfactants selected from the group consisting of ethers, glycol ethers, ethanolamides, sulfonylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, sorbitan fatty acid alcohol ethoxylates and sorbitan fatty acid ester ethoxylates), nonionic surfactants (e.g., one or more nonionic surfactants selected from the group consisting of alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.,), glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pyrrolidones, sugar-based alkyl polyglycosides, sulfonylamides, sorbitan fatty acid alcohol ethoxylates, sorbitan fatty acid ester ethoxylates, sorbitan fatty acid ester and tertiary acetylenic glycols), styrene acrylic polymers, modified styrene acrylic polymers and/or zwitterionic surfactants (e.g., one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidycholine and sphingomyelins).

66. The inoculant composition of any one of the preceding paragraphs, wherein said inoculant composition comprises one or more agriculturally acceptable soaps and/or organosilicone surfactants, optionally one or more alkali metal salts of fatty acids.

67. The inoculant composition of any one of the preceding paragraphs, wherein said inoculant composition comprises one or more agriculturally acceptable anti-freezing agents, optionally ethylene glycol, glycerin, propylene glycol and/or urea.

68. The composition of any one of the preceding paragraphs, wherein said inoculant composition comprises, consists essentially of or is an amorphous liquid.

69. The inoculant composition of any one of the preceding paragraphs, wherein said inoculant composition comprises, consists essentially of or is an amorphous solid.

70. The inoculant composition of any one of the preceding paragraphs, wherein said inoculant composition comprises, consists essentially of or is a powder or granuale, optionally a spray-dried powder, freeze-dried powder, spray-freeze-dried powder, fluidized bed-dried powder, spray-dried granuale, freeze-dried granuale, spray-freeze-dried granulae or fluidized bed-dried granuale.

71. The inoculant composition ofany one of the preceding paragraphs, wherein microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% of more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92,%, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38.39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

72. The inoculant composition of any one of the preceding paragraphs, wherein at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain table following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more, desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 5660, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 day s or more.

73. The inoculant composition of any one of the preceding paragraphs, wherein at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units per gram and/or milliliter of inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 4° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more, and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1.0.2, 0.25, 0.5, 0.75, 1, 1.5, 2, 2.5, 3, 3.5, 4.4.5, 5, 6, 7, 8, 9, 10, 11, 12, 13, 14, 15, 16, 17, 18, 19, 20, 21 days or more.

74. A coated plant propagation material, comprising, consisting essentially of, or consisting of a plant propagation material, optionally a seed, and a coating that covers at least a portion of the outer surface of said plant propagation material, said coating comprising, consisting essentially of, or consisting of the inoculation composition of any one of paragraphs 1-73.

75. The coated plant propagation material paragraph 74, wherein said coating comprises, consists essentially of, or consists of an inner coating lay er that comprises said one or more microorganisms and an outer coating layer that is devoid of said one or more microorganisms.

76. The coated plant propagation material of any one of paragraphs 74-75, wherein said coating comprises, consists essentially of or is an amorphous liquid.

77. The coated plant propagation material of any one of paragraphs 74-75, wherein said coating comprises, consists essentially of or is an amorphous solid.

78. The coated plant propagation material of any one of paragraphs 74-75, wherein said coating comprises, consists essentially of or is a powder or granuale, optionally a spray dried powder, freeze-dried powder, spray-freeze-dried powder or fluidized bed-dried granuale 79. The coated plant propagation material of any one of paragraphs 74-75, wherein said coating comprises about $1\times10^1$ to about $1\times10^{12}$ colony-forming units of said one or more microorganisms, optionally $1\times10^4$, $1\times10^5$, $1\times10^6$, $1\times10^7$ or more colony-forming units.

80. A kit, comprising the inoculant composition of any one of paragraphs 1 to 73 or the coated plant propagation material of any one of paragraphs 74-79 and a container housing said inoculant composition or coated plant propagation material.

81. The kit of paragraph 80, wherein said container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

82. The kit of any one of paragraphs 80-81, wherein said container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

83. The kit of any one of paragraphs 80-82, wherein said container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

84. The kit of any one of paragraphs 80-83, wherein said container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

85. The kit of any one of paragraphs 90-84, wherein said kit further comprises one or more oxygen-absorbing compound, optionally activated carbon, iron powder, sodium chloride, ferrous carbonate, one or more metal halide catalysts and/or sodium hydrogen carbonate.

86. A plant treated with the inoculant composition of any one of paragraphs 1-73.

87. A plant germinated from the coated plant propagation material of any one of paragraphs 74-79.

88. A plant part harvested from the plant of any one of paragraphs 86-87.

89. A processed product produced from the plant part of paragraph 88.

90. A crop comprising, consisting essentially of, or consisting of a plurality of the plant or plant part of any one of paragraphs 86-87.

91. A method, comprising, consisting essentially of, or consisting of applying the inoculant composition of any one of paragraphs 1-73 to a plant.

92. A method, comprising, consisting essentially of, or consisting of applying the inoculant composition of any one of paragraphs 1-73 to a plant propagation material.

93. The method of paragraph 92, further comprising planting said plait propagation material in a growth medium, optionally soil.

94. The method of paragraph 93, wherein said plant propagation material is planted in soil in which plants of the same genus were cultivated in at least one of the three years prior to said planting, optionally in each of the one, two or three years immediately preceding said planting.

95. The method of any one of paragraphs 93-94, wherein said inoculant composition is applied to the plant propagation material at the time of planting.

96. The method of any one of paragraphs 93-94, wherein said inoculant composition is applied to the plant propagation material at least 1, 2, 3, 4, 5, 6, 7, 8, 9, 10, 11, 12, 15, 18, 21, 24, 27, 30, 33, 36, 39, 42, 45, 48 hours or more prior to planting.

97. The method of any one of paragraphs 93-94, wherein said inoculant composition is applied to the plant propagation material at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more prior to planting.

98. The method of any one of paragraphs 93-94, wherein said inoculant composition is applied to the plant propagation material about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting.

99. A method comprising, consisting essentially of, or consisting of planting the coated plant propagation material of any one of paragraphs 74-79 in a growth medium, optionally soil 100. The method of any one of paragraphs 93-99, further comprising growing a plant or plant part from the plant propagation material.

101. The method of paragraph 100, further comprising applying the inoculant composition of any one of paragraphs 1-73 to the plant that grows from the plant propagation material.

102. A method, comprising, consisting essentially of or consisting of:

applying the inoculant composition of any one of paragraphs 1-73 to a seed and/or to the plant that grows from said seed;

applying a second composition to said seed and/or to the plant that grows from said seed, said second composition comprising:

one or more agriculturally beneficial microorganisms, optionally one or more diazotrophs, one or more phosphate-solubilizing microorganisms, one or more mycorrhizal fungi and/or one or more biopesticides, optionally one or more bioacaricides, one or more biofungicides, one or more bioinsecticides and/or one or more bionematicides;

one or more biostimulants, optionally one or more seaweed extracts, myo-inositol and/or glycine;

one or more nutrients, optionally one or more vitamins (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine);

one or more fungicides, optionally one or more of the fungicides expressly disclosed above, one or more herbicides, optionally one or more of the herbicides expressly disclosed above, one or more insecticides, optionally one or more of the insecticides expressly disclosed above;

one or more nematicides, optionally one or more of the nematicides expressly disclosed above;

one or more lipo-chitooligosaccharides, optionally one or more of the lipo-chitooligosaccharides represented by formulas I-IV and/or one or more of the lipo-chitooligosaccharides represented by structures V-XXXIII;

one or more chitooligosaccharides, optionally one or more of the chitooligosaccharides represented by formulas XXXIV-XXXV and/or one or more of the chitooligosaccharides represented by structures XXXVI-XXXIX, one or more chitinous compounds, optionally one or more chitins and/or one or more chitosans; one or more flavonoids, optionally one or more anthocyanidins, such as cyanidin, delphinidin, malvidin, pelargonidin, peonidin and/or petunidin, anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC)

epicatechin 3-gallate (ECg), epigallocatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones e.g., biochanin A, daidzein, formononetin, genistein and/or glycitein), isoflavanes (e.g., equol, ionchocarpane and/or laxifloranone), isoflavandiols, isoflavenes (e.g., glabrene, haginin D and/or 2-methoxy judaicin), coumestans (e.g., coumestrol, plicadin and/or wedelolactone), pterocarpans and/or roetonoids, and/or one or more analogues, derivatives, hydrates, isomers, polymers, salts and solvates thereof, such as neoflavonoids (e.g., calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-I, erycristagallin, glycinol, glyceollidins, glyceollins, glycyrrhizol, maackiain, medicarpin, morisianine, orientanol, phaseolin, pisatin, striatine and/or trifolirhizin);

jasmonic acid and/or one or more derivatives thereof;

linoleic acid and/or one or more derivatives thereof;

linolenic acid and/or one or more derivatives thereof;

one or more karrakins, optionally one or more karrakins represented by formula XXXX; and/or one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

103. The coated plant propagation material, kit, plant, plant part, processed product, crop or method of any one of paragraphs 74-102, wherein said plant propagation material or plant is a monocot.

104. The coated plant propagation material, kit, plant, plant part, processed product, crop or method of any one of paragraphs 74-102, wherein said plant propagation material or plant is a dicot.

105. The coated plant propagation material, kit, plant, plant part, processed product, crop or method of any one of paragraphs 74-102, wherein said plant propagation material or plant is leguminous.

106. The coated plant propagation material, kit, plant, plant part, processed product, crop or method of any one of paragraphs 74-102, wherein said plant propagation material or plant is non-leguminous 107. The coated plant propagation material, kit, plant, plant part, processed product, crop or method of any one of paragraphs 74-102, wherein said plant propagation material or plant is of the family Amaranthaceae, optionally chard, spinach, sugar beet, or *quinoa.*

108. The coated plant propagation material, kit, plant, plant part, processed product, crop or method of any one of paragraphs 74-102, wherein said plant propagation material or plant is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

109. The coated plant propagation material, kit, plant, plant part, processed product, crop or method of any one of paragraphs 74-102, wherein said plant propagation material or plant is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana.*

110. The coated plant propagation material, kit, plant, plant part, processed product, crop or method of any one of paragraphs 74-102, wherein said plant propagation material or plant is of the family Cucurbitaceae, optionally cantaloupe, cucumber, honeydew, melon, pumpkin, squash (e.g., acorn squash, butternut squash, summer squash), watermelon, or zucchini.

111. The coated plant propagation material, kit, plant, plant part, processed product, crop or method of any one of paragraphs 74-102, wherein said plant propagation material or plant is of the family Fabaceae, optionally alfalfa, beans, carob, clover, guar, lentils, mesquite, peas, peanuts, soybeans, tamarind, tragacanth, or vetch.

112. The coated plant propagation material, kit, plant, plant part, processed product, crop or method of any one of paragraphs 74-102, wherein said plant propagation material or plant is of the family Malvaceae, optionally cacao, cotton, durian, hibiscus, kenaf, kola, or okra.

113. The coated plant propagation material, kit, plant, plant part, processed product, crop or method of any one of paragraphs 74-102, wherein said plant propagation material or plant is of the family Poaceae, optionally bamboo, barley, corn, fonio, lawn grass (e.g., Bahia grass. Bermudagrass, bluegrass, Buffalograss. Centipede grass, Fescue, or *Zoysia*), millet, oats, ornamental grasses, rice, rye, sorghum, sugar cane, triticale, or wheat.

114. The coated plant propagation material, kit, plant, plant part, processed product, crop or method of any one of paragraphs 74-102, wherein said plant propagation material or plant is of the family Polygonaceae, optionally buckwheat.

115. The coated plant propagation material, kit, plant, plant part, processed product, crop or method of any one of paragraphs 74-102, wherein said plant propagation material or plant is of the family Rosaceae, optionally almonds, apples, apricots, blackberry, blueberry, cherries, peaches, plums, quinces, raspberries, roses, or strawberries.

116. The coated plant propagation material, kit, plant, plant part, processed product, crop or method of any one of paragraphs 74-102, wherein said plant propagation material or plant is of the family Solanaceae, optionally bell peppers, chili peppers, eggplant, *petunia*, potato, tobacco, or tomato.

117. The coated plant propagation material, kit, plant, plant part, processed product, crop or method of any one of paragraphs 74-102, wherein said plant propagation material or plant is of the family Vitaceae, optionally grape.

118. A method of enhancing the stability and/or survivability of one or more microorganisms in a composition, comprising, consisting essentially of, or consisting of adding one or more sugar alcohols, humic acids and/or fulvic acids to said composition.

119. The method of paragraph 118, wherein said composition comprises one or more maltodextrins, optionally one or more maltodextrins having a dextrose equivalent value of about 10, 11, 12, 13, 14, 15, 16, 17, 18, 19, 20, 21, 22, 23, 24 or 25, 120. The method of paragraph 118, wherein said composition comprises one or more maltodextrins, optionally one or more maltodextrins having a dextrose equivalent value of about 15 to about 20.

121. The method of any one of paragraphs 118-120, wherein said composition comprises one or more monosaccharides, optionally arabinose, fructose and/or glucose.

122. The method of any one of paragraphs 118-121, wherein said composition comprises one or more disaccharides, optionally maltose, sucrose and/or trehalose.

123. The method of any one of paragraphs 118-122, wherein said composition comprises one or more oxidation control components, optionally ascorbic acid and/or glutathione.

124. The method of any one of paragraphs 118-123, wherein said composition comprises one or more UV protectants, optionally one or more lignosulfates.

125. The method of any one of paragraphs 118-124, wherein said one more sugar alcohols comprises, consists essentially of or consists of sorbitol and/or xylitol.

126. The method of any one of paragraphs 118-125, wherein said one more humic acids comprises, consists essentially of or consists of potassium humate and/or sodium humate.

127. The method of any one of paragraphs 118-125, wherein said one more fulvic acids comprises, consists essentially of or consists of potassium fulvate and/or sodium fulvate.

128. The method ofany one of paragraphs 118-127, wherein said one or more sugar alcohols, humic acids and/or fulvic acids is/are added until it/they comprise(s) about 0.001 to about 95% (by weight), optionally about 0.001 to about 1%, about 0.25 to about 5%, about 1 to about 10%, about 5 to about 25%, about 10% to about 30%, about 20% to about 40%, about 25% to about 50% (by weight), of said inoculant composition.

129. The method of any one of paragraphs 118-127, wherein said one or more sugar alcohols, humic acids and/or fulvic acids is/are added until it/they comprise(s) about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of said inoculant composition.

130. The method of any one of paragraphs 118-127, wherein said one or sugar alcohols, humic acids and/or fulvic acids is/are added in an amount/concentration sufficient to ensure microorganisms remain viable in inoculant compositions of the present disclosure following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more, and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

131. The method of any one of paragraphs 118-127, wherein said one or sugar alcohols, humic acids and/or fulvic acids is/are added in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 das or more 132. The method of any one of paragraphs 118-127, wherein said one or more sugar alcohols, humic acids and/or fulvic acids is/are added in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, or more colony-forming units per gram and/or milliliter of inoculant composition remain viable following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more, desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

133. The method of any one of paragraphs 118-132, further comprising adding one or more drying agents to said composition.

134. The method of paragraph 133, wherein said one or more drying agents comprises calcium stearate, one or more clays, graphite, magnesium stearate, magnesium sulfate, powdered milk, one or more silica powders, soy lecithin and/or talc.

135. The method of any one of paragraphs 118-134 further comprising adding one or more microbial extracts to said composition.

136. The method of paragraph 135, wherein said one or more microbial extracts comprises: one or more *Bacillus* extracts, optionally an extract of media comprising *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* TJ100, *B. amyloliquefaciens* MBI600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* I-1562, *B. firmus* 1-1582, *B. lichenformis* BA842 (deposited as NRRL B-50516), *B. lichenformis* BL21 (deposited as NRRL B-50134), *B. mycoides* NRRL B-21664, *B. pumilus* NRRL B-21662, *B. pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI 600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 401 I, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, *B. thuringiensis* EG 7841, *B. thuringiensis* DSM 2803, *B. thuringiensis* NB-125 and/or *B. thuringiensis* NB-176;

one or more *Bradyrhizobium* extracts, optionally an extract of media comprising *B. elkani* SEMIA 501, *B. elkani* SEM1A 587, *B. elkani* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C;

one or more *Rhizobium* extracts, optionally an extract of media comprising *R. leguminosarum* SO12A-2;

one or more *Sinorhizobium* extracts, optionally an extract of media comprising *S. fredii* CCBAUI114 and/or *S. fredii* USDA 205;

one or more *Pennicillium* extracts, optionally an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490;

one or more *Streptomyces* extracts, optionally an extract of media comprising *Streptomyces* NRRL B-30145, *Streptomyces* M1064, *S. galbus* NRRL 30232, *S. lydicus* WYEC 108 (ATCC 55445), *S. violaceusniger* YCED 9 (ATCC 55660) and/or *Streptomyces* WYE 53 IATCC 55750), one or more *Trichoderma* extracts, optionally an extract of media comprising *T. asperellum* SKT-1 (ECO-HOPEX, Kumiai Chemical Industry Co., Ltd., Japan), *T. atroviride* LC52 (SENTINEL®, Agrimm Technologies Ltd, NZ), *T. harzianum* T-22 (PLANTSHIELD®, der Finns BioWorks Inc., USA), *T. harzianum* TH-35 (ROOT PRO®, from Mycontrol Ltd., Israel). *T. harzianum* T-39 (TRICHODEX®, Mycontrol Ltd., Israel; T. 2000®, Makhteshim Ltd., Israel), *T. harziamum* ICC012 and *T. viride* TRICHOPEL (Agrimm Technologies Ltd, NZ), *T. harzianum* ICC012 and *T. viride* ICC080 (REMEDIER® WP, Isagro Ricerca. Italy), *T. polysporum* and *T. harzianum* (BINAB®, BINAB Bio-Innovation AB, Sweden), *T. stromaticum* TRICO-VAB® (C.E.P.L A.C., Brazil), *T. virens* GL-3, ATCC 58678, *T. viride* TRIECO® (Ecosense Labs. (India) Pt. Ltd, India. BO-CURE® F, T. Stanes & Co. Ltd., India), *T. viride* TV1 (Agribiotec srd, Italy), *T. viride* ICC080; and/or one or more *Yersinia* extracts, optionally an extract of media comprising *Y. entomophaga* O82KB8.

137. The inoculant composition of any one of paragraphs 135-136, wherein said one or more microbial extracts comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

138. The method of any one of paragraphs 135-136, wherein said one or more microbial extracts is added until it comprises about 0.1 to about 5% (by weight) of said composition, optionally about 0.1 to about 2% (by weight) of said composition, optionally about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of said composition.

139. Use of one or more sugar alcohols, one or more humic acids and/or one or more fulvic acids for enhancing the the stability and/or survivability of one or more microorganisms in a composition.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Unless otherwise stated, the percentages described in the following examples are weight percentages based on the total weight of the composition (e.g., seed coating) being described.

Unless otherwise stated, the microbial suspensions described in the following examples comprise microbes that were grown to stationary phase prior to use.

Examine 1

Soybean seeds (ASGROW® AG4531; Monsanto Company, St. Louis, MO) were weighed out into 200 g allotments. Each allotment of seeds was coated with 1 ml of an aqueous *Yersinia entomaphaga* O82KB8 suspension supplemented with a stabilizer Table 1.

TABLE 1

| Seed Coating (1 ml per 200 g seed) |
|---|
| *Y. entomaphaga* O82KB8 suspension + 50% stabilizer (45% Maltrin® M150 + 0.089% potassium phosphate dibasic + 0.022% potassium phosphate monobasic in deionized water) |
| *Y. entomaphaga* O82KB8 suspension + 50% stabilizer (45% sorbitol + 0.089% potassium phosphate dibasic + 0.022% potassium phosphate monobasic in deionized water) |
| *Y. entomaphaga* O82KB8 suspension + 50% stabilizer (27% Maltrin ® M150 + 18% sorbitol + 0.089% potassium phosphate dibasic + 0.022% potassium phosphate monobasic in deionized water) |

Coated seeds were dried at mom temperature and ambient humidity for 4 hours and then assayed for on-seed survivability. FIG. 1. Dried seeds were stored at room temperature (20-23° C.) and 54% relative humidity and then assayed for on-seed survivability. FIG. 1 *Yersinia* survival was enhanced when sorbitol was added to the maltodextrin stabilizer.

Soybean seeds (ASGROW® AG4531, Monsanto Company, St Louis. MO) were weighed out into 200 g allotments Each allotment of seeds was coated with 1 ml of an aqueous *Yersinia entomaphaga* O82KB8 suspension supplemented with a stabilizer. Table 2.

TABLE 2

| Seed Coating (1 ml per 200 g seed) |
|---|
| *Y. entomphaga* O82KB8 suspension + 50% stabilizer (27% Maltrin ® M150 + 18% sorbitol + 0.089% potassium phosphate dibasic + 0.022% potassium phosphate monobasic in deionized water) |
| *Y. entomaphaga* O82KB8 suspension + 50% stabilizer (27% Maltrin ® M150 + 18% xylitol + 0.089% potassium phosphate dibasic + 0.022% potassium phosphate monobasic in deionized water) |
| *Y. entomaphaga* O82KB8 suspension + 50% stabilizer (33.75% Maltrin ® M150 + 11.25% sorbitol + 0.089% potassium phosphate dibasic + 0.022% potassium phosphate monobasic in deionized water) |
| *Y. entomaphaga* O82KB8 suspension + 50% stabilizer (33.75% Maltrin ® M150 + 11.25% xylitol + 0.089% potassium phosphate dibasic + 0.022% potassium phosphate monobasic in deionized water) |
| *Y. entomaphaga* O82KB8 suspension + 50% stabilizer (33.75% Maltrin ® M100 + 11.25% sorbitol + 0.089% potassium phosphate dibasic + 0.022% potassium phosphate monobasic in deionized water) |
| *Y. entomaphaga* O82KB8 suspension + 50% stabilizer (33.75% Maltrin ® M100 + 11.25% xylitol + 0.089% potassium phosphate dibasic + 0.022% potassium phosphate monobasic in deionized water) |

Figure 2:
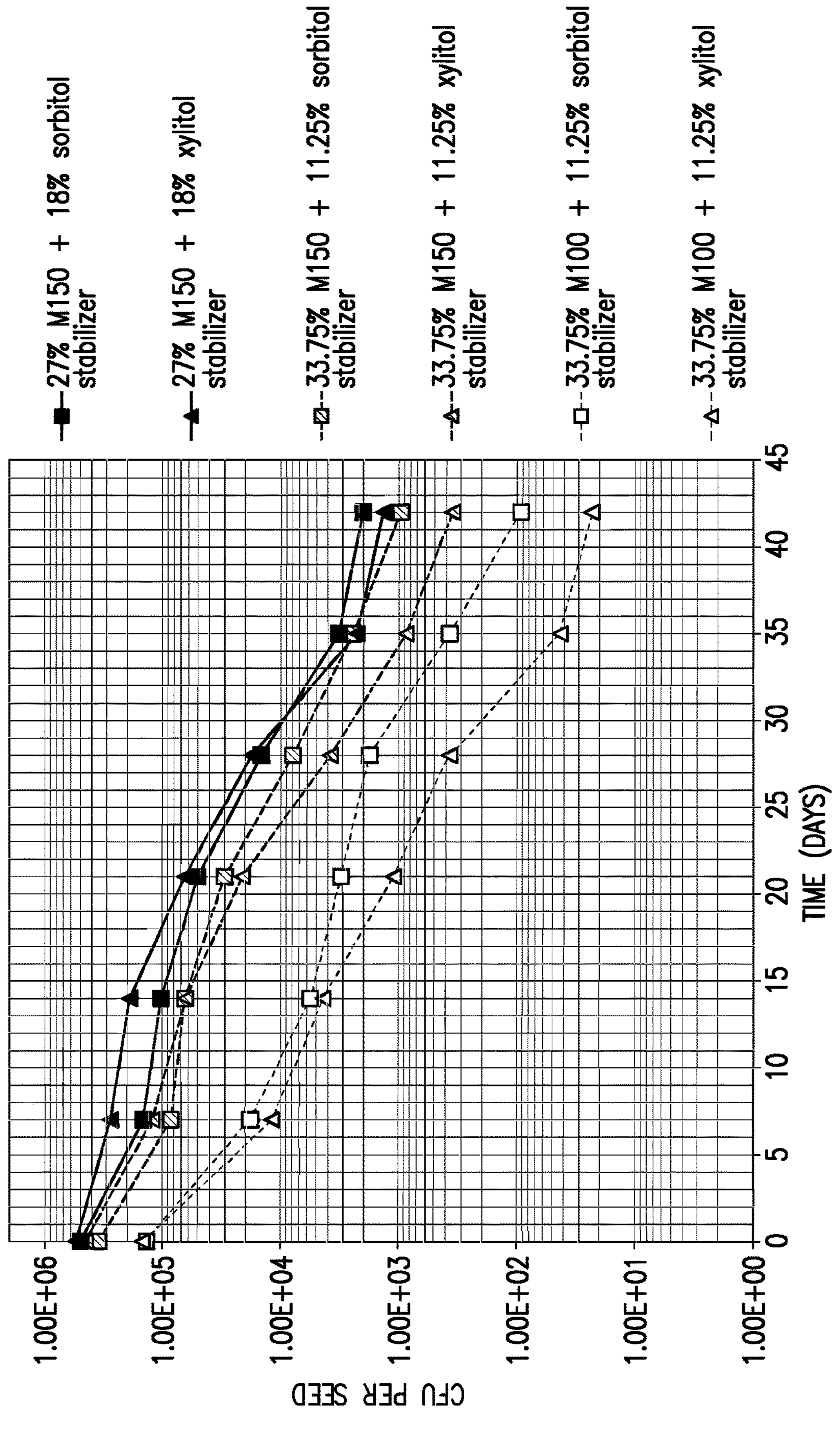

Coated seeds were dried at room temperature and ambient humidity for 4 hours and then assayed for on-seed survivability. FIG. 2. Dried seeds were stored at room temperature (20-23° C.) and 54% relative humidity and then assayed for on-seed survivability. FIG. 2. The 27% MALTRIN® M150+ 18% sorbitol stabilizer stabilized *Yersinia* survival as it did in Example 3 above. Sorbitol also stabilized *Yesinia* survival when added to a MALTRIN® M150 stabilizer at a lower concentration (11.25%) and when added to a MALTRIN® M100 stabilizer. Xylitol exhibited a similar effect, stabilizing *Yersinia* survival at each concentration and with each maltodextrin stabilizer.

Soybean seeds (ASGROW® AG4531; Monsanto Company, St. Louis, MO) were weighed out into 200 g allotments. Each allotment of seeds was coated with 188 μl of an aqueous *Yersinia entomaphaga* O82KB8 suspension supplemented with a stabilizer. Table 3.

TABLE 3

| Seed Coating (188 μl per 200 g seed) |
|---|
| *Y. entomaphaga* O82KB8 suspension + 50% stabilizer (36% Maltrin ® M100 + 24% sorbitol + 1.5% potassium phosphate dibasic + 0.019% potassium phosphate monobasic in deionized water) |
| *Y. entompahaga* O82KB8 suspension + 50% stabilizer (36% Maltrin ® M100 + 8% sorbitol + 8% fructose + 8% xylitol + 1.5% potassium phosphate dibasic + 0.019% potassium phosphate monobasic in deionized water) |
| *Y. entomaphaga* O82KB8 suspension + 50% stabilizer (36% Maltrin ® M150 + 24% sorbitol + 1.5% potassium phosphate dibasic + 0.019% potassium phosphate monobasic in deionized water) |
| *Y. entomaphaga* O82KB8 suspension + 50% stabilizer (36% Maltrin ® M150 + 8% sorbitol + 8% fructose + 8% xylitol + 1.5% potassium phosphate dibasic + 0.019% potassium phosphate monobasic in deionized water) |
| *Y. entomaphaga* O82KB8 suspension + 50% stabilizer (36% Maltrin ® M180 + 24% sorbitol + 1.5% potassium phosphate dibasic + 0.019% potassium phosphate monobasic in deionized water) |
| *Y. entomaphaga* O82KB8 suspension + 50% stabilizer (36% Maltrin ® M180 + 8% sorbitol + 8% fructose + 8% xylitol + 1.5% potassium phosphate dibasic + 0.019% potassium phosphate monobasic in deionized water) |
| *Y. entomaphaga* O82KB8 suspension + 50% stabilizer (36% Maltrin ® M200 + 24% sorbitol + 1.5% potassium phosphate dibasic + 0.019% potassium phosphate monobasic in deionized water) |
| *Y. entomaphaga* O82KB8 suspension + 50% stabilizer (36% Maltrin ® M200 + 8% sorbitol + 8% fructose + 8% xylitol + 1.5% potassium phosphate dibasic + 0.019% potassium phosphae monobasic in deionized water) |

Figure 3:
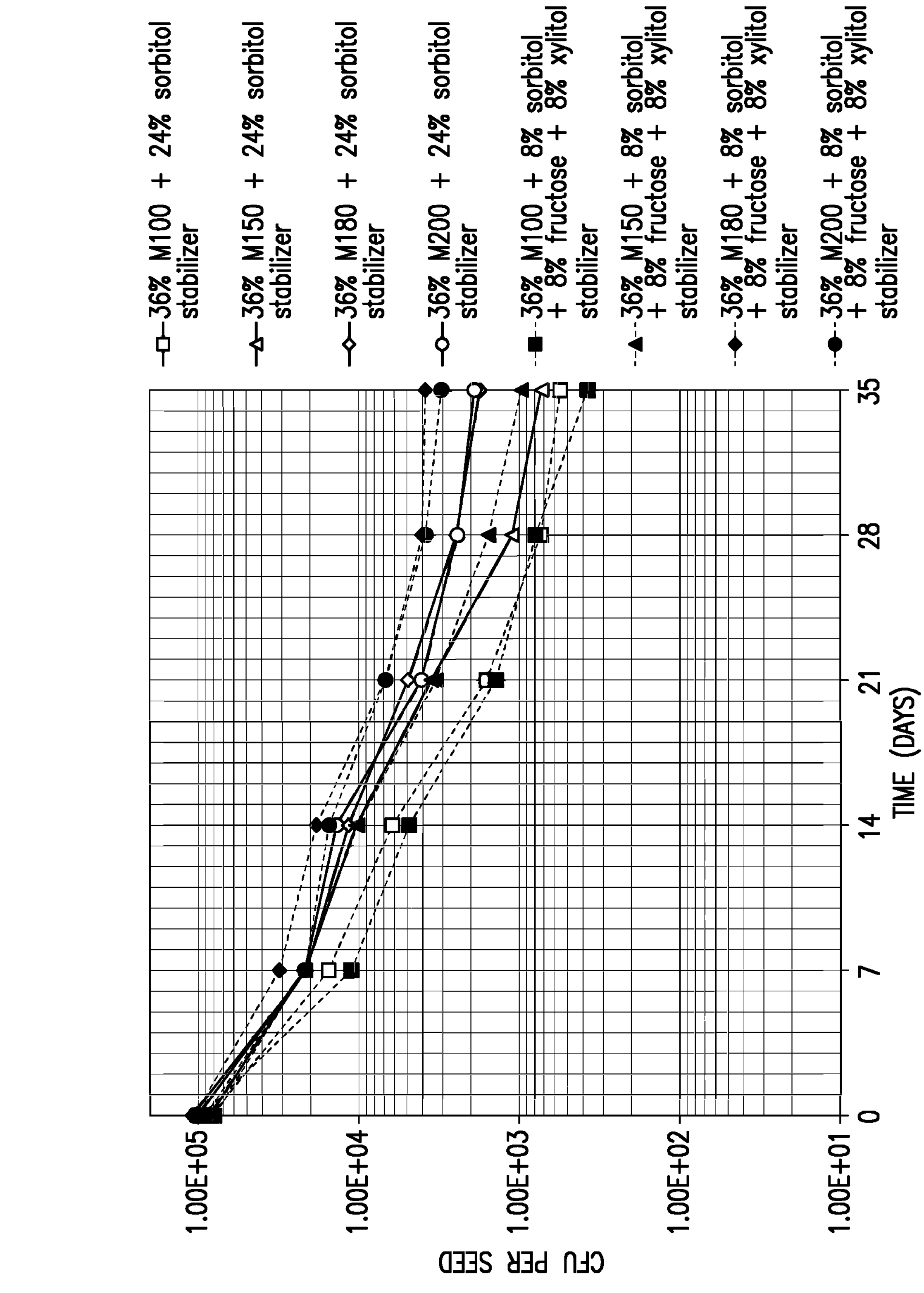

Coated seeds were dried at room temperature and ambient humidity for 4 hours and then assayed for on-seed survivability. FIG. 3. Dred seeds were stored at room temperature (20-23° C.) and 54% relative humidity and then assayed for on-seed survivability. FIG. 3 Sorbitol stabilized *Yersinia* survival when paired with MALTRIN® M100 and MALTRIN® M150 as it did in Example 4 above, *Yersinia* were further stabilized when sorbitol was paired with MALTRIN® M180 and MALTRIN® M200, *Yersinia* survival was enhanced when 24% sorbitol was replaced with 8% sorbitol+8% fructose+8% xylitol.

Example 4

Soybean seeds (ASGROW® AG4531; Monsanto Company, St. Louis, MO) were weighed out into 200 g allotments. Each allotment of seeds was coated with 1 ml of an aqueous *Yersinia entomaphaga* O82K8 suspension supplemented with a stabilizer. Table 4.

TABLE 4

| Seed Coating (1 ml per 200 g seed) |
|---|
| *Y. entomaphaga* O82KB8 suspension + 50% stabilizer (27% Maltrin ® M150 + 18% maltose monohydrate + 0.089% potassium phosphate dibasic + 0.022% potassium phosphate monobasic in deionized water) |
| *Y. entomaphaga* O82KB8 suspension + 50% stabilizer (27% Maltrin ® M150 + 13.5% maltose monohydrate + 4.5% sorbitol + 0.089% potassium phosphate dibaisc + 0.022% potassium phosphate monobasic in deionized water) |
| *Y. entomaphaga* O82KB8 suspension + 50% stabilizer (27% Maltrin ® M150 + 9% maltose monohydrate + 9% sorbitol + 0.089% potassium phosphate dibasic + 0.022% potassium phosphate monobasic in deionized water) |
| *Y. entomaphaga* O82KB8 suspension + 50% stabilizer (27% Maltrin ® M150 + 4.5% maltose monohydrate + 13.5% sorbitol + 0.089% potassium phosphate dibasic + 0.022% potassium phosphate monobasic in deionized water) |

Figure 4:
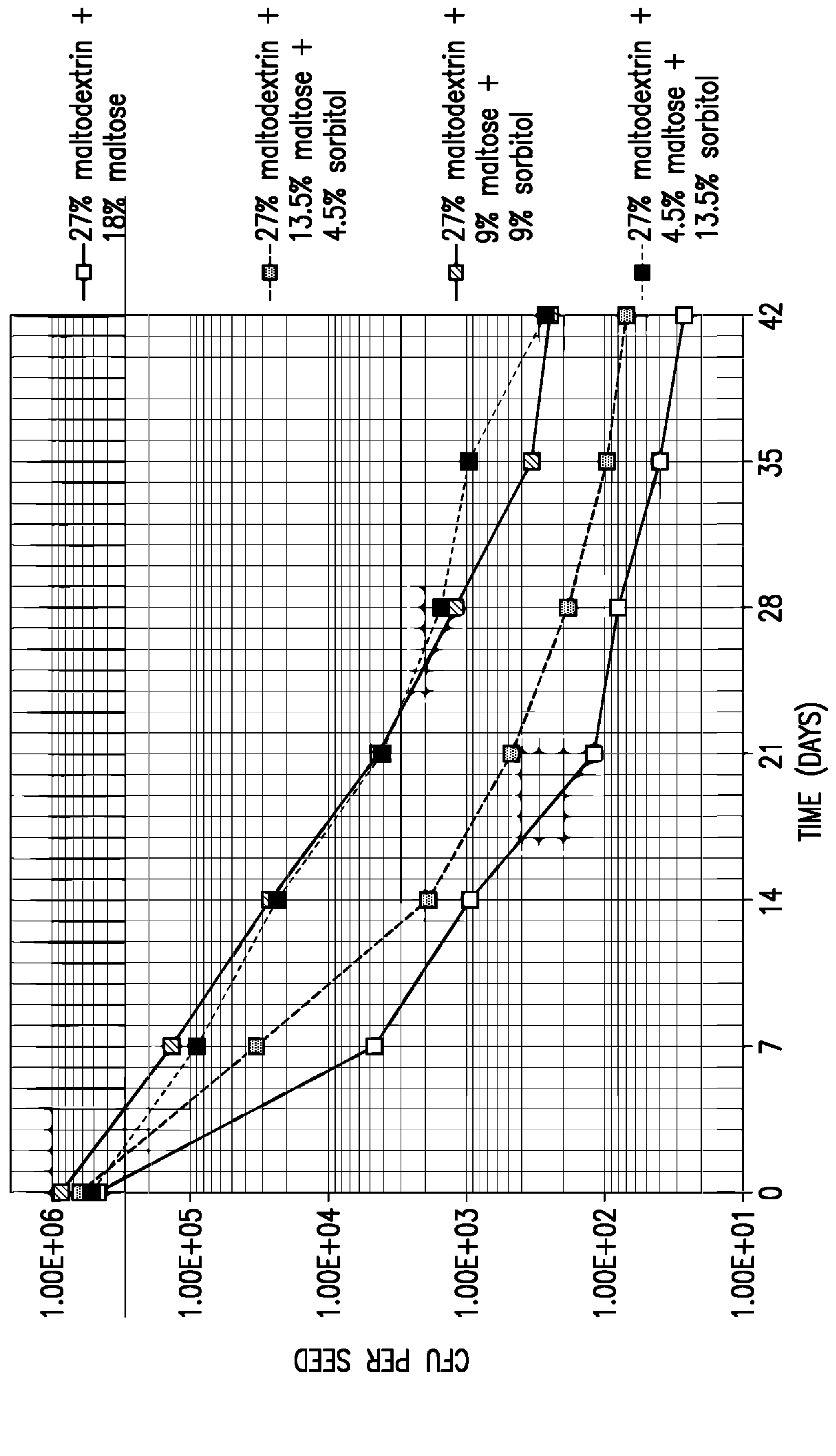

Coated seeds were dried at room temperature and ambient humidity for 4 hours and then assayed for on-seed survivability. FIG. 4. Dried seeds were stored at room temperature (20-23'C) and 54% relative humidity and then assayed for on-seed survivability. FIG. 4, *Yersinia* survival was enhanced when portions of the maltose in the maltodextrin-maltose stabilizer were replaced with sorbitol.

Example 5

Soybean seeds (ASGROW® AG4531; Monsanto Company, St. Louis, MO) were weighed out into 200 g allotments. Each allotment or seeds was coated with 1 ml of an aqueous *Yersinia entomophaga* O82KB8 suspension supplemented with a stabilizer Table 5.

TABLE 5

| Seed Coating (1 ml per 200 g seed) |
|---|
| *Y. entomaphaga* O82KB8 suspension + 50% stabilizer (36% Maltrin ® M150 + 24% maltose monohydrate + 1.5% potassium phosphate dibasic + 0.019% potassium phosphate ) monobasic in deionized water |
| *Y. entomaphaga* O82KB8 suspension + 50% stabilizer (36% Maltrin ® M150 + 24% fructose + 1.5% potassium phosphate dibasic + 0.019% potassium phosphate monobasic in deionized water) |
| *Y. entomaphaga* O82KB8 suspension + 50% stabilizer (36% Maltrin ® M150 + 24% sorbitol + 1.5% potassium phosphate dibasic + 0.019% potassium phosphate monobasic in deionized water) |
| *Y. entomaphaga* O82KB8 suspension + 50% stabilizer (36% Maltrin ® M150 + 24% xylitol + 1.5% potassium phosphate dibasic + 0.019% potassium phosphate monobasic in deionized water) |
| *Y. entomaphaga* O82KB8 suspension + 50% stabilizer (36% Maltrin ® M150 + 12% fructose + 12% sorbitol + 1.5% potassium phosphate dibasic + 0.019% potassium phosphate monobasic in deionized water) |
| *Y. entomaphaga* O82KB8 suspension + 50% stabilizer (36% Maltrin ® M150 + 12% fructose + 12% xylitol + 1.5% potassium phosphate dibasic + 0.019% potassium phosphate monobasic in deionized water) |
| *Y. entomaphaga* O82KB8 suspension + 50% stabilizer (36% Maltrin ® M100 + 12% sorbitol + 12% xylitol + 1.5% potassium phosphate dibasic + 0.019% potassium phosphate monobasic in deionized water) |
| *Y. entomaphaga* O82KB8 suspension + 50% stabilizer (36% Maltrin ® M100 + 8% fructose + 8% sorbitol + 8% xylitol + 1.5% potassium phosphate dibasic + 0.019% potassium phosphate monobasic in deionized water) |

Figure 5:
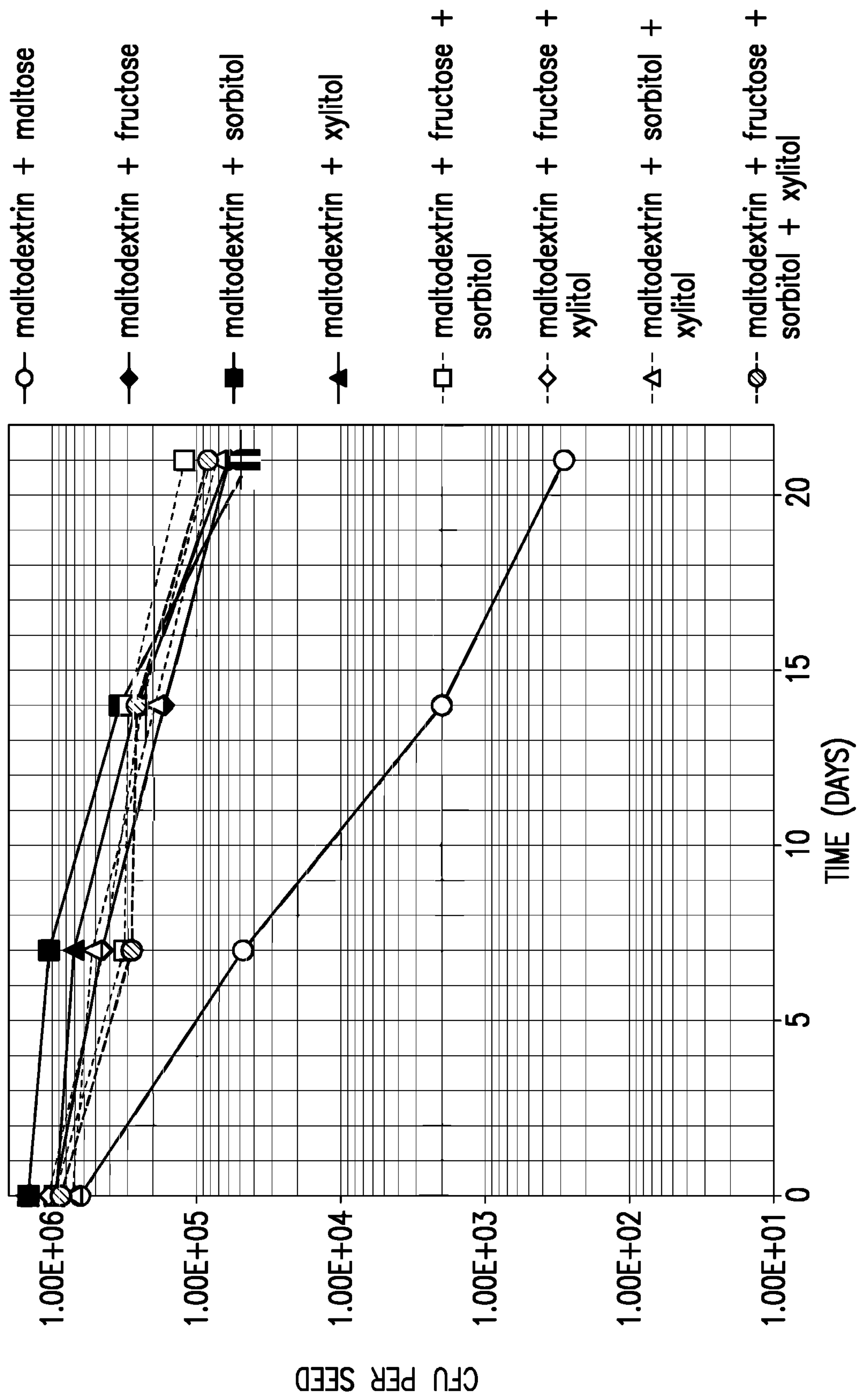

Coated seeds were dried at mom temperature and ambient humidity for 4 hours and then assayed for on-seed survivability. FIG. 5. Dried seeds were stored at room temperature (20-23° C.) and 54% relative humidity and then assayed for on-seed survivability. FIG. 5, *Yersinia* was enhanced when all of the maltose in the maltodextrin-maltose stabilizer was replaced with fructose, sorbitol, xylitol or mixtures thereof.

Example 6

Soybean seeds (ASGROW® AG2836; Monsanto Company, St. Louis, MO) were weighed out into 200 g allotments. Each allotment of seeds was coated with 188 μl of an aqueous *Bradyrhizobium japonicum* NRRL B-50626 suspension supplemented with a stabilizer Table 6.

TABLE 6

| Seed Coating (188 μl per 200 g seed) |
|---|
| *B. jabonicum* NRRL B-50626 suspension + 50% Extender for TagTeam ® |
| *B. japonicum* NRRL B-50626 suspension + 50% stabilizer (30% Maltrin ® M180 + 30% maltose monohydrate + 1.5% potassium phosphate dibasic + 0.019% potassium phosphate monobasic in deionized water) |
| *B. japonicum* NRRL B-50626 suspension + 50% stabilizer (45% Maltrin ® M180 + 7.5% fructose + 7.5% xylitol + 1.5% potassium phosphate dibasic + 0.019% potassium phosphate monobasic in deionized water) |
| *B. japonicum* NRRL B-50626 suspension + 50% stabilizer (30% Maltrin ® M180 + 15% fructose + 15% xylitol + 1.5% potassium phosphate dibasic + 0.019% potassium phosphate monobasic in deionized water) |
| *B. japonicum* NRRL B-50626 suspension + 50% stabilizer (15% Maltrin ® M180 + 22.5% fructose + 22.5% xylitol + 1.5% potassium phosphate dibasic + 0.019% potassium phosphae monobasic in deionized water) |

Figure 6:
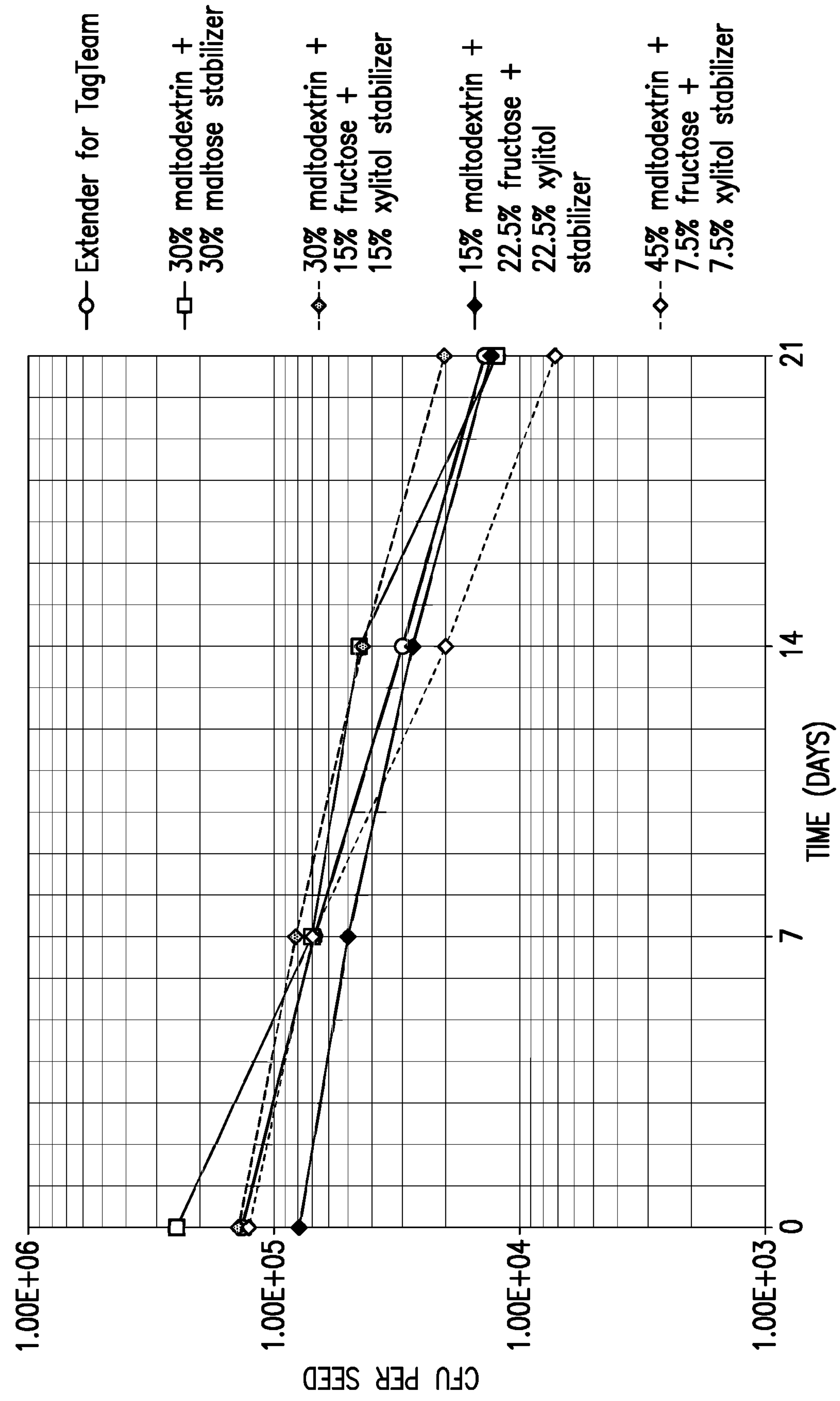
FIG. 6 is a graph showing the survivability of desiccated *Bradyrhizobium japonicum* NRRL B-50626 on soybean seeds stored at room temperature and 54% relative humidity.

Coated seeds were dried at room temperature and ambient humidity for 4 hours and then assayed for on-seed survivability. FIG. 6. Dried seeds were stored at room temperature (20-23° C.) and 54% relative humidity and then assayed for on-seed survivability. FIG. 6, *Bradyrhizobium* survival was enhanced when all of the maltose in the maltodextrin-maltose stabilizer was replaced with fructose and xylitol. Indeed, the 30% MALTRIN M180+15% fructose+15% xylitol stabilizer stabilized the *Bradyrhizobium* more than a commercially available stabilizer (Extender for TagTeam®; Monsanto Company, St. Louis, MO).

Example 7

Aqueous liquid inoculant compositions comprising $3.04 \times 10^{11}$ colony-forming units of *Bradyrhizobium japonicum* NRRL B-50626 and maltodextrin-based stabilizers (Table 7) were spray-dried using a BUCHI Mini Spray Dryer B-200 (BUCHI Corp., New Castle, DE) equipped with an ultrasonic nozzle. The flow rate of the inoculant composition was set to 8% (2.3 ml per minute). Inlet temperature was adjusted to maintain an outlet temperature of 50° C.

TABLE 7

| |
|---|
| *B. japonicum* NRRL B-50626 suspension + 14% Maltrin ® M150 + 6% maltose monohydrate + 0.089% potassium phosphate dibasic + 0.022% potassium phosphate monobasic |
| *B. japonicum* NRRL B-50626 suspension + 14% Maltrin ® M150 + 6% sorbitol + 0.089% potassium phosphate dibasic + 0.022% potassium phosphate monobasic |
| *B. japonicum* NRRL B-50626 suspension + 14% Maltrin ® M150 + 3% maltose monohydrate + 3% sorbitol + 0.089% potassium phosphate dibasic + 0.022% potassium phosphate monobasic |

Figure 7:
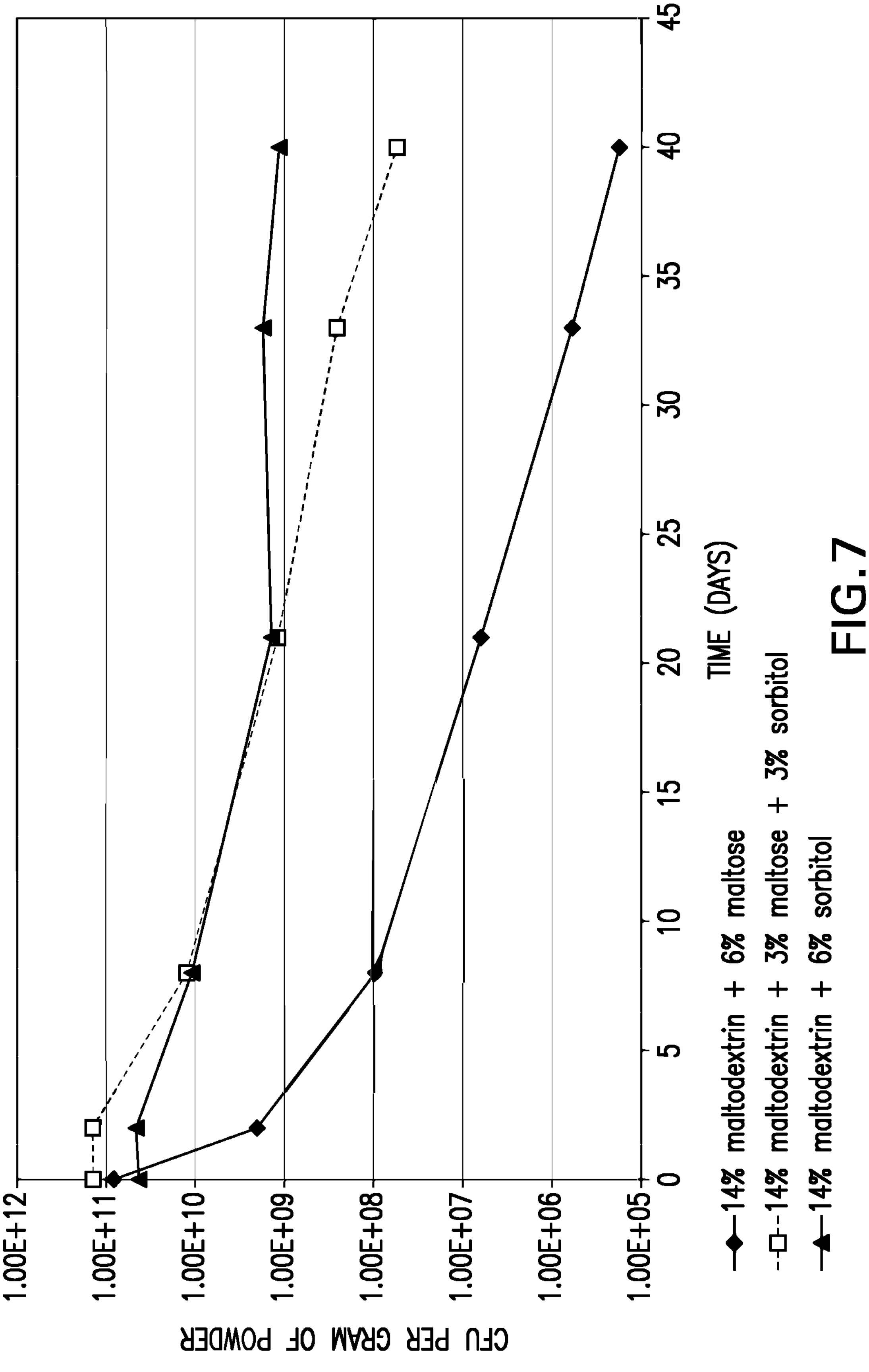
FIG. 7 is a graph showing the survivability of spray-dried *Bradyrhizobium japonicum* NRRL B-50626 on soybean seeds stored at room temperature and 54% relative humidity.

The spray-dried powders were stored at room temperature (20-23° C.) and 54% relative humidity under ambient light and then assayed for survivability. FIG. 7. The survival of spray-dried *Bradyrhizobium* was enhanced when some or all of the maltose in the maltose-maltodextrin stabilizer was replaced with sorbitol.

Example 8

Aqueous liquid inoculant compositions comprising *Yersinia entomophaga* O82KB8 (Table 8) were applied to PARAFILM® discs (2.5 cm diameter) at room temperature (20-23° C.) and ambient humidity under ambient light.

TABLE 8

| "Foliar" Treatment (five 2 μl drops per disc) |
|---|
| *Y. entomaphaga* O82KB8 suspension |
| *Y. entomaphaga* O82KB8 suspension + 0.25% Maltrin ® M150 + 0.75% maltose monohydrate |
| *Y. entomaphaga* O82KB8 suspension + 025% Maltrin ® M150 + 0.75% sorbitol |

Figure 8:
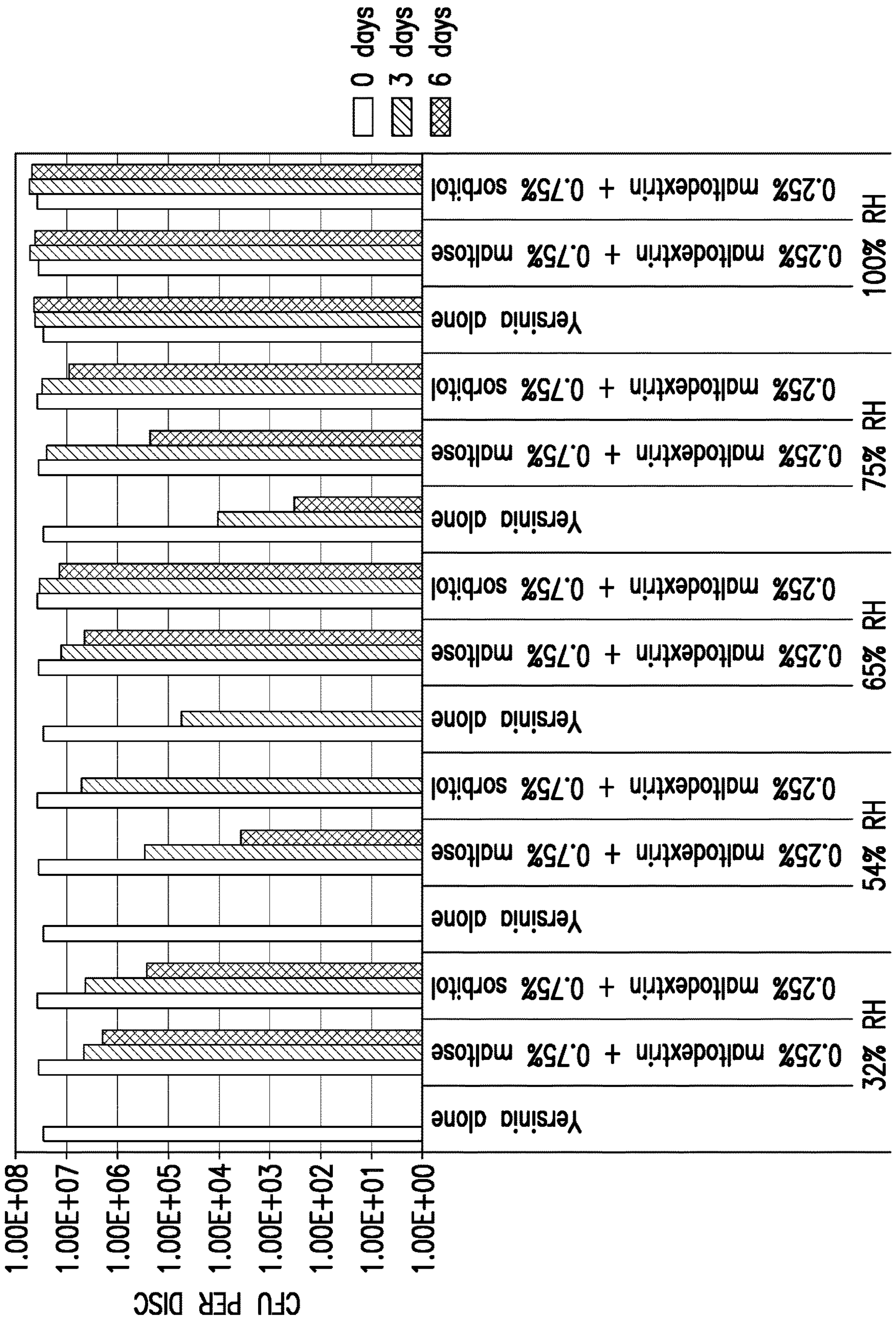
FIG. 8 is a graph showing the survivability of desiccated *Yersinia entomaphaga* O82KB8 on parafilm stored at room temperature and 32%, 54%, 65%, 75% or 100% relative humidity.

Treated discs were dried at room temperature under ambient humidity and ambient light and then assayed for survivability. FIG. 8. Treated discs were stored at room temperature (20-23° C.) and 32%, 54%, 65%, 75% or 100% relative humidity under ambient light and then assayed for survivability. FIG. 8, *Yersinia* survival was enhanced by the addition of 0.25% MALTRIN® M150+0 75% maltose or 0.25% MALTRIN® M150+0.75% sorbitol.

Example 9

Aqueous liquid inoculant compositions comprising *Yersinia entomophaga* O82KB8 (Table 9) were applied to PARAFILM® discs (2.5 cm diameter) at room temperature (20-23° C.) and ambient humidity under ambient light.

TABLE 9

| "Foliar" Treatment (five 2 μl drops per disc) |
|---|
| *Y. entomaphaga* O82KB8 suspension |
| *Y. entomaphaga* O82KB8 suspension + 3.75% Maltrin ® M150 + 1.25% maltose monohydrate + 0.089% potassium phosphate dibasic + 0.022% potassium phosphate monobasic |
| *Y. entomaphaga* O82KB8 suspension + 3.75% Maltrin ® M150 + 1.25% sorbitol + 0.089% potassium phosphate dibasic + 0.022% potassium phosphate monobasic |
| *Y. entomaphaga* O82KB8 suspension + 2.5% Maltrin ® M150 + 2.5% maltose monohydrate + 0.089% potassium phosphate dibasic + 0.022% potassium phosphate monobasic |
| *Y. entomaphaga* O82KB8 suspension + 2.5% Maltrin ® M150 + 2.5% sorbitol + 0.089% potassium phosphate dibasic + 0.022% potassium phosphate monobasic |
| *Y. entomaphaga* O82KB8 suspension + 1.25% Maltrin ® M150 + 3.75% maltose monohydrate + 0.089% potassium phosphate dibasic + 0.022% potassium phosphate monobasic |
| *Y. entomaphaga* O82KB8 suspension + 1.25% Maltrin ® M150 + 3.75% sorbitol + 0.089% potassium phosphate dibasic + 0.022% potassium phosphate monobasic |

Figure 9:
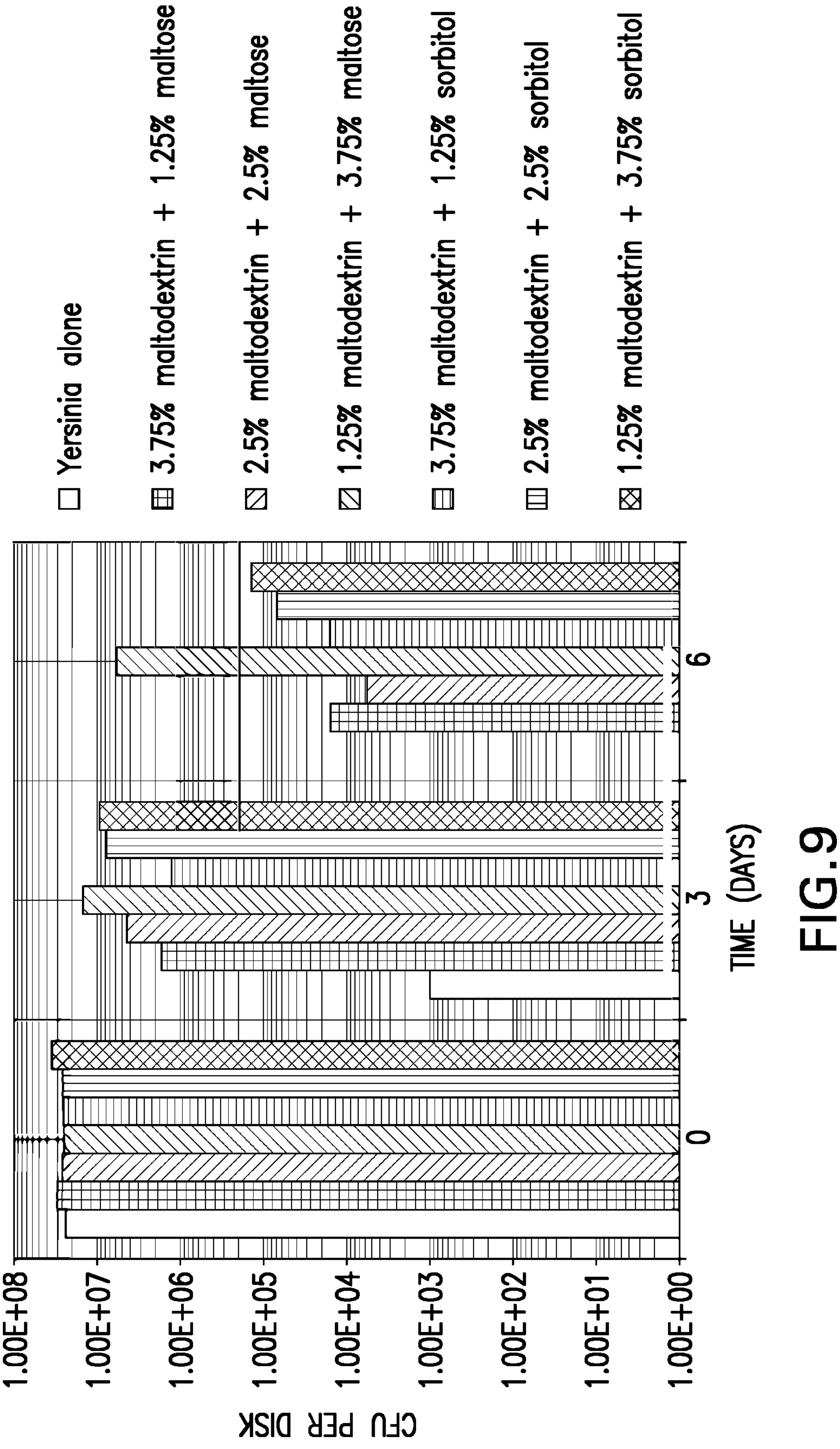
FIGS. 9-10 are graphs showing the survivability of desiccated *Yersinia entomaphaga* O82KB8 on parafilm stored at room temperature and 75% relative humidity.

Treated discs were dried at room temperature under ambient humidity and ambient light and then assayed for survivability. FIG. 9. Treated discs were stored at room temperature (20-23° C.) and 75% relative humidity under ambient light and then assayed for survivability. FIG. 9, *Yersinia* survival was enhanced by the addition of each of the maltodextrin-maltose and maltodextrin-sorbitol stabilizers.

Example 10

Aqueous liquid inoculant compositions comprising *Yersinia entomophaga* O82KB8 (Table 10) were applied to PARAFILM® discs (2.5 cm diameter) at room temperature (20-23° C.) and ambient humidity under ambient light.

TABLE 10

| "Foliar" Treatment (five 2 μl drops per disc) |
|---|
| *Y. entomaphaga* O82KB8 suspension |
| *Y. entomaphaga* O82KB8 suspension + 3% glycerol |
| *Y. entomaphaga* O82KB8 suspension + 4.25% Maltrin ® M150 + 0.75% sorbitol + 0.089% potassium phosphate dibasic + 0.022% potassium phosphate monobasic |
| *Y. entomaphaga* O82KB8 suspension + 3.5% Maltrin ® M150 + 1.5% sorbitol + 0.089% potassium phosphate dibasic + 0.022% potassium phosphate monobasic |
| *Y. entomaphaga* O82KB8 suspension + 2.5% Maltrin ® M150 + 2.5% sorbitol + 0.089% potassium phosphate dibasic + 0.022% potassium phosphate monobasic |

Figure 10:
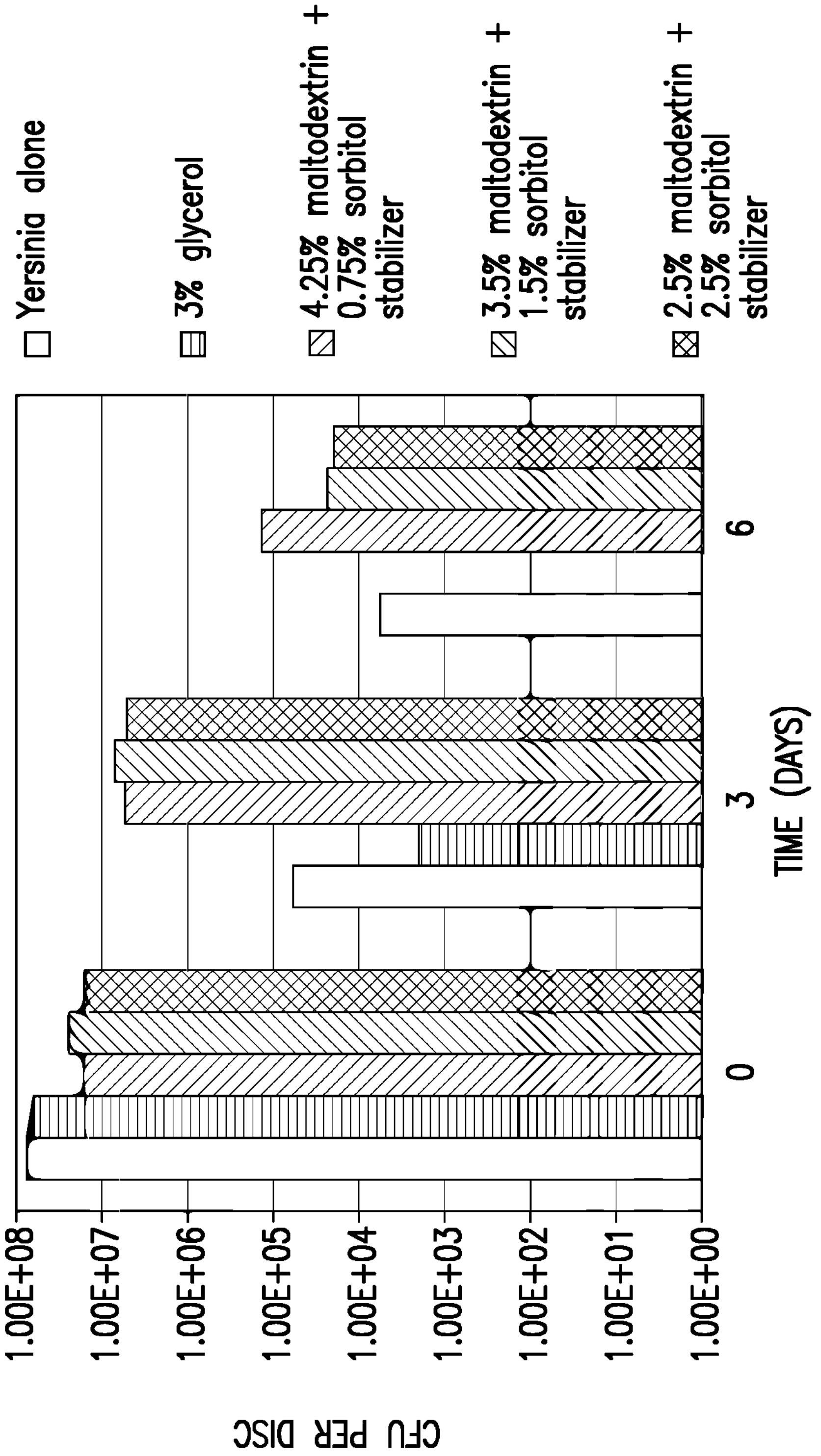

Treated discs were dried at room temperature under ambient humidity and ambient light and then assayed for survivability. FIG. 10. Treated discs were stored at mom temperature (20-23° C.) and 75% relative humidity under ambient light and then assayed for survivability. FIG. 10, *Yersinia* survival was enhanced by each of the maltodextrin-sorbitol stabilizers.

Example 11

Aqueous liquid inoculant compositions comprising *Yersinia entomophaga* O82KB8 (Table 11) were applied to PARAFILM® discs (2.5 cm diameter) at room temperature (20-23° C.) and ambient humidity, under ambient light.

TABLE 11

| "Foliar" Treatment (five 2 μl drops per disc) |
|---|
| *Y. entomaphaga* O82KB8 suspension + 0.25% Maltrin ® M150 + 0.75% maltose monohydrate + 0.089% potassium phosphate dibasic + 0.022% potassium phosphate monobasic |
| *Y. entomaphaga* O82KB8 suspension + 0.25% Maltrin ® M150 + 0.75% fructose + 0.089% potassium phosphate dibasic + 0.022% potassium phosphate monobasic |
| *Y. entomaphaga* O82KB8 suspension + 0.25% Maltrin ® M150 + 0.75% sorbitol + 0.089% potassium phosphate dibasic + 0.022% potassium phosphate monobasic |
| *Y. entomaphaga* O82KB8 suspension + 0.25% Maltrin ® M150 + 0.75% xylitol + 0.089% potassium phosphate dibasic + 0.022% potassium phosphate monobasic |
| *Y. entomaphaga* O82KB8 suspension + 0.25% Maltrin ® M150 + 0.375% fructose + 0.375% sorbitol + 0.089% potassium phosphate dibasic + 0.022% potassium phosphate monobasic |
| *Y. entomaphaga* O82KB8 suspension + 0.25% Maltrin ® M150 + 0.375% fructose + 0.375% xylitol + 0.089% potassium phosphate dibasic + 0.022% potassium phosphate monobasic |
| *Y. entomaphaga* O82KB8 suspension + 0.25% Maltrin ® M150 + 0.375% sorbitol + 0.375% xylitol + 0.089% potassium phosphate dibasic + 0.022% potassium phosphate monobasic |
| *Y. entomaphaga* O82KB8 suspension + 0.25% Maltrin ® M150 + 0.25% fructose + 0.25% sorbitol + 0.25% xylitol + 0.089% potassium phosphate dibasic + 0.022% potassium phosphate monobasic |

Figure 11:
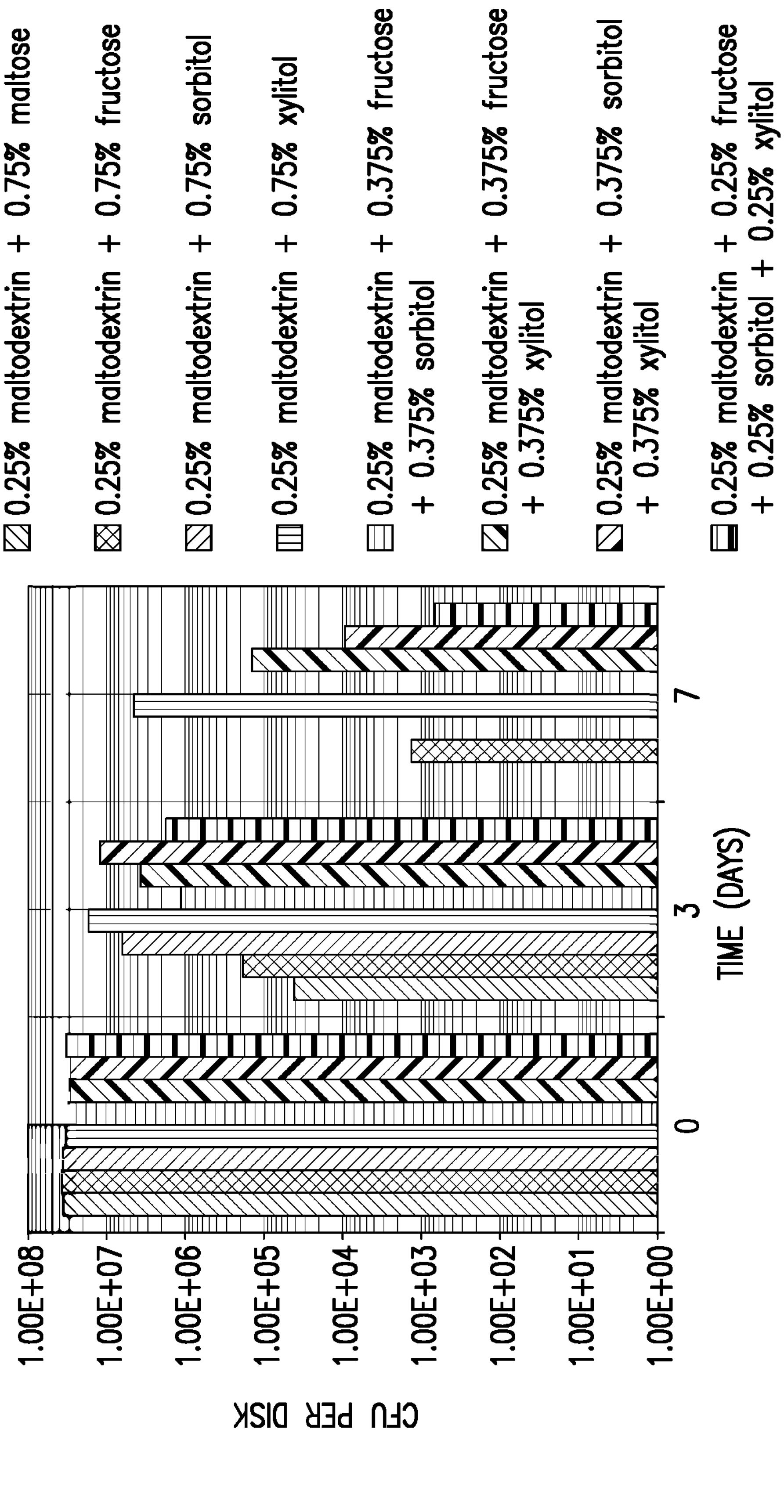
FIG. 11 is a graph showing the survivability of desiccated *Yersinia entomaphaga* O82KB8 on parafilm stored at room temperature and 54% relative humidity.

Treated discs were dried at room temperature under ambient humidity and ambient light and then assayed for survivability. FIG. 11. Treated discs were stored at room temperature (20-23° C.) and 54% relative humidity under ambient light and then assayed for survivability. FIG. 11, *Yersinia* survival was enhanced when all of the maltose in the maltodextrin-maltose stabilizer was replaced with fructose, sorbitol, xylitol or mixtures thereof.

Example 12

Aqueous liquid inoculant compositions comprising *Yersinia entomophaga* O82KB8 (Table 12) were applied to PARAFILM® discs (2.5 cm diameter) at room temperature (20-23'C) and ambient humidity under ambient light.

TABLE 12

| "Foliar" Treatment (five 2 µl drops per disc) |
|---|
| *Y. entomaphaga* O82KB8 suspension |
| *Y. entomaphaga* O82KB8 suspension + 1.25% Maltrin ® M150 + 3.75% soibitol + 0.089% potassium phosphate dibasic + 0.022% potassium phosphate monobasic |

Figure 12:
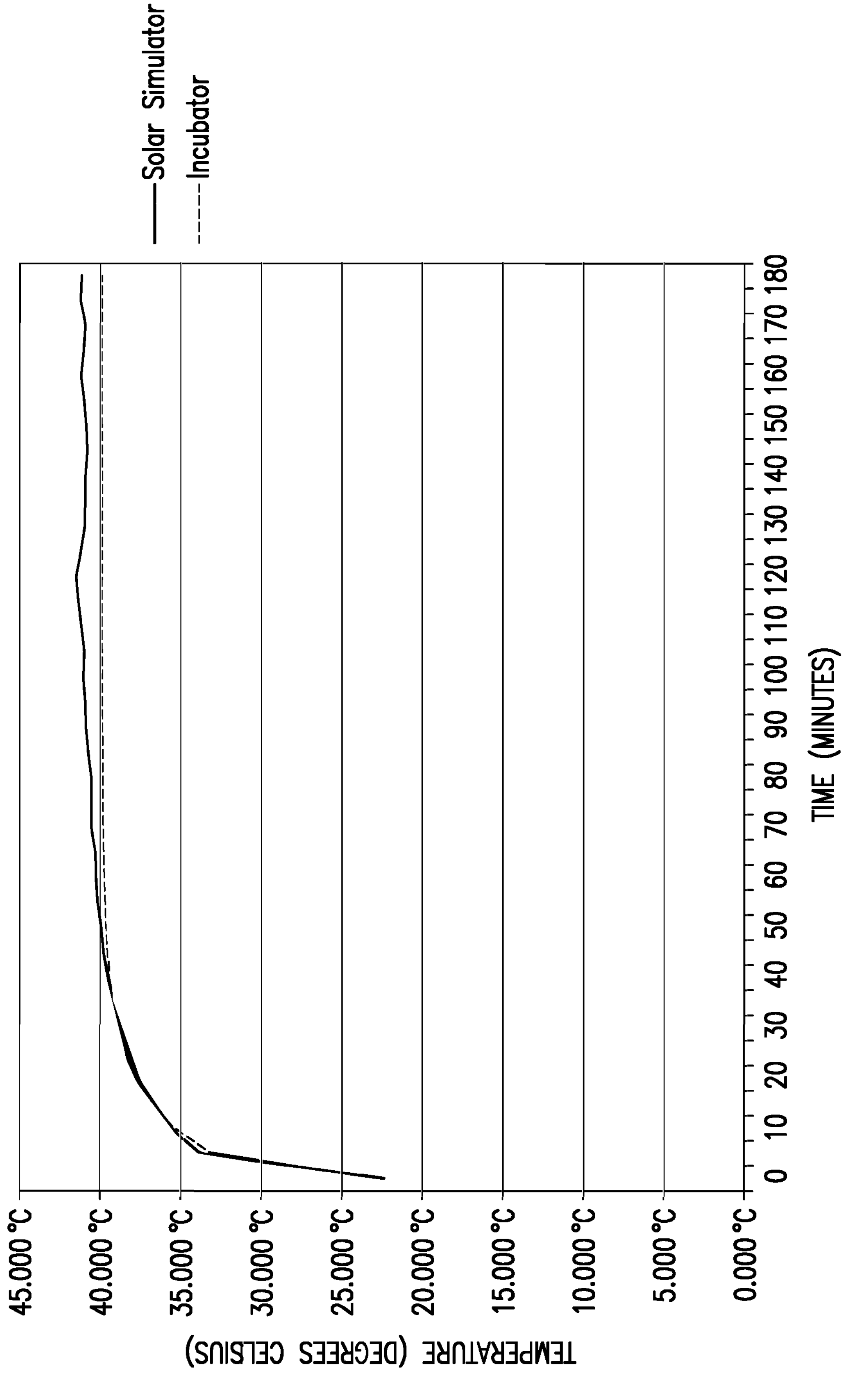
FIGS. 12-13 are graphs showing the temperatures and relative humidities measured under the Oriel Sol1A™ Class ABB Solar Simulator (light intensity of 100 mW at 300 nm) and in the dark incubator references in Examples 18-23.
Figure 13:
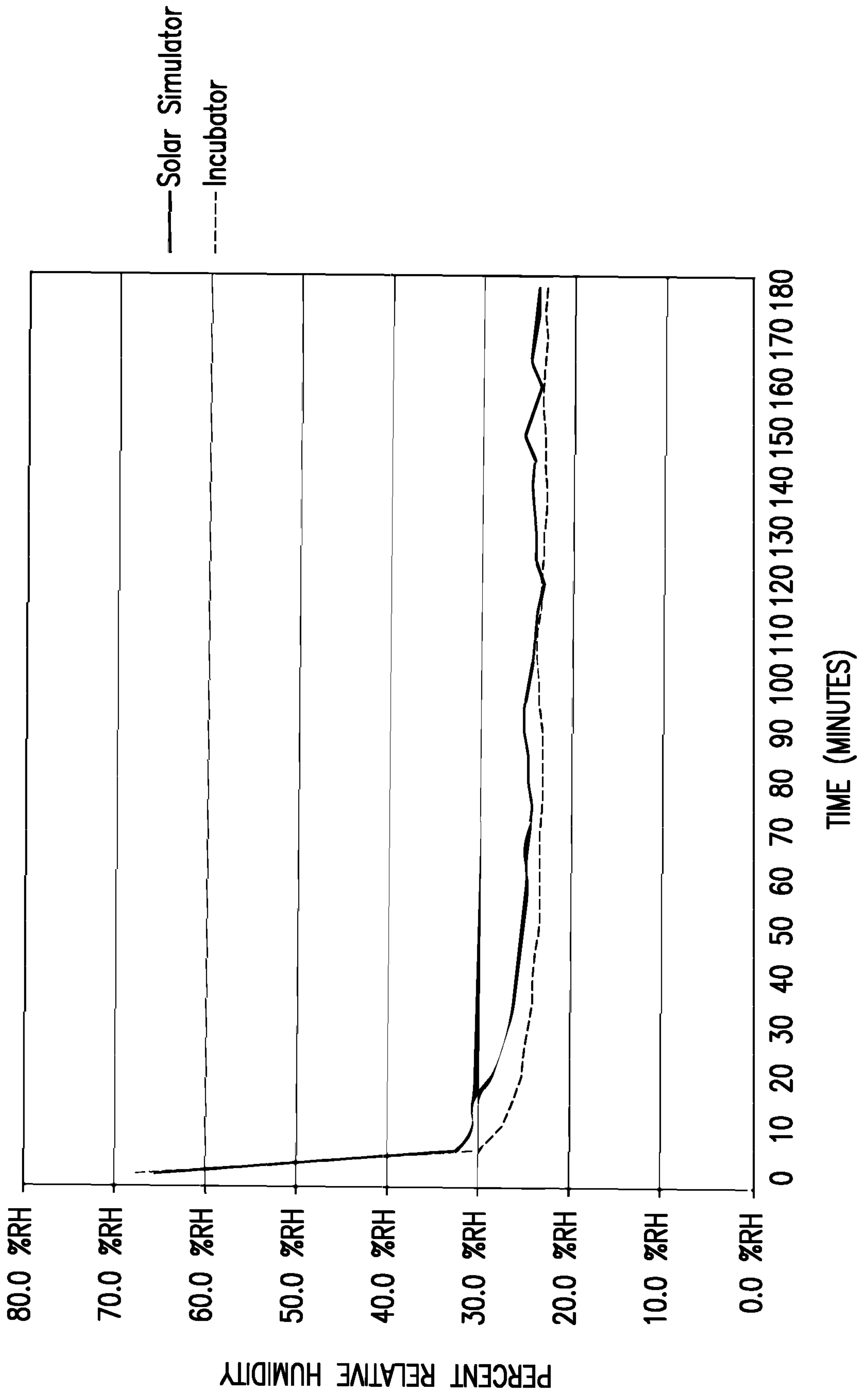
Figure 14:
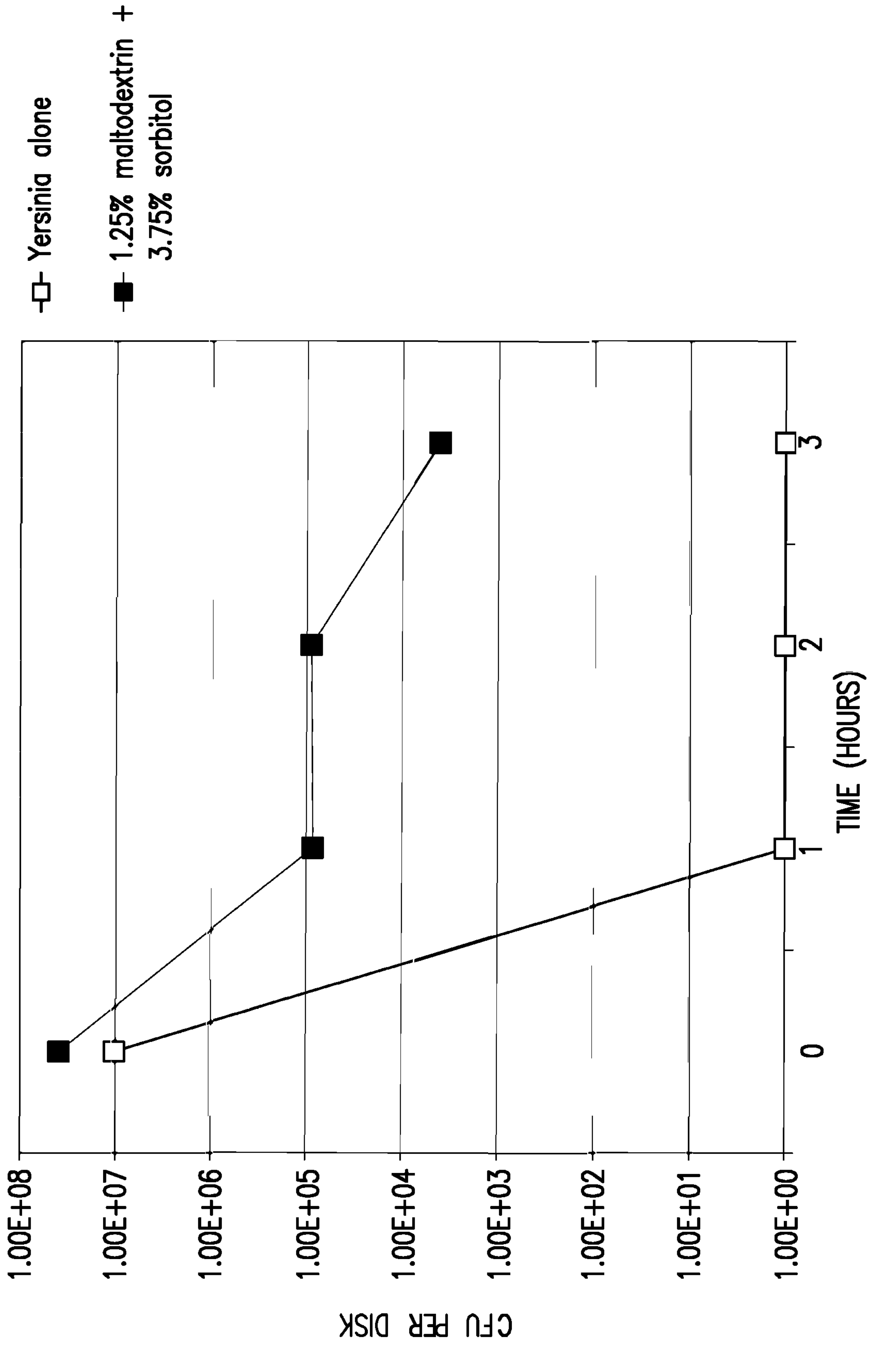
FIGS. 14-19 are graphs showing the survivability of desiccated *Yersinia entomaphaga* O82KB8 on parafilm stored under the Oriel Sol1A™ Class ABB Solar Simulator (light intensity of 100 mW at 300 nm) or in a dark incubator.

Treated discs were dried at room temperature under ambient humidity and ambient light and then assayed for survivability. FIG. 14. Treated discs were stored under an Oriel Sol1A™ Class ABB Solar Simulator (light intensity of 100 mW at 300)nm) or in a dark incubator and then assayed for survivability. The temperatures and relative humidities of the solar simulator and the incubator were kept virtually identical for the duration of the experiment. FIGS. 12-13. As shown in FIG. 14, the stabilizing medium enhanced *Yersinia* survival.

Example 13

Aqueous liquid inoculant compositions comprising *Yersinia entomophaga* O82KB8 (Table 13) were applied to PARAFILM® discs (2.5 cm diameter) at room temperature (20-23° C.) and ambient humidity under ambient light.

TABLE 13

| "Foliar" Treatment (five 2 µl drops per disc) |
|---|
| *Y. entomaphaga* O82KB8 suspension + 1.25% Maltrin ® M150 + 3.75% sorbitol + 0.089% potassium phosphate dibasic + 0.022% potassium phosphate monobasic |
| *Y. entomaphaga* O82KB8 suspension + 1.25% Maltrin ® M150 + 3.75% sorbitol + 0.089% potassium phosphate dibasic + 0.022% potassium phosphate monobasic + 1% calcium lignosulfate |
| *Y. entomaphaga* O82KB8 suspension + 1.25% Maltrin ® M150 + 3.75% sorbitol + 0.089% potassium phosphate dibasic + 0.022% potassium phosphate monobasic + 1% sodium lignosulfate |
| *Y. entomaphaga* O82KB8 suspension + 1.25% Maltrin ® M150 + 3.75% sorbitol + 0.089% potassium phosphate dibasic + 0.022% potassium phosphate monobasic + 1% DL-tryptophan |

Figure 15:
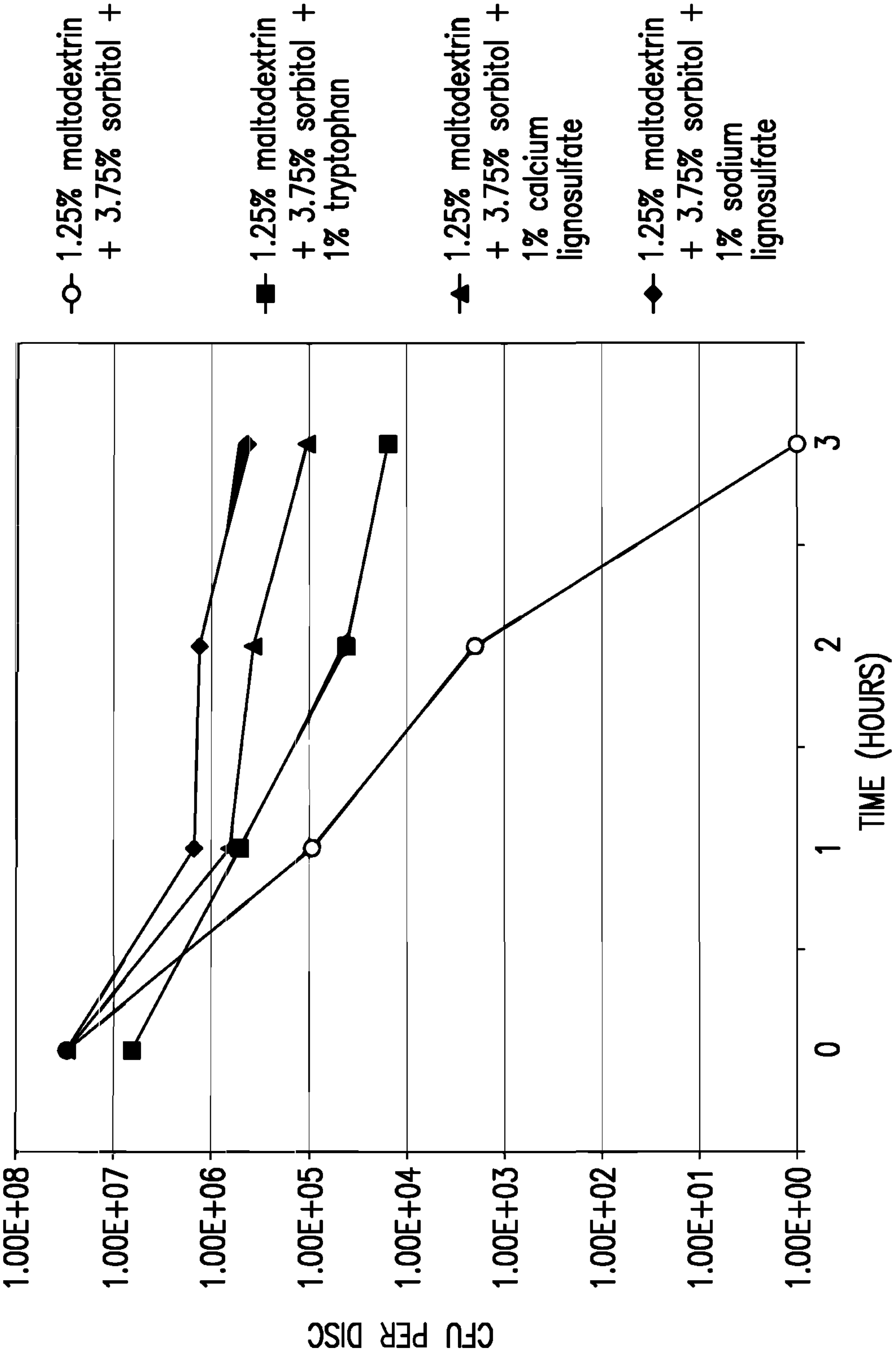

Treated discs were dried at room temperature under ambient humidity and ambient light and then assayed for survivability FIG. 15. Treated discs were stored under an Oriel Sol1A™ Class ABBSolar Simulator (light intensity of 100 mW at 300 nm; approximately 41° C. approximately 23% relative humidity) and assayed for survivability. As shown in FIG. 15, the addition of a UV protectant to the stabilizing medium further enhanced *Yersinia* survival.

Example 14

Aqueous liquid inoculant compositions comprising *Yersinia entomophaga* s2 KB 8 (Table 14) were applied to PARAFILM® discs (2.5 cm diameter) at room temperature (20-23° C.) and ambient humidity under ambient light.

TABLE 14

| "Foliar" Treatment (five 2 µl drops per disc) |
|---|
| *Y. entomaphaga* O82KB8 suspension + 0.25% Maltrin ® M150 + 0.75% sorbitol + 0.089% potassium phosphate dibasic + 0.022% potassium phosphate monobasic + 1% calcium lignosulfate |
| *Y. entomaphaga* O82KB8 suspension + 0.25% Maltrin ® M150 + 0.75% sorbitol + 0.089% potassium phosphate dibasic + 0.022% potassium phosphate monobasic + 1% sodium lignosulfate |
| *Y. entomaphaga* O82KB8 suspension + 1.25% Maltrin ® M150 + 3.75% sorbitol + 0.089% potassium phosphate dibasic + 0.022% potassium phosphate monobasic + 1% calcium lignosulfate |
| *Y. entomaphaga* O82KB8 suspension + 1.25% Maltrin ® M150 + 3.75% soibitol + 0.089% potassium phosphate dibasic + 0.022% potassium phosphate monobasic + 1% sodium lignosulfate |

Figure 16:
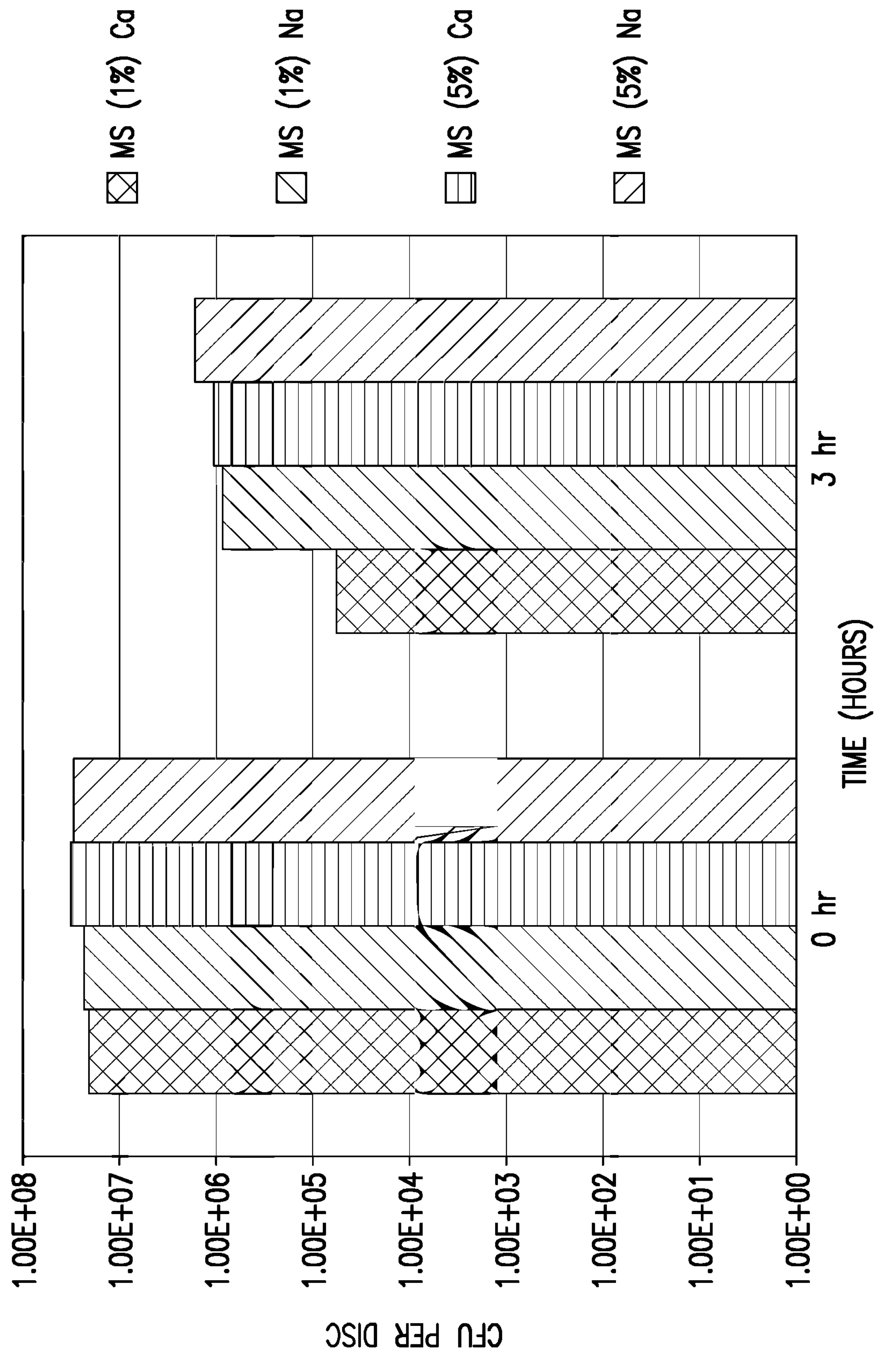

Treated discs were dried at room temperature under ambient humidity and ambient light and then assayed for survivability. FIG. 16. Treated discs were stored under an Orel Sol1A™ Class ABBSolar Simulator (light intensity of 100 mW at 300 nm; approximately 41° C.; approximately 23% relative humidity) and assayed for survivability. FIG. 16.

Example 15

Aqueous liquid inoculant compositions comprising *Yersinia entomophaga* O82KB8 (Table 15) were applied to PARAFILM® discs (2.5 cm diameter) at room temperature (20-23° C.) and ambient humidity under ambient light.

TABLE 15

| "Foliar" Treatment (five 2 µl drops per disc) |
|---|
| *Y. entomaphaga* O82KB8 suspension + 0.25% Maltrin ® M150 + 0.75% sorbitol + 0.089% potassium phosphate dibasic + 0.022% potassium phosphate monobasic + 0.1% calcium lignosulfate (Borresperse Ca) |
| *Y. entomaphaga* O82KB8 suspension + 0.25% Maltrin ® M150 + 0.75% sorbitol + 0.089% potassium phosphate dibasic + 0.022% potassium phosphate monobasic + 0.1% sodium lignosulfate (Borresperse Na) |
| *Y. entomaphaga* O82KB8 suspension + 0.25% Maltrin ® M150 + 0.75% soibitol + 0.089% potassium phosphate dibasic + 0.022% potassium phosphate monobasic + 0.1% sodium lignosulfate (Marasperse CBOS-4) |
| *Y. entomaphaga* O82KB8 suspension + 0.25% Maltrin ® M150 + 0.75% sorbitol + 0.089% potassium phosphate dibasic + 0.022% potassium phosphate monobasic + 1% calcium lignosulfate (Borresperse Ca) |
| *Y. entomaphaga* O82KB8 suspension + 0.25% Maltrin ® M150 + 0.75% sorbitol + 0.089% potassium phosphate dibasic + 0.022% potassium phosphate monobasic + 1% sodium lignosulfate (Borresperse Na) |
| *Y. entomaphaga* O82KB8 suspension + 0.25% Maltrin ® M150 + 0.75% sorbitol + 0.089% potassium phosphate dibasic + 0.022% potassium phosphate monobasic + 1% sodium lignosulfate (Marasperse CBOS-4) |

Figure 17:
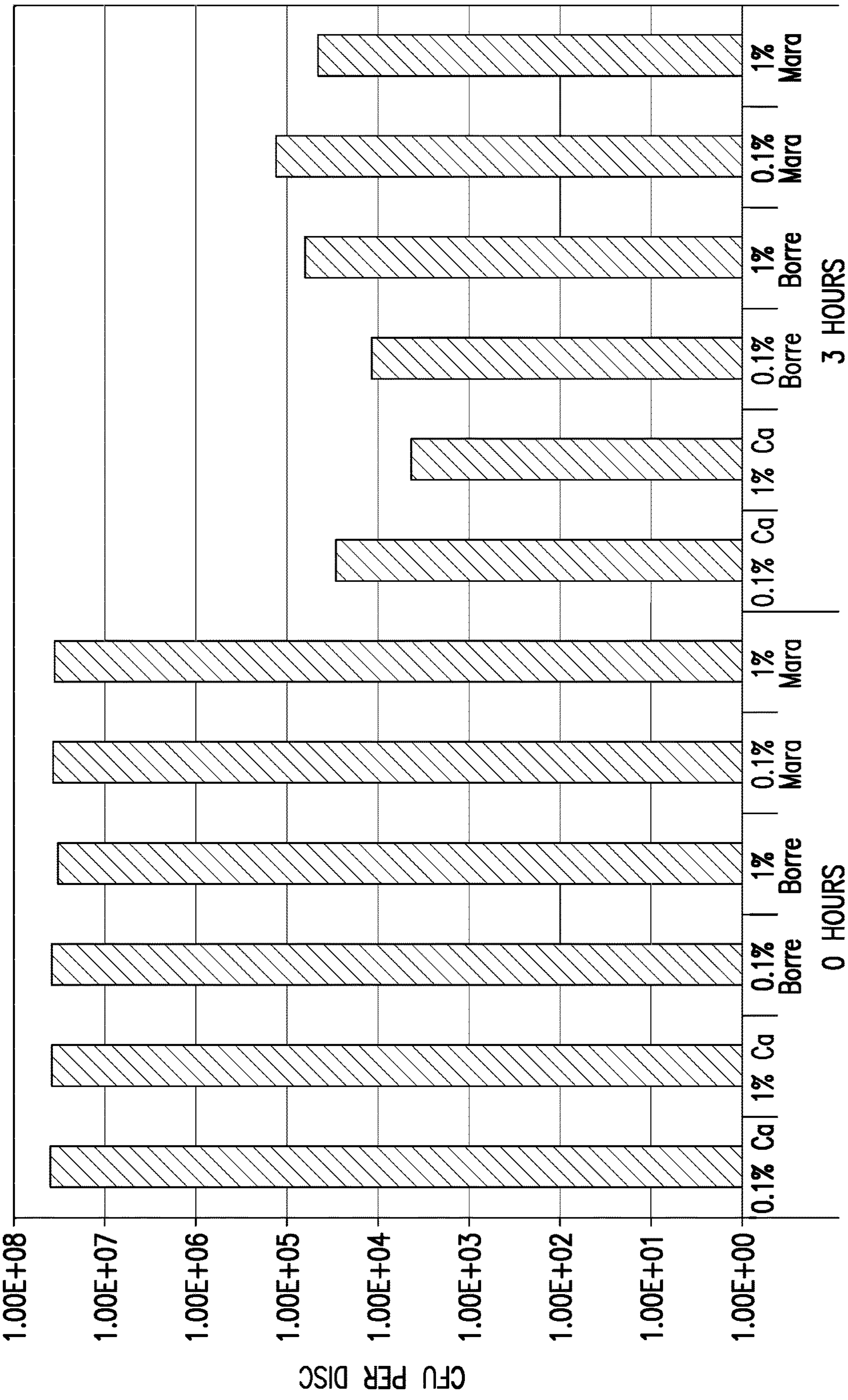

Treated discs were dried at room temperature under ambient humidity and ambient light and then assayed for survivability. FIG. 17 Treated discs were stored under an Oriel Soil A™ Class ABBSolar Simulator (light intensity of 100 mW at 300 nm; approximately 41° C.; approximately 23% relative humidity) and assayed for survivability. FIG. 17.

Example 16

Aqueous liquid inoculant compositions comprising *Yersinia entomophaga* O82KB8 (Table 16) were applied to PARAFILM® discs (2.5 cm diameter) at room temperature (20-23° C.) and ambient humidity under ambient light.

TABLE 16

| "Foliar" Treatment (five 2 µl drops per disc) |
|---|
| *Y. entomaphaga* O82KB8 suspension + 0.25% Maltrin ® M150 + 0.75% maltose monohydrate + 0.089% potassium phosphate dibasic + 0.022% potassium phosphate monobasic + sodium lignosulfate (Marasperse CBOS-4) |
| *Y. entomaphaga* O82KB8 suspension + 0.25% Maltrin ® M150 + 0.75% sorbitol + 0.089% potassium phosphate dibasic + 0.022% potassium phosphate monobasic + 0.1% sodium lignosulfate (Marasperse CBOS-4) |
| *Y. entomaphaga* O82KB8 suspension + 0.25% Maltrin ® M150 + 0.75% |

TABLE 16-continued

| "Foliar" Treatment (five 2 μl drops per disc) |
| --- |
| xylitol + 0.089% potassium phosphate dibasic + 0.022% potassium phosphate monobasic + 0.1% sodium lignosulfate (Marasperse CBOS-4) |

Figure 18:
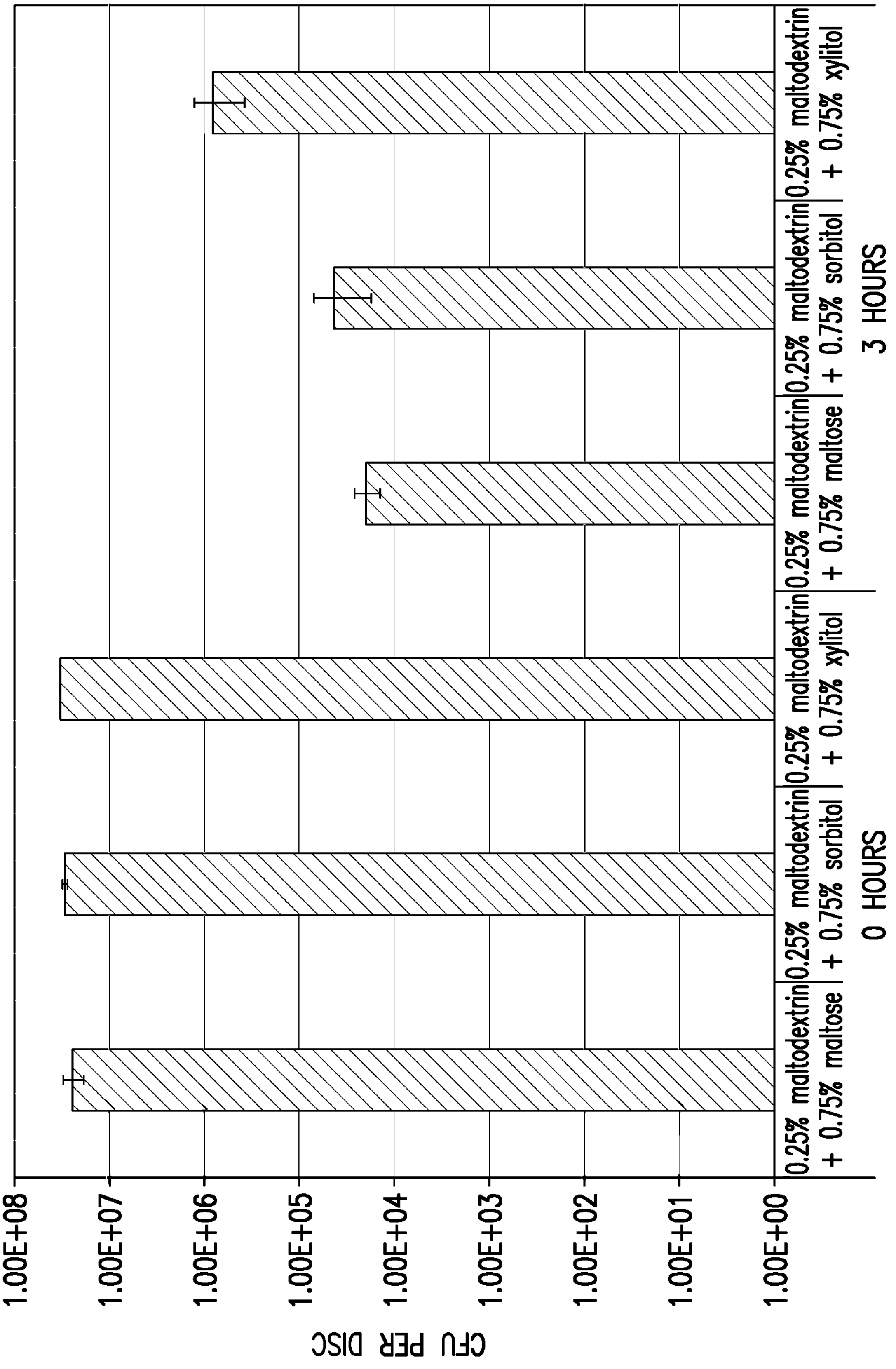

Treated discs were dried at room temperature under ambient humidity and ambient light and then assayed for survivability. FIG. 18 Treated discs were stored under an Oriel Sol1A™ Class ABBSolar Simulator (light intensity of 100 mW at 300 nm; approximately 41° C.; approximately 23% relative humidity) and assayed for survivability. As shown in FIG. 18, *Yersinia* survival was enhanced when all of the maltose in the maltodextrin-maltose stabilizer was replaced with sorbitol or xylitol.

Example 17

Aqueous liquid inoculant compositions comprising *Yersinia entomophaga* O82KB8 (Table 17) was applied to PARAFILM® discs (2.5 cm diameter) at room temperature (20-23° C.) and ambient humidity under ambient light.

TABLE 17

| "Foliar" Treatment (five 2 μl drops per disc) |
| --- |
| *Y. entomophaga* O82KB8 suspension + 0.25% Maltrin ® M150 + 0.75% maltose monohydrate + 0.089% potassium phosphate dibasic + 0.022% potassium phosphate monobasic |
| *Y. entomophaga* O82KB8 suspension + 0.25% Maltrin ® M150 + 0.75% xylitol + 0.089% potassium phosphate dibasic + 0.022% potassium phosphate monobasic |
| *Y. entomophaga* O82KB8 suspension + 0.25% Maltrin ® M150 + 0.75% maltose monohydrate + 0.089% potassium phosphate dibasic + 0.022% potassium phosphate monobasic + 0.1% sodium lignosulfate (Marasperse Na) |
| *Y. entomophaga* O82KB8 suspension + 0.25% Maltrin ® M150 + 0.75% xylitol + 0.089% potassium phosphate dibasic + 0.022% potassium phosphate monobasic + 0.1% sodium lignosulfate (Marasperse Na) |

Figure 19:
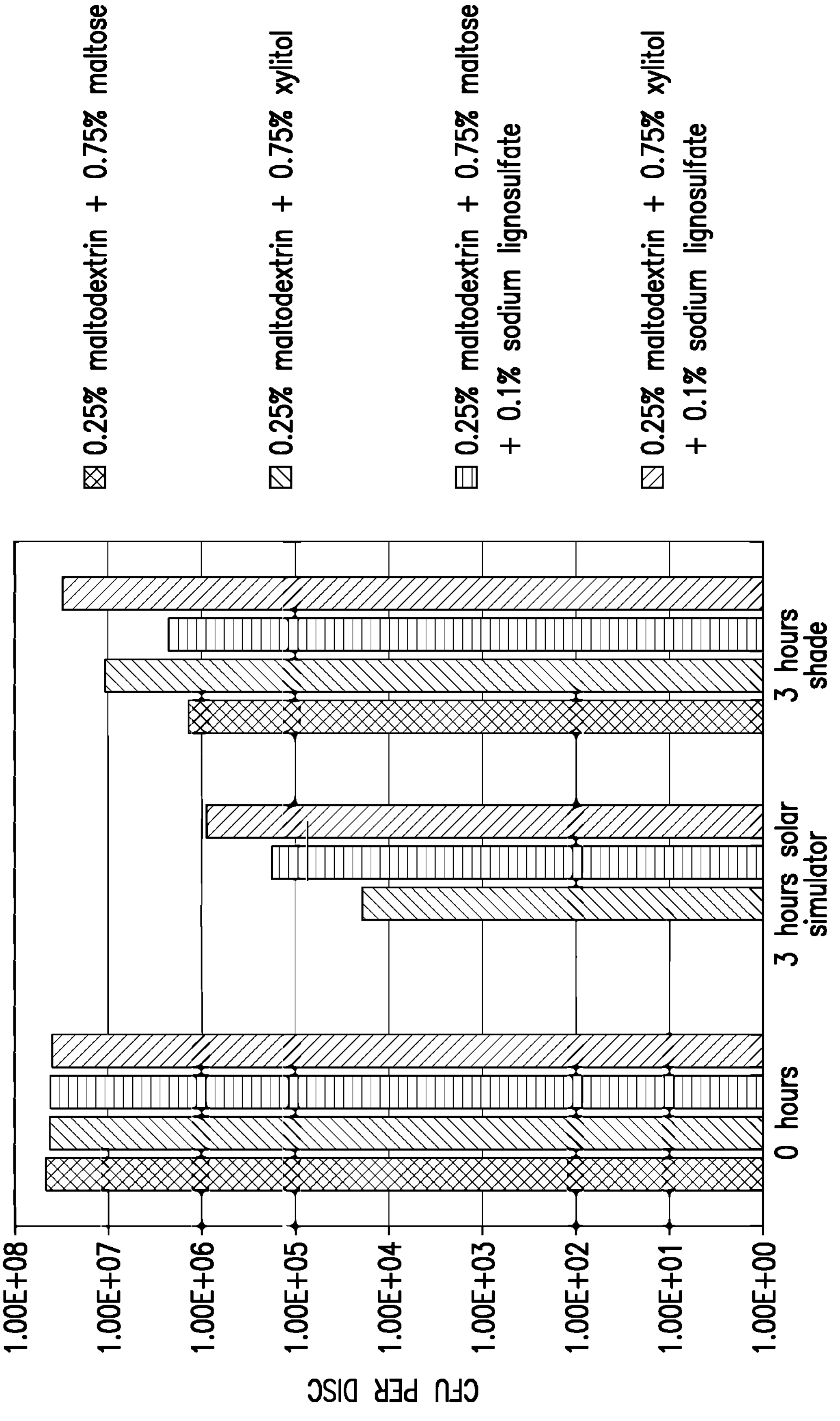

Treated discs were dried at room temperature under ambient humidity and ambient light and then assayed for survivability. FIG. 19. Treated discs were stored underpan Oriel Sol1A™ Class ABB Solar Simulator (light intensity of 100 mW at 300 nm) or in a dark incubator and then assayed for survivability. As shown in FIG. 19, *Yersinia* survival was enhanced when all of the maltose in the maltodextrin-maltose stabilizer was replaced with xylitol Enhanced survival with xylitol was observed in each of the test conditions both under the solar simulator and in the shade, as well as with and without sodium lignosulfate.

Example 18

Aqueous liquid inoculant compositions comprising *Yersinia entomophaga* O82KB8 (Table 189 were applied to parafilm discs (2.5 cm diameter) at room temperature (20-23° C.) and ambient humidity under ambient light.

TABLE 18

| "Foliar" Treatment (five 2 μl drops per disc) |
| --- |
| *Y. entomophaga* O82KB8 suspension + 0.25% Maltrin ® M150 + 0.75% maltose monohydrate + 0.089% potassium phosphate dibasic + 0.022% potassium phosphate monobasic + 0.1% calcium lignosulfate (Borresperse Ca) |
| *Y. entomophaga* O82KB8 suspension + 0.25% Maltrin ® M150 + 0.75% maltose monohydrate + 0.089% potassium phosphate dibasic + 0.022% potassium phosphate monobasic + 0.1% sodium lignosulfate (Borresperse Na) |
| *Y. entomophaga* O82KB8 suspension + 0.25% Maltrin ® M150 + 0.75% maltose monohydrate + 0.089% potassium phosphate dibasic + 0.022% potassium phosphate monobasic + 0.1% sodium lignosulfate (Marasperse CBOS-4) |
| *Y. entomophaga* O82KB8 suspension + 0.25% Maltrin ® M150 + 0.75% maltose monohydrate + 0.089% potassium phosphate dibasic + 0.022% potassium phosphate monobasic + 0.1% humic acid (Borregro HA-2) |
| *Y. entomophaga* O82KB8 suspension + 0.25% Maltrin ® M150 + 0.75% maltose monohydrate + 0.089% potassium phosphate dibasic + 0.022% potassium phosphate monobasic + 1% calcium lignosulfate (Borresperse Ca) |
| *Y. entomophaga* O82KB8 suspension + 0.25% Maltrin ® M150 + 0.75% maltose monohydrate + 0.089% potassium phosphate dibasic + 0.022% potassium phosphate monobasic + 1% sodium lignosulfate (Borresperse Na) |
| *Y. entomophaga* O82KB8 suspension + 0.25% Maltrin ® M150 + 0.75% maltose monohydrate + 0.089% potassium phosphate dibasic + 0.022% potassium phosphate monobasic + 1% sodium lignosulfate (Marasperse CBOS-4) |
| *Y. entomophaga* O82KB8 suspension + 0.25% Maltrin ® M150 + 0.75% maltose monohydrate + 0.089% potassium phosphate dibasic + 0.022% potassium phosphate monobasic + 1% humic acid (Borregro HA-2) |

Figure 20:
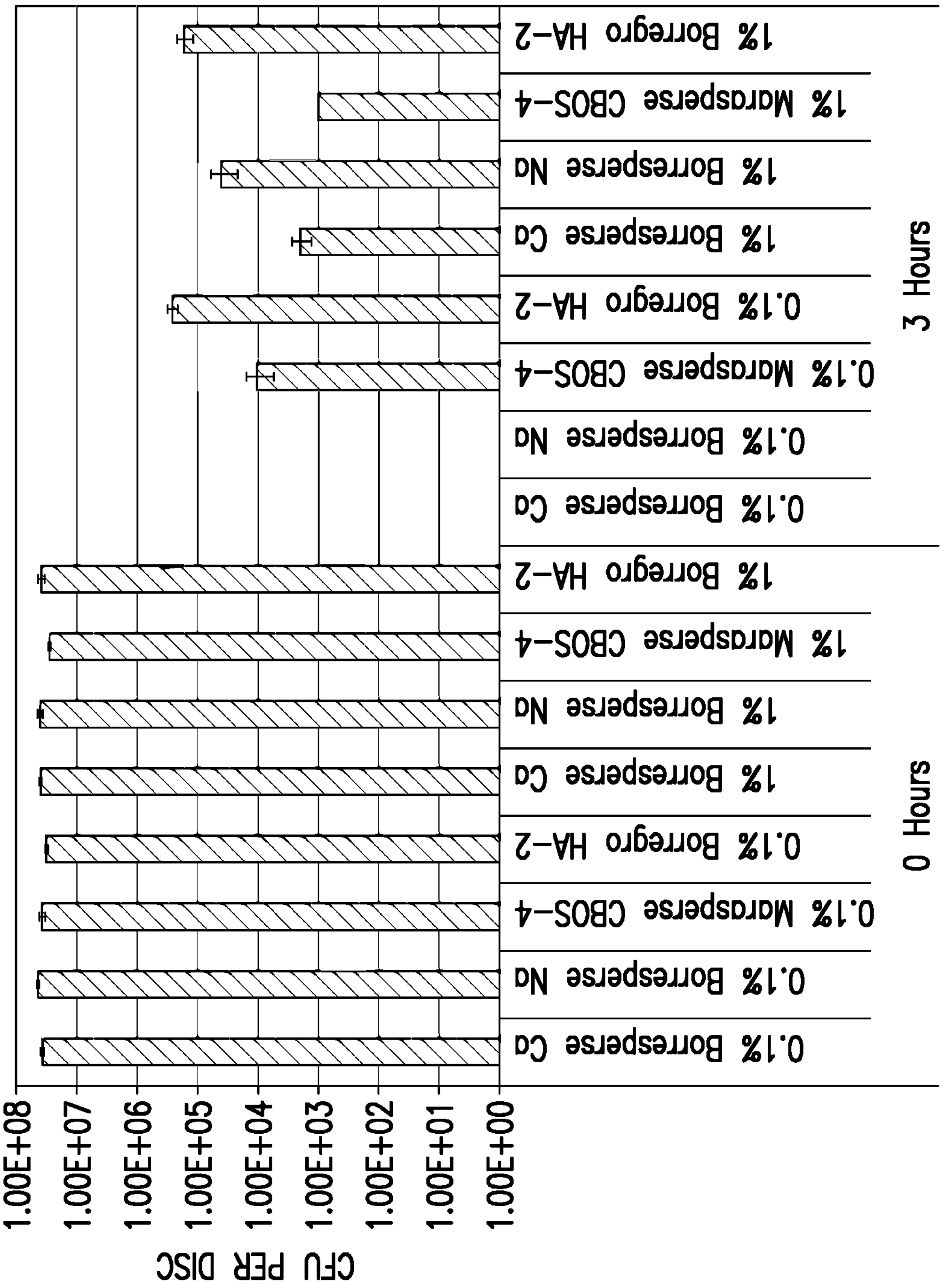
FIGS. 20-23 are graphs showing the survivability of desiccated *Yersinia entomaphaga* O82KB8 on parafilm stored under the Oriel Sol1A™ Class ABB Solar Simulator (light intensity of 100 mW at 300 nm) or in a dark incubator.

Treated discs were dried at room temperature under ambient humidity and ambient light and then assayed for survivability. FIG. 20. Treated discs were stored under an Oriel Sol1A™ Class ABB Solar Simulator (light intensity of 100 mW at 300 nm; approximately 41° C.; approximately 23% relative humidity) and assayed for survivability. FIG. 20. Humic acid enhanced *Yersinia* survival as compared to each of the lignosulfate additives.

Example 19

Aqueous liquid inoculant compositions comprising *Yersinia entomophaga* O82KB8 (Table 19) were applied to parafilm discs (2.5 cm diameter) at room temperature (20-23° C.) and ambient humidity under ambient light.

TABLE 19

| "Foliar" Treatment (five 2 μl drops per disc) |
| --- |
| *Y. entomophaga* O82KB8 suspension + 0.25% Maltrin ® M150 + 0.75% sorbitol + 0.089% potassium phosphate dibasic + 0.022% potassium phosphate monobasic + 0.1% calcium lignosulfate (Borresperse Ca) |
| *Y. entomophaga* O82KB8 suspension + 0.25% Maltrin ® M150 + 0.75% sorbitol + 0.089% potassium phosphate dibasic + 0.022% potassium phosphate monobasic + 0.1% sodium lignosulfate (Borresperse Na) |
| *Y. entomophaga* O82KB8 suspension + 0.25% Maltrin ® M150 + 0.75% sorbitol + 0.089% potassium phosphate dibasic + 0.022% potassium phosphate monobasic + 0.1% sodium lignosulfate (Marasperse CBOS-4) |
| *Y. entomophaga* O82KB8 suspension + 0.25% Maltrin ® M150 + 0.75% sorbitol + 0.089% potassium phosphate dibasic + 0.022% potassium phosphate monobasic + 0.1% humic acid (Borregro HA-2) |
| *Y. entomophaga* O82KB8 suspension + 0.25% Maltrin ® M150 + 0.75% sorbitol + 0.089% potassium phosphate dibasic + 0.022% potassium phosphate monobasic + 1% calcium lignosulfate (Borresperse Ca) |
| *Y. entomophaga* O82KB8 suspension + 0.25% Maltrin ® M150 + 0.75% sorbitol + 0.089% potassium phosphate dibasic + 0.022% potassium phosphate monobasic + 1% sodium lignosulfate (Borresperse Na) |
| *Y. entomophaga* O82KB8 suspension + 0.25% Maltrin ® M150 + 0.75% sorbitol + 0.089% potassium phosphate dibasic + 0.022% potassium phosphate monobasic + 1% sodium lignosulfate (Marasperse CBOS-4) |
| *Y. entomophaga* O82KB8 suspension + 0.25% Maltrin ® M150 + 0.75% sorbitol + 0.089% potassium phosphate dibasic + 0.022% potassium phosphate monobasic + 1% humic acid (Borregro HA-2) |

Figure 21:
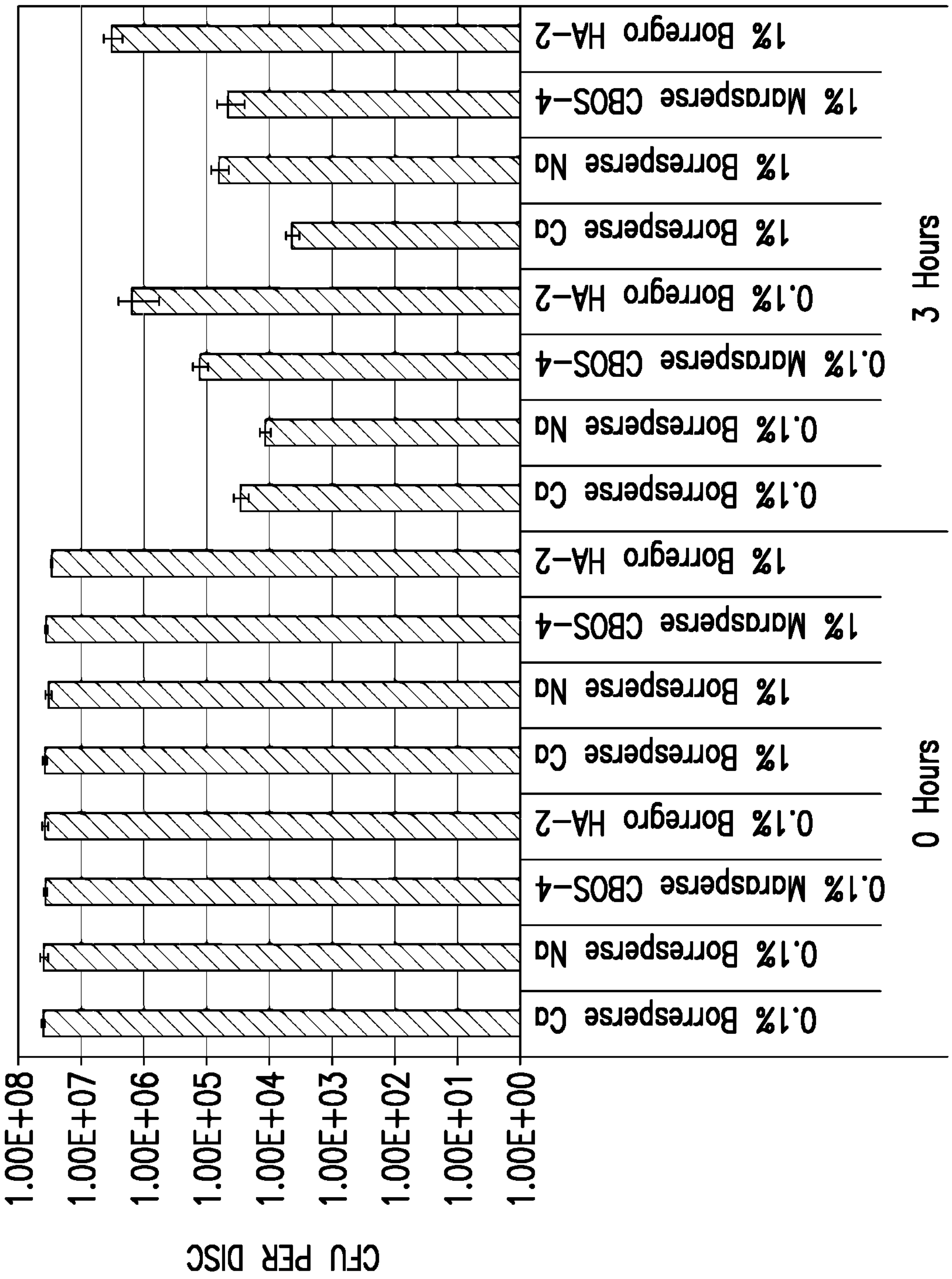

Treated discs were dried at room temperature under ambient humidity and ambient light and then assayed for survivability. FIG. 21. Treated discs were stored under an Oriel SolA™ Class ABB Solar Simulator (light intensity of 100 mW at 300 nm; approximately 41° C.; approximately 23% relative humidity) and assayed for survivability. FIG. 21. Humic acid enhanced *Yersinia* survival as compared to each of the lignosulfate additives.

Example 20

Aqueous liquid inoculant compositions comprising *Yersinia entomophaga* O82KB8 (Table 20) were applied to parafilm discs (2.5 cm diameter) at room temperature (20-23° C.) and ambient humidity under ambient light.

TABLE 20

| "Foliar" Treatment (five 2 µl drops per disc) |
|---|
| *Y. entomaphaga* O82KB8 suspension + 0.25% Maltrin ® M150 + 0.75% maltose monohydrate + 0.089% potassium phosphate dibasic + 0.022% potassium phosphate monobasic + 0.1% humic acid (Borregro HA-2) |
| *Y. entomaphaga* O82KB8 suspension + 0.25% Maltrin ® M150 + 0.75% sorbitol + 0.089% potassium phosphate dibasic + 0.022% potassium phosphate monobasic + 0.1% humic acid (Borregro HA-2) |
| *Y. entomaphaga* O82KB8 suspension + 0.25% Maltrin ® M150 + 0.75% xylitol + 0.089% potassium phosphate dibasic + 0.022% potassium phosphate monobasic + 0.1% humic acid (Borregro HA-2) |

Figure 22:
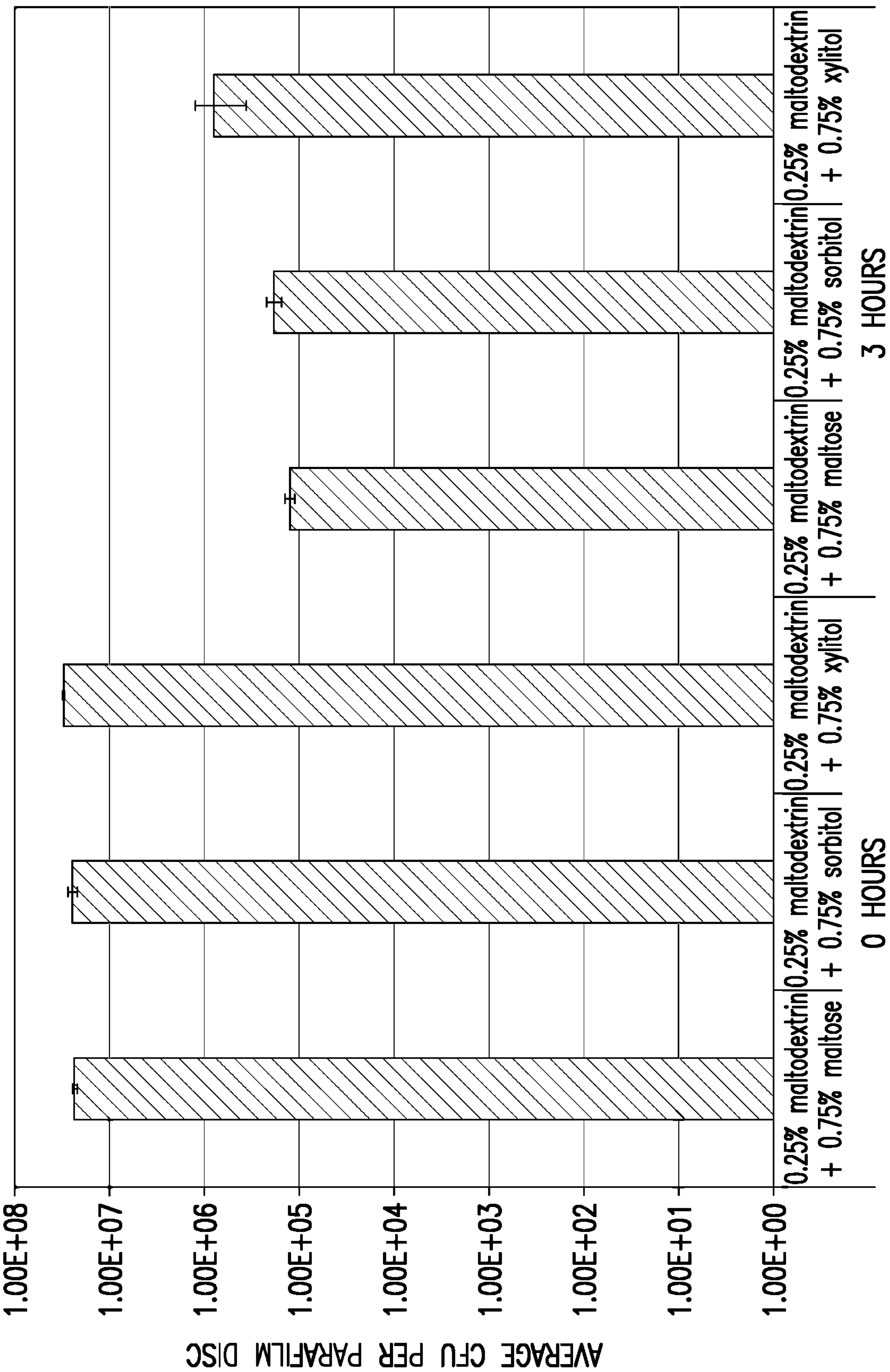

Treated discs were dried at room temperature under ambient humidity and ambient light and then assayed for survivability. FIG. 22. Treated discs were stored under an Oriel Sol1A™ Class ABB Solar Simulator (light intensity of 100 mW at 300 nm; approximately, 41° C.; approximately 23% relative humidity) and assayed for survivability. FIG. 22.

Example 21

Aqueous liquid inoculant compositions comprising *Yersinia entomophaga* O82KB8 (Table 21) were applied to parafilm discs (2.5 cm diameter) at room temperature (20-23° C.) and ambient humidity under ambient light.

TABLE 21

| "Foliar" Treatment (five 2 µl drops per disc) |
|---|
| *Y. entomaphaga* O82KB8 suspension + 0.25% Maltrin ® M150 + 0.75% maltose monohydrate + 0.089% potassium phosphate dibasic + 0.022% potassium phosphate monobasic + 0.1% humic acid (Borregro HA-2) |
| *Y. entomaphaga* O82KB8 suspension + 0.25% Maltrin ® M150 + 0.75% xylitol + 0.089% potassium phosphate dibasic + 0.022% potassium phosphate monobasic + 0.1% humic acid (Borregro HA-2) |

Figure 23:
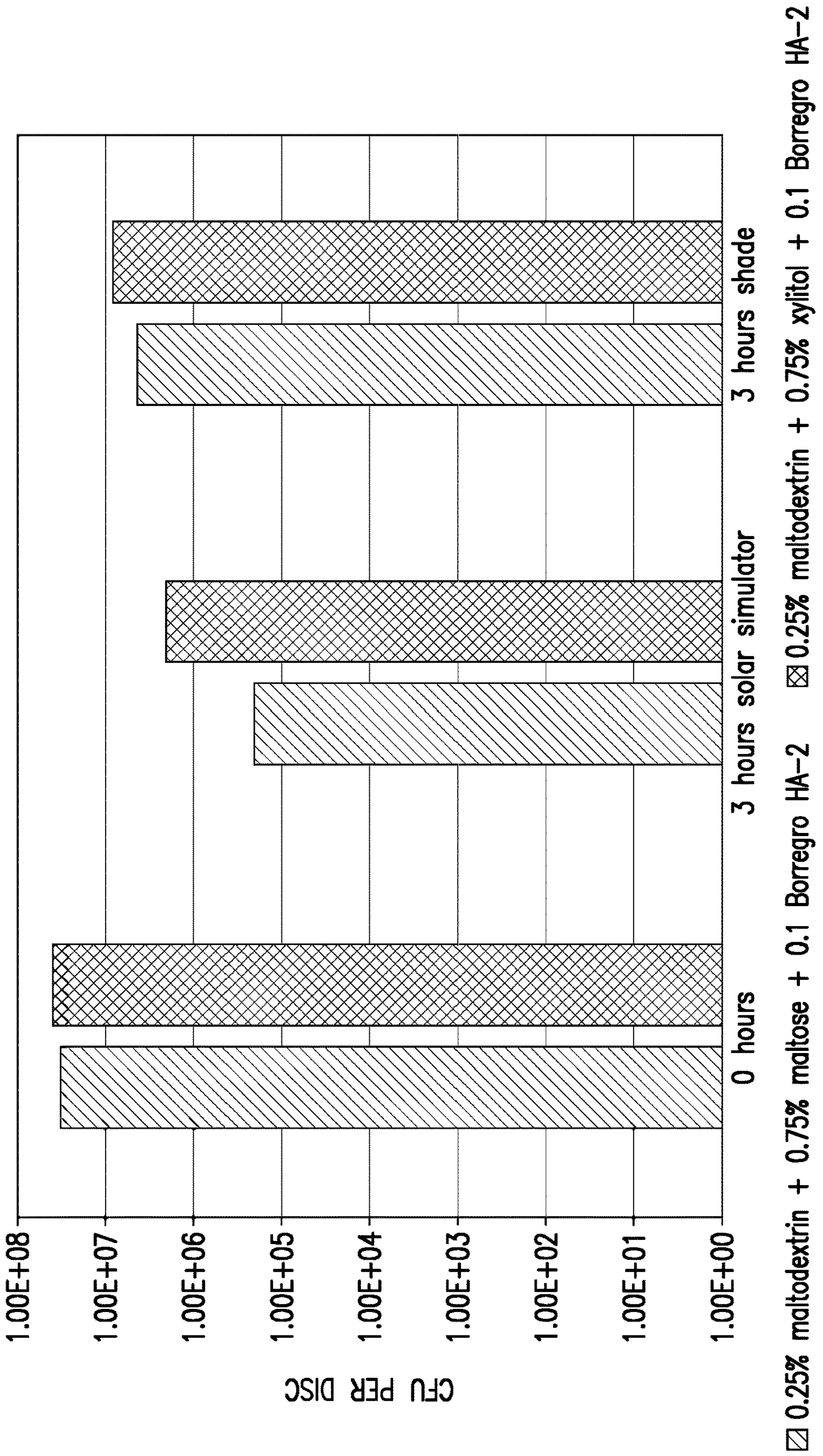

Treated discs were dried at room temperature under ambient humidity and ambient light and then assayed for survivability. FIG. 23 Treated discs were stored under an Oriel Sol1A™ Class ABB Solar Simulator (light intensity of 100 mW at 300 nm; approximately 41° C.; approximately 23% relative humidity) or in a dark incubator (approximately 41° C.; approximately 23% relative humidity) and assayed for survivability. FIG. 23.

APPENDIX A

*Acinetobacter, Actinomycetes, Aegerita, Agrobacterium* (e.g., *A. radiobacter* strains such as K1026 and K84), *Akanthomyces, Alcaligenes, Alternaria, Aminobacter* (e.g., *A. aganoensis, A. aminovorans, A. anthyllidis, A. ciceronei, A. lissarensis, A. niigataensis*), *Ampelomyces* (e.g., *A. quisqualis* strains such as M-10), *Anabaena* (e.g., *A. aequalis, A. affinis, A, angstumalis angstumalis, A, angstumalis marchita, A. aphanizomendoides, A. azollae, A. bornetiana, A. catenula, A. cedrorum, A. circinalis, A. confervoides, A. constricta, A. cyanobacterium, A. cyradeae, A. cylindrica, A. echinispora, A. felisii, A. flos-aquae flos-aquae, A. flos-aquae minor, A. flos-aquae treleasei, A. helicoidea, A, inaequalis, A. lapponica, A. laxa, A. lemmermannii, A. levanderi, A. limnetica, A. macrospora macraspora, A. macrospora robusta, A. monticulosa, A, nostoc, A. ascillarioides, A. planctonica, A. raciborski, A. scheremetievi, A. sphaerica, A. spiroides crassa, A. spiroides sprroides, A. subcylindrica, A, torulosa, A. unispora, A. varibilis, A. verrucosa, A. viguieri, A. wisconsinense, A. zerlingii*), *Arthrobacter, Arthrbotrys* (e.g., *A. aggregata, A. alaskana, A. ameropora, A, anomala, A. apscheronica, A. arthrobotryoides, A. azerbaijanica, A. bakunika, A. botryospora, A. brochopaga, A. chazarica, A. chilensis, A. cladodes, A. calvispora, A. compacta, A. conoides, A. constringens, A. cylindrospora, A. dactyloides, A. deflectans, A. dendroides, A. doliiformis, A. drechsleri, A. elegans, A. ellipsospora, A. entomopaga, A. ferox, A. foliicola, A. fruticulosa, A. globospora, A. hatospora, A. hertziana, A, indica, A. irregularis, A. javanica, A. kirghizica, A. longa, A. longiphora, A. longiramulifera, A. longispora, A. mangrovispora, A. megaspora, A. microscaphoides, A. microspora, A. multisecundaria, A. musiformis, A. nematopaga, A, nonseptata, A. oligospora, A. oudemansii, A. oviformis, A. perpasta, A. polycephala, A. pseudoclavata, A. pyriformis, A. recta, A. robusta, A. rosea, A. scaphoides, A. sclerhypha, A. shahriari, A. shizishanna, A. sinensis, A. soprunovii, A. stilbacea, A. straminicola, A. superba, A. tabrizica, A. venusta, A. vermicola, A. yunnanensis*), *Aschersonia, Ascophaera, Aspergillus* (e.g., *A. flavus* strains such as NRRL 21882, *A. parasitcus*), *Aulosira* (e.g., *A. aenigmatica, A. africana, A. bohemensis, A. bombayensis, A. confluens, A. fertilissima, A. fertilissma* var. *tenius, A. fritschii, A. godoyana, A. implexa, A. laxa, A. plantonica, A. prolifica, A. pseudoramosa, A. schaminslandii, A. striata, A. terrestris, A, thermalis*), *Aureobacterium, Aureobasidium* (e.g., *A. pullulans* strains such as DSM 14940 and DSM 14941), *Azobacter, Azorhobium* (e.g., *A. caulinodans, A. doebereinerae, A oxalatiphilum*), *Azospirillum* (e.g., *A. amazonense* strains such as BR 11140 (SpY2T), *A. brasilense* strains such as INTA Az-39, AZ39, XOH, BR 11002, BR 11005, Ab-V5 and Ab-V6, *A. canadense, A. doebereinerae, A. formosense, A. halopraeferans, A. irakense, A. largimobile, A. lipoferum* strains such as BR 11646, *A. melinis, A. oryzae, A. picis, A. rugosum, A. thiophilum, A. zeae*), *Azotobacter* (e.g., *A. agilis, A. armeniacus, A.* sp. AR. *A. beijerinkii, A. chroococcum*, A. DCU26, A. FA8, *A. nigricans, A. paspali, A. salinestris, A. tropicalis, A. vinelandii*), *Bacillus* (e.g., *B. amyloliquefaciens* strains such as D747, NRRL B-50349. TJ1000 (also known as 1BE, isolate ATCC BAA-390), FZB24, FZB42, IN937a, IT-45, TJ1000, MB1600, BS27 (deposited as NRRL B-5015), BS2084 (deposited as NRRL B-500I3), 15AP4 (deposited as ATCC PTA-6507), 3AP4 (deposited as ATCC PTA-6506), LSSA01 (deposited as NRRL B-50104), ABP278 (deposited as NRRL B-50634). 1013 (deposited as NRRL B-50509), 918 (deposited as NRRL B-50508), 22CP1 (deposited as ATCC PTA-6508) and BS18 (deposited as NRRL B-50633), *B. cereus* strains such as I-1562, *B. firmus* strains such as 1-1582. *B. laevolacticus, B. lichenformis* strains such as BAS42 (deposited as NRRL B-50516) and BL21 (deposited as NRRL B-50134), *B. macerns, B. firmus, B. mycoides* strains such as NRRL B-21664, *B. pasteurii, B. pumillus* strains such as NRRL B-21662, NRRL B-30087, ATCC 55608, ATCC 55609, GB34. KFP9F and QST 2808, *B.*

*sphaericus, B. subtilis* strains such as ATCC 55078, ATCC 55079. MBI 600, NRRL B-21661, NRRL B-21665, CX-9060, GB03, GB07, QST-713. FZB24, D747 and 3BPS (deposited as NRRL B-50510), *B. thuringiensis* strains such as ATCC 13367, GC-91, NRRL B-21619, ABTS-1857, SAN 4011, ABG-6305, ABG-6346, AM65-52, SA-12, SB4, ABTS-351, HD-1, EG 2348, EG 7826, EG 7841, DSM 2803, NB-125 and NB-176), *Beijerinckia, Beauveria* (e.g., *B. bassiana* strains such as ATCC 26851, ATCC 48023, ATCC 48585, ATCC 74040, ATCC-74250, DSM 12256 and PPRI 5339), *Beijerinckia, Blastodendrion, Bosea* (e.g., *B. eneae, B. lathyri, B. lupini, B. massiliensis, B. minantitlanensis, B. robiniae, B. thioxidans, B. vestrisii*), *Bradyrhizobium* (e.g., *B. arachidis, B. bete, B. canariense, B. cytisi, B. daqingense, B. dentrificans, B. diazoefficiens, B. elkanii* strains such as SEMIA 501, SEMIA 587 and SEMIA 5019, *B. ganzhouense, B. huanghuauhaiense, B. icense, B. ingae, B. iriomotense, B. japonicum* strains such as NRRL B-50586 (also deposited as NRRL B-59565), NRRL B-50587 (also deposited as NRRL B-59566), NRRL B-50588 (also deposited as NRRL B-59567). NRRL B-50589 (also deposited as NRRL B-59568). NRRL B-50590 (also deposited as NRRL B-59569), NRRL B-50591 (also deposited as NRRL B-59570), NRRL B-50592 (also deposited as NRRL B-59571), NRRL B-50593 (also deposited as NRRL B-59572). NRRL B-50594 (also deposited as NRRL B-50493). NRRL B-50608, NRRL B-50609. NRRL B-50610, NRRL B-50611, NRRL B-50612, NRRL B-50726, NRRL B-50727, NRRL B-50728, NRRL B-50729, NRRL B-50730, SEMIA 566, SEMIA 5079, SEMIA 5080, USDA 6, USDA 110, USDA 122, USDA 123, USDA 127, USDA 129 and USDA 532C, *B. jicama, B. lablabi, B. liaoningense, B. manausense, B. neotropicale, B. oligotrophicum, B. ottawaense, B. pachyrhizi, B. paxllaeri, B. retamae, B. rifense, B. valentinum, B. yuanmingense*), *Burkholderia* (e.g., *B. acidipaludis, B. ambifaria, B, andropogonis, B, anthina, B. arboris, B. bannensis, B. bryophila, B. caledonica, B. carbensis, B. caryphylli, B. cenocepacua, B. choica, B. cocovenenans, B. contaminans, B. denitrificans, B. diazotrophica, B. diffusa, B. dilworthii, B. dolosa, B. eburnea, B. endofungorum, B. ferrariae, B. fungorum, B. ginsengisoli, B. gladioli, B. glathei, B. glumae, B. graminis, B. grimmiae, B. heleia, B. hospital, B. humi, B. kururiensis, B. lata, B. latens, B. mallei, B. megapolitana, B. metallica, B. mimosarum, B. multivorans, B, nodosa, B, norimbergensis, B. oklahomensis, B. phenazinium, R. phenohruptrix, B. phymatum, B. phytofirmans, B. pickettii, B. plantarii, B. pseudomallei, B. pseudomultivorans, B. pyrrocinia, B. rhizoxinica, B. rhynchosiae, B. sabiae, B. sacchari, B. sartisoli, B. sediminicola, B. seminalis, B. silvatlantica, B. singaporensis, B. soli, B. sordidcola, B. sp.* strains such as A396, *B. sprentiae, B. stabtilis, B. symbiotica, B. telluris, B. terrae, B. terrestris, B. terricola, B. thailandensis, B. tropica, B. tuberum, B. ubonensis, B. udeis, B. unamae, B. vandii, B. vietnamiensis, B. xenovorans, B. zhejiangensis*), *Brevibacillus, Burkholderia* (e.g., *B.* sp, nov. rinojensis), *Calonectria, Candida* (e.g., *C. oleophila* such I-182, *C. saitoana*), *Candidatus* (e.g., *C. burkholderia calva, C. Burkholderia crenata, C. burkholderia hispidae, C. burkholderia kirkii, C. burkholderia mamillata, C. burkholderia nigropunctata, C. burkholderia rigidae, C. burkholdena schumannianae, C. burkholderia verschuerenii, C. burkholderia virens, C. phyroplasma allocasuarinae, C. phytoplasma americanum, C. phytoplasma asteris, C. phytoplasma aurantifolia, C. phytoplasma australiense, C. phytoplasma balanitae, C. phytoplasma brasihense, C. phytoplasma caricae, C. phytoplasma castaneae, C. phytoplasma cocosnigeriae, C. phytoplasma cocostanzaniae, C. phytoplasma convolvuh, C. phytoplasma costaricanum, C. phytoplasma cynodontis, C. phytoplasma fragariae, C. phytoplasma fraxini, C. phytoplasma graminis, C. phyloplasma japonicum, C. phytoplasma luffae, C. phytoplasma lycopersici, C. phytoplasma malasianum, C. phytoplasma mali, C. phytoplasma omanense, C. phytoplasma oryzae, C. phytoplasma palmae, C. phytoplasma palmicola, C. phytoplasma phoenicium, C phytoplasma pini, C. phytoplasma pruni, C. phytoplasma prunorum, C. phytoplasma pyri, C. phytoplasma rhamni, C. phytoplasma rubi, C. phytoplasma solani, C. phytoplasma spartii, C. phytoplasma sudamericanum, C. phytoplasma tamaricis, C. phytoplasma trifolii, C. phytoplasma ulmi, C. phytoplasma vitis, C. phytoplasma ziziphi*), *Chromobacterium* (e.g., *C. subtsugae* NRRL B-30655 and PRAA4-1, *C. vaccinia* strains such as NRRL B-50880, *C. violaceum*), *Chryseomonas, Clavibacter, Clonastachys* (e.g., *C. rosea* f, *catenulata* (also referred to as *Gliocladium catenulatum*) strains such as JI446). *Clostridium, Coelenmomyces, Coelomycidium, Colletotrichum* (e.g., *C. gloeosporioides* strains such as ATCC 52634). *Comomonas, Conidiobolus, Coniothyrium* (e.g., *C. minitans* strains such as CON/M191-08), *Cordyceps, Corynebacterium, Couchia, Cryphonectria* (e.g., *C. parasitica*), *Cryptococcus* (e.g., *C. albidus*), *Cryptophlebia* (e.g., *C. leucotreta*), *Culicinomyces, Cupriavidus* (e.g., *C. alkaliphilus, C. basilensis, C. campinensis, C. gilardii, C. laharis, C. metallidurans, C. numazuensis, C. oxalaticus, C. pampae, C. pauculus, C. pinatubonensis, C. respiraculi, C. tarwanensis*), *Curtobacterium, Cydia* (e.g., *C. pomonella* strains such as V03 and V22), *Dactylaria* (e.g., *D. candida*), *Delftia* (e.g., *D. acidovorans* strains such as RAY209). *Desulforibito, Desulfovabrio, Devosia* (e.g., *D. neptuniae*), *Dilophosphora* (e.g., *D. alopecuri*), *Engyodontium, Enterobacter, Entomophaga, Entomophthora, Erynia, Escherichia* (e.g., *E. intermedia*), *Eupenicillium, Exiguobacaterium, Filariomyces, Filobasidiella, Flavobacterium* (e.g., F. H492), *Frankia* (e.g., *F. alni*), *Fusarium* (e.g., *F. laterium, F. oxysporum, F. solani*), *Gibellula, Gigaspora* (e.g., *G. margarita*), *Gliocladium* (e.g., *G. virens* strains such as ATCC 52045 and GL-2I), *Glomus* (e.g., *G. aggregatum, G. brasilianum, G. clorum, G. deserticola, G. etunicatum, G. fasciculatum, G. intradices* strains such as RTI-801, *G. monosporum, G. mosseae*), *Gluconobacter, Halospirulina, Harposporium* (e.g., *H. anguillulae*), *Hesperomyces, Hirsutella* (e.g., *H. minnesotensis, H. rhossiliensis, H. thomsonii* strains such as ATCC 24874), *Hydrogenophage, Hymenoscyphous* (e.g., *H. ericae*), *Hymenostilbe, Hypocrella, Isaria* (e.g., *I. fumosorosea* strains such as Apopka-97 (deposited as ATCC 20874)), *Klebsiella* (e.g., *K. pneumoniae, K. oxytoca*), *Kluyvera, Laccaria* (e.g., *L. bicolor, L. laccata*), *Lactobacillus, Lagenidium, Lecanicillium* (e.g., *L. lecanii* strains such as KV01, *L. longisporum* strains such as KV42 and KV71), *Leptolegnia, Lysobacter* (e.g., *L. antibioticus* strains such as 13-1 and HS124, *L. enzymogenes* strains such as 3.1T8), *Massospora, Meristacrum* (e.g., *M. asterospermum*), *Mesorhizobium* (e.g., *M. abyssinicae, M. albiziae, M. alhagi, M. amorphae, M. australicum, M. camelthorni, M. caraganae, M. chacoense, M. ciceri, M. gobiense, M. hawassense, M. robiniae, M. sangai, M. mediterraneum, M. metallidurans, M. muleiense, M. opportunistum, M. plurifarium, M. qingshengii, M. robiniae, M. sangaii, M. septentrionale, M. shangrilense, M. shonense, M. silamurunense, M. tamadayense, M. tarimense, M. temperatum, M. thiogangeticum, M. tianshanense*), *Metarhizium* (e.g., *M. anisopliae* (also referred to as *M. brunneum, Metarrhizium anisopliae*, and green muscadine) strains such as IMI 330189, FI-985. FI-1045, F52 (deposited as DSM 3884, DSM 3885, ATCC 90448, SD 170 and ARSEF 7711) and ICIPE 69), *M. flavoviride* strains such as ATCC 32969), *Methylobacterium* (e.g., *M. adhaesivum, M. aerolatum, M. aminovorans, M. aquaticum, M. braciatum, M. bradythecii, M. bullatum, M. cerastii, M. chloromethanicum, M. dankookense, M. dichloromethanicum, M. extorquens, M. fujisawaense, M. gnaphalii, M. goesingense, M. gossipiicola, M. gregans, M. haplocladii, M. hispanicum, M, iners, M. isbiliense, M. jeotgali, M. komagatae, M. longum, M. lusitanum, M. marchantiae, M. mesophilicum, M, nodulans, M, organophilum, M, oryzac, M. oxalidis, M. persicinum, M. phyllosphaerae, M. platani, M. podarium, M. populi, M. radiotolerans, M. rhodesianum, M. rhodinum, M. salsuginis, M. soli, M. suomiense, M. tardum, M. tarhaniae, M. thiocyanatum, M. thurigiense, M. trifolii, M. variable, M. zatmanii*), *Metschikowia* (e.g., *M. fructicola*), *Microbacterium* (e.g., *M. laevaniformans*), *Microdochium* (e.g., *M. dimerum*), *Microsphaeropsis* (e.g., *M. ochraea* P130A), *Microvirga* (e.g., *M. aerilata, M. aerophila, M. flocculans, M. guangxiensis, M. lotononidis, M. lupini, M. subterranea, M. vignae, M. zambiensis*), *Monacrosporium* (e.g., *M. cionopagum*), *Mucor, Muscodor* (e.g., *M. albus* such NRRL 30547, QST 20799 and SA-13, *M. roseus* strains such as NRRL 30548), *Mycoderma, Myiophagus, Myriangium, Myrothecium* (e.g., *M. verrucaria*), *Nectria, Nematoctonus* (e.g., *N. geogenius, N. leiosporus*), *Neozygites, Nomuraea* (e.g., *N. rileyi* strains such as SA86101, GU87401, SR86151, CG128 and VA9101), *Nostoc* (e.g., *N. azollae. N. caeruleum, N. carneum, N. commmutum, N. commune, N ellipsosporum, N. flagelliforme, N. linckia, N. longstaffi, N. microscopicum, N. muscorum, N. paludosum, N. pruniforme, N. punctifrome, N. sphaericum, N. sphaeroides, N. spongiaeforme, N. verrucosum*), *Ochrobactrum* (e.g., *O. anthrops, O. cicero, O. cytisi, O. daejeonense, O. gallinifaecis, O. grigonense, O. guangzhouense, O. haematophilum, O, intermedium, O. lupini, O, oryzae, O. pectoris, O. pituitosum, O. pseudointermedium, O. pseudogrignonense, O. rhizosphaerae, O. thiophenivorans, O. tritici*), *Oidiodendron, Paecilomyces* (e.g., *P. fumosoroseus* strains such as FE991 and FE 9901, *P. lilacinus* strains such as 251, DSM 15169 and BCP2), *Paenibacillus* (e.g., *P. alvei* strains such as NAS6G6, *P. azotofixans, P. polymyxa* strains such as ABP166 (deposited as NRRL B-50211)), *Pandora, pantoea* (e.g., *P. agglomerans* strains such as NRRL B-21856, *P. vagans* strains such as C9-1), *Paraglomus* (e.g., *P. brazilianum*), *Paraisaria, Pasteria, Pasteuria* (e.g., *P. nishizawae* strains such as Pn1, *P. penetrans, P ramose, P. sp.* strains such as ATCC PTA-9643 and ATCC SD-5832, *P. thornea, P. usage*), *Penicillium* (e.g., *P. albidum, P. aurantiogriseum, P. bilaiae* (formerly known as *P. bilaii* and *P. bilaji*) strains such as ATCC 18309, ATCC 20851, ATCC 22348, NRRL 50162, NRRL 50169, NRRL 50776, NRRL 50777, NRRL 50778, NRRL 50777, NRRL 50778, NRRL 50'779, NRRL 50780, NRRL 50781, NRRL 50782, NRRL 50783, NRRL 50784, NRRL 50785, NRRL 50786, NRRL 50787, NRRL 50788 and RS7B-SD1, *P. brevicompactum* strains such as AgRF18, *P. canescens* strains such as ATCC 10419, *P. chyrsogemum, P. citreonigrum, P. cirinum, P. digitatum, P. expansum* strains such as ATCC 24692 and YT02, *P. fellatanum* strains such as ATCC 48694, *P. frequentas, P. fuscum, P. fussiporus, P. gaestrivorus* strains such as NRRL 50170, *P. glabrum* strains such as DAOM 239074 and CBS 229 28, *P. glaucum, P. griseofulvum, P. implicatum, P. janthinellum* strains such as ATCC 10455, *P. lanosocoeruleum* strains such as ATCC 48919, *P. hilacinum, P. minioluteum, P. montanense, P. nigricans, P. oxalicum, P. pinetorum, P. pinophilum, P. purpurogenum, P. radicum* strains such as ATCC 201836, FRR 4717, FRR 4719 and N93/47267, *P. raitstrickii* strains such as ATCC 10490, *P. rugulosum, P. simplicissimum, P. solitum, P. variable, P. velutinum, P. viridicatum*), *Phingobacterium, Phlebiopsis* (e.g., *P. gigantea*), *Photorhabdus, Phyllobacterium* (e.g., *P. bourgognense, P. brassicacearum, P. catacumbae, P. endophyticum, P. ifriqiyense, P. leguminum, P. loti, P. myrinacearum, P. sophorae, P. trifolii*), *Pichia* (e.g., *P. anomala* strains such as WRL-076), *Pisohthus* (e.g., *P. tinctorius*), *Planktothricoides, Plectonema, Pleurodesmospora, Pochonia* (e.g., *P. chlamydopora*), *Podonectria, Polycephalomyces, Prochlorocoous* (e.g., *P. marinus*), *Prochloron* (e.g., *P. didemni*), *Prochlorothrix, Pseudogisbellula, Pseudomonas* (e.g., *P. agarici, P. antartica, P. aurantiaca, P. aurantiaca, P. azotifigens, P. Azotoformans, P. balearica, P. blatchfordae, P. brassicacearum, P. brenneri, P. cannabina, P. cedrina, P. cepacia, P. chlororaphis* strains such as MA 342, *P. congelans, P corrugata, P. costantinii, P. denitrificans, P. entomophila, P. fluorescens* strains such as ATCC 27663, CL 145A and A506, *P. fragii, P. fuscovaginae, P. fulva, P. gessardii, P. jessenii* strains such as PS06, *P. kilonensis, P. koreensis, P. libanensis, P. lili, P. lundensis, P. lutea, P. luteola, P. mandelii, P. marginalis, P. meditrranea, P. meridana, P. migulae, P. moraviensis, P. mucidolens, P, orientalis, P, oryzihabitans, P. palleroniana, P. panacis, P. parafulva, P. peli, P. pertucinogena, P. plecoglossicida, P. protogens, P. proteolytica, P. putida, P. pyrocina* strains such as ATCC 15958, *P. rhodesiae, P. sp.* strains such as DSM 13134, *P. striata, P. stutzeri, P. syringae, P. synxantha, P. taetrolens, P. thisvervalensis, P, tolaasii, P. veronii*), *Pseudozyma* (e.g., *P. flocculosa* strains such as PF-A22 UL), *Pythium* (e.g., *P. oligandrum* strains such as DV 74), *Rhizobium* (e.g., *R. aggregatum, R. alamii, R. alkalisoli, P. alvei, P. azibense, P. borbori, R. calliandrae, R. cauense, R. cellulosilyticum, R. daejeonense, R. endolithicum, R. endophyticum, R, etli, R. fabae, R. flavum, R. fredii, R. freirei, R. galegae, R. gallicum, R. giardinii, R. grahamii, R. hainanense, R. halophytocola, R. halotolerans, R. helanshanense, R. herbae, R. huautlense, R, indigoferae, R. jaguaris, R. kummingense, R. laguerreae, R. larrymoorei, R. leguminosarum* strains such as SO12A-2 (IDAC 080305-01), *R. lemnae, R. leucaenae, R. loessense, R. lupini, R. lustanum, R. mayense, R. mesoamericanum, R. mesosinicum, R. miluonense, R. mongolense, R. multihospitium, R. naphthalenivorans, R. nepotum, R, oryzae, R. pakistanensis, R. paknamense, R. paranaense, R. petrolearium, R. phaseoli, R. phenanthrenilyticum, R. pisi, R. pongamiae, R. populi, R. Pseudoryzae, R. pusense, R. qilianshanese, R. radiobacter, R. rhizogenes, R. rhizoryzae, R. rozettiformans, R. rubi, R. selenitireeducens, R. skierneiwicense, R. snulacinae, R. soli, R. sophorae, R. sophoriradicis, R. sphaerophysae, R. straminoryzae, R. subbaraonis, R. sullae, R. taibaishanense, R tarimense, R. tibeticum, R. trifolii* strains such as RP113-7, *R. tropici* strains such as SEMIA 4080, *R. tubonense, R. undicola, R. vallis, R. viciae* strains such as P1NP3Cst, SU303 and WSM 1455, *R. vignae, R. vitis, R. yanglingense, R. yantingense*), *Rhizoctonia, Rhizopogon* (e.g., *R. amylopogon, R. fulvigleba, R. luteolus, R. villosuli*), *Rhodococcus, Saccharopolyspora* (e.g., *S. spinosa*), *Scleroderma* (e.g., *S. cepa S. citrinum*), *Septobasidium, Serratia, Shinella* (e.g., *S. kummerowiae*), *Sinorhizoium* (e.g., *S. abri, S. adhaerens, S. americanum, S. arboris, S. chiapanecum, S. fredii* strains such as CCBAU114 and USDA 205, *S. garamanticus, S. indiaense, S. kostiense, S. kummerowiae, S. medicae, S. meliloti* strains such as MSDJ0848, *S. mexicanus, S. numidicus, S. psoraleae, S. saheli, S. sesbaniae, S.*

*sojae, S. terangae, S. xinjiangense*), *Sorosporella, Sphaerodes* (e.g., *S. mycoparastica* strains such as IDAC 301008-01), *Spodoptera* (e.g., *S. littoralis*), *Sporodiniella, Steinernema* (e.g., *S. carpocapsae, S. feltiae, S. kraussei* strains such as L137), *Stenotrophomonas, Streptomyces* (e.g., *S. cacaoi* strains such as ATCC 19093, *S. galbus* strains such as NRRL 30232, *S. griseoviridis* strains such as K61, *S. lydicus* strains such as WYEC 108, *S. violaceusniger* strains such as YCED-9 (deposited as ATCC 55660)), *Streptosporangium, Stillbella, Swaminathania, Talaromyces* (e.g., *T. aculeatus, T. flavus* strains such as V117b), *Tetranacrium, Thiobacillus, Tilachlidium, Tolypocladium, Tolypothrix, Torrubiella, Torulospora, Trenomyces, Trichoderma* (e.g. *T. asperellum* strains such as SKT-1 and ICC 012, *T. atroviride* strains such as LC52 and CNCM 1-1237, *T. fertile* strains such as JM41R, *T. gamsii* strains such as ICC 080, *T. hamatum* strains such as ATCC 52198, *T. harzianum strains such as ATCC* 52445, KRL-AG2, T-22, TH-35, T-39 and ICC012, *T. polysporum, T. reesi* strains such as ATCC 28217 *T. stromaticum, T. virens* strains such as ATCC 58678, G1-3, GL-21 and G-41, *T. viridae* strains such as ATCC 52440, ICC080 and TV1), *Typhula, Ulocladium* (e.g., *U. oudemansii* strains such as HRU3), *Uredinella, Variovorax, Verticillium* (e.g., *V. chlamydosporum, V. lecanii* strains such as ATCC 46578), *Vibrio, Xanthobacter, Xanthomonas, Xenorhadbus, Yersinia* (e.g., *Y. entomophaga* strains such as O82KB8), *Zoophthora*

That which is claimed:

1. An aqueous liquid inoculant composition comprising one or more sugar alcohols, one or more disaccharides, one or more maltodextrins having an average dextrose equivalent value of about 15 to about 20, and one or more Gram-negative, non-spore-forming microorganisms, wherein said sugar alcohol(s), disaccharide(s), and maltodextrin(s) are present in a sugar alcohol:(disaccharide and maltodextrin) ratio of about 15:85 to about 25:75.

2. The aqueous liquid inoculant composition of claim 1, wherein said one or more sugar alcohols comprises sorbitol.

3. The aqueous liquid inoculant composition of claim 1, wherein said one or more sugar alcohols comprises xylitol.

4. The aqueous liquid inoculant composition of claim 1, wherein said one or more disaccharides comprise maltose.

5. The aqueous liquid inoculant composition of claim 1, wherein said sugar alcohol(s), disaccharide(s), and maltodextrin(s) are present in a sugar wherein said sugar alcohol(s), disaccharide(s), and maltodextrin(s) are alcohol:(disaccharide and maltodextrin) ratio of about 20:80.

6. The aqueous liquid inoculant composition of claim 1, wherein said maltodextrin(s) and said sugar alcohol(s) are present in a maltodextrin:sugar alcohol ratio of about 25:75.

7. The aqueous liquid inoculant composition of claim 1, comprising about $1\times10^{1}$ to about $1\times10^{12}$ colony-forming units of said Gram-negative, non-spore-forming microorganisms per gram and/or milliliter of said aqueous liquid inoculant composition.

8. The aqueous liquid inoculant composition of claim 1, comprising at least $1\times10^{4}$ colony-forming units of said Gram-negative, non-spore-forming microorganisms per gram and/or milliliter of said aqueous liquid inoculant composition.

9. The aqueous liquid inoculant composition of claim 1, further comprising one or more carboxymethyl celluloses and/or polyvinyl alcohols.

10. The aqueous liquid inoculant composition of claim 1, wherein said one or more sugar alcohols, said one or more disaccharides, and said one or more maltodextrins comprise about 25 to about 50% of said aqueous liquid inoculant composition (w/w, based upon the total weight of said aqueous liquid inoculant composition).

11. The aqueous liquid inoculant composition of claim 1, further comprising one more lipo-chitooligosaccharides.

12. The aqueous liquid inoculant composition of claim 1, wherein said one or more sugar alcohols, said one or more disaccharides and said one or more maltodextrins collectively comprise about 5 to about 25% of said aqueous liquid inoculant composition (w/w, based upon the total weight of said aqueous liquid inoculant composition).

13. The aqueous liquid inoculant composition of claim 1, wherein said one or more sugar alcohols, said one or more disaccharides, and said one or more maltodextrins collectively comprise about 1 to about 10% of said aqueous liquid inoculant composition (w/w, based upon the total weight of said aqueous liquid inoculant composition).

14. The aqueous liquid inoculant composition of claim 1, further comprising one or more humic acids.

15. The aqueous liquid inoculant composition of claim 1, wherein said one or more sugar alcohols, said one or more disaccharides, and said one or more maltodextrins collectively comprise about 0.25 to about 5% of said aqueous liquid inoculant composition (w/w, based upon the total weight of said aqueous liquid inoculant composition).

16. A method, comprising applying the aqueous liquid inoculation composition of claim 1 to a plant propagation material.

17. A method, comprising applying the aqueous liquid inoculant composition of claim 1 to a plant.

18. A coated plant propagation material, comprising a plant propagation material and a coating that covers at least a portion of an outer surface of said seed, said coating comprising the aqueous liquid inoculant composition of claim 1.

19. A method, comprising applying the aqueous liquid inoculant composition of claim 1 to foliage.

20. A method, comprising drying the aqueous liquid inoculant composition of claim 1 to produce a powder or granule comprising said one or more Gram-negative, non-spore-forming microorganisms, said one or more sugar alcohols, said one or more disaccharides, and said one or more maltodextrins.

21. A method of improving the stability of a Gram-negative, non-spore-forming microorganism in an aqueous composition, said method comprising introducing into said aqueous composition one or more sugar alcohols, one or more disaccharides and one or more maltodextrins having an average dextrose equivalent value of about 15 to about 20 in a sugar alcohol:(disaccharide and maltodextrin) ratio of about 15:85 to about 25:75.

22. The method of 21, further comprising drying said aqueous composition after said introducing to produce a powder or granule comprising said Gram-negative, non-spore-forming microorganism, said one or more sugar alcohols, said one or more disaccharides, and said one or more maltodextrins.

* * * * *